(12) United States Patent
Alfaro et al.

(10) Patent No.: US 11,780,821 B2
(45) Date of Patent: Oct. 10, 2023

(54) INHIBITORS OF FIBROBLAST ACTIVATION PROTEIN

(71) Applicant: Praxis Biotech LLC, San Francisco, CA (US)

(72) Inventors: Jennifer Alfaro, Santiago (CL); Sebastian Belmar, Santiago (CL); Sebastian Bernales, Piedmont, CA (US); Brahmam Pujala, Greater Noida (IN); Dayanand Panpatil, Noida (IN); Bhawana Bhatt, Noida (IN)

(73) Assignee: PRAXIS BIOTECH LLC, San Francisco, CA (US)

(*) Notice: Subject to any disclaimer, the term of this patent is extended or adjusted under 35 U.S.C. 154(b) by 0 days.

(21) Appl. No.: 16/221,398

(22) Filed: Dec. 14, 2018

(65) Prior Publication Data
US 2019/0185451 A1 Jun. 20, 2019

Related U.S. Application Data

(60) Provisional application No. 62/599,630, filed on Dec. 15, 2017.

(51) Int. Cl.
| | | |
|---|---|---|
| C07D 401/12 | (2006.01) | |
| A61P 3/04 | (2006.01) | |
| A61P 3/10 | (2006.01) | |
| A61P 35/00 | (2006.01) | |
| C07D 207/34 | (2006.01) | |
| C07D 401/14 | (2006.01) | |
| C07D 403/12 | (2006.01) | |
| C07D 405/12 | (2006.01) | |
| C07D 405/14 | (2006.01) | |
| C07D 413/14 | (2006.01) | |
| C07D 471/04 | (2006.01) | |
| C07D 491/048 | (2006.01) | |

(52) U.S. Cl.
CPC .......... *C07D 401/12* (2013.01); *A61P 3/04* (2018.01); *A61P 3/10* (2018.01); *A61P 35/00* (2018.01); *C07D 207/34* (2013.01); *C07D 401/14* (2013.01); *C07D 403/12* (2013.01); *C07D 405/12* (2013.01); *C07D 405/14* (2013.01); *C07D 413/14* (2013.01); *C07D 471/04* (2013.01); *C07D 491/048* (2013.01)

(58) Field of Classification Search
CPC . C07D 401/12; C07D 410/10; A61K 31/4439
USPC ....................................... 546/279.1; 514/343
See application file for complete search history.

(56) References Cited

U.S. PATENT DOCUMENTS

| | | | | |
|---|---|---|---|---|
| 8,183,280 B2* | 5/2012 | Evans | .................. | C07D 207/16 514/423 |
| 9,346,814 B2* | 5/2016 | Jansen | .................. | C07D 401/12 |
| 11,504,364 B2 | 11/2022 | Pujala et al. | | |
| 2006/0089312 A1 | 4/2006 | Bachovchin | | |
| 2006/0276435 A1 | 12/2006 | Cohen et al. | | |
| 2007/0098781 A1 | 5/2007 | Loeffler et al. | | |
| 2010/0081701 A1 | 4/2010 | Evans et al. | | |
| 2010/0291020 A1 | 11/2010 | Arora et al. | | |
| 2012/0045509 A1 | 2/2012 | Loeffler et al. | | |
| 2014/0357650 A1 | 12/2014 | Jansen | | |
| 2020/0206216 A1 | 7/2020 | Pujala | | |
| 2020/0216417 A1 | 7/2020 | Bernales | | |
| 2022/0089573 A1 | 3/2022 | Jakob et al. | | |

FOREIGN PATENT DOCUMENTS

| | | |
|---|---|---|
| EA | 028422 B1 | 11/2017 |
| RU | 2447063 C2 | 4/2012 |
| WO | 2001081337 A1 | 11/2001 |
| WO | 2001096295 A2 | 12/2001 |
| WO | 2003000250 A1 | 1/2003 |
| WO | 2003002553 A2 | 1/2003 |
| WO | 2003037327 A1 | 5/2003 |
| WO | 2003074500 A2 | 9/2003 |
| WO | 2004071454 A2 | 8/2004 |
| WO | 2007085895 A2 | 8/2007 |
| WO | 2009116067 A2 | 9/2009 |
| WO | 2010083570 A1 | 7/2010 |
| WO | 2013107820 A1 | 7/2013 |
| WO | 2017011831 A1 | 1/2017 |
| WO | 2017189569 A1 | 11/2017 |
| WO | 2018111969 A1 | 6/2018 |
| WO | 2018111989 A1 | 6/2018 |
| WO | 2019083990 A2 | 5/2019 |
| WO | 2019118932 A1 | 6/2019 |
| WO | 2019154886 A1 | 8/2019 |
| WO | 2020132661 A2 | 6/2020 |
| WO | 2020142742 A1 | 7/2020 |
| WO | 2020144375 A9 | 10/2020 |

OTHER PUBLICATIONS

Fitzgerald et al., "The role of, etc.," Cancer and Metastasis Reviews, 39: 783-803.. (Year: 2020).*
Kelly, "Fibroblast activation, etc.," Drug Resistance Updates 8, 51-58.. (Year: 2005).*
Martinez-Garza et al., "Fibroblast Growth, etc.," Int. J. Mol. Sci., 20, pp. 1-21. (Year: 2019).*
Simone, Oncology: Introduction, Cecil Textbook of Medicine, ed. Bennett et al. W.B. Saunders CO. 20th ed. vol. 1, pp. 1004-1010. (Year: 1996).*
Gura, Systems for Identifiying New Drugs Are Often Faulty, Cancer Models, Science, vol. 278 No. 5340. pp 1041-1042. (Year: 1997).*
Johnson et al., Relationships between drug activity in NCI preclinical in vitro and in vivo and early clinical trials, British J of Cancer, 64(10): 1424-1431. (Year: 2001).*
Pearce et al., Failure modes in anticancer drug discovery and development, Cancer Drug Design and Discovery ed by Stephen Neidle, chap. 18, pp. 424-435. (Year: 2008).*

(Continued)

*Primary Examiner* — David K O'Dell
(74) *Attorney, Agent, or Firm* — Morrison & Foerster LLP

(57) ABSTRACT

Compounds and compositions for modulating fibroblast activation protein (FAP) are described. The compounds and compositions may find use as therapeutic agents for the treatment of diseases, including hyperproliferative diseases.

16 Claims, 16 Drawing Sheets

(56) References Cited

OTHER PUBLICATIONS

Pure et al., "Pro-tumorigenic roles of, etc.," Oncogene 37:4343-4357. (Year: 2018).*
Schuppan et al., "Liver fibrosis, etc.," Matrix Biol. 68-69, 435-451.. (Year: 2018).*
Juillerat-Jeannert et al., "Fibroblast activation, etc.," Expert Opinion on Therapeutic Targets, 21(10), 977-991. (Year: 2017).*
Wauman et al., "The dipeptidyl peptidase, etc.," Frontiers in Immunology, 6, article 387. (Year: 2015).*
Vliegen et al., "The expression of proline, etc.," Ann Transl Med, 5(6): 130.. (Year: 2017).*
Kelly et al., "Firbroblast Activation, etc.," International review of Cell and Molecular Biology, 297, 83-116. (Year: 2012).*
Hamson et al., "Understanding fibroblast, etc.," Proteomics Clin. Appl., 8, 454-463. (Year: 2014).*
Jansen, Koen "Potent and selective inhibitors of fibroblast activation protein (FAP)" Dissertation University of Antwerp, 2014.*
Aertgeerts, K. et al. (May 2005). "Structural and Kinetic Analysis of the Substrate Specificity of Human Fibroblast Activation Protein $\alpha^*$," J. Biol. Chem. 280(20):19441-19444.
Brokopp, C.E. et al. (2011). "Fibroblast Activation Protein Is Induced By Inflammation and degrades Type I Collagen In Thin-Cap Fibroatheromata," Eur. Heart J. 32(21):2713-2722.
Camacho, R.C. et al. (Sep. 5, 2013, e-pub. Jul. 3, 2013). "Pegylated Fgf21 Rapidly Normalizes Insulin-Stimulated Glucose Utilization In Diet-Induced Insulin Resistant Mice," Eur. J. Pharmacol. 715(1-3):41-45.
Chen, L. et al. (Aug. 9, 2017). "PKM2 Aggravates Palmitate-Induced Insulin Resistance in HepG2 Cells via STAT3 Pathway," Biochem. Biophys. Res. Commun. 492(1):109-115.
Cohen, S.J. et al. (Aug. 2008). "Fibroblast Activation Protein and Its Relationship to Clinical Outcome in Pancreatic Adenocarcinoma," Pancreas 37(2):154-158.
Coppage, A.L. et al. (2016). "Human FGF-21 Is a Substrate of Fibroblast Activation Protein," PLoS One 11 (3):e0151269, 10 pages.
Cunningham, C.C. (Sep. 2007). "Talabostat," Expert Opin Investig Drugs 16(9):1459-1465.
Dong, J.Q., et al. (2015, e-pub. May 2, 2015). "Pharmacokinetics and Pharmacodynamics of PF-05231023, A Novel Long-Acting FGF21 Mimetic, In a First-In-Human Study," Br. J. Clin. Pharmacol. 80(5):1051-1063.
Dunshee, D.R. et al. (Mar. 11, 2016). "Fibroblast Activation Protein Cleaves and Inactivates Fibroblast Growth Factor 21," J. Biol. Chem. 291(11):5986-5996.
Eager, R.M. et al. (Jul. 30, 2009). "Phase II Assessment Of Talabostat and Cisplatin In Second-Line Stage IV Melanoma," BMC Cancer 9:263, 11 pages.
Eager, R.M., et al. (Aug. 2009, e-pub. Jun. 5, 2009). "Phase II Trial Of Talabostat and Docetaxel In Advanced Non-Small Cell Lung Cancer,"Clin. Oneal. R. Coll. Radiol. 21(6):464-472.
Gaich, G. et al. (Sep. 3, 2013). "The Effects of LY2405319, an FGF21 Analog, in Obese Human Subjects with Type 2 Diabetes," Cell Metab 18(3):333-340.
Hager, T., et al. (Mar. 5, 2013, e-pub. Feb. 19, 2013). "Differential Enzyme-Linked Immunosorbent Assay And Ligand-Binding Mass Spectrometry For Analysis Of Biotransformation Of Protein Therapeutics: Application To Various FGF21 Modalities," Anal Chem. 85(5):2731-2738.
Hecht, R. et al. (Nov. 27, 2012). "Rationale-Based Engineering of a Potent Long-Acting FGF21 Analog for the Treatment of Type 2 Diabetes," PLoS One 7(11):e49345.
Henry, L.R. et al. (Mar. 15, 2007). "Clinical Implications Of Fibroblast Activation Protein In Patients With Colon Cancer," Clin. Cancer Res. 13(6):1736-1741.
Hugo, W. et al. (Mar. 24, 2016). "Genomic and Transcriptomic Features Of Response To Anti-PD-1 Therapy In Metastatic Melanoma," Cell 165(1):35-44.

International Search Report and Written Opinion of the International Searching Authority, dated Apr. 29, 2020, for PCT Application No. PCT/US2020/012260, filed Jan. 3, 2020, ten pages.
International Search Report and Written Opinion of the International Searching Authority, dated Feb. 27, 2019, for PCT Application No. PCT/US2018/65859, filed Dec. 14, 2018, 15 pages.
Jansen, K. et al. (Mar. 11, 2014). "Extended Structure-Activity Relationship and Pharmacokinetic Investigation of (4-Quinolinoyl)glycyl-2-cyanopyrrolidine Inhibitors of Fibroblast Activation Protein (FAP)," J. Med. Chem. 57(7):3053-3074.
Ju, M.J. et al. (2009). "Peritumoral Activated Hepatic Stellate Cells Predict Poor Clinical Outcome in Hepatocellular Carcinoma After Curative Resection," Am. J. Clin. Pathol. 131(4):498-510.
Kharitonenkov, A. et al. (Jun. 2005). "FGF-21 As A Novel Metabolic Regulator," J. Clin. Invest. 115(6):1627-1635.
Kharitonenkov, A, et al. (Feb. 2007, e-pub. Oct. 26, 2006). "The Metabolic State of Diabetic Monkeys Is Regulated by Fibroblast Growth Factor-21,"Endocrinology 148(2):774-781.
Lee, K.N. et al. (2011). "Enhancement Of Fibrinolysis By Inhibiting Enzymatic Cleavage Of Precursor $\alpha 2$-Antiplasmin," J. Thromb. Haemost. 9(5):987-996.
Lee, K.N. et al. (Jun. 16, 2009). "Using Substrate Specificity of Antiplasmin-Cleaving Enzyme for Fibroblast Activation Protein Inhibitor Design," Biochemistry, 48(23):5149-5158, 22 pages.
Levy, M.T. et al. (1999). "Fibroblast Activation Protein: A Cell Surface Dipeptidyl Peptidase and Gelatinase Expressed by Stellate Cells at the Tissue Remodelling Interface in Human Cirrhosis," Hepatology 29(6):1768-1778.
Li, J. et al. (Aug. 15, 2012). "An Activatable Near Infrared Fluorescent Probe for In Vivo Imaging of Fibroblast Activation Protein-alpha," Bioconjug Chem. 23(8):1704-1711, 17 pages.
Markan, K.R. et al. (May 2016). "Metabolic Fibroblast Growth Factors (FGFs): Mediators Of Energy Homeostasis," Semin. Cell Dev. Biol. 53:85-93, 21 pages.
Micanovic, R., et al. (May 2009. e-pub. Dec. 30, 2008). "Differentcf N- and C-Termini In The Functional Activity Of FGF21," J. Cell Physiol. 219(2):227-234.
Mu, J. et al. (Feb. 2012). "FGF21 Analogs of Sustained Action Enabled by Orthogonal Biosynthesis Demonstrate Enhanced Antidiabetic Pharmacology in Rodents," Diabetes 61(2):505-512.
Narra, K. et al. (2007, e-pub. Nov. 1, 2007). "Phase II Trial Of Single Agent Val-Boropro (Talabostat) Inhibiting Fibroblast Activation Protein In Patients With Metastatic Colorectal Cancer," Cancer Biol. Ther. 6(11):1691-1699.
Niedermeyer, J et al. (Feb. 2000). "Targeted Disruption of Mouse Fibroblast Activation Protein," Mol. Cell Biol. 20(3):1089-1094.
O'Brien, P. et al. (2008). "Seprase; An Overview Of An Important Matrix Serine Protease," Biochim. Biophys. Acta 1784(9):1130-1145, 57 pages.
Park, J.E. et al. (Dec. 17, 1999). "Fibroblast Activation Protein, a Dual Specificity Serine Protease Expressed in Reactive Human Tumor Stromal Fibroblasts," J. Biol. Chem. 274(51):36505-36512.
PubChem SID 104103293, Substance Record CHEBI:558344, seven pages.
Ryabtsova, O. et al. (2012, e-pub. Apr. 4, 2012). "Acylated Gly-(2-Cyano)Pyrrolidines As Inhibitor of Fibroblast Activation Protein (FAP) and the Issued of FAP/Prolyl Oligopeptidase (PREP)-Selectivity," Bioorganic & Medicinal Chemistry Letters 22:3412-3417.
Sánchez-Garrido, M.A. et al. (2016). "Fibroblast Activation Protein (FAP) as a Novel Metabolic Target," Molecular Metabolism pp. 1-44.
Santos, A.M. et al. (Dec. 2009). "Targeting Fibroblast Activation Protein Inhibits Tumor Stromagenesis and Growth In Mice," Clin. Invest. 119(12):3613-3625.
Tsu, H. et al. (2006). "2-[3-[2-[(2S)-2-Cyano-1Pyrrolidinyl]-2-Oxoethylamino]-3-Methyl-1-Oxobutyl]-1,2,3,4-Tetrahydroisoquinoline:A Potent, Selective, and Orally Bioavailable Dipeptide-Derived Inhibitor of Dipeptidyl Peptidase IV," Journal of Medicinal Chemistry 49(1):373-380. 2 pages.
Wen, X. et al. (2016). "Fibroblast Activation Protein-α-Positive Fibroblasts Promote Gastric Cancer Progression and Resistance to Immune Checkpoint Blockade," Oncol Res. 25:629-640.

(56) References Cited

OTHER PUBLICATIONS

Xu, J. et al. (2009, e-pub. Aug. 25, 2009). "Acute Glucose-Lowering And Insulin-Sensitizing Action Of FGF21 In Insulin-Resistant Mouse Models—Association With Liver and Adipose Tissue Effects," Am. J. Physiol. Endocrinol. Metab. 297(5):E1105-1114.

Yellapu, N. et al. (Jan. 2014, e-pub. May 31, 2013). Design, Synthesis, in Silico, and in Vitro evaluation of Novel Pyrimidine Phosphonates with Cytotoxicity against Breast Cancer Cells, Med. Chem. Res. 23:317-328.

Yie, J. et al. (2009, e-pub. Dec. 4, 2008). "FGF21 N- and C-Termini Play Different Roles In Receptor Interaction and Activation," FEBS Lett. 583(1):19-24.

Zhen, E.Y. et al. (2016). "Circulating FGF21 Proteolytic Processing Mediated By Fibroblast Activation Protein," Biochem J. 473(5):605-614.

International Preliminary Report on Patentability, dated Jun. 16, 2020, for PCT Application No. PCT/US2018/65859, filed Dec. 14, 2018, 10 pages.

International Search Report and Written Opinion of the International Searching Authority, dated Jun. 8, 2020, for PCT Application No. PCT/US2019/68189, filed Dec. 21, 2019, 11 pages.

PubChem-CID-10376593. Create date Oct. 25, 2006 (modify date Apr. 18, 2020). "1-[(2S)-2-Amino-3-methylpentanoyl]-3,3-difluoroazetidine-2-carbonitrile," 11 pages.

Invitation to Pay Additional Fees form PCT/ISA/206 dated Feb. 21, 2020, for International Patent Application No. PCT/US2020/012260 filed Jan. 3, 2020, two pages.

Invitation to Pay Additional Fees form PCT/ISA/206 dated Mar. 11, 2020, for International Patent Application No. PCT/US19/68189 filed Dec. 21, 2019, two pages.

International Preliminary Report on Patentability, dated Jun. 16, 2021, dated Apr. 29, 2020, for PCT Application No. PCT/US2020/012260, filed Jan. 3, 2020, 6 pages.

International Preliminary Report on Patentability, dated Jun. 16, 2021, dated Jun. 8, 2020, for PCT Application No. PCT/US2019/068189, filed Dec. 21, 2019, 7 pages.

McMahon, G. (2000). "VEGP Receptor Signaling in Tumor Angiogenesis," The Oncologist 5(Suppl 1):3-10.

Pinedo, H.M. et al. (2000). "Translational Research: The Role of VEGF in Tumor Angiogenesis," The Oncologist 5 (Suppl. 1):1-2.

Jansen, K. et al. (May 9, 2013). "Selective Inhibitors Of Fibroblast Activation Protein (FAP) With A (4-Quinolinoyl)-Glycyl-2-Cyanopyrrolidine Scaffold," ACS Medicinal Chemistry Letters 4(5):491-496.

Third Party Observations Against EP Application 18887574.4, Applicant Praxis Biotech LLC, dated Nov. 15, 2021, 19 pages.

Third Party Observations Against EP Application 199012881.1, Applicant Praxis Biotech LLC, dated Dec. 1, 2021, 22 pages.

Poplawski, S.E. et al. (May 9, 2013). "Identification Of Selective and Potent Inhibitors Of Fibroblast Activation Protein and Prolyl Oligopeptidase," Journal Of Medicinal Chemistry 56(9):3467-3477, pages A-K.

\* cited by examiner

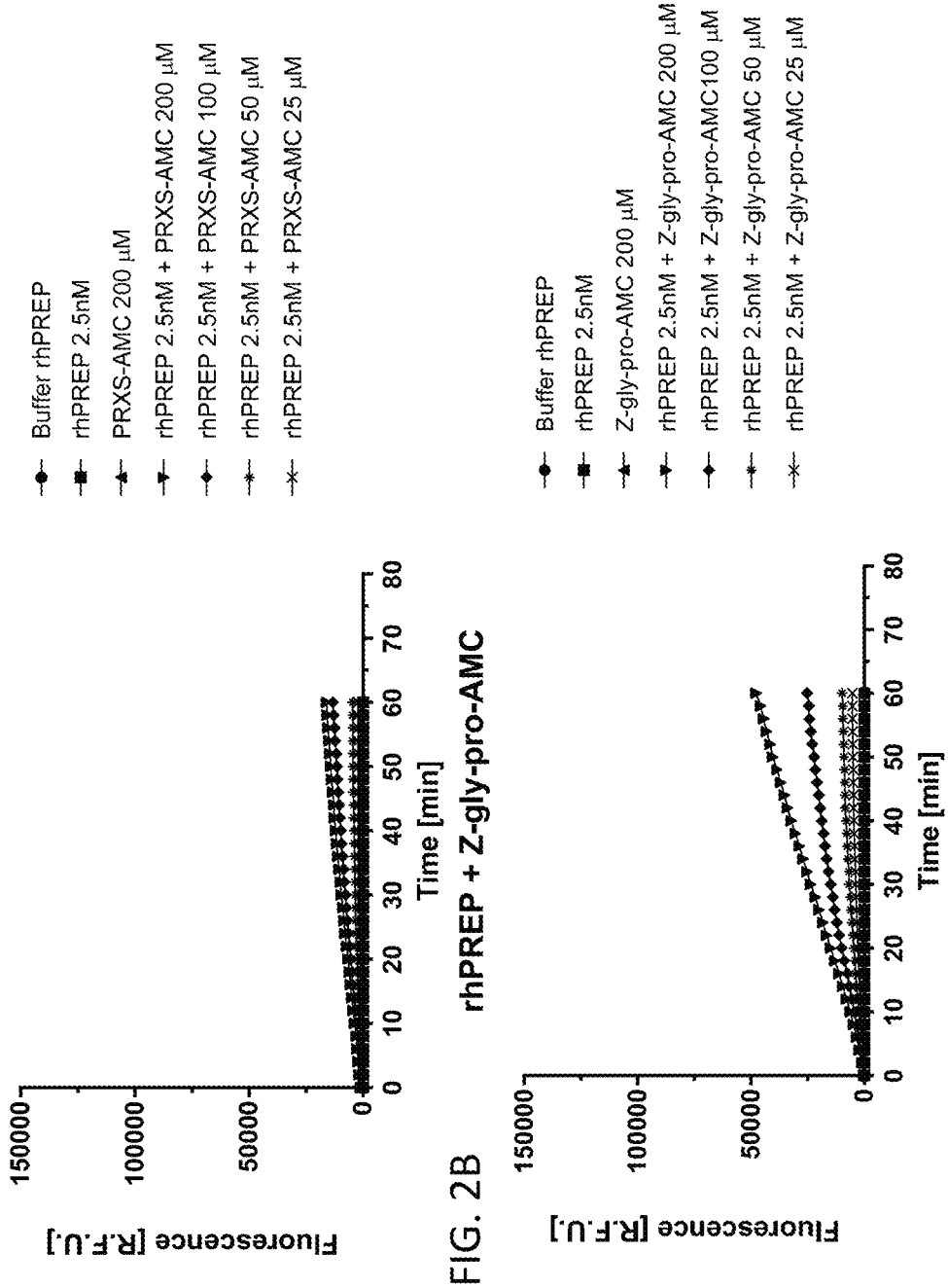

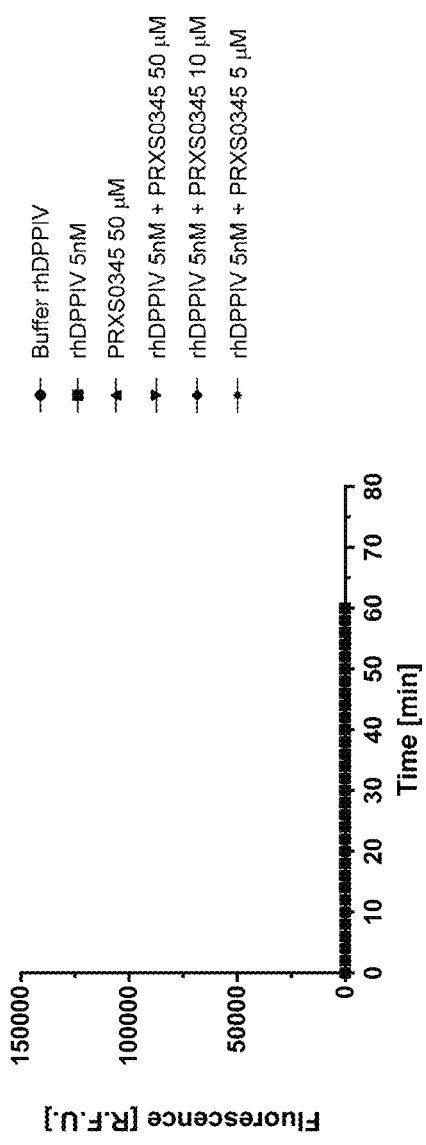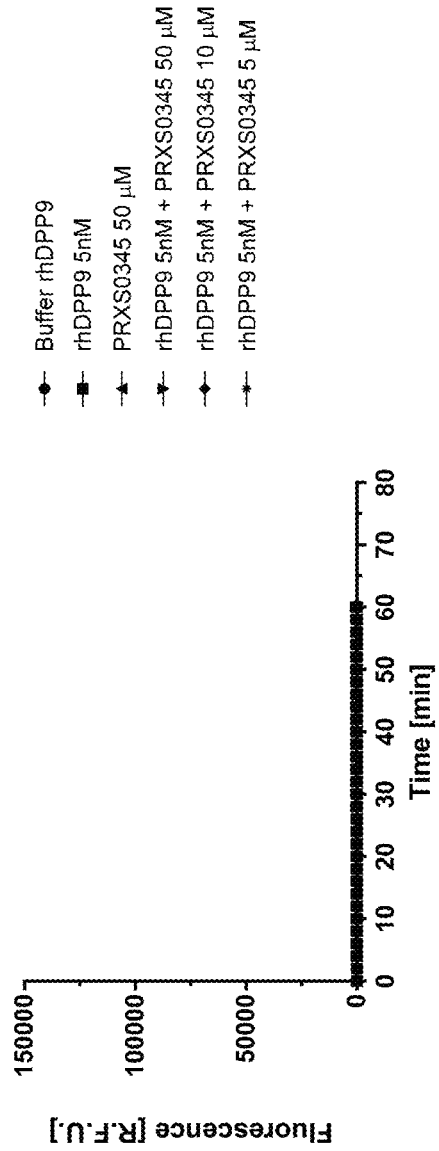
FIG. 3A rhDPPIV + PRXS-AMC
FIG. 3B rhDPP9 + PRXS-AMC

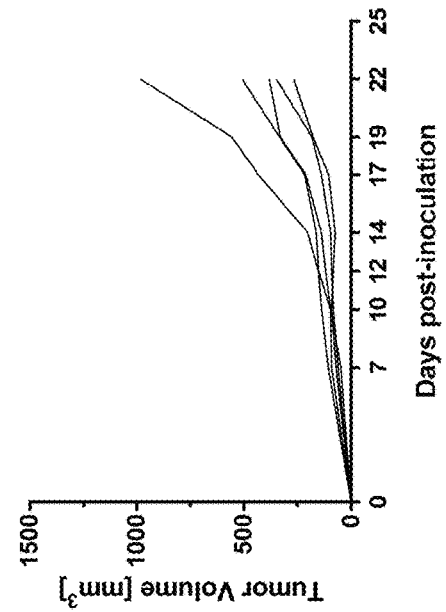
FIG. 9
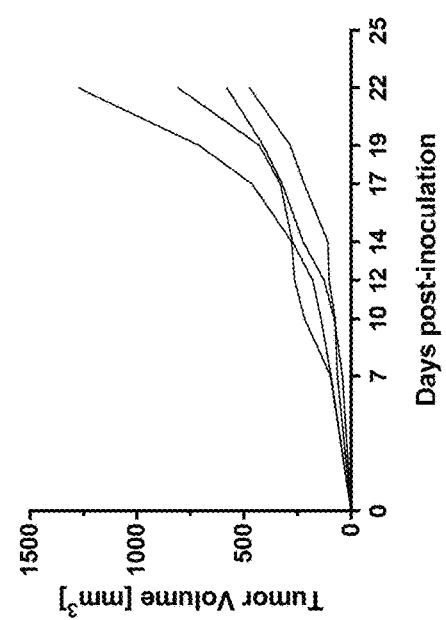
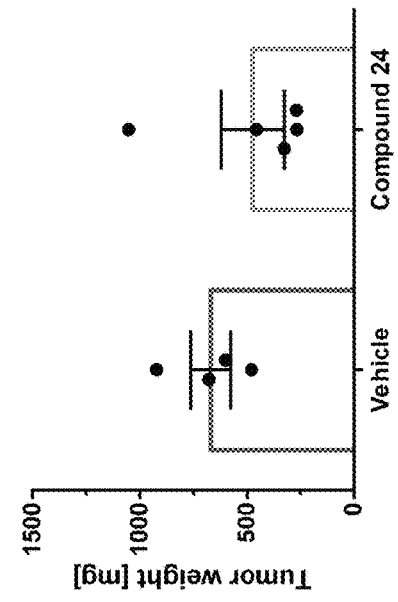
FIG. 10

INHIBITORS OF FIBROBLAST ACTIVATION PROTEIN

CROSS-REFERENCE TO RELATED APPLICATIONS

This application claims priority benefit of U.S. Provisional Patent Application No. 62/599,630, filed Dec. 15, 2017, the disclosure of which is incorporated herein by reference in its entirety.

FIELD OF THE INVENTION

The present disclosure relates generally to therapeutic agents that may be useful in modulating fibroblast activation protein.

BACKGROUND

Fibroblast activation protein (FAP), also referred to as FAPα, Seprase or α2-antiplasmin converting enzyme, is a type II integral membrane serine protease that belongs to the prolyl oligopeptidase family S9, which also includes DPPII, DPPIV, DPP8, DPP9, and PREP enzymes. This family is characterized for having an exo-dipeptidyl peptidase (DPP) activity. FAP is the only member that also has an endopeptidase activity (Aertgeerts, K., et al. J Biol Chem, 2005. 280(20): p. 19441-4). FAP has a high degree of homology with DPPIV. It is mainly found as a cell surface homodimer but it has also been reported to form heterodimers with DPPIV in vivo (O'Brien, P., et al. Biochim Biophys Acta, 2008. 1784(9): p. 1130-45). Purported physiological substrates of FAP endopeptidase activity include α2-antiplasmin, type I collagen, gelatin, and Fibroblast growth factor 21 (FGF21) (Lee, K. N., et al., Biochemistry, 2009. 48(23): p. 5149-58), and for the exopeptidase activity include Neuropeptide Y, B-type natriuretic peptide, substance P and peptide YY (Brokopp, C. E., et al., Eur Heart J, 2011. 32(21): p. 2713-22; Coppage, A. L., et al., PLoS One, 2016. 11(3): p. e0151269; Dunshee, D. R., et al., J Biol Chem, 2016. 291(11): p. 5986-96; Lee, K. N., et al., J Thromb Haemost, 2011. 9(5): p. 987-96).

FAP has been implicated in diseases involving proliferation, tissue remodeling, chronic inflammation and/or fibrosis, including but not limited to fibrotic disease, wound healing, keloid formation, osteoarthritis, rheumatoid arthritis and related disorders involving cartilage degradation, atherosclerotic disease, and Crohn's disease.

FAP expression is related to poor prognosis in several types of cancer including gastric cancer, pancreatic adenocarcinoma and hepatocellular carcinoma, (Wen, X., et al., Oncol Res, 2016; Cohen, S. J., et al., Pancreas, 2008. 37(2): p. 154-8; Ju, M. J., et al., Am J Clin Pathol, 2009. 131(4): p. 498-510) and in colon cancer, increased FAP expression has been associated with a more aggressive disease (Henry, L. R., et al., Clin Cancer Res, 2007. 13(6): p. 1736-41). Purportedly, FAPα on CAFs has critical roles in regulating antitumor immune response by inducing tumor-promoting inflammation (Chen, L., et al., Biochem Biophys Res Commun, 2017; Wen, X., et al., Oncol Res, 2016; Hugo, W., et al., Cell, 2016. 165(1): p. 35-44).

Val-boroPro (Talabostat, PT-100) is the only FAP inhibitor that reached clinical stages. This compound was originally developed as a DPPIV inhibitor and subsequently evaluated as a FAP inhibitor regardless of its lack of selectivity (Cunningham, C. C., Expert Opin Investig Drugs, 2007. 16(9): p. 1459-65). This agent was tested in Phase II in a variety of cancers in combination with standard cytotoxic chemotherapy, however endpoints for efficacy were not met (Eager, R. M., et al., BMC Cancer, 2009. 9: p. 263; Narra, K., et al., Cancer Biol Ther, 2007. 6(11): p. 1691-9; Eager, R. M., et al., Clin Oncol R Coll Radiol, 2009. 21(6): p. 464-72). Two Phase III trials were early terminated, apparently because of both safety and efficacy concerns (Jansen, K., et al., J Med Chem, 2014. 57(7): p. 3053-74). Since Val-boroPro rapidly loses protease inhibitory activity due to cyclization upon standing in pH 7.8, effective concentrations were difficult to achieve in patients given the clinical toxicities seen with this agent at higher doses (Narra, K., et al., Cancer Biol Ther, 2007. 6(11): p. 1691-9).

There is scope to improve FAP inhibitor selectivity and the properties of the inhibitors to improve safety and efficacy in vivo.

BRIEF SUMMARY

Provided herein are compounds, salts thereof, pharmaceutical compositions of the foregoing and methods of making and using the same. In one aspect is provided a compound of formula (I):

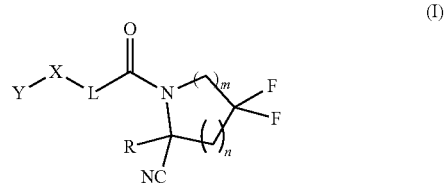

or a pharmaceutically acceptable salt thereof, wherein:
R is hydrogen, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of R are independently optionally substituted by $R^d$;
m is 0, 1, 2, 3, or 4;
n is 0, 1, 2, 3, or 4,
wherein m+n is 1, 2, 3, or 4;
X is —C(=O)—, —O—, —CH(OH)—, —S—, —S(=O)—, or —S(=O)$_2$—;
L is

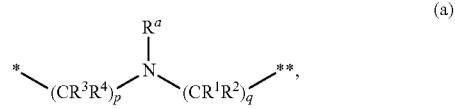

wherein
* represents the point of attachment to the Y—X— moiety,
** represents the point of attachment to the remainder of the molecule,
$R^a$ is hydrogen, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^a$ are independently optionally substituted by $R^e$, $R^1$ and $R^2$, independently of each other and independently at each occurrence, are hydrogen, $C_1$-$C_2$ alkyl, $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^1$ and $R^2$ are independently optionally substituted by $R^f$, or $R^1$ and $R^2$ are taken together with the carbon atom or atoms to which they are attached to form a 3- to 8-membered cycloalkylene optionally substituted by $R^f$, q is 1, 2, or 3, $R^3$ and $R^4$, independently of each other and independently at each occurrence, are hydrogen, $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^3$ and $R^4$ are independently optionally substituted by $R^g$, or $R^3$ and $R^4$ are taken together with the carbon atom to which they are attached to form a 3- to 8-membered cycloalkylene optionally substituted by $R^g$, and p is 0, 1, or 2;

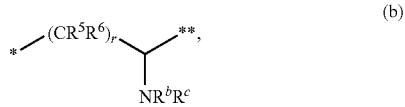
(b)

wherein

* represents the point of attachment to the Y—X— moiety,

** represents the point of attachment to the remainder of the molecule, $R^5$ and $R^6$, independently of each other and independently at each occurrence, are H, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^5$ and $R^6$ are independently optionally substituted by $R^h$, $R^b$ and $R^c$ are independently H, $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, 5- to 10-membered heteroaryl, $C_6$-$C_{14}$ aryl, or —C(=O)OR$^{17}$, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^b$ and $R^c$ are independently optionally substituted by $R^i$, and r is 1, 2, or 3; or

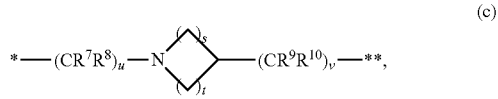
(c)

wherein

* represents the point of attachment to the Y—X— moiety,

** represents the point of attachment to the remainder of the molecule, $R^7$ and $R^8$, independently of each other and independently at each occurrence, are hydrogen, $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^7$ and $R^8$ are independently optionally substituted by $R^j$, or $R^7$ and $R^8$ are taken together with the carbon atom to which they are attached to form a 3- to 8-membered cycloalkylene optionally substituted by $R^j$, $R^9$ and $R^{10}$, independently of each other and independently at each occurrence, are H, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^9$ and $R^{10}$ are independently optionally substituted by $R^k$, s is 1, 2, or 3, t is 1, 2, or 3, wherein s+t is 2, 3, or 4, u is 0 or 1, and v is 0 or 1;

Y is $C_6$-$C_9$ aryl optionally substituted by $R^{11}$, 6- to 10-membered heteroaryl optionally substituted by $R^{12}$, or 3- to 12-membered heterocyclyl optionally substituted by $R^{13}$, wherein when Y is phenyl or naphthyl, the phenyl or naphthyl of Y is substituted by at least one $R^{11}$, and wherein when L is *—NH—CH$_2$—** and Y is optionally substituted quinolinyl, the optionally substituted quinolinyl of Y is connected to the parent structure at the 2-, 3-, 5-, 6-, 7-, or 8-position, wherein $R^{11}$, $R^{12}$, and $R^{13}$, independently of each other and independently at each occurrence, are $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, halogen, cyano, oxo, —OR$^{14}$, —NR$^{15}$R$^{16}$, —SR$^{14}$, —NO$_2$, —C=NH(OR$^{14}$), —C(O)R$^{14}$, —OC(O)R$^{14}$, —C(O)OR$^{14}$, —C(O)NR$^{15}$R$^{16}$, —NR$^{14}$C(O)R$^{15}$, —NR$^{14}$C(O)OR$^{15}$, —NR$^{14}$C(O)NR$^{15}$R$^{16}$, —S(O)R$^{14}$, —S(O)$_2$R$^{14}$, —NR$^{14}$S(O)R$^{15}$, —NR$^{14}$S(O)$_2$R$^{15}$, —S(O)NR$^{15}$R$^{16}$, —S(O)$_2$NR$^{15}$R$^{16}$, or —P(O)(OR$^{15}$)(OR$^{16}$), wherein each $R^{11}$, $R^{12}$, and $R^{13}$ is independently optionally substituted by $R^L$;

each $R^{14}$ is independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{14}$ are independently optionally substituted by halogen, —OH, oxo, cyano, or $C_1$-$C_6$ alkyl optionally substituted by halogen, —OH, or oxo;

$R^{15}$ and $R^{16}$, independently of each other and independently at each occurrence, are hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{15}$ and $R^{16}$ are independently optionally substituted by halogen, —OH, oxo, cyano, or $C_1$-$C_6$ alkyl, optionally substituted by halogen, —OH, or oxo, or $R^{15}$ and $R^{16}$ are taken together with the atom to which they are attached to form a 3- to 6-membered heterocyclyl optionally substituted by halogen, oxo, cyano, or $C_1$-$C_6$ alkyl optionally substituted by halogen, —OH, or oxo; and $R^d$, $R^e$, $R^f$, $R^g$, $R^h$, $R^i$, $R^j$, and $R^k$, independently of each other and independently at each occurrence, are halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —$OR^{14}$, —$NR^{15}R^{16}$, cyano, or nitro; and each $R^L$ is independently halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —$OR^{14}$, —$C(O)R^{14}$, —$NR^{15}R^{16}$, cyano, oxo, or nitro.

In one aspect, provided is a compound of formula (I) or a pharmaceutically acceptable salt thereof, wherein the compound has any one or more of the following features:

(i) X is —C(═O)—, —O— or —CH(OH)—;
(ii) L is
  (a) —NH—$CR^1R^2$—, such as —NH—$CH_2$— or —NH—$CH(CH_3)$— or wherein $R^1$ and $R^2$ are taken together with the carbon atom to which they are attached to form a 3- to 8-membered cycloalkylene such as a cyclopropylene;
  (b) —$CR^5R^6$—$CH(NR^bR^c)$—, including but not limited to, when $R^6$, $R^b$, and $R^c$ are each H, and $R^5$ is H or $C_1$-$C_6$ alkyl; or

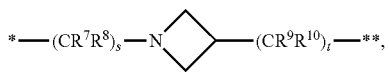

(c)

wherein * represents the point of attachment to the Y—X— moiety, ** represents the point of attachment to the remainder of the molecule, such as

(c)

(iii) Y is:
  (a) $C_6$-$C_9$ aryl optionally substituted by $R^{11}$, such as unsubstituted 2,3-dihydro-1H-inden-2-yl or a phenyl or naphthyl substituted by at least one $R^{11}$, including but not limited to when each $R^{11}$ is independently selected from halogen, trihalomethyl, cyano, and —C(═O)$NH_2$;
  (b) 6- to 10-membered heteroaryl optionally substituted by $R^{12}$, such as a pyridinyl or pyrimidinyl substituted by at least one $R^{12}$; or
  (c) 3- to 12-membered heterocyclyl optionally substituted by $R^{13}$, such as a piperidinyl substituted by at least one $R^{13}$.

In another aspect is provided a compound of formula (I), or a salt thereof, wherein the —X-L- moiety is selected from the group consisting of

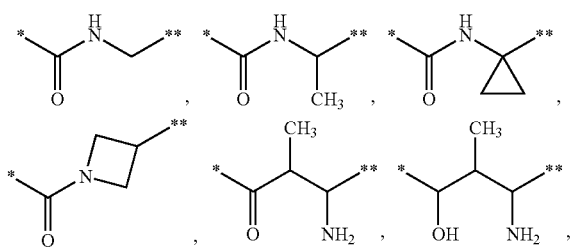

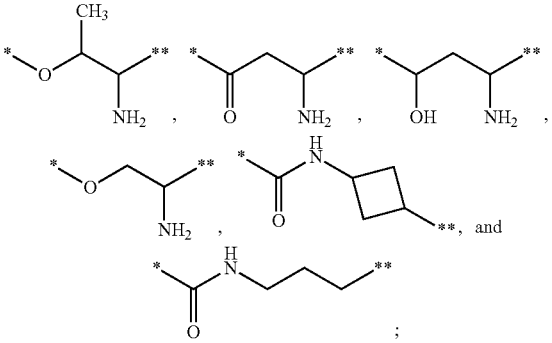

wherein * represents the point of attachment to the Y moiety, and ** represents the point of attachment to the remainder of the molecule.

Also provided is a pharmaceutical composition comprising a compound of any formula herein, including formula (I), or a pharmaceutically acceptable salt thereof, and a pharmaceutically acceptable carrier.

Also provided is a method of treating a disease or disorder mediated by fibroblast activation protein (FAP) in an individual in need thereof comprising administering to the individual a therapeutically effective amount of a compound as detailed herein, including but not limited to a compound of formula (I), or a pharmaceutically acceptable salt thereof, or a pharmaceutical composition comprising such compound or salt. Such disease or disorder in one aspect is characterized by proliferation, tissue remodeling, chronic inflammation, obesity, glucose intolerance, or insulin insensitivity. In one aspect, the disease or disorder is breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma. In a particular aspect, the disease or disorder is metastatic kidney cancer, chronic lymphocytary leukemia, pancreatic adenocarcinoma, or non-small cell lung cancer. In a further aspect, the disease or disorder is a fibrotic disease, wound healing, keloid formation, osteoarthritis, rheumatoid arthritis and related disorders involving cartilage degradation, atherosclerotic disease, Crohn's disease, or Type II diabetes. In another particular aspect is provided a method of reducing tumor growth, tumor proliferation, or tumorigenicity in an individual in need thereof, comprising administering to the individual a compound as detailed herein, such as a compound of formula (I), or a pharmaceutically acceptable salt thereof, or a pharmaceutical composition of the foregoing.

BRIEF DESCRIPTION OF THE DRAWINGS

FIG. 2A shows PRXS-AMC degradation over time by rhPREP. FIG. 2B shows Z-Gly-Pro-AMC degradation over time by rhPREP.

FIG. 3A shows PRXS-AMC degradation over time by rhDPPIV. FIG. 3B shows PRXS-AMC degradation over time by rhDPP9.

FIG. 9 shows individual recordings of tumor volume when mice were treated with test compound 24 or a control vehicle.

FIG. 10 shows mean and standard error of mean (SEM) of the total mass of the tumors when mice were treated with test compound 24 or a control vehicle.

DETAILED DESCRIPTION

Figure 1A:
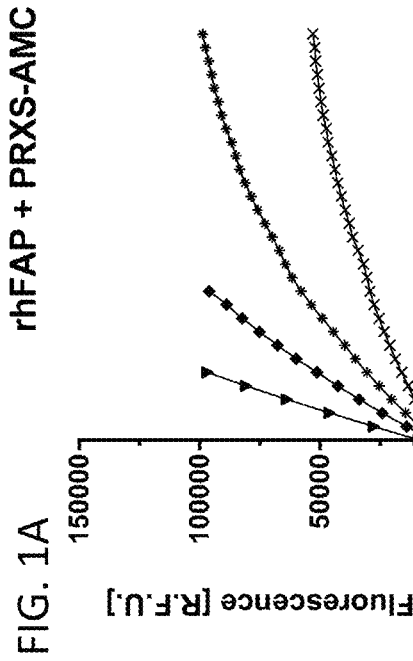
FIG. 1A shows PRXS-AMC degradation over time by rhFAP.

Described herein are compounds according to formula (I):

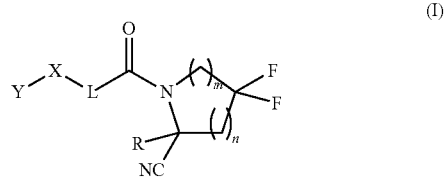

and pharmaceutically acceptable salts thereof. The compounds can be useful for inhibiting fibroblast activation protein (FAPα). In certain embodiments, the compound is used to treat a disease or a disorder mediated by FAPα in an individual. Such diseases or disorders can include or be characterized by proliferation, tissue remodeling, chronic inflammation, obesity, glucose intolerance, and/or insulin insensitivity. In some embodiments, the compound is used to treat cancer.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C=C) and having the number of carbon atoms designated (i.e., $C_3$-$C_{10}$ means three to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

Where applicable, a heteroaryl group may be depicted in a tautomeric form. Such compounds would be considered to be heteroaryl even if certain tautomeric forms are, for example, heterocyclyl. For example, the heteroaryl group

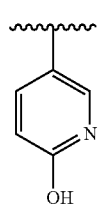

may be depicted in the heterocyclic tautomeric form

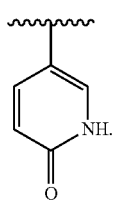

Regardless of which tautomer is shown, the group is considered to be heteroaryl.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. Beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. The methods described herein contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that aspects and embodiments described herein as "comprising" include "consisting of" and "consisting essentially of" embodiments.

When a composition is described as "consisting essentially of" the listed components, the composition contains the components expressly listed, and may contain other components which do not substantially affect the disease or condition being treated such as trace impurities. However, the composition either does not contain any other components which do substantially affect the disease or condition being treated other than those components expressly listed; or, if the composition does contain extra components other than those listed which substantially affect the disease or condition being treated, the composition does not contain a sufficient concentration or amount of those extra components to substantially affect the disease or condition being treated. When a method is described as "consisting essentially of" the listed steps, the method contains the steps listed, and may contain other steps that do not substantially affect the disease or condition being treated, but the method does not contain any other steps which substantially affect the disease or condition being treated other than those steps expressly listed.

When a moiety is indicated as substituted by "at least one" substituent, this also encompasses the disclosure of exactly one substituent.

Compounds

In one aspect, provided is a compound of formula (I):

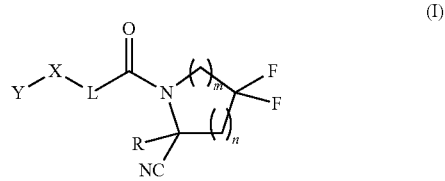

or a pharmaceutically acceptable salt thereof, wherein:

R is hydrogen, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of R are independently optionally substituted by $R^a$;

m is 0, 1, 2, 3, or 4;

n is 0, 1, 2, 3, or 4, wherein m+n is 1, 2, 3, or 4;

X is —C(=O)—, —O—, —CH(OH)—, —S—, —S(=O)—, or —S(=O)$_2$—;

L is

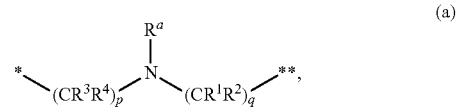

wherein

\* represents the point of attachment to the Y—X— moiety,

\*\* represents the point of attachment to the remainder of the molecule, $R^a$ is hydrogen, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^a$ are independently optionally substituted by $R^e$, $R^1$ and $R^2$, independently of each other and independently at each occurrence, are hydrogen, $C_1$-$C_2$ alkyl, $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^1$ and $R^2$ are independently optionally substituted by $R^f$, or $R^1$ and $R^2$ are taken together with the carbon atom or atoms to which they are attached to form a 3- to 8-membered cycloalkylene optionally substituted by $R^f$, q is 1, 2, or 3, $R^3$ and $R^4$, independently of each other and independently at each occurrence, are hydrogen, $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^3$ and $R^4$ are independently optionally substituted by $R^g$, or $R^3$ and $R^4$ are taken together with the carbon atom to which they are attached to form a 3- to 8-membered cycloalkylene optionally substituted by $R^g$, and p is 0, 1, or 2;

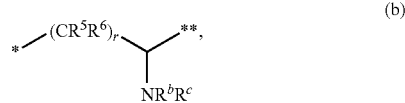
(b)

wherein

* represents the point of attachment to the Y—X— moiety,

** represents the point of attachment to the remainder of the molecule, $R^5$ and $R^6$, independently of each other and independently at each occurrence, are H, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^5$ and $R^6$ are independently optionally substituted by $R^h$, $R^b$ and $R^c$ are independently H, $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, 5- to 10-membered heteroaryl, $C_6$-$C_{14}$ aryl, or —C(=O)O$R^{17}$, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^b$ and $R^c$ are independently optionally substituted by $R^i$, and r is 1, 2, or 3; or

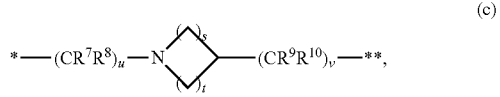
(c)

wherein

* represents the point of attachment to the Y—X— moiety,

** represents the point of attachment to the remainder of the molecule, $R^7$ and $R^8$, independently of each other and independently at each occurrence, are hydrogen, $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^7$ and $R^8$ are independently optionally substituted by $R^j$, or $R^7$ and $R^8$ are taken together with the carbon atom to which they are attached to form a 3- to 8-membered cycloalkylene optionally substituted by $R^j$, $R^9$ and $R^{10}$, independently of each other and independently at each occurrence, are H, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^9$ and $R^{10}$ are independently optionally substituted by $R^k$, s is 1, 2, or 3, t is 1, 2, or 3, wherein s+t is 2, 3, or 4, u is 0 or 1, and v is 0 or 1;

Y is $C_6$-$C_9$ aryl optionally substituted by $R^{11}$, 6- to 10-membered heteroaryl optionally substituted by $R^{12}$, or 3- to 12-membered heterocyclyl optionally substituted by $R^{13}$, wherein when Y is phenyl or naphthyl, the phenyl or naphthyl of Y is substituted by at least one $R^{11}$, and wherein when L is *—NH—CH$_2$—** and Y is optionally substituted quinolinyl, the optionally substituted quinolinyl of Y is connected to the parent structure at the 2-, 3-, 5-, 6-, 7-, or 8-position, wherein $R^{11}$, $R^{12}$, and $R^{13}$, independently of each other and independently at each occurrence, are $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, halogen, cyano, oxo, —O$R^{14}$, —N$R^{15}R^{16}$, —S$R^{14}$, —NO$_2$, —C=NH(O$R^{14}$), —C(O)$R^{14}$, —OC(O)$R^{14}$, —C(O)O$R^{14}$, —C(O)N$R^{15}R^{16}$, —N$R^{14}$C(O)$R^{15}$, —N$R^{14}$C(O)O$R^{15}$, —N$R^{14}$C(O)N$R^{15}R^{16}$—S(O)$R^{14}$, —S(O)$_2R^{14}$, —N$R^{14}$S(O)$R^{15}$, —N$R^{14}$S(O)$_2R^{15}$, —S(O)N$R^{15}R^{16}$, —S(O)$_2$N$R^{15}R^{16}$, or —P(O)(O$R^{15}$)(O$R^{16}$), wherein each $R^{11}$, $R^{12}$, and $R^{13}$ is independently optionally substituted by $R^L$;

each $R^{14}$ is independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{14}$ are independently optionally substituted by halogen, —OH, oxo, cyano, or $C_1$-$C_6$ alkyl optionally substituted by halogen, —OH, or oxo;

$R^{15}$ and $R^{16}$, independently of each other and independently at each occurrence, are hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{15}$ and $R^{16}$ are independently optionally substituted by halogen, —OH, oxo, cyano, or $C_1$-$C_6$ alkyl, optionally substituted by halogen, —OH, or oxo, or $R^{15}$ and $R^{16}$ are taken together with the atom to which they are attached to form a 3- to 6-membered heterocyclyl optionally substituted by halogen, oxo, cyano, or $C_1$-$C_6$ alkyl optionally substituted by halogen, —OH, or oxo;

$R^d$, $R^e$, $R$, $R^g$, $R^h$, $R^i$, $R^j$, and $R^k$, independently of each other and independently at each occurrence, are halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —$OR^{14}$, —$NR^{15}R^{16}$, cyano, or nitro; and each $R^L$ is independently halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —$OR^{14}$, —$C(O)R^{14}$, —$NR^{15}R^{16}$, cyano, oxo, or nitro.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to R of formula (I) may be combined with every description, variation, embodiment or aspect of Y, X, L, m, and/or n the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae Ia, Ib, II, IIa, IIb, III, IIIa, IIIb, IV, IVa, IVb, V, Va, Vb, VI, VIa, VIb, VII, VIIa, VIIb, VIII, VIIIa and VIIIb detailed herein, and are equally described, the same as if each and every description, variation, embodiment or aspect were separately and individually listed for all formulae.

In some embodiments, the compound of formula (I) is of the formula (Ia):

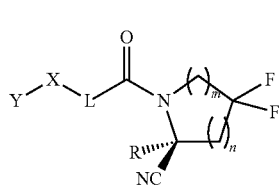

(Ia)

or a salt thereof, wherein Y, X, L, R, m, and n are as defined for formula (I).

In some embodiments, the compound of formula (I) is of the formula (Ib):

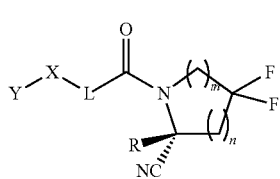

(Ib)

or a salt thereof, wherein Y, X, L, R, m, and n are as defined for formula (I).

In some embodiments of the compound of formula (I), where m is 1 and n is 1, the compound is of the formula (II):

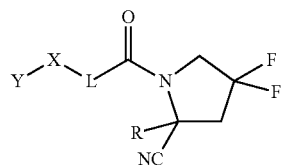

(II)

or a salt thereof, wherein Y, X, L, and R are as defined for formula (I).

In some embodiments, the compound of formula (II) is of the formula (IIa):

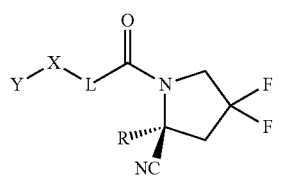

(IIa)

or a salt thereof, wherein Y, X, L, and R are as defined for formula (I).

In some embodiments, the compound of formula (II) is of the formula (IIb):

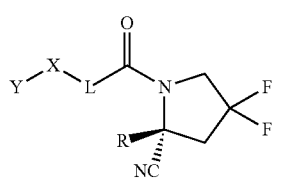

(IIb)

or a salt thereof, wherein Y, X, L, and R are as defined for formula (I).

In some embodiments of the compound of formula (II), where L is —NH—$CH_2$—, the compound is of the formula (III):

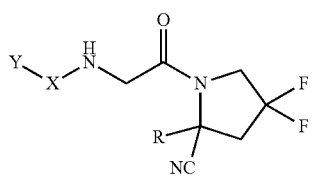

(III)

or a salt thereof, wherein Y, X, and R are as defined for formula (I).

In some embodiments, the compound of formula (III) is of the formula (IIIa):

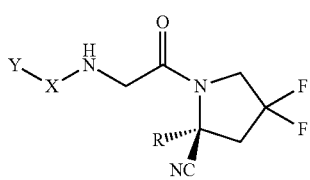

(IIIa)

or a salt thereof, wherein Y, X, and R are as defined for formula (I).

In some embodiments, the compound of formula (III) is of the formula (IIIb):

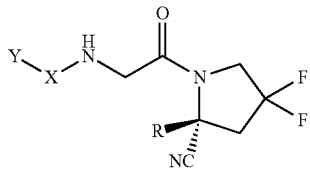

(IIIb)

or a salt thereof, wherein Y, X, and R are as defined for formula (I).

In some embodiments, the compound of formula (III) is of the formula (III-1):

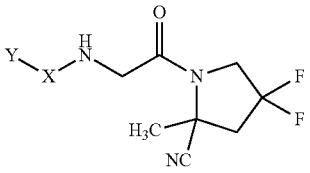

(III-1)

or a salt thereof, wherein Y and X are as defined for formula (I).

In some embodiments of the compound of formula (II), where L is —NH—CH(CH$_3$)—, the compound is of the formula (IV):

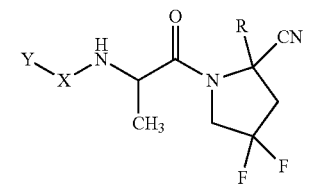

(IV)

or a salt thereof, wherein Y, X, and R are as defined for formula (I). In one aspect of a compound of formula (IV), the carbon bearing the methyl group of L is in the S configuration. In one aspect of a compound of formula (IV), the carbon bearing the methyl group of L is in the R configuration.

In some embodiments, the compound of formula (IV) is of the formula (IVa):

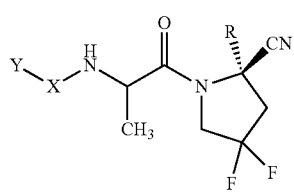

(IVa)

or a salt thereof, wherein Y, X, and R are as defined for formula (I). In one aspect of a compound of formula (IVa), the carbon bearing the methyl group of L is in the S configuration. In one aspect of a compound of formula (IVa), the carbon bearing the methyl group of L is in the R configuration.

In some embodiments, the compound of formula (IV) is of the formula (IVb):

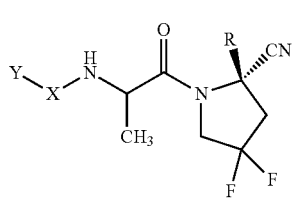

(IVb)

or a salt thereof, wherein Y, X, and R are as defined for formula (I). In one aspect of a compound of formula (IVb), the carbon bearing the methyl group of L is in the S configuration. In one aspect of a compound of formula (IVb), the carbon bearing the methyl group of L is in the R configuration.

In some embodiments of the compound of formula (II), the compound is of the formula (V):

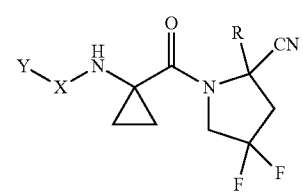

(V)

or a salt thereof, wherein Y, X, and R are as defined for formula (I).

In some embodiments, the compound of formula (V) is of the formula (Va):

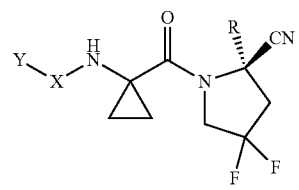

(Va)

or a salt thereof, wherein Y, X, and R are as defined for formula (I).

In some embodiments, the compound of formula (V) is of the formula (Vb):

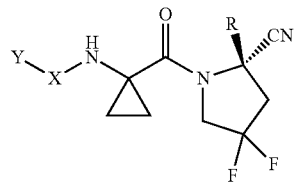

(Vb)

or a salt thereof, wherein Y, X, and R are as defined for formula (I).

In some embodiments of the compound of formula (II), the compound is of the formula (VI):

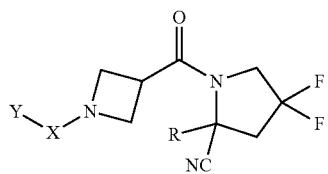

(VI)

or a salt thereof, wherein Y, X, and R are as defined for formula (I).

In some embodiments, the compound of formula (VI) is of the formula (VIa):

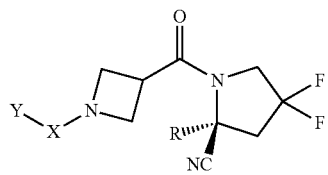

(VIa)

or a salt thereof, wherein Y, X, and R are as defined for formula (I).

In some embodiments, the compound of formula (VI) is of the formula (VIb):

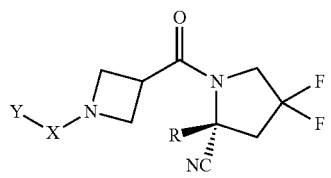

(VIb)

or a salt thereof, wherein Y, X, and R are as defined for formula (I).

In some embodiments of the compound of formula (II), where L is —$CH_2$—$CH(NH_2)$—, the compound is of the formula (VII):

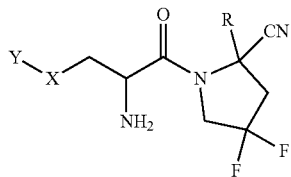

(VII)

or a salt thereof, wherein Y, X, and R are as defined for formula (I). In one aspect of a compound of formula (VII), the carbon bearing the —$NH_2$ group of L is in the S configuration. In one aspect of a compound of formula (VII), the carbon bearing the —$NH_2$ group of L is in the R configuration.

In some embodiments, the compound of formula (VII) is of the formula (VIIa):


(VIIa)

or a salt thereof, wherein Y, X, and R are as defined for formula (I). In one aspect of a compound of formula (VIIa), the carbon bearing the —$NH_2$ group of L is in the S configuration. In one aspect of a compound of formula (VIIa), the carbon bearing the —$NH_2$ group of L is in the R configuration.

In some embodiments, the compound of formula (VII) is of the formula (VIIb):

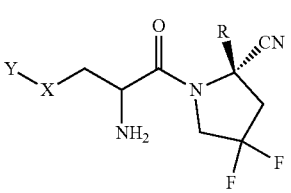

(VIIb)

or a salt thereof, wherein Y, X, and R are as defined for formula (I). In one aspect of a compound of formula (VIIb), the carbon bearing the —$NH_2$ group of L is in the S configuration. In one aspect of a compound of formula (VIIb), the carbon bearing the —$NH_2$ group of L is in the R configuration.

In some embodiments of the compound of formula (II), where L is —$CH(CH_3)$—$CH(NH_2)$—, the compound is of the formula (VIII):

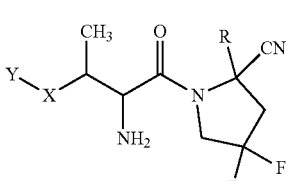

(VIII)

or a salt thereof, wherein Y, X, and R are as defined for formula (I). In one aspect of a compound of formula (VIII), the carbon bearing the —NH₂ group of L is in the S configuration. In one aspect of a compound of formula (VIII), the carbon bearing the —NH₂ group of L is in the R configuration. In one aspect of a compound of formula (VIII), the carbon bearing the methyl group of L is in the S configuration. In one aspect of a compound of formula (VIII), the carbon bearing the methyl group of L is in the R configuration.

In some embodiments, the compound of formula (VIII) is of the formula (VIIIa):

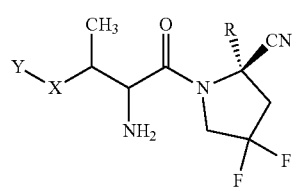

(VIIIa)

or a salt thereof, wherein Y, X, and R are as defined for formula (I). In one aspect of a compound of formula (VIIIa), the carbon bearing the —NH₂ group of L is in the S configuration. In one aspect of a compound of formula (VIIIa), the carbon bearing the —NH₂ group of L is in the R configuration. In one aspect of a compound of formula (VIIIa), the carbon bearing the methyl group of L is in the S configuration. In one aspect of a compound of formula (VIIIa), the carbon bearing the methyl group of L is in the R configuration.

In some embodiments, the compound of formula (VIII) is of the formula (VIIIb):

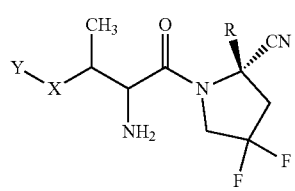

(VIIIb)

or a salt thereof, wherein Y, X, and R are as defined for formula (I). In one aspect of a compound of formula (VIIIb), the carbon bearing the —NH₂ group of L is in the S configuration. In one aspect of a compound of formula (VIIIb), the carbon bearing the —NH₂ group of L is in the R configuration. In one aspect of a compound of formula (VIIIb), the carbon bearing the methyl group of L is in the S configuration. In one aspect of a compound of formula (VIIIb), the carbon bearing the methyl group of L is in the R configuration. In some embodiments of the compound of formula (II), the compound is of the formula (IX):

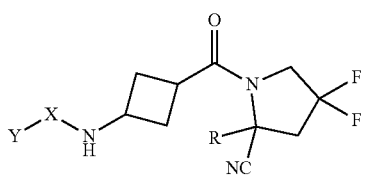

(IX)

or a salt thereof, wherein Y, X, and R are as defined for formula (I). In one aspect of a compound of formula (IX), the 1,3-cyclobutylene is the cis isomer. In one aspect of a compound of formula (IX), the 1,3-cyclobutylene is the tran isomer.

In some embodiments, the compound of formula (IX) is of the formula (IXa):

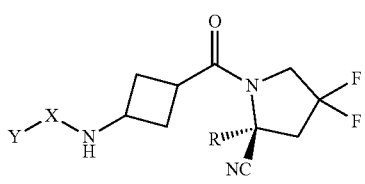

(IXa)

or a salt thereof, wherein Y, X, and R are as defined for formula (I). In one aspect of a compound of formula (IXa), the 1,3-cyclobutylene is the cis isomer. In one aspect of a compound of formula (IXa), the 1,3-cyclobutylene is the tran isomer.

In some embodiments, the compound of formula (IX) is of the formula (IXb):

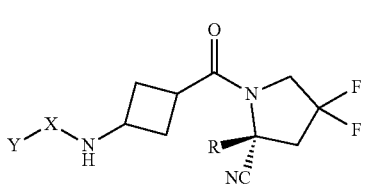

(IXb)

or a salt thereof, wherein Y, X, and R are as defined for formula (I). In one aspect of a compound of formula (IXb), the 1,3-cyclobutylene is the cis isomer. In one aspect of a compound of formula (IXb), the 1,3-cyclobutylene is the tran isomer.

In some embodiments of the compound of formula (II), where L is —NH—CH₂—, the compound is of the formula (X):

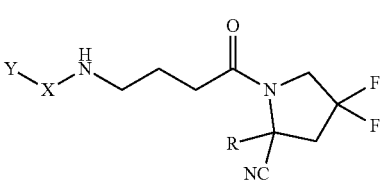

(X)

or a salt thereof, wherein Y, X, and R are as defined for formula (I).

In some embodiments, the compound of formula (X) is of the formula (Xa):

(Xa)

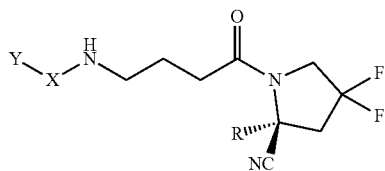

or a salt thereof, wherein Y, X, and R are as defined for formula (I).

In some embodiments, the compound of formula (X) is of the formula (Xb):

(Xb)

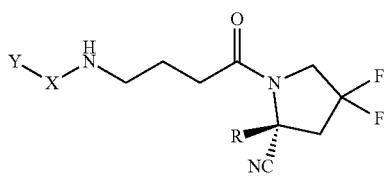

or a salt thereof, wherein Y, X, and R are as defined for formula (I).

In one variation a compound of formula (I), or a salt thereof, is provided wherein X is —C(=O)—, —O— or —CH(OH)—. In another variation a compound of formula (I), or a salt thereof, is provided wherein X is —S—, —S(=O)—, or —S(=O)$_2$—. In some embodiments of the compound of formula (I), or a salt thereof, X is —C(=O)—. In other embodiments of the compound of formula (I), or a salt thereof, X is —O—. All variations of X apply equally to any applicable formulae herein, such as formulae Ia, Ib, II, IIa, IIb, III, IIIa, IIIb, IV, IVa, IVb, V, Va, Vb, VI, VIa, VIb, VII, VIIa, VIIb, VIII, VIIIa and VIIIb.

In some embodiments of the compound of formula (I), or a salt thereof, L is

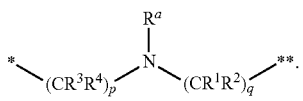

In a particular such embodiment, $R^a$ is H, and $R^1$, $R^2$, $R^3$ and $R^4$, if present, are each H. In one embodiment, L is

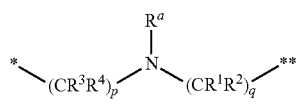

and X is —C=O. In another embodiment, L is

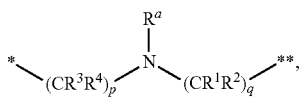

X is —C=O and p is 0.

In some embodiments, L is

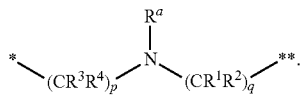

In one particular variation, $R^1$ and $R^2$ are attached to the same carbon atom. In another particular variation, $R^1$ and $R^2$ are attached to different carbon atoms.

In some embodiments, L is —N($R^a$)—$CR^1R^2$— (i.e., p is 0). In one particular variation, L is —NH—$CR^1R^2$—. In another particular variation, L is —NH—CH$_2$—. In another particular variation, L is —NH—CH(CH$_3$)—. In another particular variation, L is —NH—$CR^1R^2$—, wherein $R^1$ and $R^2$ are taken together with the carbon atom or atoms to which they are attached to form a 3- to 8-membered cycloalkylene (e.g., cyclopropylene).

In some embodiments, L is —N($R^a$)—$(CR^1R^2)_3$— (i.e., p is 0). In one particular variation, L is —NH—$(CR^1R^2)_3$—. In another particular variation, L is —NH—$(CH_2)_3$—. In another particular variation, L is —NH—$(CR^1R^2)_3$—, wherein $R^1$ and $R^2$ from two non-adjacent carbons are taken together with the carbon atoms to which they are attached and interstitial carbon to form a 3- to 8-membered cycloalkylene (e.g., 1,3-cyclobutylene).

In other embodiments of the compound of formula (I), or a salt thereof, L is

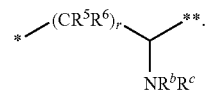

In one such embodiment, X is —C=O. In another such embodiment, X is —O—. In a further such embodiment, X is —CH(OH)—. In yet another such embodiment, X is —S—. In still another such embodiment, X is —S(=O)—. In still another such embodiment, X is —S(=O)$_2$. In one aspect of such embodiments, r is 1. In another aspect of such embodiments, r is 2. In still another aspect of such embodiments, r is 3. In any embodiment provided where L is

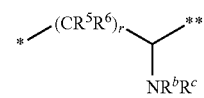

one variation, $R^b$ and $R^c$ are both H. In any embodiment provided where L is

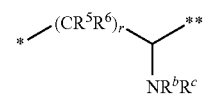

in another variation, $R^b$ and $R^c$ are both H, r is 1, $R^5$ is H and $R^6$ is a $C_1$-$C_6$ alkyl such as methyl.

In some of these embodiments, L is —$CR^5R^6$—CH(NR$^b$R$^c$)— (i.e., r is 1). In one particular variation, L is —CH($R^5$)—CH(NH$_2$)—, including but not limited to aspects wherein $R^5$ is hydrogen or $C_1$-$C_6$ alkyl. In one particular variation, L is —CH₂—CH(NH₂)—. In another particular variation, L is —CH(CH₃)—CH(NH₂)—.

In some embodiments of the compound of formula (I), or a salt thereof, L is

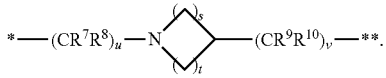

In one such embodiment, X is —C=O. In another such embodiment, X is —O—. In a further such embodiment, X is —S—. In still another such embodiment, X is —S(=O)—. In still another such embodiment, X is —S(=O)₂. In a particular variation, L is

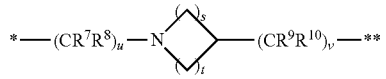

and u is 0. In another variation, L is

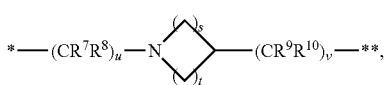

u is 0 and X is selected from the group consisting of —C=O, —O—, —S—, —S(=O)— and —S(=O)₂. In any embodiment or variation where L is

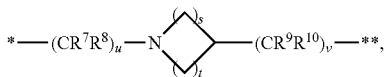

in one aspect, s is 1 and t is 1.
In one variation, L is

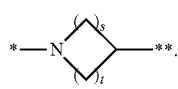

In another particular variation, L is

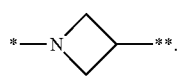

In one variation, L is

and X is selected from the group consisting of —C=O, —O—, —S—, —S(=O)— and —S(=O)₂.

In one variation, provided herein is a compound of formula (I), or a salt thereof, wherein the —X-L- moiety is selected from the group consisting of:

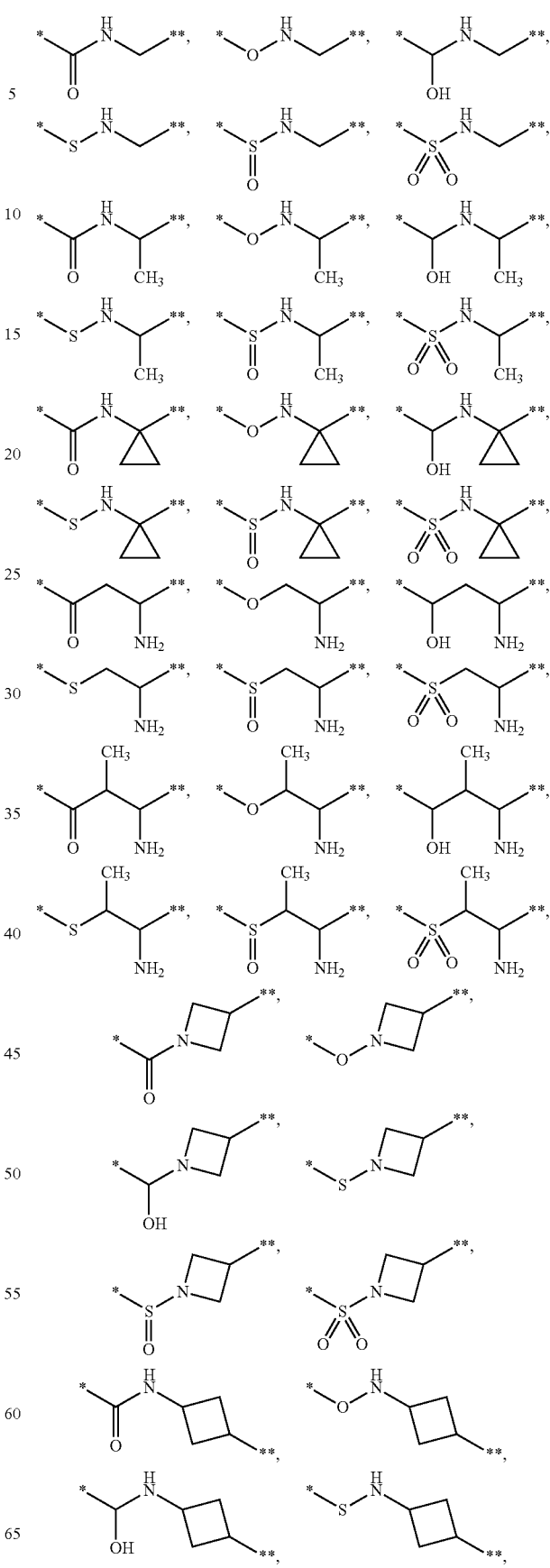

-continued

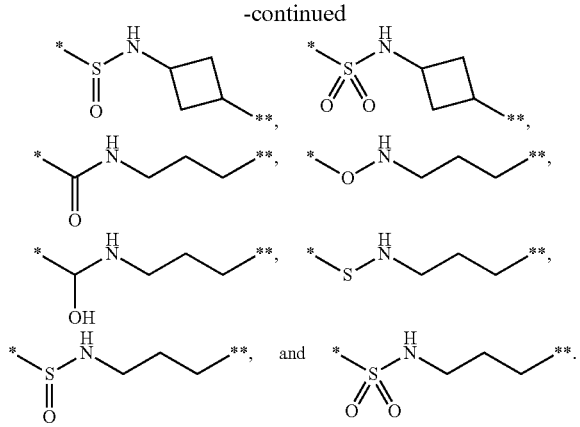

wherein * represents the point of attachment to the Y moiety and ** represents the point of attachment to the remainder of the molecule.

In another variation is provided a compound of formula (I), or a salt thereof, wherein the —X-L- moiety is selected from the group consisting of:

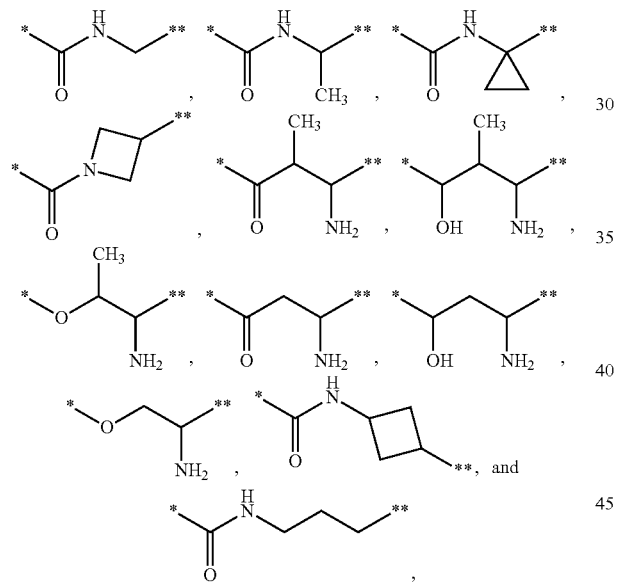

wherein * represents the point of attachment to the Y moiety and ** represents the point of attachment to the remainder of the molecule.

In one aspect, provided is a compound of formula (I) or a pharmaceutically acceptable salt thereof, wherein the compound has any one or more of the following features:
(i) X is —C(=O)—, —O— or —CH(OH)—;
(ii) L is:
  (a) —NH—$(CR^1R^2)_q$—, wherein $R^1$ and $R^2$, independently of each other and independently at each occurrence, are hydrogen or $C_1$-$C_2$ alkyl, or $R^1$ and $R^2$ groups attached to the same carbon atom are taken together with the carbon atom to which they are attached to form a 3- to 5-membered cycloalkylene, or $R^1$ and $R^2$ groups attached to two different carbon atoms are taken together with the carbon atoms to which they are attached to form a 3- to 5-membered cycloalkylene (examples of such —NH—$(CR^1R^2)_q$-moieties include

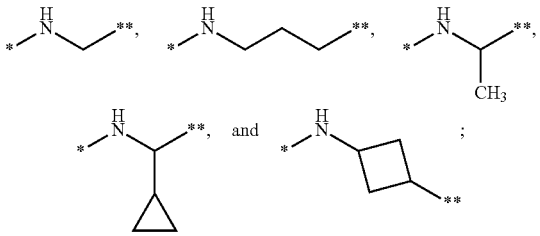

(b) —$CR^5R^6$—$CH(NH_2)$—, wherein $R^5$ and $R^6$, independently of each other and independently at each occurrence, are hydrogen or $C_1$-$C_2$ alkyl, (examples of such —$CR^5R^6$—$CH(NH_2)$— moieties include (c)

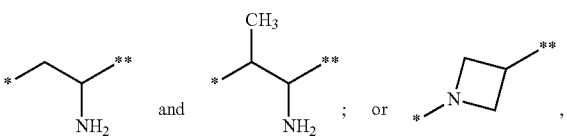

wherein * represents the point of attachment to the Y—X— moiety and ** represents the point of attachment to the remainder of the molecule; and
(iii) Y is:
  (a) $C_6$-$C_9$ aryl optionally substituted by $R^{11}$, such as unsubstituted 2,3-dihydro-1H-inden-2-yl or a phenyl or naphthyl substituted by at least one $R^{11}$, including but not limited to when each $R^{11}$ is independently selected from halogen, trihalomethyl, cyano, and —C(=O)$NH_2$;
  (b) 6- to 10-membered heteroaryl optionally substituted by $R^{12}$, such as a pyridinyl, pyrimidinyl, pyridin-2 (1H)-onyl, quinolin-6-yl, optionally substituted by $R^{12}$, wherein $R^{12}$ is phenyl or —OH; or
  (c) 3- to 12-membered heterocyclyl optionally substituted by $R^{13}$, such as 2H-pyran-2-only, isoindolinyl, piperidin-2-only and piperidinyl substituted by at least one $R^{13}$.

In one aspect of this variation, (i), (ii)(a), and (iii)(a) apply. In another variation, (i), (ii)(a), and (iii)(b) apply apply. In another variation, (i), (ii)(a), and (iii)(c) apply. In another variation, (i), (ii)(b), and (iii)(a) apply. In another variation, (i), (ii)(b), and (iii)(b) apply. In another variation, (i), (ii)(b), and (iii)(c) apply. In another variation, (i), (ii)(c), and (iii)(a) apply. In another variation, (i), (ii)(c), and (iii)(b) apply. In another variation, (i), (ii)(c), and (iii)(c) apply.

All variations of L, or combinations of X and L, apply equally to any applicable formulae herein, such as formulae Ia, Ib, II, IIa, IIb, III, IIIa, IIIb, IV, IVa, IVb, V, Va, Vb, VI, VIa, VIb, VII, VIIa, VIIb, VIII, VIIIa and VIIIb.

In some embodiments, Y is $C_6$-$C_9$ aryl optionally substituted by $R^{11}$, 6- to 10-membered heteroaryl optionally substituted by $R^{12}$, or 3- to 12-membered heterocyclyl optionally substituted by $R^{13}$, wherein when Y is phenyl or naphthyl, the phenyl or naphthyl of Y is substituted by at least one $R^{11}$, and wherein when L is *—NH—$CH_2$—** and Y is optionally substituted quinolinyl, the optionally substituted quinolinyl of Y is connected to the parent structure at the 2-, 3-, 5-, 6-, 7-, or 8-position, In some embodiments, Y is $C_6$-$C_9$ aryl optionally substituted by $R^{11}$. In one aspect, Y is phenyl optionally substituted by $R^{11}$. In one variation, Y is substituted with 1 to 3 $R^{11}$ moieties which may be the same or different. In some embodiments, Y is phenyl substituted by 1 to 5 $R^{11}$ independently selected from halogen, trihalomethyl, cyano, and —C(=O)NH$_2$. In another particular embodiment, Y is a monosubstituted phenyl, such as phenyl substituted at the C4 position by $R^{11}$. In a particular variation, Y is phenyl substituted in the C4 position by cyano or —C(=O)NH$_2$. In another particular embodiment, Y is a disubstituted phenyl, such as phenyl substituted at the C2 and C4 positions or the C3 and C4 positions by two $R^{11}$ groups, which may be the same or different. In one aspect, the phenyl of Y is substituted with or two $R^{11}$ groups selected from the group consisting of cyano, —C(=O)NH$_2$, halogen and trihalomethyl. In another embodiment, Y is optionally substituted 2,3-dihydro-1H-inden-2-yl.

In some embodiments, Y is 6- to 10-membered heteroaryl optionally substituted by $R^{12}$, wherein when L is *—NH—CH$_2$—** and Y is optionally substituted quinolinyl, the optionally substituted quinolinyl of Y is connected to the parent structure at the 2-, 3-, 5-, 6-, 7-, or 8-position. In another embodiment, Y is quinolin-6-yl optionally substituted by $R^{12}$. In another embodiment, Y is quinolin-4-yl optionally substituted by $R^{12}$ and L is *—CH$_2$—CH(NH$_2$)—** or *—CH(CH$_3$)—CH(NH$_2$)—**. In another embodiment, Y is pyridin-4-yl optionally substituted by $R^{12}$. In another embodiment, Y is pyrimidin-4-yl optionally substituted by $R^{12}$ and optionally fused to $C_6$-$C_{14}$ aryl or $C_5$-$C_{10}$ cycloalkyl, which $C_6$-$C_{14}$ aryl or $C_5$-$C_{10}$ cycloalkyl are optionally substituted by $R^{12}$.

In some embodiments, Y is quinolin-6-yl optionally substituted by $R^{12}$, wherein $R^{12}$ is —OH or phenyl.

In some embodiments, Y is pyridin-3-yl substituted by $R^{12}$. In one variation, Y is pyridin-3-yl substituted by $R^{12}$, wherein $R^{12}$ is independently selected from optionally substituted $C_6$-$C_{14}$ aryl or —OR$^{14}$. In one variation, Y is pyridin-3-yl substituted in the C2 position by $R^{12}$, wherein $R^{12}$ is optionally substituted $C_6$-$C_{14}$ aryl. In one variation, Y is pyridin-3-yl substituted in the C6 position by $R^{12}$, wherein $R^{12}$ is —OR$^{14}$. In one variation, Y is pyridin-3-yl substituted in the C2 by optionally substituted $C_6$-$C_{14}$ aryl and substituted in the C6 position by —OR$^{14}$.

In some embodiments, Y is pyridin-4-yl substituted by $R^{12}$ in the C3 position. In one variation, Y is pyridin-4-yl substituted in the C3 position by $R^{12}$, wherein $R^{12}$ is independently selected from optionally substituted $C_1$-$C_6$ alkyl, optionally substituted $C_2$-$C_6$ alkenyl, optionally substituted $C_3$-$C_8$ cycloalkyl, optionally substituted $C_4$-$C_8$ cycloalkenyl, OR$^{14}$, NR$^{15}$R$^{16}$, optionally substituted pyridinyl, optionally substituted quinolinyl, optionally substituted indolyl, optionally substituted indazolyl, optionally substitute pyridin-2(1H)-onyl, optionally substituted phenyl, and optionally substituted 3- to 12-membered heterocyclyl.

In some embodiments, Y is pyridin-4-yl substituted in the C3 position by $R^{12}$, wherein $R^{12}$ is pyridinyl optionally substituted by $C_1$-$C_6$ alkyl. In another embodiment, Y is pyridin-4-yl substituted in the C3 position by $R^{12}$, wherein $R^{12}$ is indolyl optionally substituted by $C_1$-$C_6$ alkyl. In another embodiment, Y is pyridin-4-yl substituted in the C3 position by $R^{12}$, wherein $R^{12}$ is phenyl optionally substituted by $C_1$-$C_6$ alkyl, halogen, or $C_1$-$C_6$ alkoxy. In another embodiment, Y is pyridin-4-yl substituted in the C3 position by $R^{12}$, wherein $R^{12}$ is cyclopropyl optionally substituted by $C_1$-$C_6$ alkyl or —OR$^{14}$. In another embodiment, Y is pyridin-4-yl substituted in the C3 position by $R^{12}$, wherein $R^{12}$ is —OR$^{14}$, and $R^{14}$ is optionally substituted $C_1$-$C_6$ alkyl or optionally substituted phenyl.

In one variation, when Y is a 6-membered heteroaryl (e.g., pyridin-4-yl) substituted by $C_1$-$C_2$ alkyl, wherein the $C_1$-$C_2$ alkyl is substituted by $R^L$, $R^L$ is selected from the group consisting of halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —OR$^{14}$, —C(O)R$^{14}$, cyano, oxo, and nitro.

In one variation, when Y is a 6-membered heteroaryl (e.g., pyridin-4-yl) substituted by $C_1$-$C_2$ alkyl, wherein the $C_1$-$C_2$ alkyl is substituted by $R^L$, $R^L$ is selected from the group consisting of halogen and $C_6$-$C_{14}$ aryl.

In some embodiments, Y is pyrimidin-4-yl optionally substituted by $R^{12}$ and optionally fused to $C_6$-$C_{14}$ aryl or $C_5$-$C_{10}$ cycloalkyl, which $C_6$-$C_{14}$ aryl or $C_5$-$C_{10}$ cycloalkyl are optionally substituted by $R^{12}$. In a particular embodiment, Y is pyrimidin-4-yl fused to $C_6$-$C_{14}$ aryl, wherein $C_6$-$C_{14}$ aryl is optionally substituted by $R^{12}$. In a further embodiment, Y is unsubstituted quinazolin-4-yl. In another particular embodiment, Y is pyrimidin-4-yl fused to $C_5$-$C_{10}$ cycloalkyl, wherein $C_5$-$C_{10}$ cycloalkyl is optionally substituted by $R^{12}$. In a further embodiment, Y is 6,7-dihydro-5H-cyclopenta[d]pyrimidin-4-yl.

In some embodiments, Y is 2H-pyran-2-onyl optionally substituted by $R^{12}$ and optionally fused to $C_6$-$C_{14}$ aryl, which $C_6$-$C_{14}$ aryl is optionally substituted by $R^{12}$. In a further embodiment, Y is 2H-pyran-2-on-5-yl fused to $C_6$-$C_{14}$ aryl, wherein 2H-pyran-2-onyl or $C_6$-$C_{14}$ aryl are optionally substituted by $R^{12}$. In yet another embodiment, Y is 1H-isochromen-1-on-4-yl optionally substituted by halogen.

In some embodiments, Y is B' or a tautomer thereof. Thus, it is understood that in some embodiments, Y is

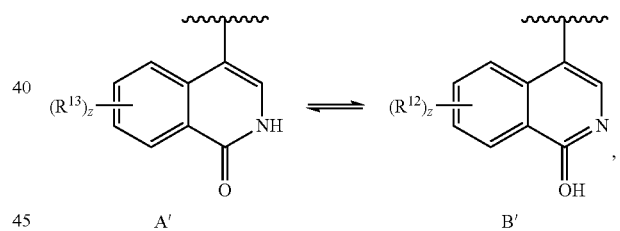

A'  B' wherein z is 0, 1, 2, 3, 4, or 5; ⇌ indicates tautomerism between A' and B'; and $R^{12}$ and $R^{13}$ are identical for any pair of tautomers. In some embodiments, Y is D' or a tautomer thereof. Thus, it is understood that in some embodiments, Y is

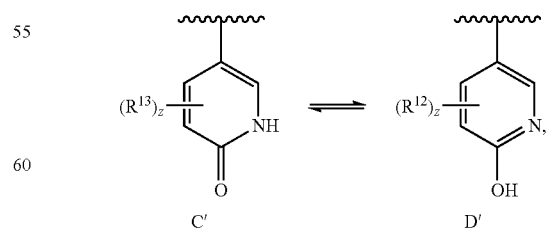

C'  D' wherein z is 0, 1, 2, 3, 4, or 5; ⇌ indicates tautomerism between C' and D'; and $R^{12}$ and $R^{13}$ are identical for any pair of tautomers.

In one embodiment, Y is selected from the group consisting of

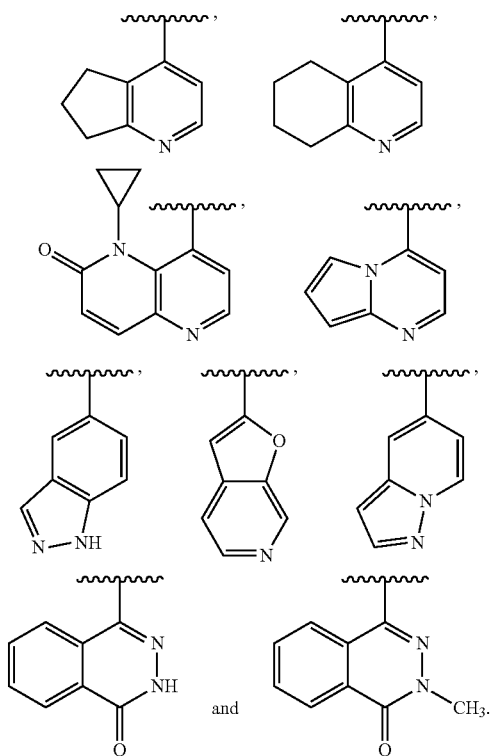

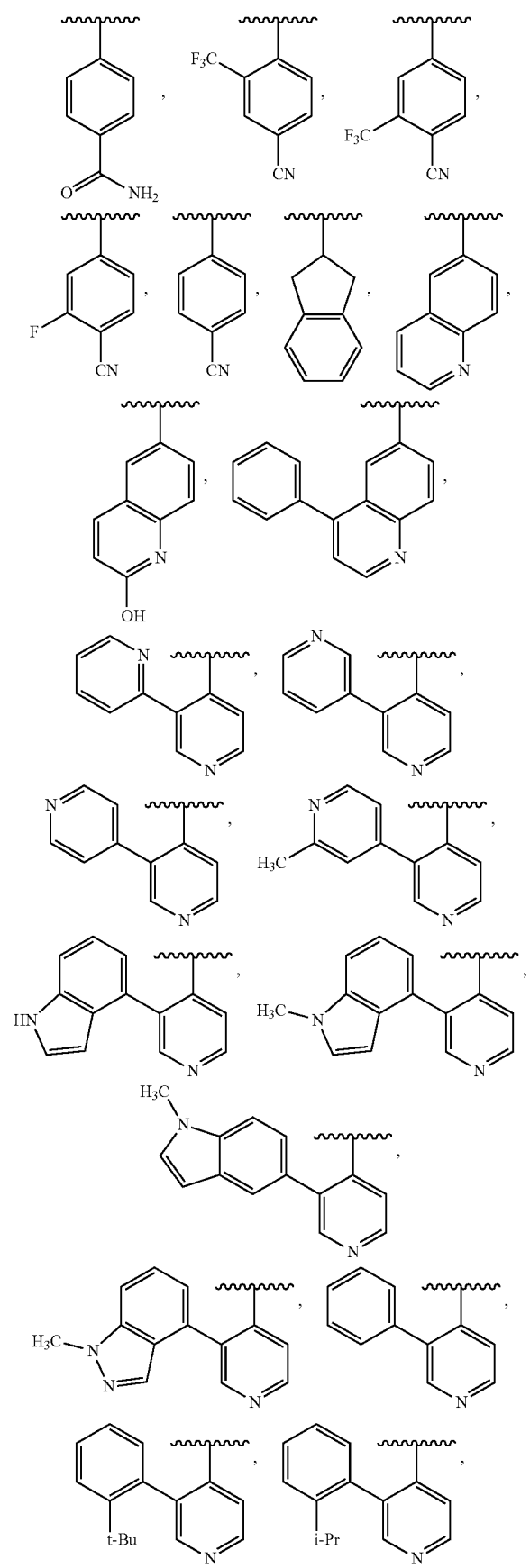

In some embodiments, Y is pyridin-2(1H)-onyl optionally substituted by $R^{12}$ and optionally fused to $C_6$-$C_{14}$ aryl or 5- to 10-membered heterocyclyl, which $C_6$-$C_{14}$ aryl or 5- to 10-membered heterocyclyl, independently of each other and independently at each occurrence, are optionally substituted by $R^{12}$. In a further embodiment, Y is pyridin-2(1H)-on-5-yl optionally substituted by $C_1$-$C_6$ alkyl (e.g., methyl) or $C_6$-$C_{14}$ aryl (e.g., phenyl, also referred to herein as "Ph")). In yet another embodiment, Y is pyridin-2(1H)-on-5-yl optionally substituted by $R^{12}$ and optionally fused to $C_6$-$C_{14}$ aryl, which $C_6$-$C_{14}$ aryl is optionally substituted by $R^{12}$. In a further embodiment, Y is isoquinolin-1(2H)-on-4-yl optionally substituted by $R^{12}$, such as halogen (e.g., fluoro), $C_1$-$C_6$ alkyl (e.g., methyl), $C_6$-$C_{14}$ aryl (e.g., phenyl), or $C_3$-$C_8$ cycloalkyl (e.g., cyclopropyl). In yet another embodiment, Y is pyridin-2(1H)-on-5-yl optionally substituted by $R^{12}$ and optionally fused to 5- to 10-membered heterocyclyl, which 5- to 10-membered heterocyclyl, is optionally substituted by $R^{12}$. In a further embodiment, Y is unsubstituted 7,8,9,10-tetrahydropyrido[1,2-a]azepin-4(6H)-on-1-yl.

In some embodiments, Y is 3- to 12-membered heterocyclyl optionally substituted by $R^{13}$. In a particular embodiment, Y is unsubstituted isoindolin-2-yl. In another embodiment, Y is piperidin-2-on-5-yl optionally substituted by $R^{13}$, such as $C_1$-$C_6$ alkyl (e.g., ethyl) and $C_6$-$C_{14}$ aryl (e.g., phenyl).

In some of these embodiments, Y is selected from the group consisting of:

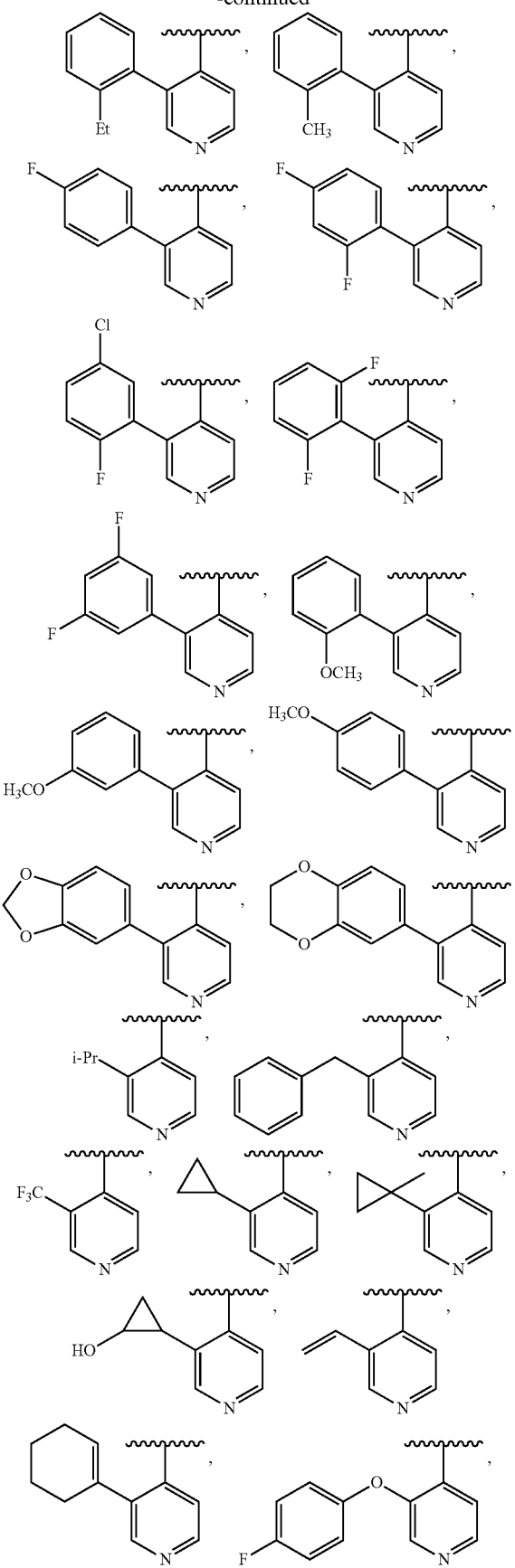
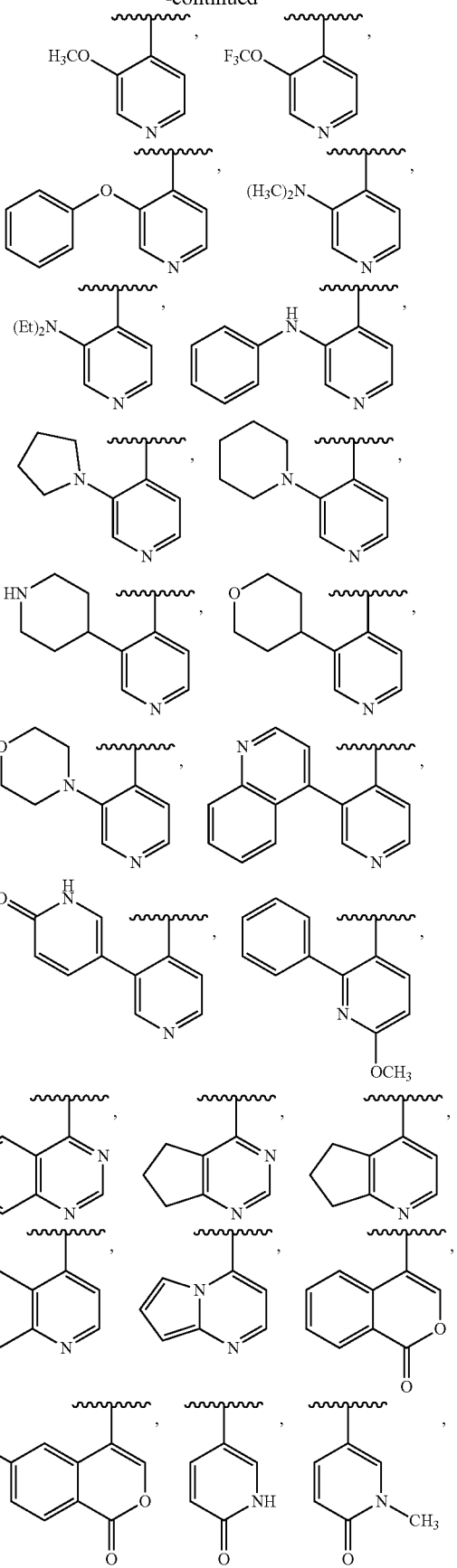

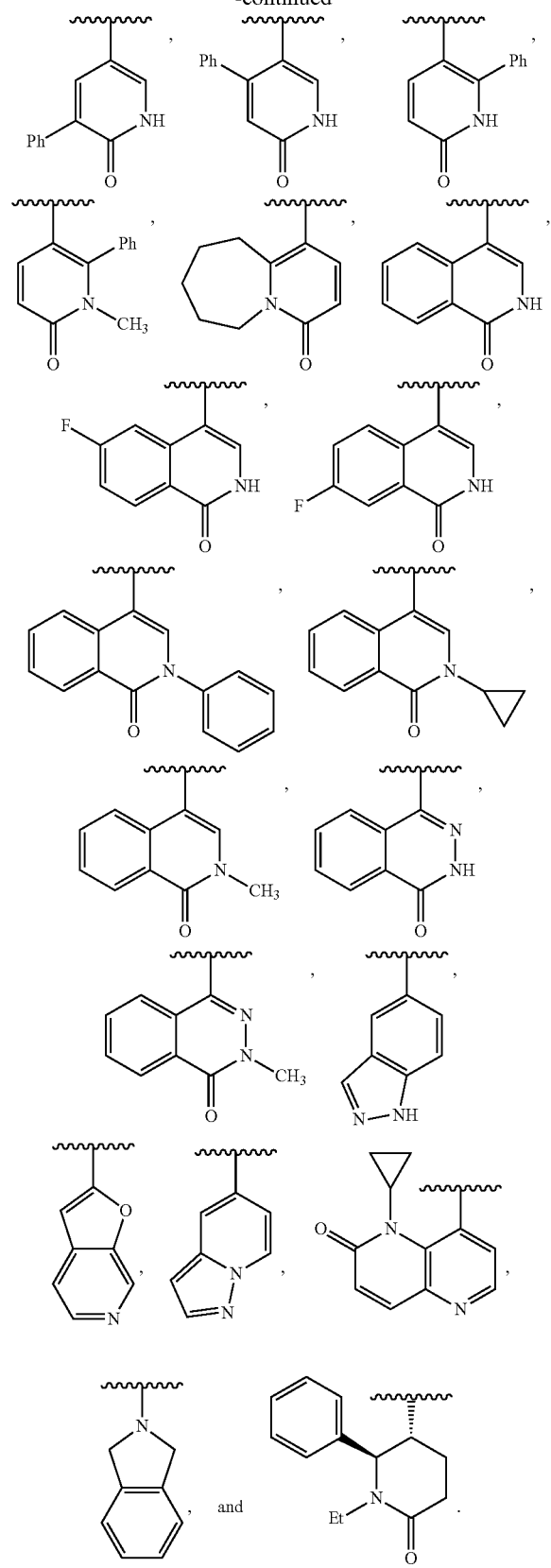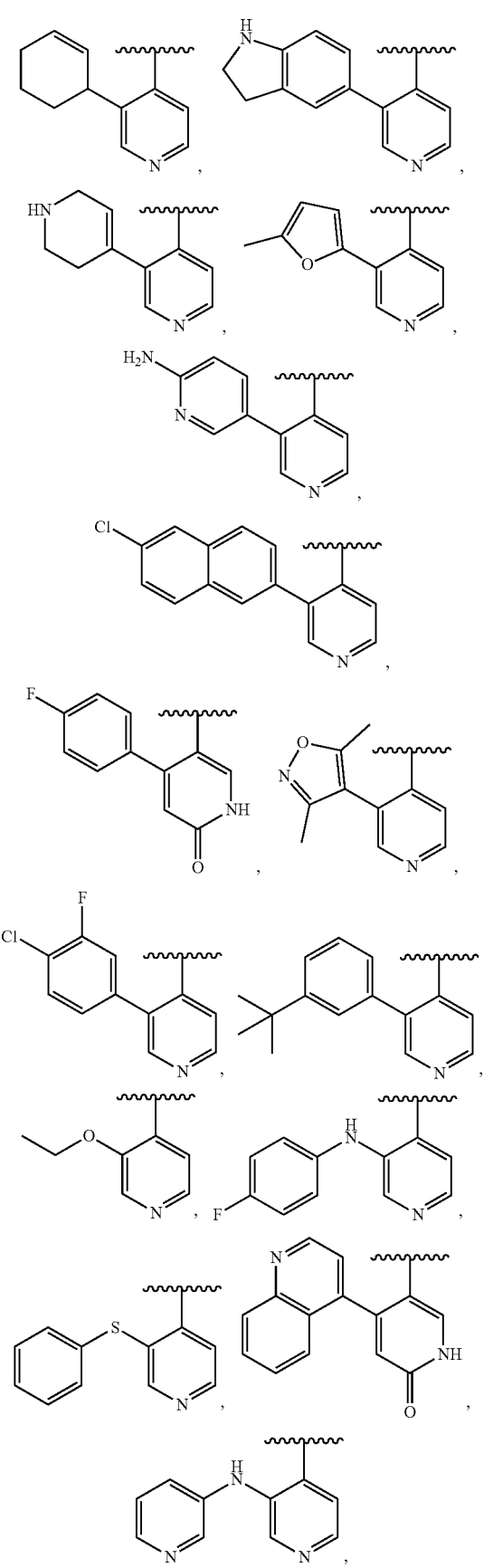
In some of these embodiments, Y is selected from the group consisting of:

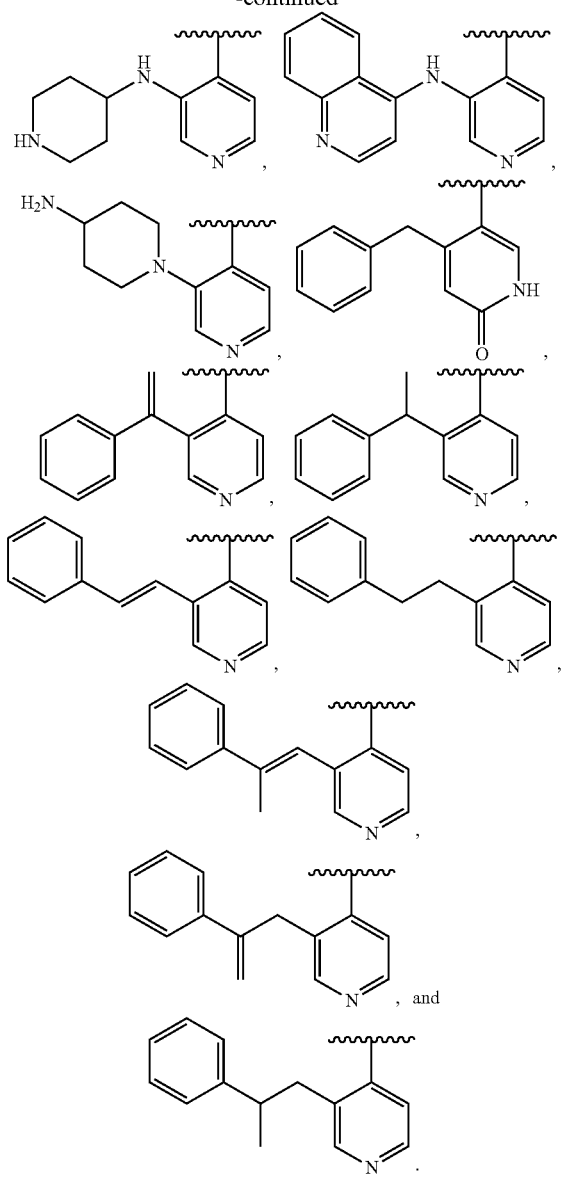

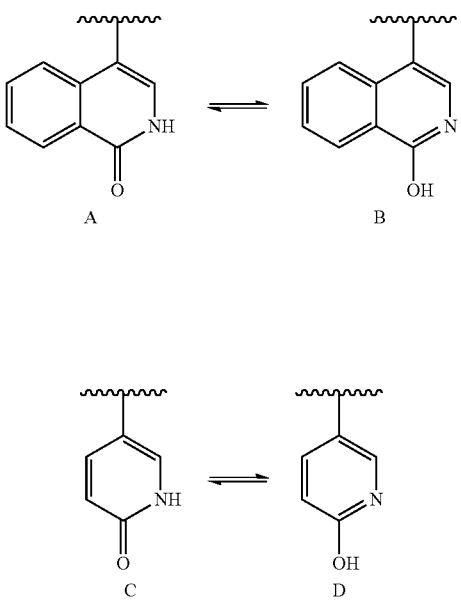

All variations of Y apply equally to any applicable formulae herein, such as formulae Ia, Ib, II, IIa, IIb, III, IIIa, IIIb, IV, IVa, IVb, V, Va, Vb, VI, VIa, VIb, VII, VIIa, VIIb, VIII, VIIIa and VIIIb.

Also provided are salts of compounds referred to herein, such as pharmaceutically acceptable salts. The invention also includes any or all of the stereochemical forms, including any enantiomeric or diastereomeric forms, and any tautomers or other forms of the compounds described.

Some of the compounds described herein exist in equilibrium with a tautomeric form. For example, amide A is a tautomeric form of B and imidic acid B is a tautomeric form of A. Similarly, amide C is a tautomeric form of D and imidic acid D is a tautomeric form of C. Amide A exists in equilibrium with a tautomeric form of imidic acid B, and amide C exists in equilibrium with a tautomeric form of imidic acid D. Regardless of which tautomeric form is depicted, the compounds are understood by one of ordinary skill in the art to comprise both the amide and the imidic acid tautomers.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 1.

TABLE 1

| Compound No. | Structure |
|---|---|
| 1 | 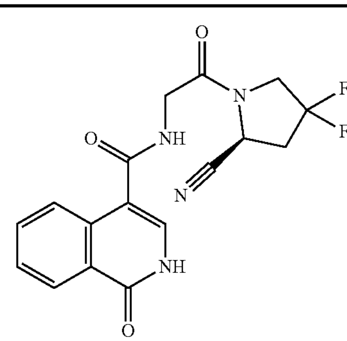 |

TABLE 1-continued

| Compound No. | Structure |
|---|---|
| 2 | (structure: 2-phenyl-1-oxo-1,2-dihydroisoquinoline-4-carboxamide linked via NHCH₂C(O) to 2-cyano-4,4-difluoropyrrolidine) |
| 3 | (structure: 2-cyclopropyl-1-oxo-1,2-dihydroisoquinoline-4-carboxamide linked via NHCH₂C(O) to 2-cyano-4,4-difluoropyrrolidine) |
| 4 | (structure: quinoline-6-carboxamide linked via NHCH₂C(O) to 2-cyano-4,4-difluoropyrrolidine) |
| 5 | (structure: 6,7-dihydro-5H-cyclopenta[d]pyrimidine-4-carboxamide linked via NHCH₂C(O) to 2-cyano-4,4-difluoropyrrolidine) |
| 6 | (structure: 6-oxo-1,6-dihydropyridine-3-carboxamide linked via NHCH₂C(O) to 2-cyano-4,4-difluoropyrrolidine) |
| 7 | (structure: 2,3-dihydro-1H-indene-2-carboxamide linked via NHCH₂C(O) to 2-cyano-4,4-difluoropyrrolidine) |
| 8 | (structure: isoindoline-2-carboxamide linked via NHCH₂C(O) to 2-cyano-4,4-difluoropyrrolidine) |
| 9 | (structure: 2-methyl-1-oxo-1,2-dihydroisoquinoline-4-carboxamide linked via NHCH₂C(O) to 2-cyano-4,4-difluoropyrrolidine) |
| 10 | (structure: 2-hydroxyquinoline-6-carboxamide linked via NHCH₂C(O) to 2-cyano-4,4-difluoropyrrolidine) |
| 11 | (structure: 4-carbamoylbenzamide linked via NHCH₂C(O) to 2-cyano-4,4-difluoropyrrolidine) |

TABLE 1-continued
| Compound No. | Structure |
|---|---|
| 12 | 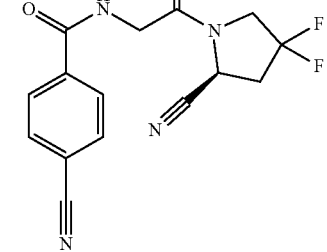 |
| 13 | 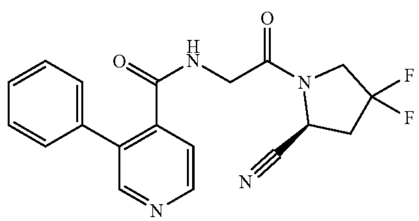 [SMILES: N#C[C@@H]1CC(F)(F)CN1C(=O)CNC(=O)c1ccncc1-c1ccccc1] |
| 14 | 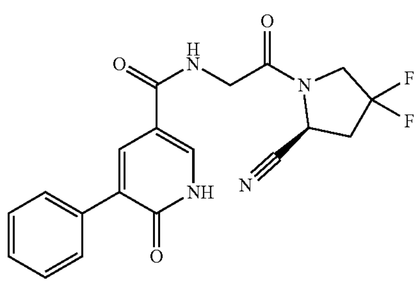 [SMILES: N#C[C@@H]1CC(F)(F)CN1C(=O)CNC(=O)c1c[nH]c(=O)c(-c2ccccc2)c1] |
| 15 | 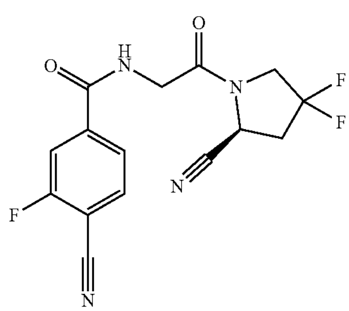 [SMILES: N#Cc1ccc(C(=O)NCC(=O)N2CC(F)(F)C[C@H]2C#N)cc1F] |
| 16 | 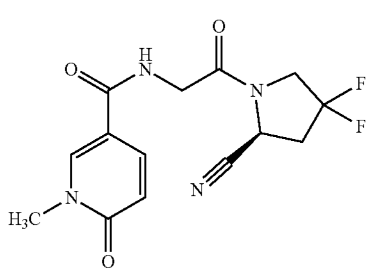 [SMILES: Cn1cc(C(=O)NCC(=O)N2CC(F)(F)C[C@H]2C#N)ccc1=O] |
| 17 | |
| 18 | |
| 19 | |
| 20 | |
| 21 | |

TABLE 1-continued

| Compound No. | Structure |
|---|---|
| 22 | (isochromen-1-one-4-carboxamide linked via NH-CH2-C(O) to 4,4-difluoro-2-cyanopyrrolidine) |
| 23 | (1-oxo-1,2-dihydroisoquinoline-4-carboxamide linked via NH-C(cyclopropylidene)-C(O) to 4,4-difluoro-2-cyanopyrrolidine) |
| 24 | (3-cyclopropylpyridine-4-carboxamide linked via NH-CH2-C(O) to 4,4-difluoro-2-cyanopyrrolidine) |
| 25 | (1-oxo-1,2-dihydroisoquinoline-4-carboxamide linked via NH-CH(CH3)-C(O) to 4,4-difluoro-2-cyanopyrrolidine) |
| 26 | (6-fluoro-1-oxo-1,2-dihydroisoquinoline-4-carboxamide linked via NH-CH2-C(O) to 4,4-difluoro-2-cyanopyrrolidine) |
| 27 | (7-fluoro-1-oxo-1,2-dihydroisoquinoline-4-carboxamide linked via NH-CH2-C(O) to 4,4-difluoro-2-cyanopyrrolidine) |
| 28 | (6-fluoro-isochromen-1-one-4-carboxamide linked via NH-CH2-C(O) to 4,4-difluoro-2-cyanopyrrolidine) |
| 29 | (4-phenyl-6-oxo-1,6-dihydropyridine-3-carboxamide linked via NH-CH2-C(O) to 4,4-difluoro-2-cyanopyrrolidine) |
| 30 | (2-phenyl-6-oxo-1,6-dihydropyridine-3-carboxamide linked via NH-CH2-C(O) to 4,4-difluoro-2-cyanopyrrolidine) |
| 31 | (2-phenyl-1-methyl-6-oxo-1,6-dihydropyridine-3-carboxamide linked via NH-CH2-C(O) to 4,4-difluoro-2-cyanopyrrolidine) |
| 32 | (1-oxo-1,2-dihydroisoquinoline-4-carbonyl-azetidine-3-carbonyl linked to 4,4-difluoro-2-cyanopyrrolidine) |

TABLE 1-continued

| Compound No. | Structure |
|---|---|
| 33 | 3-(dimethylamino)-N-(2-((S)-2-cyano-4,4-difluoropyrrolidin-1-yl)-2-oxoethyl)isonicotinamide |
| 34 | 3-(diethylamino)-N-(2-((S)-2-cyano-4,4-difluoropyrrolidin-1-yl)-2-oxoethyl)isonicotinamide |
| 35 | 3-(4-fluorophenoxy)-N-(2-((S)-2-cyano-4,4-difluoropyrrolidin-1-yl)-2-oxoethyl)isonicotinamide |
| 36 | 3-methoxy-N-(2-((S)-2-cyano-4,4-difluoropyrrolidin-1-yl)-2-oxoethyl)isonicotinamide |
| 37 | 3-cyclopropyl-N-(2-((S)-2-cyano-4,4-difluoropyrrolidin-1-yl)-2-oxoethyl)isonicotinamide |
| 38 | 3-(trifluoromethyl)-N-(2-((S)-2-cyano-4,4-difluoropyrrolidin-1-yl)-2-oxoethyl)isonicotinamide |
| 39 | 3-isopropyl-N-(2-((S)-2-cyano-4,4-difluoropyrrolidin-1-yl)-2-oxoethyl)isonicotinamide |
| 40 | 3-vinyl-N-(2-((S)-2-cyano-4,4-difluoropyrrolidin-1-yl)-2-oxoethyl)isonicotinamide |
| 41 | 3-(pyrrolidin-1-yl)-N-(2-((S)-2-cyano-4,4-difluoropyrrolidin-1-yl)-2-oxoethyl)isonicotinamide |
| 42 | 3-(piperidin-1-yl)-N-(2-((S)-2-cyano-4,4-difluoropyrrolidin-1-yl)-2-oxoethyl)isonicotinamide |
| 43 | 3-(cyclohex-1-en-1-yl)-N-(2-((S)-2-cyano-4,4-difluoropyrrolidin-1-yl)-2-oxoethyl)isonicotinamide |
| 44 | 3-(benzo[d][1,3]dioxol-5-yl)-N-(2-((S)-2-cyano-4,4-difluoropyrrolidin-1-yl)-2-oxoethyl)isonicotinamide |
| 45 | 3-(2,3-dihydrobenzo[b][1,4]dioxin-6-yl)-N-(2-((S)-2-cyano-4,4-difluoropyrrolidin-1-yl)-2-oxoethyl)isonicotinamide |

TABLE 1-continued

| Compound No. | Structure |
|---|---|
| 46 | 3-(2,6-difluorophenyl)-N-(2-((S)-2-cyano-4,4-difluoropyrrolidin-1-yl)-2-oxoethyl)isonicotinamide |
| 47 | 3-(3,5-difluorophenyl)-N-(2-((S)-2-cyano-4,4-difluoropyrrolidin-1-yl)-2-oxoethyl)isonicotinamide |
| 48 | 3-(2-methylpyridin-4-yl)-N-(2-((S)-2-cyano-4,4-difluoropyrrolidin-1-yl)-2-oxoethyl)isonicotinamide |
| 49 | 3-(1-methyl-1H-indol-5-yl)-N-(2-((S)-2-cyano-4,4-difluoropyrrolidin-1-yl)-2-oxoethyl)isonicotinamide |
| 50 | 3-benzyl-N-(2-((S)-2-cyano-4,4-difluoropyrrolidin-1-yl)-2-oxoethyl)isonicotinamide |
| 51 | 3-(isoquinolin-4-yl)-N-(2-((S)-2-cyano-4,4-difluoropyrrolidin-1-yl)-2-oxoethyl)isonicotinamide |
| 52 | 3-(4-fluorophenyl)-N-(2-((S)-2-cyano-4,4-difluoropyrrolidin-1-yl)-2-oxoethyl)isonicotinamide |
| 53 | 3-(2,4-difluorophenyl)-N-(2-((S)-2-cyano-4,4-difluoropyrrolidin-1-yl)-2-oxoethyl)isonicotinamide |
| 54 | 3-(5-chloro-2-fluorophenyl)-N-(2-((S)-2-cyano-4,4-difluoropyrrolidin-1-yl)-2-oxoethyl)isonicotinamide |
| 55 | 3-(2-methoxyphenyl)-N-(2-((S)-2-cyano-4,4-difluoropyrrolidin-1-yl)-2-oxoethyl)isonicotinamide |
| 56 | 3-(3-methoxyphenyl)-N-(2-((S)-2-cyano-4,4-difluoropyrrolidin-1-yl)-2-oxoethyl)isonicotinamide |
| 57 | 3-(4-methoxyphenyl)-N-(2-((S)-2-cyano-4,4-difluoropyrrolidin-1-yl)-2-oxoethyl)isonicotinamide |
| 58 | 3-(pyridin-2-yl)-N-(2-((S)-2-cyano-4,4-difluoropyrrolidin-1-yl)-2-oxoethyl)isonicotinamide |

TABLE 1-continued

| Compound No. | Structure |
|---|---|
| 59 | (structure) |
| 60 | (structure) |
| 61 | (structure) |
| 62 | (structure) |
| 63 | (structure) |
| 64 | (structure) |
| 65 | (structure) |
| 66 | (structure) |
| 67 | (structure) |
| 68 | (structure) |
| 69 | (structure) |
| 70 | (structure) |
| 71 | (structure) |

TABLE 1-continued

| Compound No. | Structure |
|---|---|
| 72 | (structure) |
| 73 | (structure) |
| 74 | (structure) |
| 75 | (structure) |
| 76 | (structure) |
| 77 | (structure) |
| 78 | (structure) |
| 79 | (structure) |
| 80 | (structure) |
| 81 | (structure) |
| 82 | (structure) |
| 83 | (structure) |

TABLE 1-continued

| Compound No. | Structure |
|---|---|
| 84 | (furo[3,2-c]pyridine-2-carbonyl structure) |
| 85 | (pyrazolo[1,5-a]pyridine-5-carbonyl structure) |
| 86 | (6-methoxy-2-phenylpyridine-3-carbonyl structure) |
| 87 | (3-(1-methyl-1H-indazol-4-yl)pyridine-4-carbonyl structure) |
| 88 | (3-morpholinopyridine-4-carbonyl structure) |
| 89 | (3-(1-methylcyclopropyl)pyridine-4-carbonyl structure) |
| 90 | (3-(2-hydroxycyclopropyl)pyridine-4-carbonyl structure) |
| 91 | (3-(piperidin-4-yl)pyridine-4-carbonyl structure) |
| 92 | (3-(tetrahydro-2H-pyran-4-yl)pyridine-4-carbonyl structure) |
| 93 | (6,7-dihydro-5H-cyclopenta[b]pyridine-4-carbonyl structure) |
| 94 | (5,6,7,8-tetrahydroquinoline-4-carbonyl structure) |
| 95 | (pyrrolo[1,2-a]pyrimidine-4-carbonyl structure) |
| 96 | (3-(trifluoromethoxy)pyridine-4-carbonyl structure) |

TABLE 1-continued

| Compound No. | Structure |
|---|---|
| 97 | (structure) |
| 98 | (structure) |
| 99 | (structure) |
| 100 | (structure) |
| 101 | (structure) |
| 102 | (structure) |
| 103 | (structure) |
| 104 | (structure) |

Additional representative compounds are listed in Table 1-A.

TABLE 1-A

| Compound No. | Structure |
|---|---|
| 105 | (structure) |
| 106 | (structure) |
| 107 | (structure) |
| 108 | (structure) |

TABLE 1-A-continued

| Compound No. | Structure |
|---|---|
| 109 | 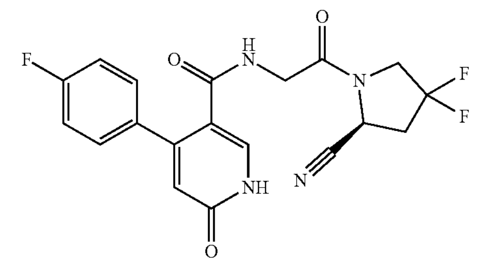 [SMILES: N#C[C@@H]1CC(F)(F)CN1C(=O)CNC(=O)c1c[nH]c(=O)cc1-c1ccc(F)cc1] |
| 110 | 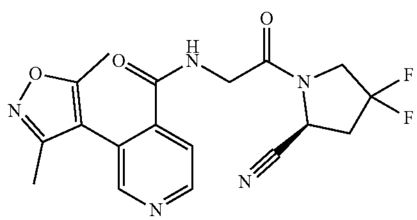 [SMILES: Cc1noc(C)c1-c1cnccc1C(=O)NCC(=O)N1CC(F)(F)C[C@H]1C#N] |
| 111 | 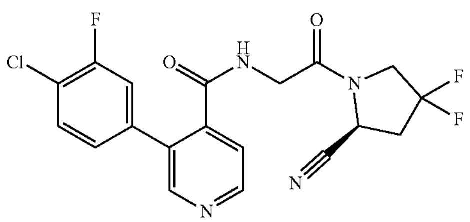 [SMILES: N#C[C@@H]1CC(F)(F)CN1C(=O)CNC(=O)c1ccncc1-c1ccc(Cl)c(F)c1] |
| 112 | 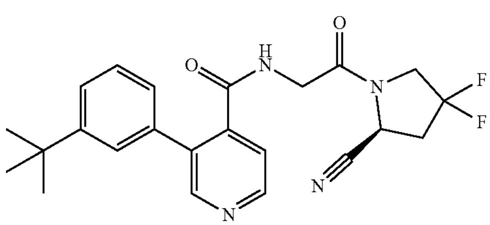 [SMILES: CC(C)(C)c1cccc(-c2cnccc2C(=O)NCC(=O)N2CC(F)(F)C[C@H]2C#N)c1] |
| 113 | 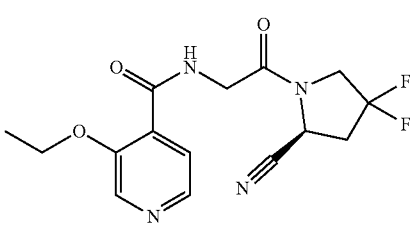 [SMILES: CCOc1cnccc1C(=O)NCC(=O)N1CC(F)(F)C[C@H]1C#N] |
| 114 | 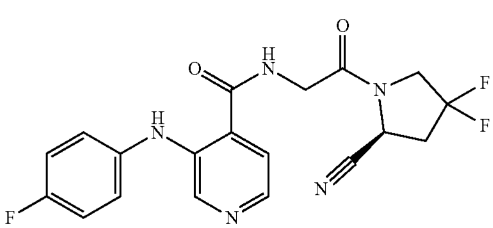 [SMILES: N#C[C@@H]1CC(F)(F)CN1C(=O)CNC(=O)c1ccncc1Nc1ccc(F)cc1] |
| 115 | |
| 116 | |
| 117 | |
| 118 | |
| 119 | |
| 120 | |

TABLE 1-A-continued

| Compound No. | Structure |
|---|---|
| 121 | 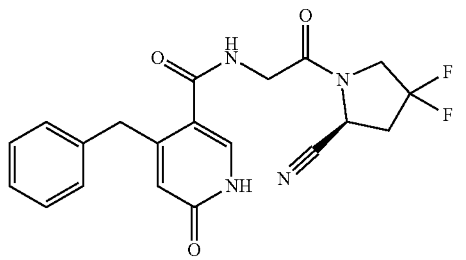 [SMILES: N#C[C@@H]1CC(F)(F)CN1C(=O)CNC(=O)c1c[nH]c(=O)cc1Cc1ccccc1] |
| 122 | 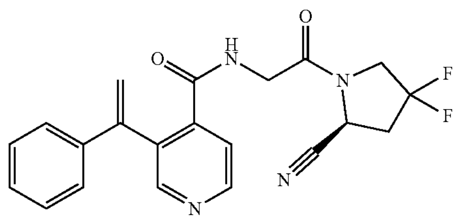 [SMILES: C=C(c1ccccc1)c1cnccc1C(=O)NCC(=O)N1CC(F)(F)C[C@H]1C#N] |
| 123 | 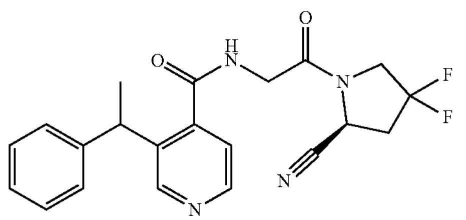 [SMILES: CC(c1ccccc1)c1cnccc1C(=O)NCC(=O)N1CC(F)(F)C[C@H]1C#N] |
| 123a | 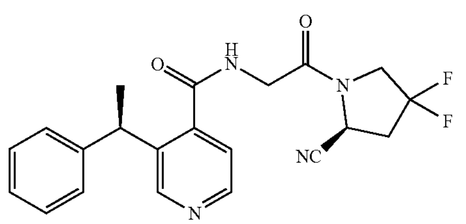 [SMILES: C[C@H](c1ccccc1)c1cnccc1C(=O)NCC(=O)N1CC(F)(F)C[C@H]1C#N] |
| 123b | 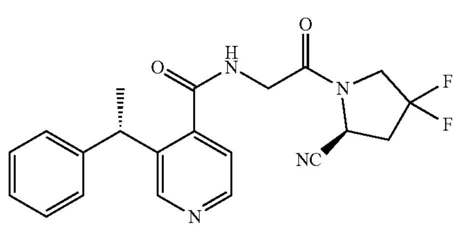 [SMILES: C[C@@H](c1ccccc1)c1cnccc1C(=O)NCC(=O)N1CC(F)(F)C[C@H]1C#N] |
| 124 | 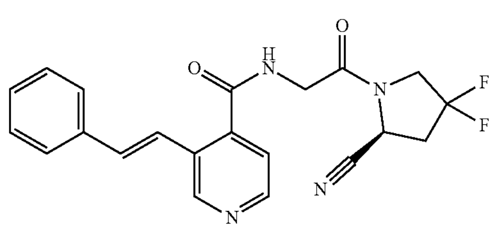 [SMILES: N#C[C@@H]1CC(F)(F)CN1C(=O)CNC(=O)c1ccncc1/C=C/c1ccccc1] |

TABLE 1-A-continued

| Compound No. | Structure |
|---|---|
| 125 | |
| 126 | |
| 127 | |
| 128 | |
| 129 | |

Certain compounds depicted in Table 1 or Table 1-A exist as tautomers. Regardless of which tautomer is shown, all tautomeric forms are intended.

In some embodiments, provided herein is a compound described in Table 1, or a tautomer thereof, or a salt of any of the foregoing, and uses thereof. In some embodiments, provided herein is a compound described in Table 1 or a pharmaceutically acceptable salt thereof. In some embodiments, provided herein is a compound described in Table 1-A, or a tautomer thereof, or a salt of any of the foregoing, and uses thereof. In some embodiments, provided herein is a compound described in Table 1-A or a pharmaceutically acceptable salt thereof. In some embodiments, provided herein is a compound described in Table 1 or 1-A, or a tautomer thereof, or a salt of any of the foregoing, and uses thereof. In some embodiments, provided herein is a compound described in Table 1 or 1-A or a pharmaceutically acceptable salt thereof.

In some embodiments, provided herein is a compound selected from Compound Nos. 1-129, or a tautomer thereof, or a salt of any of the foregoing, and uses thereof. In some embodiments, provided herein is a compound selected from Compound Nos. 1-129, or a pharmaceutically acceptable salt thereof.

In some embodiments, provided is a compound selected from Compound Nos. 1-129, or a stereoisomer thereof (including a mixture of two or more stereoisomers thereof), or a salt thereof. In some embodiments, the compound is a salt of a compound selected from Compound Nos. 1-129, or a stereoisomer thereof.

In one variation, the compound detailed herein is selected from the group consisting of:

N-(2-(2-cyano-4,4-difluoropyrrolidin-1-yl)-2-oxoethyl)-1-oxo-1,2-dihydroisoquinoline-4-carboxamide;
N-(2-(2-cyano-4,4-difluoropyrrolidin-1-yl)-2-oxoethyl)-1-oxo-2-phenyl-1,2-dihydroisoquinoline-4-carboxamide;
N-(2-(2-cyano-4,4-difluoropyrrolidin-1-yl)-2-oxoethyl)-2-cyclopropyl-1-oxo-1,2-dihydroisoquinoline-4-carboxamide;
N-(2-(2-cyano-4,4-difluoropyrrolidin-1-yl)-2-oxoethyl)quinoline-6-carboxamide;
N-(2-(2-cyano-4,4-difluoropyrrolidin-1-yl)-2-oxoethyl)-6,7-dihydro-5H-cyclopenta[d]pyrimidine-4-carboxamide;
N-(2-(2-cyano-4,4-difluoropyrrolidin-1-yl)-2-oxoethyl)-6-oxo-1,6-dihydropyridine-3-carboxamide;
N-(2-(2-cyano-4,4-difluoropyrrolidin-1-yl)-2-oxoethyl)-2,3-dihydro-1H-indene-2-carboxamide;
N-(2-(2-cyano-4,4-difluoropyrrolidin-1-yl)-2-oxoethyl)isoindoline-2-carboxamide;
N-(2-(2-cyano-4,4-difluoropyrrolidin-1-yl)-2-oxoethyl)-2-methyl-1-oxo-1,2-dihydroisoquinoline-4-carboxamide;
N-(2-(2-cyano-4,4-difluoropyrrolidin-1-yl)-2-oxoethyl)-2-hydroxyquinoline-6-carboxamide;
N-(2-(2-cyano-4,4-difluoropyrrolidin-1-yl)-2-oxoethyl)terephthalamide;
4-cyano-N-(2-(2-cyano-4,4-difluoropyrrolidin-1-yl)-2-oxoethyl)-3-(trifluoromethyl)benzamide;
N-(2-(2-cyano-4,4-difluoropyrrolidin-1-yl)-2-oxoethyl)-3-phenylisonicotinamide;
N-(2-(2-cyano-4,4-difluoropyrrolidin-1-yl)-2-oxoethyl)-6-oxo-5-phenyl-1,6-dihydropyridine-3-carboxamide;
4-cyano-N-(2-(2-cyano-4,4-difluoropyrrolidin-1-yl)-2-oxoethyl)-3-fluorobenzamide;
N-(2-(2-cyano-4,4-difluoropyrrolidin-1-yl)-2-oxoethyl)-1-methyl-6-oxo-1,6-dihydropyridine-3-carboxamide;
4-cyano-N-(2-(2-cyano-4,4-difluoropyrrolidin-1-yl)-2-oxoethyl)benzamide;
4-cyano-N-(2-(2-cyano-4,4-difluoropyrrolidin-1-yl)-2-oxoethyl)-2-(trifluoromethyl)benzamide;
N-(2-(2-cyano-4,4-difluoropyrrolidin-1-yl)-2-oxoethyl)-4-phenylquinoline-6-carboxamide;
N-(2-(2-cyano-4,4-difluoropyrrolidin-1-yl)-2-oxoethyl)-1-ethyl-6-oxo-2-phenylpiperidine-3-carboxamide;
N-(2-(2-cyano-4,4-difluoropyrrolidin-1-yl)-2-oxoethyl)-4-oxo-4,6,7,8,9,10-hexahydropyrido[1,2-a]azepine-1-carboxamide;
N-(2-(2-cyano-4,4-difluoropyrrolidin-1-yl)-2-oxoethyl)-1-oxo-1H-isochromene-4-carboxamide;
N-(1-(2-cyano-4,4-difluoropyrrolidine-1-carbonyl)cyclopropyl)-1-oxo-1,2-dihydroisoquinoline-4-carboxamide;
N-(2-(2-cyano-4,4-difluoropyrrolidin-1-yl)-2-oxoethyl)-3-cyclopropylisonicotinamide;
N-(1-(2-cyano-4,4-difluoropyrrolidin-1-yl)-1-oxopropan-2-yl)-1-oxo-1,2-dihydroisoquinoline-4-carboxamide;
N-(2-(2-cyano-4,4-difluoropyrrolidin-1-yl)-2-oxoethyl)-6-fluoro-1-oxo-1,2-dihydroisoquinoline-4-carboxamide;
N-(2-(2-cyano-4,4-difluoropyrrolidin-1-yl)-2-oxoethyl)-7-fluoro-1-oxo-1,2-dihydroisoquinoline-4-carboxamide;
N-(2-(2-cyano-4,4-difluoropyrrolidin-1-yl)-2-oxoethyl)-6-fluoro-1-oxo-1H-isochromene-4-carboxamide;
N-(2-(2-cyano-4,4-difluoropyrrolidin-1-yl)-2-oxoethyl)-6-oxo-4-phenyl-1,6-dihydropyridine-3-carboxamide;
N-(2-(2-cyano-4,4-difluoropyrrolidin-1-yl)-2-oxoethyl)-6-oxo-2-phenyl-1,6-dihydropyridine-3-carboxamide;
N-(2-(2-cyano-4,4-difluoropyrrolidin-1-yl)-2-oxoethyl)-1-methyl-6-oxo-2-phenyl-1,6-dihydropyridine-3-carboxamide;
4,4-difluoro-1-(1-(1-oxo-1,2-dihydroisoquinoline-4-carbonyl)azetidine-3-carbonyl)pyrrolidine-2-carbonitrile;
N-(2-(2-cyano-4,4-difluoropyrrolidin-1-yl)-2-oxoethyl)-3-(dimethylamino)isonicotinamide;
N-(2-(2-cyano-4,4-difluoropyrrolidin-1-yl)-2-oxoethyl)-3-(diethylamino)isonicotinamide;
N-(2-(2-cyano-4,4-difluoropyrrolidin-1-yl)-2-oxoethyl)-3-(4-fluorophenoxy)isonicotinamide;
N-(2-(2-cyano-4,4-difluoropyrrolidin-1-yl)-2-oxoethyl)-3-methoxyisonicotinamide;
N-(2-(2-cyano-4,4-difluoropyrrolidin-1-yl)-2-oxoethyl)-3-(trifluoromethyl)isonicotinamide;
N-(2-(2-cyano-4,4-difluoropyrrolidin-1-yl)-2-oxoethyl)-3-isopropylisonicotinamide;
N-(2-(2-cyano-4,4-difluoropyrrolidin-1-yl)-2-oxoethyl)-3-vinylisonicotinamide;
N-(2-(2-cyano-4,4-difluoropyrrolidin-1-yl)-2-oxoethyl)-3-(pyrrolidin-1-yl)isonicotinamide;
N-[2-[2-cyano-4,4-difluoro-pyrrolidin-1-yl]-2-oxo-ethyl]-3-(1-piperidyl)pyridine-4-carboxamide;
N-(2-(2-cyano-4,4-difluoropyrrolidin-1-yl)-2-oxoethyl)-3-(cyclohex-1-en-1-yl)isonicotinamide;
3-(benzo[d][1,3]dioxol-5-yl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(2,3-dihydrobenzo[b][1,4]dioxin-6-yl)isonicotinamide;
N-(2-(2-cyano-4,4-difluoropyrrolidin-1-yl)-2-oxoethyl)-3-(2,6-difluorophenyl)isonicotinamide;
N-(2-(2-cyano-4,4-difluoropyrrolidin-1-yl)-2-oxoethyl)-3-(3,5-difluorophenyl)isonicotinamide;
N-(2-(2-cyano-4,4-difluoropyrrolidin-1-yl)-2-oxoethyl)-2'-methyl-[3,4'-bipyridine]-4-carboxamide;
N-(2-(2-cyano-4,4-difluoropyrrolidin-1-yl)-2-oxoethyl)-3-(1-methyl-1H-indol-5-yl)isonicotinamide;
3-benzyl-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(quinolin-4-yl)isonicotinamide;
N-(2-(2-cyano-4,4-difluoropyrrolidin-1-yl)-2-oxoethyl)-3-(4-fluorophenyl)isonicotinamide;
N-(2-(2-cyano-4,4-difluoropyrrolidin-1-yl)-2-oxoethyl)-3-(2,4-difluorophenyl)isonicotinamide;
3-(5-chloro-2-fluorophenyl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(2-methoxyphenyl)isonicotinamide;
N-(2-(2-cyano-4,4-difluoropyrrolidin-1-yl)-2-oxoethyl)-3-(3-methoxyphenyl)isonicotinamide;
N-(2-(2-cyano-4,4-difluoropyrrolidin-1-yl)-2-oxoethyl)-3-(4-methoxyphenyl)isonicotinamide;
N-(2-(2-cyano-4,4-difluoropyrrolidin-1-yl)-2-oxoethyl)-[2,3'-bipyridine]-4'-carboxamide;
N-(2-(2-cyano-4,4-difluoropyrrolidin-1-yl)-2-oxoethyl)-[3,3'-bipyridine]-4-carboxamide;

N-(2-(2-cyano-4,4-difluoropyrrolidin-1-yl)-2-oxoethyl)-[3,4'-bipyridine]-4-carboxamide;
3-(2-(tert-butyl)phenyl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(2-isopropylphenyl)isonicotinamide;
N-(2-(2-cyano-4,4-difluoropyrrolidin-1-yl)-2-oxoethyl)-3-(2-ethylphenyl)isonicotinamide;
N-(2-(2-cyano-4,4-difluoropyrrolidin-1-yl)-2-oxoethyl)-3-(o-tolyl)isonicotinamide;
N-(2-(2-cyano-4,4-difluoropyrrolidin-1-yl)-2-oxoethyl)-3-(1H-indol-4-yl)isonicotinamide;
N-(2-(2-cyano-4,4-difluoropyrrolidin-1-yl)-2-oxoethyl)-3-(1-methyl-1H-indol-4-yl)isonicotinamide;
N-(2-(2-cyano-4,4-difluoropyrrolidin-1-yl)-2-oxoethyl)quinazoline-4-carboxamide;
1-(2-amino-4-hydroxy-4-(1-oxo-1,2-dihydroisoquinolin-4-yl)butanoyl)-4,4-difluoropyrrolidine 2-carbonitrile;
4,4-difluoro-1-(O-(1-oxo-1,2-dihydroisoquinolin-4-yl)seryl)pyrrolidine-2-carbonitrile;
1-(2-amino-4-oxo-4-(quinolin-4-yl)butanoyl)-4,4-difluoropyrrolidine-2-carbonitrile;
1-(2-amino-4-hydroxy-4-(quinolin-4-yl)butanoyl)-4,4-difluoropyrrolidine-2-carbonitrile;
4,4-difluoro-1-(O-(quinolin-4-yl)seryl)pyrrolidine-2-carbonitrile;
1-(2-amino-4-oxo-4-(1-oxo-1,2-dihydroisoquinolin-4-yl)butanoyl)-4,4-difluoropyrrolidine-2-carbonitrile;
1-(2-amino-4-hydroxy-3-methyl-4-(1-oxo-1,2-dihydroisoquinolin-4-yl)butanoyl)-4,4-difluoropyrrolidine-2-carbonitrile;
4,4-difluoro-1-(O-(1-oxo-1,2-dihydroisoquinolin-4-yl)threonyl)pyrrolidine-2-carbonitrile;
1-(2-amino-3-methyl-4-oxo-4-(quinolin-4-yl)butanoyl)-4,4-difluoropyrrolidine-2-carbonitrile;
1-(2-amino-4-hydroxy-3-methyl-4-(quinolin-4-yl)butanoyl)-4,4-difluoropyrrolidine-2-carbonitrile;
4,4-difluoro-1-(O-(quinolin-4-yl)threonyl)pyrrolidine-2-carbonitrile;
1-(2-amino-3-methyl-4-oxo-4-(1-oxo-1,2-dihydroisoquinolin-4-yl)butanoyl)-4,4-difluoropyrrolidine-2-carbonitrile;
N-(2-(2-cyano-4,4-difluoropyrrolidin-1-yl)-2-oxoethyl)-4-oxo-3,4,4a,8a-tetrahydrophthalazine-1-carboxamide;
N-[2-[2-cyano-4,4-difluoro-pyrrolidin-1-yl]-2-oxo-ethyl]-3-methyl-4-oxo-phthalazine-1-carboxamide;
N-(4-(2-cyano-4,4-difluoropyrrolidin-1-yl)-4-oxobutyl)-1-oxo-1,2-dihydroisoquinoline-4-carboxamide;
N-(2-(2-cyano-4,4-difluoropyrrolidin-1-yl)-2-oxoethyl)-1H-indazole-5-carboxamide;
N-(2-(2-cyano-4,4-difluoropyrrolidin-1-yl)-2-oxoethyl)furo[2,3-c]pyridine-2-carboxamide;
N-(2-(2-cyano-4,4-difluoropyrrolidin-1-yl)-2-oxoethyl)pyrazolo[1,5-a]pyridine-5-carboxamide;
N-(2-(2-cyano-4,4-difluoropyrrolidin-1-yl)-2-oxoethyl)-6-methoxy-2-phenylnicotinamide;
N-(2-(2-cyano-4,4-difluoropyrrolidin-1-yl)-2-oxoethyl)-3-(1-methyl-1H-indazol-4-yl)isonicotinamide;
N-[2-[2-cyano-4,4-difluoro-pyrrolidin-1-yl]-2-oxo-ethyl]-3-morpholino-pyridine-4-carboxamide;
N-(2-(2-cyano-4,4-difluoropyrrolidin-1-yl)-2-oxoethyl)-3-(1-methylcyclopropyl)isonicotinamide;
N-(2-(2-cyano-4,4-difluoropyrrolidin-1-yl)-2-oxoethyl)-3-(2-hydroxycyclopropyl)isonicotinamide;
N-(2-(2-cyano-4,4-difluoropyrrolidin-1-yl)-2-oxoethyl)-3-(piperidin-4-yl)isonicotinamide;
N-(2-(2-cyano-4,4-difluoropyrrolidin-1-yl)-2-oxoethyl)-3-(tetrahydro-2H-pyran-4-yl)isonicotinamide;
N-(2-(2-cyano-4,4-difluoropyrrolidin-1-yl)-2-oxoethyl)-6,7-dihydro-5H-cyclopenta[b]pyridine-4-carboxamide;
N-(2-(2-cyano-4,4-difluoropyrrolidin-1-yl)-2-oxoethyl)-5,6,7,8-tetrahydroquinoline-4-carboxamide;
N-(2-(2-cyano-4,4-difluoropyrrolidin-1-yl)-2-oxoethyl)pyrrolo[1,2-a]pyrimidine-4-carboxamide;
N-(2-(2-cyano-4,4-difluoropyrrolidin-1-yl)-2-oxoethyl)-3-(trifluoromethoxy)isonicotinamide;
N-(2-(2-cyano-4,4-difluoropyrrolidin-1-yl)-2-oxoethyl)-3-phenoxyisonicotinamide;
N-(2-(2-cyano-4,4-difluoro-2-methylpyrrolidin-1-yl)-2-oxoethyl)-1-oxo-1,2-dihydroisoquinoline-4-carboxamide;
N-(2-(2-cyano-4,4-difluoropyrrolidin-1-yl)-2-oxoethyl)-6'-oxo-1',6'-dihydro-[3,3'-bipyridine]-4-carboxamide;
N-(2-(2-cyano-4,4-difluoropyrrolidin-1-yl)-2-oxoethyl)-5-cyclopropyl-6-oxo-5,6-dihydro-1,5-naphthyridine-4-carboxamide;
N-(3-(2-cyano-4,4-difluoropyrrolidine-1-carbonyl)cyclobutyl)-1-oxo-1,2-dihydroisoquinoline-4-carboxamide;
N-(2-(2-cyano-4,4-difluoropyrrolidin-1-yl)-2-oxoethyl)-3-(phenylamino)isonicotinamide;
N-(2-(2-cyano-4,4-difluoropyrrolidin-1-yl)-2-oxoethyl)-3-(cyclohex-2-en-1-yl)isonicotinamide;
N-(2-(2-cyano-4,4-difluoropyrrolidin-1-yl)-2-oxoethyl)-3-(indolin-5-yl)isonicotinamide;
N-(2-(2-cyano-4,4-difluoropyrrolidin-1-yl)-2-oxoethyl)-1',2',3',6'-tetrahydro-[3,4'-bipyridine]-4-carboxamide;
N-(2-(2-cyano-4,4-difluoropyrrolidin-1-yl)-2-oxoethyl)-3-(5-methylfuran-2-yl)isonicotinamide;
6'-amino-N-(2-(2-cyano-4,4-difluoropyrrolidin-1-yl)-2-oxoethyl)-[3,3'-bipyridine]-4-carboxamide;
3-(6-chloronaphthalen-2-yl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-4-(4-fluorophenyl)-6-oxo-1,6-dihydropyridine-3-carboxamide;
N-(2-(2-cyano-4,4-difluoropyrrolidin-1-yl)-2-oxoethyl)-3-(3,5-dimethylisoxazol-4-yl)isonicotinamide;
3-(4-chloro-3-fluorophenyl)-N-(2-(2-cyano-4,4-difluoropyrrolidin-1-yl)-2-oxoethyl)isonicotinamide;
3-(3-(tert-butyl)phenyl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-ethoxyisonicotinamide;
N-(2-(2-cyano-4,4-difluoropyrrolidin-1-yl)-2-oxoethyl)-3-((4-fluorophenyl)amino)isonicotinamide;
N-(2-(2-cyano-4,4-difluoropyrrolidin-1-yl)-2-oxoethyl)-3-(phenylthio)isonicotinamide;
N-(2-(2-cyano-4,4-difluoropyrrolidin-1-yl)-2-oxoethyl)-6-oxo-4-(quinolin-4-yl)-1,6-dihydropyridine-3-carboxamide;
N-(2-(2-cyano-4,4-difluoropyrrolidin-1-yl)-2-oxoethyl)-3-(pyridin-3-ylamino)isonicotinamide;
N-(2-(2-cyano-4,4-difluoropyrrolidin-1-yl)-2-oxoethyl)-3-(piperidin-4-ylamino)isonicotinamide;
N-(2-(2-cyano-4,4-difluoropyrrolidin-1-yl)-2-oxoethyl)-3-(quinolin-4-ylamino)isonicotinamide;
3-(4-aminopiperidin-1-yl)-N-(2-(2-cyano-4,4-difluoropyrrolidin-1-yl)-2-oxoethyl)isonicotinamide;
4-benzyl-N-(2-(2-cyano-4,4-difluoropyrrolidin-1-yl)-2-oxoethyl)-6-oxo-1,6-dihydropyridine-3-carboxamide;
N-(2-(2-cyano-4,4-difluoropyrrolidin-1-yl)-2-oxoethyl)-3-(1-phenylvinyl)isonicotinamide;
N-(2-(2-cyano-4,4-difluoropyrrolidin-1-yl)-2-oxoethyl)-3-(1-phenylethyl)isonicotinamide;

N-(2-(2-cyano-4,4-difluoropyrrolidin-1-yl)-2-oxoethyl)-3-styrylisonicotinamide;

N-(2-(2-cyano-4,4-difluoropyrrolidin-1-yl)-2-oxoethyl)-3-phenethylisonicotinamide;

N-(1-(2-cyano-4,4-difluoropyrrolidin-1-yl)-1-oxopropan-2-yl)-3-phenylisonicotinamide;

N-(2-(2-cyano-4,4-difluoropyrrolidin-1-yl)-2-oxoethyl)-3-(2-phenylprop-1-en-1-yl)isonicotinamide;

N-(2-(2-cyano-4,4-difluoropyrrolidin-1-yl)-2-oxoethyl)-3-(2-phenylallyl)isonicotinamide, and N-(2-(2-cyano-4,4-difluoropyrrolidin-1-yl)-2-oxoethyl)-3-(2-phenylpropyl)isonicotinamide.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described, such as the compounds of Table 1. The structure or name is intended to embrace all possible stereoisomers of a compound depicted. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$ $^{13}N$, $^{15}O$, $^{17}O$, $^{32}P$, $^{35}S$, $^{18}F$, $^{36}Cl$. Certain isotope labeled compounds (e.g. $^3H$ and $^{14}C$) is useful in compound or substrate tissue distribution studies. Incorporation of heavier isotopes such as deuterium ($^2H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol.

Compounds of the formula (I-1) can be prepared according to Scheme 1, wherein R, $R^1$, $R^2$, Y, m, n and q are as detailed herein for formula (I), or any variation thereof detailed herein; Z and $Z^1$ are leaving groups; and $PG^1$ is an amine protecting group.

Scheme 1

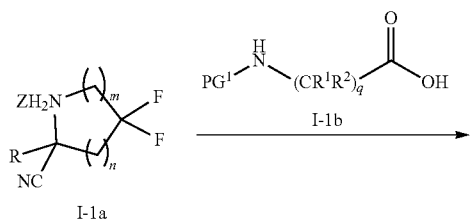

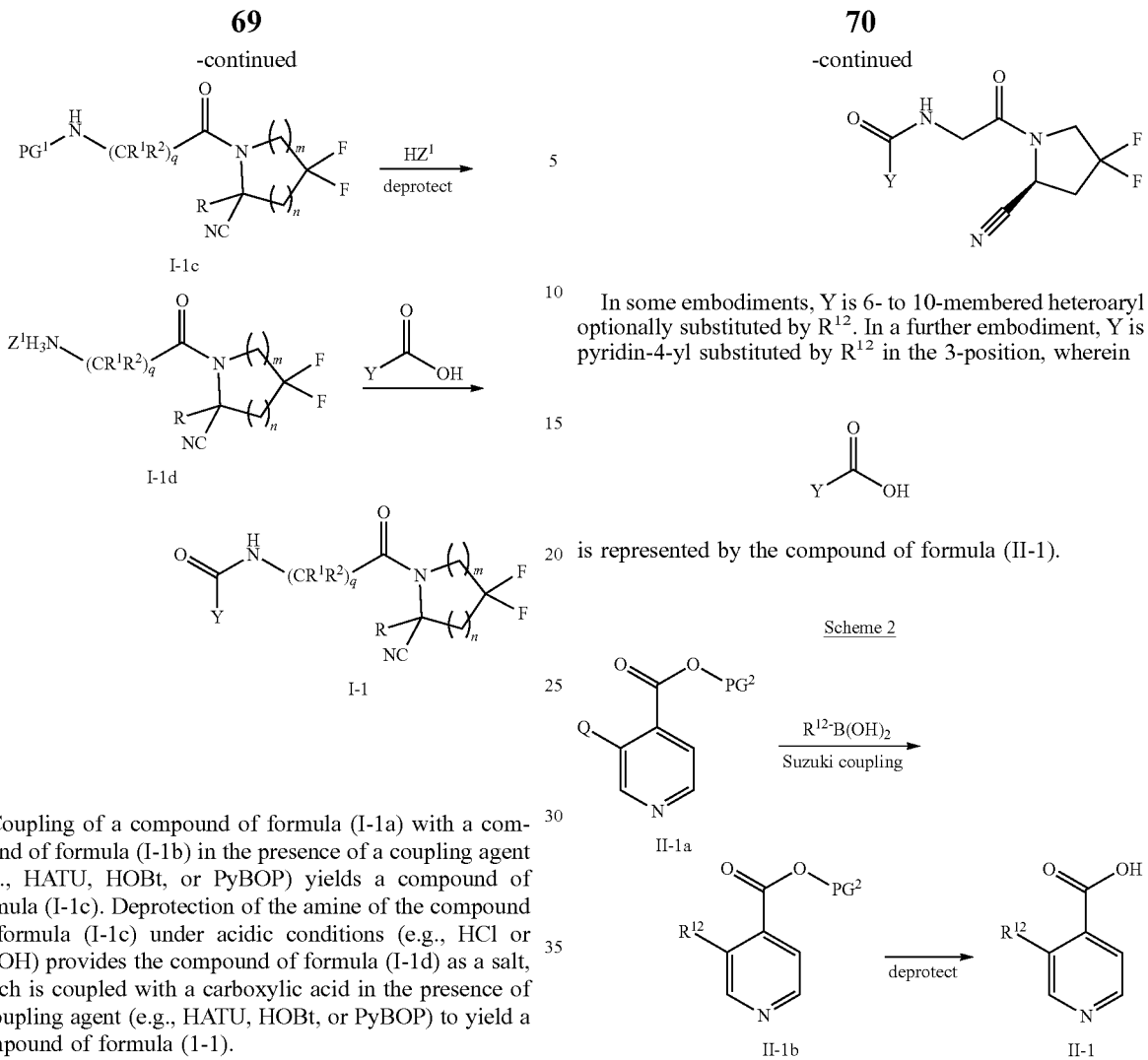

Coupling of a compound of formula (I-1a) with a compound of formula (I-1b) in the presence of a coupling agent (e.g., HATU, HOBt, or PyBOP) yields a compound of formula (I-1c). Deprotection of the amine of the compound of formula (I-1c) under acidic conditions (e.g., HCl or pTsOH) provides the compound of formula (I-1d) as a salt, which is coupled with a carboxylic acid in the presence of a coupling agent (e.g., HATU, HOBt, or PyBOP) to yield a compound of formula (1-1).

An exemplary embodiment of the preparative method in Scheme 1 is shown in Scheme 1a.

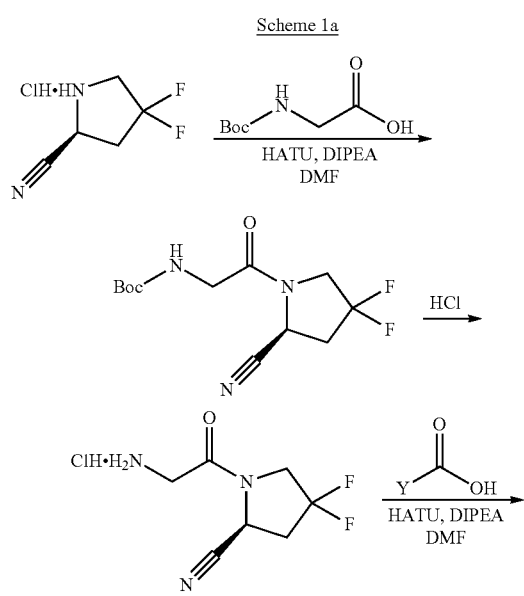

In some embodiments, Y is 6- to 10-membered heteroaryl optionally substituted by $R^{12}$. In a further embodiment, Y is pyridin-4-yl substituted by $R^{12}$ in the 3-position, wherein is represented by the compound of formula (II-1).

It is understood that the schemes above may be modified to arrive at various compounds of the invention by selection of appropriate reagents and starting materials. For a general description of protecting groups and their use, see P. G. M. Wuts and T. W. Greene, Greene's Protective Groups in Organic Synthesis 4*th* edition, Wiley-Interscience, New York, 2006.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Compositions comprising a compound provided herein are also described. In one variation, the composition comprises a compound or salt thereof and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use and Uses

Compounds and compositions detailed herein, such as a pharmaceutical composition comprising a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease or disorder in an individual in need thereof comprising administering a compound described herein or any embodiment, variation, or aspect thereof, or a pharmaceutically acceptable salt thereof. In some embodiments, the compound, pharmaceutically acceptable salt thereof, or composition is administered to the individual according to a dosage and/or method of administration described herein.

The compounds or salts thereof described herein and compositions described herein are believed to be effective for treating a variety of diseases and disorders. In some embodiments, a compound or salt thereof described herein or a composition described herein may be used in a method of treating a disease or disorder mediated by fibroblast activation protein (FAP). In some embodiments, the disease or disorder is characterized by proliferation, tissue remodeling, fibrosis, chronic inflammation, excess alcohol consumption, or abnormal metabolism.

In some embodiments, a compound or salt thereof described herein or a composition described herein may be used in a method of treating a disease or disorder mediated by a physiological substrate of FAP peptidase activity. In some embodiments the FAP peptidase activity is endopeptidase activity. In some embodiments, the physiological substrate of FAP endopeptidase activity is α2-antiplasmin, type I collagen, gelatin, and Fibroblast growth factor 21 (FGF21). In some embodiments the FAP peptidase activity is exopeptidase activity. In some embodiments, the physiological substrate of FAP exopeptidase activity is Neuropeptide Y, B-type natriuretic peptide, substance P and peptide YY. In some embodiments, a compound or salt thereof described herein or a composition described herein may be used in a method of treating a disease or disorder mediated by FGF21.

In some embodiments, a compound or salt thereof described herein or a composition described herein may be used in a method of treating a FGF21-associated disorder, such as obesity, type I- and type II diabetes, pancreatitis, dyslipidemia, hyperlipidemia conditions, non-alcoholic fatty liver disease (NAFLD), non-alcoholic steatohepatitis (NASH), insulin resistance, hyperinsulinemia, glucose intolerance, hyperglycemia, metabolic syndrome, acute myocardial infarction, hypertension, cardiovascular diseases, atherosclerosis, peripheral arterial disease, apoplexy, heart failure, coronary artery heart disease, renal disease, diabetic complications, neuropathy, gastroparesis, disorder associated with a serious inactivation mutation in insulin receptor, and other metabolic disorders. In some embodiments, the FGF21-associated disorder is diabetes, obesity, dyslipidemia, metabolic syndrome, non-alcoholic fatty liver disease, non-alcoholic steatohepatitis or cardiovascular diseases.

In some embodiments, a compound or salt thereof described herein or a composition described herein may be used in a method of treating a disease or disorder characterized by proliferation, tissue remodeling, fibrosis, chronic inflammation, excess alcohol consumption, or abnormal metabolism.

In some embodiments, a compound or salt thereof described herein or a composition described herein may be used in a method of treating cancer, such as breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma. In some embodiments, the compound, salt, or composition may be used in a method of treating metastatic kidney cancer, chronic lymphocytary leukemia, pancreatic adenocarcinoma, or non-small cell lung cancer.

In some embodiments, the administration of the compound, salt, or composition reduces tumor growth, tumor proliferation, or tumorigenicity in the individual. In some embodiments, the compound, salt, or composition may be used in a method of reducing tumor growth, tumor proliferation, or tumorigenicity in an individual in need thereof. In some embodiments, tumor growth is slowed or arrested. In some embodiments, tumor growth is reduced at least about 10%, 20%, 30%, 40%, 50%, 60%, 70%, 80%, 90% or more. In some embodiments, the tumor is reduced in size. In some embodiments, tumor metastasis is prevented or slowed. In some embodiments, the tumor growth, tumor proliferation, or tumorigenicity is compared to the tumor growth, tumor proliferation, or tumorigenicity in the individual prior to the administration of the compound, salt, or composition. In some embodiments, the tumor growth, tumor proliferation, or tumorigenicity is compared to the tumor growth, tumor proliferation, or tumorigenicity in a similar individual or group of individuals. Methods of measuring tumor growth, tumor proliferation, and tumorigenicity are known in the art, for example by repeated imaging of the individual.

In some embodiments, a compound or salt thereof described herein or a composition described herein may be used in in a method of treating fibrotic disease, thrombosis, wound healing, keloid formation, osteoarthritis, rheumatoid arthritis and related disorders involving cartilage degradation, atherosclerotic disease, Crohn's disease, hepatic cirrhosis, idiopathic pulmonary fibrosis, myocardial hypertrophy, diastolic dysfunction, obesity, glucose intolerance, insulin insensitivity, or diabetes mellitus. In some embodiments, the hepatic cirrhosis is viral hepatitis-induced, alcohol-induced, or biliary cirrhosis. In some embodiments, the diabetes mellitus is type II diabetes. In some embodiments, the disease or disorder is fibrotic liver degeneration.

In some embodiments, provided herein is a method of inhibiting FAP. The compounds or salts thereof described herein and compositions described herein are believed to be effective for inhibiting FAP.

In some embodiments, the method of inhibiting FAP comprises inhibiting FAP in a cell by administering or delivering to the cell a compound described herein, or a pharmaceutically acceptable salt thereof, or a pharmaceutical composition described herein. In some embodiments, the cell is a fibroblast, such as a myofibroblast, a keloid fibroblast, a cancer associated fibroblast (CAF), or a reactive stromal fibroblast, among others cells with FAP expression.

In some embodiments, the method of inhibiting FAP comprises inhibiting FAP in a tumor or in plasma by administering or delivering to the tumor or plasma a compound described herein, or a pharmaceutically acceptable salt thereof, or a pharmaceutical composition described herein.

In some embodiments, the inhibition of FAP comprises inhibiting an endopeptidase and/or exopeptidase activity of FAP. In some embodiments, FAP is inhibited by at least about 10%, 20%, 30%, 40%, 50%, 60%, 70%, 80%, 90%, 95%, 98% or more. Inhibition of FAP can be determined by methods known in the art.

In some embodiments, the compound, salt thereof, or composition inhibits FAP with an $IC_{50}$ of less than about 1 µM, such as less than about 750 nM, 600 nM, 500 nM, 300 nM, 200 nM, 100 nM, 80 nM, 60 nM, 40 nM, 25 nM, or less. In some embodiments, the compound, salt thereof, or composition inhibits FAP with an $IC_{50}$ between about 7 nM and 1 µM, such between about 10 nM and 600 nM, 15 nM and 200 nM, or 20 nM and 180 nM. In some aspects, the half maximal inhibitory concentration ($IC_{50}$) is a measure of the effectiveness of a substance in inhibiting a specific biological or biochemical function. In some aspects, the $IC_{50}$ is a quantitative measure that indicates how much of an inhibitor is needed to inhibit a given biological process or component of a process such as an enzyme, cell, cell receptor or microorganism by half. Methods of determining $IC_{50}$ in vitro and in vivo are known in the art.

In some embodiments, the compounds or salts thereof described herein and compositions described herein are administered in an amount wherein DPPII, DPPIV, DPP8, DPP9, and/or PREP activity is not inhibited or is inhibited to a lesser extent. In some embodiments, inhibition of FAP is at least or at least about 2 fold greater than inhibition of DPPII, DPPIV, DPP8, DPP9, and/or PREP activity, for example at least or at least about 3 fold, 4 fold, 5 fold, 8 fold, 10 fold, 15 fold, 30 fold, 50 fold, 60 fold, 75 fold, or 100 fold greater.

Provided herein is a method of enhancing an immune response in an individual comprising administering to the individual a compound described herein, or a pharmaceutically acceptable salt thereof, or a pharmaceutical composition described herein. In some embodiments, the individual has cancer. In some embodiments, the enhanced immune response is directed to a tumor or cancerous cell. By way of example and not wishing to be bound by theory, FAP is believed to suppress immune responses, especially in the context of cancer, therefore inhibiting FAP may enhancing the immune response of an individual. Accordingly, provided herein are methods of treating cancer in an individual in need thereof comprising administering to the individual a compound described herein, or a pharmaceutically acceptable salt thereof, or a pharmaceutical composition described herein, wherein an immune response of the individual is increased.

Provided herein is a method of increasing the level of FGF21 expression in an individual comprising administering to the individual a compound described herein, or a pharmaceutically acceptable salt thereof, or a pharmaceutical composition described herein. Also provided herein is a method of increasing the level of FGF21 or an FGF21 analog in an individual comprising administering to the individual a compound described herein, or a pharmaceutically acceptable salt thereof, or a pharmaceutical composition described herein. In some embodiments, the method further comprises administering FGF21 or an FGF21 analog, such as a mutated FGF21, pegylated FGF21, PF-05231023, or LY2405319.

FGF21 is a peptidic endocrine hormone secreted primarily by the liver (Markan, K. R. et al. Semin Cell Dev Biol, 2016, 53: 85-93). Upon entering circulation, FGF21 functions by signaling to specific tissues regulating carbohydrate and lipid metabolism (Kharitonenkov, A., et al., J Clin Invest, 2005, 115(6): 1627-35). FGF21 stimulates glucose uptake in adipocytes and is believed to protective against obesity and insulin insensitivity. Pharmacological administration of FGF21 to diabetic and obese animal models markedly ameliorates obesity, insulin resistance, dyslipidemia, fatty liver, and hyperglycemia in rodents (Markan, K. R. et al. Semin Cell Dev Biol, 2016, 53: 85-93). Small clinical trials have demonstrated that FGF21 analogs are efficacious in inducing weight loss and correcting hyperinsulinemia, dyslipidemia, and hypoadiponectinemia in obese individuals with type 2 diabetes (Gaich, G., et al., Cell Metab, 2013, 18(3): p. 333-40; Dong, J. Q., et al., Br J Clin Pharmacol, 2015, 80(5): 1051-63.

By way of example and not wishing to be bound by theory, FAP is believed to be the enzyme responsible for cleavage and inactivation of FGF21; therefore inhibiting FAP may increase levels of FGF21 expression and may augment endogenous and/or exogenous FGF21 action. FGF21 interacts with FGFR1 through its N-terminus and with β-Klotho through its C-terminus. This C-terminal region of FGF21 is essential to activate the receptor complex to initiate signaling (Micanovic, R., et al., J Cell Physiol, 2009, 219(2): 227-34; Yie, J., et al., FEBS Lett, 2009, 583(1): 19-24). Recently, FAPα has been identified as the protease responsible for the inactivation of circulating FGF21 through the C-terminal cleavage at Pro171 (Dunshee, D. R., et al., J Biol Chem, 2016, 291(11): 5986-96; Coppage, A. L., et al., PLoS One, 2016, 11(3): e0151269; Zhen, E. Y., et al., Biochem J, 2016, 473(5): 605-14). In rodents and primates, the half-life of exogenously administrated human FGF21 is short (~0.5-2 h) as result of FAP-mediated enzymatic degradation and susceptibility to renal clearance (Hager, T., et al., Anal Chem, 2013, 85(5): 2731-8; Xu, J., et al., Am J Physiol Endocrinol Metab, 2009, 297(5): E1105-14; Kharitonenkov, A., et al., Endocrinology, 2007, 148(2): 774-81). Common half-life extension strategies have improved significantly the PK properties of these FGF21 analogs in vivo; however, proteolytic processing still persists in these analogs (Hecht, R., et al., PLoS One, 2012, 7(11): e49345; Mu, J., et al., Diabetes, 2012, 61(2): 505-12; Camacho, R. C., et al., Eur J Pharmacol, 2013, 715(1-3): 41-5).

Accordingly, provided herein are methods of treating diabetes mellitus, insulin insensitivity, and/or obesity in an individual in need thereof comprising administering to the individual a compound described herein, or a pharmaceutically acceptable salt thereof, or a pharmaceutical composition described herein. In some embodiments, the method further comprises administering FGF21 or an FGF21 analog. In some embodiments, the FGF21 analog is pegylated FGF21, PF-05231023, or LY2405319. Also provided herein are methods of treating diabetes mellitus, insulin insensitivity, and/or obesity in an individual in need thereof comprising administering to the individual a compound described herein, or a pharmaceutically acceptable salt thereof, or a pharmaceutical composition described herein, wherein FGF21 expression is increased. In some embodiments, the diabetes mellitus is type II diabetes.

In some embodiments, the individual is a mammal. In some embodiments, the individual is a primate, bovine, ovine, porcine, equine, canine, feline, lapine, or rodent. In some embodiments, the individual is a human. In some embodiments, the individual has any of the diseases or disorders disclosed herein. In some embodiments, the individual is a risk for developing any of the diseases or disorders disclosed herein.

In some embodiments, the individual is human. In some embodiments, the human is at least about or is about any of 21, 25, 30, 35, 40, 45, 50, 55, 60, 65, 70, 75, 80, or 85 years old. In some embodiments, the human is a child. In some embodiments, the human is less than about or about any of 21, 18, 15, 12, 10, 8, 6, 5, 4, 3, 2, or 1 years old.

Also provided herein are uses of a compound described herein or a pharmaceutically acceptable salt thereof, or a pharmaceutical composition described herein, in the manufacture of a medicament. In some embodiments, the manufacture of a medicament is for the treatment of a disorder or disease described herein. In some embodiments, the manufacture of a medicament is for the prevention and/or treatment of a disorder or disease mediated by FAP.

Combination Therapy

As provided herein, compounds or salts thereof described herein and compositions described herein may be administered with an additional agent to treat any of the diseases and disorders disclosed herein.

In some embodiments, (a) a compound described herein, or a pharmaceutically acceptable salt thereof, or a pharmaceutical composition described herein and (b) an additional agent are sequentially administered, concurrently administered or simultaneously administered. In certain embodiments, (a) a compound described herein, or a pharmaceutically acceptable salt thereof, or a pharmaceutical composition described herein and (b) an additional agent are administered with a time separation of about 15 minutes or less, such as about any of 10, 5, or 1 minutes or less. In certain embodiments, (a) a compound described herein, or a pharmaceutically acceptable salt thereof, or a pharmaceutical composition described herein and (b) an additional agent are administered with a time separation of about 15 minutes or more, such as about any of 20, 30, 40, 50, 60, or more minutes. Either (a) a compound described herein, or a pharmaceutically acceptable salt thereof, or a pharmaceutical composition described herein and (b) an additional agent may be administered first. In certain embodiments, (a) a compound described herein, or a pharmaceutically acceptable salt thereof, or a pharmaceutical composition described herein and (b) an additional agent are administered simultaneously.

In some embodiments, the additional agent targets an immune checkpoint protein. In some embodiments, the additional agent is an antibody that targets an immune checkpoint protein. In some embodiments, the additional agent targets PD-1, PD-L1, PD-L2, CTLA4, TIM3, LAG3, CCR4, OX40, OX40L, IDO, and A2AR. In some embodiments, the additional agent is an anti-PD-1 antibody, an anti-PD-L1 antibody, or an anti-CTLA-4 antibody.

In some embodiments, the additional agent is an inducer of FGF21 expression, such as a PPARα agonist. In some embodiment, the PPARα agonist is fibrate or fenofibrate. In some embodiments, the additional agent is FGF-21 or an FGF-21 analog. In some embodiments, the FGF-21 analog is a mutated FGF21 and/or pegylated FGF21. In some embodiments, the FGF-21 analog is PF-05231023 or LY2405319.

In some embodiments, the additional agent is a KLB/FGFR complex agonist, a DDPIV antagonist, a GLP-1 receptor agonist, or a glucagon receptor agonist.

Provided herein is a method of enhancing an immune response in an individual comprising administering to the individual (a) a compound described herein, or a pharmaceutically acceptable salt thereof, or a pharmaceutical composition described herein and (b) an agent that targets an immune checkpoint protein. In some embodiments, the individual has cancer. In some embodiments, the enhanced immune response is directed to a tumor or cancerous cell.

Also provided herein are methods of treating cancer in an individual in need thereof comprising administering to the individual (a) a compound described herein, or a pharmaceutically acceptable salt thereof, or a pharmaceutical composition described herein and (b) an agent that targets an immune checkpoint protein, wherein an immune response of the individual is increased.

Provided herein is a method of increasing the level of FGF21 expression in an individual comprising administering to the individual (a) a compound described herein, or a pharmaceutically acceptable salt thereof, or a pharmaceutical composition described herein and (b) an agent that induces FGF21 expression.

Also provided herein are methods of treating diabetes mellitus, insulin insensitivity, and/or obesity in an individual in need thereof comprising administering to the individual (a) a compound described herein, or a pharmaceutically acceptable salt thereof, or a pharmaceutical composition described herein and (b) an agent that induces FGF21 expression, wherein FGF21 expression is increased. In some embodiments, the diabetes mellitus is type II diabetes.

As provided herein, compounds or salts thereof described herein and compositions described herein are administered as part of a treatment regimen that includes an exercise regimen, such as strength-training or cardiovascular exercise. In some embodiments, the compounds or salts thereof described herein and compositions described herein are administered with an additional agent and as part of a treatment regimen that includes an exercise regimen, such as strength-training or cardiovascular exercise. In some embodiments, the exercise regimen comprises exercising at least once per week, such as twice per week, 3× per week, 4× per week, 5× per week, 6× per week, or 7× per week. In some embodiments, the exercise regimen comprises exercising at least one day per week, such as two days per week, 3 days per week, 4 days per week, 5 days per week, 6 days per week, or 7 days per week. In some embodiments, the exercise regimen comprises exercising once per day, twice per day, or 3× per day. In some embodiments, the exercise regimen comprises exercising for at least 10 minutes per session, such as for at least 15 min, 20 min, 25 min, 30 min, 35 min, 40 min, 45 min, 50 min, 55 min, 1 hour, 1.25 hours, or 1.5 hours.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Articles of Manufacture and Kits

The present disclosure further provides articles of manufacture comprising a compound described herein or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the invention, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment any disease or described herein, for example for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

All references throughout, such as publications, patents, patent applications and published patent applications, are incorporated herein by reference in their entireties.

ENUMERATED EMBODIMENTS

The following enumerated embodiments are representative of some aspects of the invention.

Embodiment 1

A compound of formula (I):

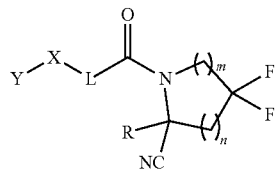
(I)

or a pharmaceutically acceptable salt thereof, wherein:
R is hydrogen, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of R are independently optionally substituted by $R^d$;
m is 0, 1, 2, 3, or 4;
n is 0, 1, 2, 3, or 4,
  wherein m+n is 1, 2, 3, or 4;
X is —C(=O)—, —O—, —CH(OH)—, —S—, —S(=O)—, or —S(=O)$_2$—;
L is

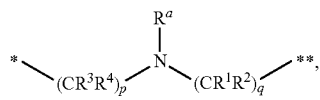
(a)

wherein
* represents the point of attachment to the Y—X— moiety,
** represents the point of attachment to the remainder of the molecule,
$R^a$ is hydrogen, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^a$ are independently optionally substituted by $R^e$,
$R^1$ and $R^2$, independently of each other and independently at each occurrence, are hydrogen, $C_1$-$C_2$ alkyl, $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^1$ and $R^2$ are independently optionally substituted by $R^f$,
or $R^1$ and $R^2$ are taken together with the carbon atom to which they are attached to form a 3- to 8-membered cycloalkylene optionally substituted by $R^f$,
q is 1, 2, or 3,
$R^3$ and $R^4$, independently of each other and independently at each occurrence, are hydrogen, $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^3$ and $R^4$ are independently optionally substituted by $R^g$,
or $R^3$ and $R^4$ are taken together with the carbon atom to which they are attached to form a 3- to 8-membered cycloalkylene optionally substituted by $R^g$, and
p is 0, 1, or 2;

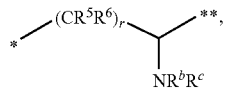
(b)

wherein
* represents the point of attachment to the Y—X— moiety,
** represents the point of attachment to the remainder of the molecule,
$R^5$ and $R^6$, independently of each other and independently at each occurrence, are H, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^5$ and $R^6$ are independently optionally substituted by $R^h$,
$R^b$ and $R^c$ are independently H, $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, 5- to 10-membered heteroaryl, $C_6$-$C_{14}$ aryl, or —C(=O)O$R^{17}$, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^b$ and $R^c$ are independently optionally substituted by $R^i$, and
r is 1, 2, or 3;

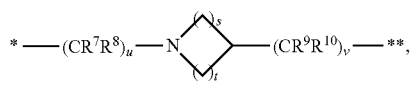
(c)

wherein
* represents the point of attachment to the Y—X— moiety,
** represents the point of attachment to the remainder of the molecule,
$R^7$ and $R^8$, independently of each other and independently at each occurrence, are hydrogen, $C_3$-$C_8$ cycloalkyl, 3- to 12-membered heteroaryl, or $C_6$-$C_{14}$ aryl, wherein the $C_3$-$C_8$ cycloalkyl, 3- to 12-membered heterocyclyl, 5- to 10-membered heteroaryl, and $C_6$-$C_{14}$ aryl of $R^7$ and $R^8$ are independently optionally substituted by $R^j$, or $R^7$ and $R^8$ are taken together with the carbon atom to which they are attached to form a 3- to 8-membered cycloalkylene optionally substituted by $R^j$, $R^9$ and $R^{10}$, independently of each other and independently at each occurrence, are H, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of $R^9$ and $R^{10}$ are independently optionally substituted by $R^k$, s is 1, 2, or 3, t is 1, 2, or 3, wherein s+t is 2, 3, or 4, u is 0 or 1, and v is 0 or 1;

Y is $C_6$-$C_9$ aryl optionally substituted by $R^{11}$, 6- to 10-membered heteroaryl optionally substituted by $R^{12}$, or 3- to 12-membered heterocyclyl optionally substituted by $R^{13}$, wherein when Y is phenyl or naphthyl, the phenyl or naphthyl of Y is substituted by at least one $R^{11}$, and wherein when L is *—NH—$CH_2$—** and Y is optionally substituted quinolinyl, the optionally substituted quinolinyl of Y is connected to the parent structure at the 2-, 3-, 5-, 6-, 7-, or 8-position, wherein $R^{11}$, $R^{12}$, and $R^{13}$, independently of each other and independently at each occurrence, are $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, halogen, cyano, oxo, —$OR^{14}$, —$NR^{15}R^{16}$, —$SR^{14}$, —$NO_2$, —C=NH($OR^{14}$), —$C(O)R^{14}$, —$OC(O)R^{14}$, —$C(O)OR^{14}$, —$C(O)NR^{15}R^{16}$, —$NR^{14}C(O)R^{15}$, —$NR^{14}C(O)OR^{15}$, —$NR^{14}C(O)NR^{15}R^{16}$, —$S(O)R^{14}$, —$S(O)_2R^{14}$, —$NR^{14}S(O)R^{15}$, —$NR^{14}S(O)_2R^{15}$, —$S(O)NR^{15}R^{16}$, —$S(O)_2NR^{15}R^{16}$, or —$P(O)(OR^{15})(OR^{16})$, wherein each $R^{11}$, $R^{12}$, and $R^{13}$ is independently optionally substituted by $R^L$;

each $R^{14}$ is independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{14}$ are independently optionally substituted by halogen, —OH, oxo, cyano, or $C_1$-$C_6$ alkyl optionally substituted by halogen, —OH, or oxo;

$R^{15}$ and $R^{16}$, independently of each other and independently at each occurrence, are hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{15}$ and $R^{16}$ are independently optionally substituted by halogen, —OH, oxo, cyano, or $C_1$-$C_6$ alkyl, optionally substituted by halogen, —OH, or oxo, or $R^{15}$ and $R^{16}$ are taken together with the atom to which they are attached to form a 3- to 6-membered heterocyclyl optionally substituted by halogen, oxo, cyano, or $C_1$-$C_6$ alkyl optionally substituted by halogen, —OH, or oxo;

$R^d$, $R^e$, $R^f$, $R^g$, $R^h$, $R^i$, $R^j$, and $R^k$, independently of each other and independently at each occurrence, are halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —$OR^{14}$, —$NR^{15}R^{16}$, cyano, or nitro; and each $R^L$ is independently halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —$OR^{14}$, —$C(O)R^{14}$, —$NR^{15}R^{16}$, cyano, oxo, or nitro.

Embodiment 2

The compound of embodiment 1, or a salt thereof, wherein X is —C(=O)—.

Embodiment 3

The compound of embodiment 1, or a salt thereof, wherein X is —O—.

Embodiment 4

The compound of embodiment 1, or a salt thereof, wherein X is —CH(OH)—.

Embodiment 5

The compound of any one of embodiments 1 to 4, or a salt thereof, wherein L is —NH—$CR^1R^2$—.

Embodiment 6

The compound of embodiment 5, or a salt thereof, wherein L is —NH—$CH_2$—.

Embodiment 7

The compound of embodiment 5, or a salt thereof, wherein L is —NH—CH($CH_3$)—.

Embodiment 8

The compound of embodiment 5, or a salt thereof, wherein L is —NH—$CR^1R^2$—, wherein $R^1$ and $R^2$ are taken together with the carbon atom to which they are attached to form a 3- to 8-membered cycloalkylene.

Embodiment 9

The compound of embodiment 8, or a salt thereof, wherein $R^1$ and $R^2$ are taken together with the carbon atom to which they are attached to form a cyclopropylene.

Embodiment 10

The compound of any one of embodiments 1 to 4, or a salt thereof, wherein L is

—$CR^5R^6$—CH($NR^bR^c$)—.

Embodiment 11

The compound of embodiment 10, or a salt thereof, wherein L is —$CR^5R^6$—CH($NR^bR^c$)—, wherein $R^6$, $R^b$, and $R^c$ are H, and $R^5$ is H or $C_1$-$C_6$ alkyl.

Embodiment 12

The compound of any one of embodiments 1 to 4, or a salt thereof, wherein L is

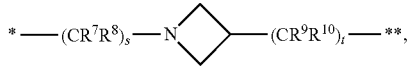

wherein * represents the point of attachment to the Y—X— moiety, ** represents the point of attachment to the remainder of the molecule.

Embodiment 13

The compound of embodiment 12, or a salt thereof, wherein L is

wherein * represents the point of attachment to the Y—X— moiety, and ** represents the point of attachment to the remainder of the molecule.

Embodiment 14

The compound of any one of embodiments 1 to 13, or a salt thereof, wherein Y is $C_6$-$C_9$ aryl optionally substituted by $R^{11}$, 6- to 10-membered heteroaryl optionally substituted by $R^{12}$, or 3- to 12-membered heterocyclyl optionally substituted by $R^{13}$.

Embodiment 15

The compound of embodiment 14, or a salt thereof, wherein Y is $C_6$-$C_9$ aryl optionally substituted by $R^{11}$, wherein when Y is phenyl or naphthyl, the phenyl or naphthyl of Y is substituted by at least one $R^{11}$.

Embodiment 16

The compound of embodiment 15, wherein Y is phenyl substituted by 1 to 5 $R^{11}$, which are independently selected from halogen, trihalomethyl, cyano, and —C(=O)$NH_2$.

Embodiment 17

The compound of embodiment 15, wherein Y is unsubstituted 2,3-dihydro-1H-inden-2-yl.

Embodiment 18

The compound of embodiment 14, or a salt thereof, wherein Y is 6- to 10-membered heteroaryl optionally substituted by $R^{12}$, wherein when L is *—NH—$CH_2$—** and Y is optionally substituted quinolinyl, the optionally substituted quinolinyl of Y is connected to the parent structure at the 2-, 3-, 5-, 6-, 7-, or 8-position.

Embodiment 19

The compound of embodiment 18, or a salt thereof, wherein either:

(a) L is *—$CH_2$—CH($NH_2$)—** or *—CH($CH_3$)—CH($NH_2$)—** and Y is quinolin-4-yl optionally substituted by $R^{12}$ or (b) L is *—NH—$CH_2$—**, Y is quinolin-6-yl optionally substituted by $R^{12}$, which $R^{12}$ is independently selected from —OH and phenyl.

Embodiment 20

The compound of embodiment 18, or a salt thereof, wherein Y is pyridin-4-yl substituted by $R^{12}$ in the 3-position.

Embodiment 21

The compound of embodiment 20, or a salt thereof, wherein $R^{12}$ is pyridinyl optionally substituted by $C_1$-$C_6$ alkyl.

Embodiment 22

The compound of embodiment 20, or a salt thereof, wherein $R^{12}$ is indolyl optionally substituted by $C_1$-$C_6$ alkyl.

Embodiment 23

The compound of embodiment 20, or a salt thereof, wherein $R^{12}$ is phenyl optionally substituted by $C_1$-$C_6$ alkyl, halogen, or $C_1$-$C_6$ alkoxy.

Embodiment 24

The compound of embodiment 18, or a salt thereof, wherein Y is pyrimidin-4-yl optionally substituted by $R^{12}$ and optionally fused to $C_6$-$C_{14}$ aryl or $C_5$-$C_{10}$ cycloalkyl, wherein $C_6$-$C_{14}$ aryl and $C_5$-C The compound of embodiment 24, or a salt thereof, wherein Y is pyrimidin-4-yl fused to $C_6$-$C_{14}$ aryl, wherein $C_6$-$C_{14}$ aryl is optionally substituted by $R^{12}$.

Embodiment 26

The compound of embodiment 24, or a salt thereof, wherein Y is optionally substituted pyridin-3-yl, unsubstituted quinazolin-4-yl or unsubstituted 6,7-dihydro-5H-cyclopenta[d]pyrimidin-4-yl.

Embodiment 27

The compound of embodiment 18, or a salt thereof, wherein Y is 2H-pyran-2-on-5-yl optionally substituted by $R^{12}$ and optionally fused to $C_6$-$C_{14}$ aryl, which $C_6$-$C_{14}$ aryl is optionally substituted by $R^{12}$.

Embodiment 28

The compound of embodiment 27, or a salt thereof, wherein Y is 1H-isochromen-1-on-4-yl optionally substituted by halogen.

Embodiment 29

The compound of embodiment 18, or a salt thereof, wherein Y is pyridin-2(1H)-on-5-yl optionally substituted by $R^{12}$ and optionally fused to $C_6$-$C_{14}$ aryl or 5- to 10-membered heterocyclyl, which $C_6$-$C_{14}$ aryl or 5- to 10-membered

Embodiment 30

The compound of embodiment 29, or a salt thereof, wherein Y is pyridin-2(1H)-on-5-yl optionally substituted by $C_1$-$C_6$ alkyl or $C_6$-$C_{14}$ aryl.

Embodiment 31

The compound of embodiment 29, or a salt thereof, wherein Y is unsubstituted 7,8,9,10-tetrahydropyrido[1,2-a]azepin-4(6H)-on-1-yl.

Embodiment 32

The compound of embodiment 29, or a salt thereof, wherein Y is isoquinolin-1(2H)-on-4-yl optionally substituted by halogen, $C_1$-$C_6$ alkyl, $C_6$-$C_{14}$ aryl, or $C_3$-$C_8$ cycloalkyl.

Embodiment 33

The compound of embodiment 14, or a salt thereof, wherein Y is 3- to 12-membered heterocyclyl optionally substituted by $R^{13}$.

Embodiment 34

The compound of embodiment 33, or a salt thereof, wherein Y is unsubstituted isoindolin-2-yl.

Embodiment 35

The compound of embodiment 33, or a salt thereof, wherein Y is piperidin-2-on-5-yl optionally substituted by $C_1$-$C_6$ alkyl or $C_6$-$C_{14}$ aryl.

Embodiment 36

The compound of any one of embodiments 1 to 35, or a salt thereof, wherein m=n=1.

Embodiment 37

The compound of any one of embodiments 1 to 36, or a salt thereof, wherein R is hydrogen.

Embodiment 38

The compound of embodiment 1, or a salt thereof, wherein the —X-L- moiety is selected from the group consisting of wherein * represents the point of attachment to the Y moiety, and ** represents the point of attachment to the remainder of the molecule.

Embodiment 39

A pharmaceutical composition comprising a compound of any one of embodiments 1-38, or a pharmaceutically acceptable salt thereof, and a pharmaceutically acceptable carrier.

Embodiment 40

A method of treating a disease or disorder mediated by fibroblast activation protein (FAP) in an individual in need thereof comprising administering to the individual a therapeutically effective amount of a compound of any one of embodiments 1-38, or a pharmaceutically acceptable salt thereof, or a pharmaceutical composition of embodiment 39.

Embodiment 41

A method of treating a disease or disorder characterized by proliferation, tissue remodeling, chronic inflammation, obesity, glucose intolerance, or insulin insensitivity in an individual in need thereof, comprising administering to the individual a therapeutically effective amount of a compound of any one of embodiments 1-38, or a pharmaceutically acceptable salt thereof, or a pharmaceutical composition of embodiment 39.

Embodiment 42

The method of embodiments 40 or 41, wherein the disease or disorder is breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma.

Embodiment 43

The method of embodiment 42, wherein the disease or disorder is metastatic kidney cancer, chronic lymphocytary leukemia, pancreatic adenocarcinoma, or non-small cell lung cancer.

Embodiment 44

The method of embodiments 40 or 41, wherein the disease or disorder is fibrotic disease, wound healing, keloid formation, osteoarthritis, rheumatoid arthritis and related disorders involving cartilage degradation, atherosclerotic disease, Crohn's disease, or Type II diabetes.

Embodiment 45

A method of reducing tumor growth, tumor proliferation, or tumorigenicity in an individual in need thereof, comprising administering to the individual a compound of any one of embodiments 1-38, or a pharmaceutically acceptable salt thereof, or a pharmaceutical composition of embodiment 39.

Embodiment 46

A method of inhibiting FAP in an individual comprising administering to the individual a compound of any one of embodiments 1-38, or a pharmaceutically acceptable salt thereof, or a pharmaceutical composition of embodiment 39.

Embodiment 47

A method of inhibiting FAP in a cell comprising administering or delivering to the cell a compound of any one of embodiments 1-38, or a pharmaceutically acceptable salt thereof, or a pharmaceutical composition of embodiment 39, or a metabolite of the foregoing.

Embodiment 48

The method of embodiment 47, wherein the cell is a fibroblast.

Embodiment 49

The method of embodiments 47 or 48, wherein the cell is a cancer associated fibroblast (CAF) or a reactive stromal fibroblast.

Embodiment 50

A method of inhibiting FAP in a tumor comprising administering or delivering to the tumor a compound of any one of embodiments 1-38, or a pharmaceutically acceptable salt thereof, or a pharmaceutical composition of embodiment 39, or a metabolite of the foregoing.

Embodiment 51

A method of inhibiting FAP in plasma comprising administering or delivering to the plasma a compound of any one of embodiments 1-38, or a pharmaceutically acceptable salt thereof, or a pharmaceutical composition of embodiment 39, or a metabolite of the foregoing.

Embodiment 52

The method of any one of embodiments 46-51, wherein inhibiting FAP comprises inhibiting an endopeptidase activity of FAP.

Embodiment 53

The method of any one of embodiments 46-51, wherein inhibiting FAP comprises inhibiting an exopeptidase activity of FAP.

Embodiment 54

A method of enhancing an immune response in an individual comprising administering (a) an immune checkpoint inhibitor and (b) a compound of any one of embodiments 1-38, or a pharmaceutically acceptable salt thereof, or a pharmaceutical composition of embodiment 39.

Embodiment 55

A method of increasing the level of FGF21 expression in an individual comprising administering to the individual a compound of any one of embodiments 1-38, or a pharmaceutically acceptable salt thereof, or a pharmaceutical composition of embodiment 39.

Embodiment 56

The method of embodiment 55, further comprising administering an inducer of FGF21 expression Embodiment 57. The method of embodiment 56, wherein the inducer of FGF21 expression is PPARα agonist.

Embodiment 58

The method of embodiment 57, wherein the PPARα agonist is fibrate or fenofibrate.

Embodiment 59

The composition of embodiment 39 for use as a human or veterinary medicament.

Embodiment 60

Use of a compound of any one of embodiments 1-38, or a pharmaceutically acceptable salt thereof, or a pharmaceutical composition of embodiment 39, in the manufacture of a medicament for the prevention and/or treatment of a disorder or disease mediated by FAP.

EXAMPLES

Synthetic Examples

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

Example 1

Synthesis of (S)—N-(2-(2-cyano-4,4-difluoropyrrolidin-1-yl)-2-oxoethyl)-1-oxo-1,2-dihydroisoquinoline-4-carboxamide

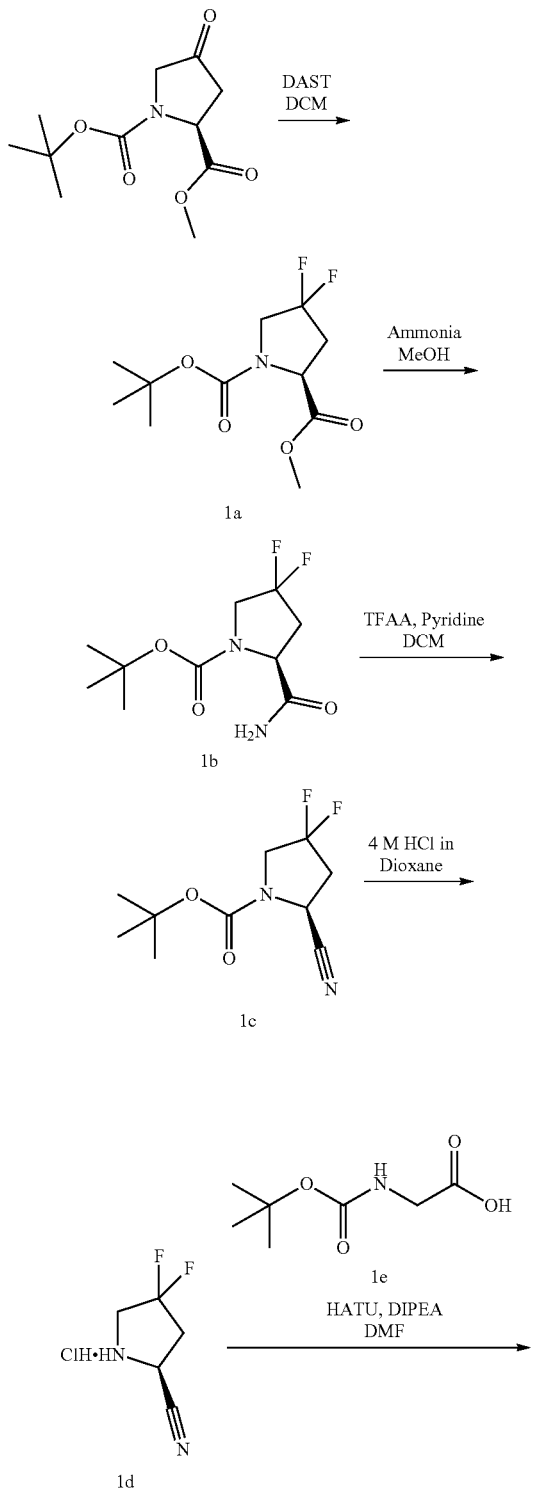

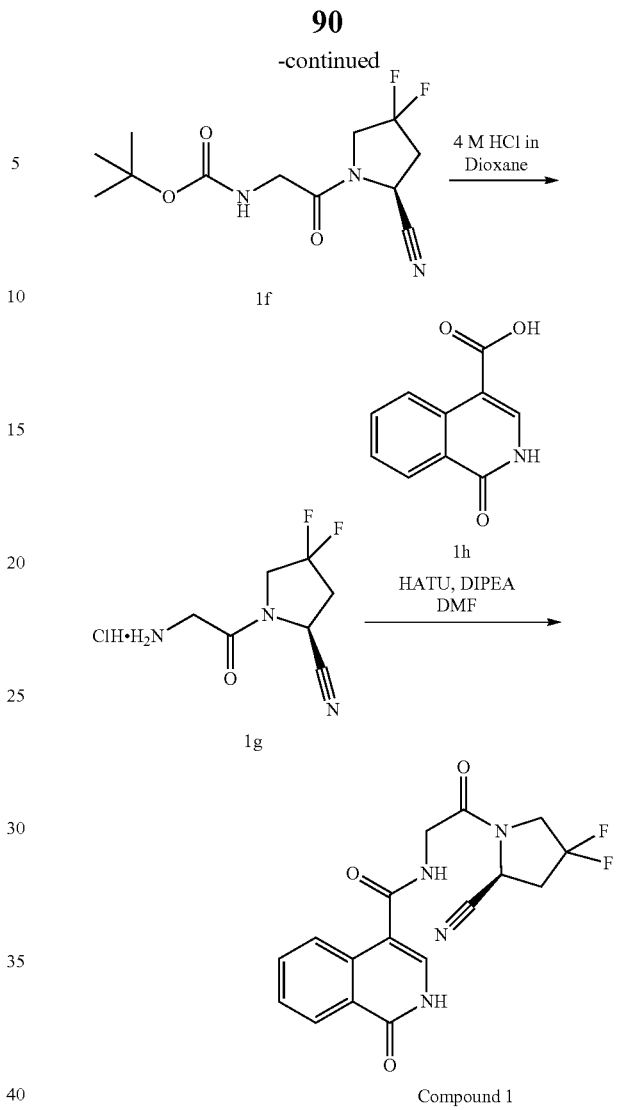

Compound 1

Compound 1a: To a stirred solution of 1-(tert-butyl) 2-methyl (S)-4-oxopyrrolidine-1,2-dicarboxylate (1.9 g, 7.36 mmol, 1.0 equiv.), in DCM (15 mL), was added DAST (2.6 ml, 19.85 mmol, 2.6 equiv) drop wise at 0° C. over a period of 30 min, the reaction mixture was stirred at RT for overnight. Progress of the reaction was monitored by NMR. Water (50 mL) was added to the reaction mixture, stirred for 5 min and extracted with DCM (50 mL×3). Combined organic layer was washed with saturated sodium bicarbonate solution (100 mL), brine (100 mL), dried over anhydrous sodium sulphate and concentrated under reduced pressure to obtain 1-(tert-butyl) 2-methyl (S)-4,4-difluoropyrrolidine-1, 2-dicarboxylate (1.25 g, 61% Yield) as a red oil.

$^1$H NMR (400 MHz, DMSO-$d_6$) δ 4.41-4.53 (m, 1H), 3.65-3.84 (m, 5H), 2.82-3.01 (m, 2H), 1.41 (s, 4H), 1.35 (s, 5H).

Compound 1b: To a stirred solution of 1-(tert-butyl) 2-methyl (S)-4,4-difluoropyrrolidine-1,2-dicarboxylate (200 mg, 0.75 mmol, 1.0 equiv.) in MeOH (1.0 mL) was added a solution of 7.0 M in ammonia in methanol (5.0 mL) drop wise at 0° C. The mixture was allowed to stir at RT for 12 h. Progress of the reaction was monitored by NMR. After completion of reaction the solvent was evaporated under reduced pressure and the obtained crude material was crystallized by hexane and pentane to afford tert-butyl (S)-2- carbamoyl-4,4-difluoropyrrolidine-1-carboxylate (185 mg, 98% Yield) as an off-white solid.

$^1$H NMR (400 MHz, DMSO-$d_6$) δ 7.48 (d, J=15.16 Hz, 1H), 7.16 (br. s., 1H), 4.24 (dd, J=5.87, 8.80 Hz, 1H), 3.58-3.83 (m, 2H), 2.77 (dd, J=8.31, 13.69 Hz, 1H), 2.20-2.38 (m, 1H), 1.26-1.55 (m, 9H).

Compound 1c: To a stirred solution of tert-butyl (S)-2-carbamoyl-4,4-difluoropyrrolidine-1-carboxylate (100 mg, 0.4 mmol, 1.0 equiv) in DCM (5.0 mL), pyridine (0.36 ml, 0.48 mmol, 1.2 equiv) was added dropwise at 0° C. The reaction mixture was allowed to stir for 15 min at 0° C. Trifluoroacetic anhydride (54.72 mg, 0.48 mmol, 1.2 equiv) was added drop wise at 0° C. The reaction mixture was allowed stir for 1 h at RT. The reaction progress was monitored by NMR and TLC, after completion of reaction, quenched by water (20 mL), and extracted with ethyl acetate (50 mL×3). Combined organic layer was washed with saturated NaHCO$_3$ solution (10 mL) and brine (20 mL), dried over anhydrous sodium sulphate and concentrated under reduced pressure. The crude product obtained was purified by combi-flash chromatography (0-30% ethyl acetate in hexane as an eluent) to obtain tert-butyl (S)-2-cyano-4,4-difluoropyrrolidine-1-carboxylate (70 mg, 76% Yield).

$^1$H NMR (400 MHz, DMSO-$d_6$) δ 4.96 (d, J=8.80 Hz, 1H), 3.65-3.89 (m, 2H), 2.82-3.03 (m, 1H), 2.75 (br. s., 1H), 1.35-1.56 (m, 9H).

Compound 1d: To a stirred solution of tert-butyl (S)-2-cyano-4,4-difluoropyrrolidine-1-carboxylate (250 mg, 1.07 mmol, 1.0 equiv) in acetonitrile (10 mL) was added 4.0 M HCl in dioxan (0.5 mL) drop wise at 0° C. over a period of 10 min. The resultant reaction mixture was allowed to stir at RT for 16 h. Progress of the reaction was monitored by TLC and NMR. The reaction mixture was concentrated under reduced pressure, the crude material obtained was washed with ethyl acetate and hexane (1:1 (20 mL)) to obtain (S)-4,4-difluoropyrrolidine-2-carbonitrile hydrochloride (70 mg, 38% Yield) as an off-white solid.

$^1$H NMR (400 MHz, DMSO-$d_6$) δ 4.56-4.67 (m, 1H), 3.27-3.50 (m, 2H), 2.54-2.75 (m, 2H).

Compound 1f: To a stirred solution of (tert-butoxycarbonyl) glycine (921.8 mg, 5.26 mmol, 1.5 equiv.) and HATU (2667 mg, 7.025 mmol, 2.0 equiv) in DMF (10 mL) was added (S)-4,4-difluoropyrrolidine-2-carbonitrile hydrochloride (590 mg, 3.51 mmol, 1.0 equiv) and stirred for 10 min. DIPEA (1.8 mL, 10.53 mmol, 3.0 equiv) was added and the reaction mixture was allowed to stir for 16 h at RT. Progress of the reaction monitored by NMR and TLC. The reaction mixture was diluted with cold water (50 mL) and extracted with ethyl acetate (50 mL×3). Combined organic layer was washed with water (25 mL×4), dried over anhydrous sodium sulphate and concentrated under reduced pressure. The crude material obtained was purified by combi flash chromatography to obtain tert-butyl (S)-(2-(2-cyano-4,4-difluoropyrrolidin-1-yl)-2-oxoethyl)carbamate (300 mg, 30% Yield).

$^1$H NMR (400 MHz, DMSO-$d_6$) δ 7.08 (t, J=5.92 Hz, 1H), 4.98-5.16 (m, 1H), 4.09-4.24 (m, 1H), 3.93-4.09 (m, 1H), 3.77 (d, J=6.14 Hz, 2H), 2.71-2.97 (m, 2H), 1.31-1.42 (m, 9H).

Compound 1g: To a stirred solution of tert-butyl (S)-(2-(2-cyano-4,4-difluoropyrrolidin-1-yl)-2-oxoethyl)carbamate (300 mg, 1.03 mmol, 1.0 equiv) in acetonitrile (10 mL) was added 4.0M HCl in dioxan (2 mL) dropwise at 0° C. over a period of 10 min. The mixture was allowed to stir at RT for 16 h. Progress of the reaction was monitored by TLC and NMR. The solvent was evaporated under reduced pressure to obtain residue which was washed with 20 mL ethyl acetate and hexane (1:1) to obtain (S)-4,4-difluoro-1-glycylpyrrolidine-2-carbonitrile hydrochloride (200 mg, 86% Yield) as an off-white solid.

$^1$H NMR (400 MHz, DMSO-$d_6$) δ 8.31 (br. s., 2H), 5.18 (d, J=7.89 Hz, 1H), 4.21 (d, J=11.40 Hz, 1H), 3.97-4.10 (m, 1H), 3.94 (br. s., 1H), 3.82 (d, J=12.28 Hz, 1H), 2.81-2.97 (m, 2H).

Compound 1: To a stirred solution of 1-oxo-1,2-dihydroisoquinoline-4-carboxylic acid (315 mg, 1.6 mmol, 1.5 equiv) and HATU (843 mg, 2.22 mmol, 2.0 equiv) in DMF (5 mL) was added (S)-4,4-difluoro-1-glycylpyrrolidine-2-carbonitrile hydrochloride (250 mg, 1.11 mmol, 1.0 equiv) and stirred for 10 min. DIPEA (429 mg, 3.33 mmol, 3.0 equiv.) was added and the mixture was allowed to stir at RT for 16 h. The reaction progress was monitored by NMR and TLC. The reaction mixture was diluted with cold water (50 mL) and extracted with ethyl acetate (50 mL×3). Combined organic layer was washed with water (50 mL×3), dried over anhydrous sodium sulphate and concentrated under reduced pressure. The crude product obtained was purified by reversed phase HPLC to obtain (S)—N-(2-(2-cyano-4,4-difluoropyrrolidin-1-yl)-2-oxoethyl)-1-oxo-1,2-dihydroisoquinoline-4-carboxamide (38 mg, 6% Yield) as an off-white solid.

LCMS 361 [M+H]$^+$ $^1$H NMR (400 MHz, DMSO-$d_6$) δ 11.62 (br. s., 1H), 8.68 (t, J=5.62 Hz, 1H), 8.25 (t, J=8.31 Hz, 2H), 7.75 (t, J=7.09 Hz, 1H), 7.47-7.62 (m, 2H), 5.03-5.18 (m, 1H), 4.22-4.36 (m, 1H), 3.99-4.20 (m, 3H), 2.77-2.98 (m, 2H).

Example 2

Synthesis of (S)—N-(2-(2-cyano-4,4-difluoropyrrolidin-1-yl)-2-oxoethyl)-1-oxo-2-phenyl-1,2-dihydroisoquinoline-4-carboxamide

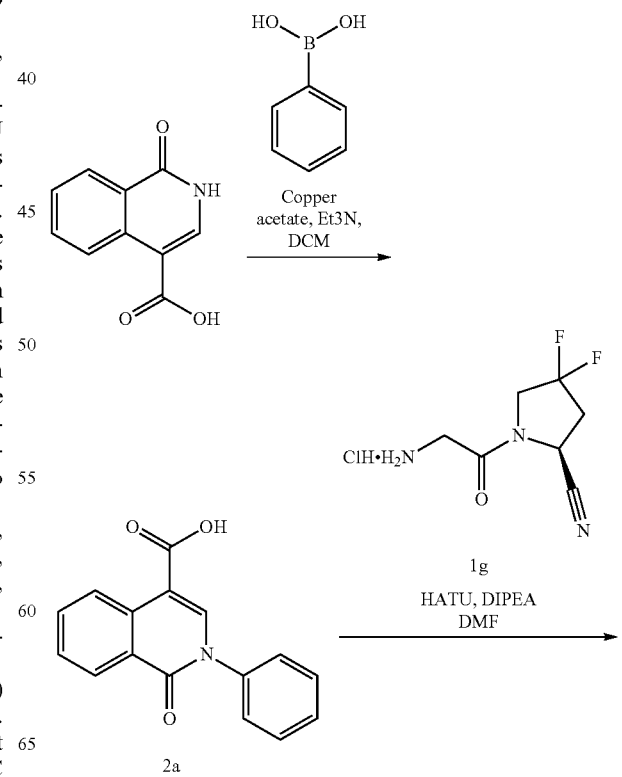

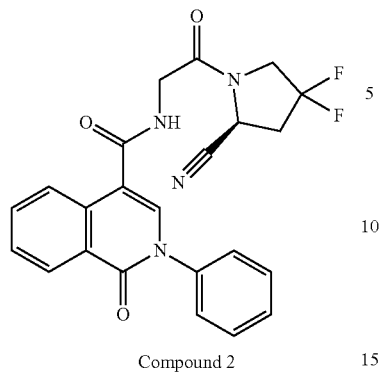

Compound 2

Compound 2a: To a stirred solution of 1-oxo-1,2-dihydroisoquinoline-4-carboxylic acid (500 mg, 2.6 mmol, 1 equiv) in DCM (10 mL), was added phenylboronic acid (480 mg, 3.9 mmol, 1.5 equiv), copper acetate (2360 mg, 13 mmol, 5 equiv), molecular sieves and Et$_3$N (4 mL, 26 mmol, 10 equiv). The reaction mixture was allowed to stir for overnight at RT. Progress of the reaction was monitored by TLC and LCMS. After completion of the reaction, the reaction mixture was passed through the Celite® bed and the filtrate was concentrated under reduced pressure to obtain crude, which was diluted with water (100 mL) and washed with ethyl acetate (100 mL). Aqueous layer was acidified with 3N HCl (30 mL) to pH-3 and extracted with ethyl acetate (100 mL×2). Organic layer was dried over anhydrous sodium sulphate and concentrated under reduced pressure to obtain 1-oxo-2-phenyl-1,2-dihydroisoquinoline-4-carboxylic acid (650 mg, 93%) as a white solid.

LCMS 266 [M+H]$^+$

Compound 2: To a stirred solution of 1-oxo-2-phenyl-1,2-dihydroisoquinoline-4-carboxylic acid (200 mg, 0.75 mmol, 1 equiv) in DMF (5 mL), was added DIPEA (0.5 mL, 3 mmol, 4 equiv) and HATU (802 mg, 2.1 mmol, 2.8 equiv) and the reaction mixture was allowed to stir for 30 min under nitrogen Atmosphere. (S)-1-(2-aminoacetyl)-4,4-difluoropyrrolidine-2-carbonitrile hydrochloride (204 mg, 0.905 mmol, 1.2 equiv) was added to above mixture and allowed to stir for overnight at RT. Progress of the reaction was monitored by TLC and LCMS. After completion of the reaction, the reaction mixture was diluted with water (30 mL) and extracted with ethyl acetate (100 mL×2). Organic layer was washed with water (100 mL), brine solution (100 mL), dried over anhydrous sodium sulphate and concentrated under reduced pressure to obtain crude compound, which was purified by reversed phase HPLC to obtain (S)—N-(2-(2-cyano-4,4-difluoropyrrolidin-1-yl)-2-oxoethyl)-1-oxo-2-phenyl-1,2-dihydroisoquinoline-4-carboxamide (Free base) (25 mg, 7%) as a white solid compound.

LCMS 437.3 [M+H]$^+$ $^1$HNMR (400 MHz, DMSO-d6) δ 8.78 (t, J=5.9 Hz, 1H), 8.35-8.27 (m, 2H), 7.82 (q, J=5.3, 3.2 Hz, 2H), 7.66-7.54 (m, 5H), 7.51 (p, J=4.6 Hz, 1H), 5.15-5.07 (m, 1H), 4.29 (ddd, J=16.2, 11.9, 4.5 Hz, 1H), 4.14 (qd, J=18.6, 17.9, 7.2 Hz, 2H), 3.29 (s, 1H), 2.99-2.73 (m, 2H).

Example 3

Synthesis of (S)—N-(2-(2-cyano-4,4-difluoropyrrolidin-1-yl)-2-oxoethyl)-2-cyclopropyl-1-oxo-1,2-dihydroisoquinoline-4-carboxamide

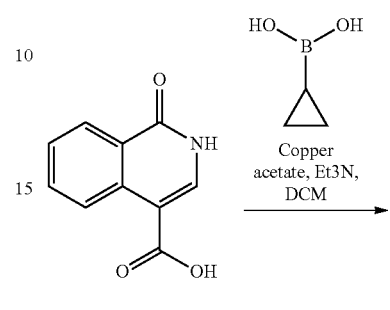

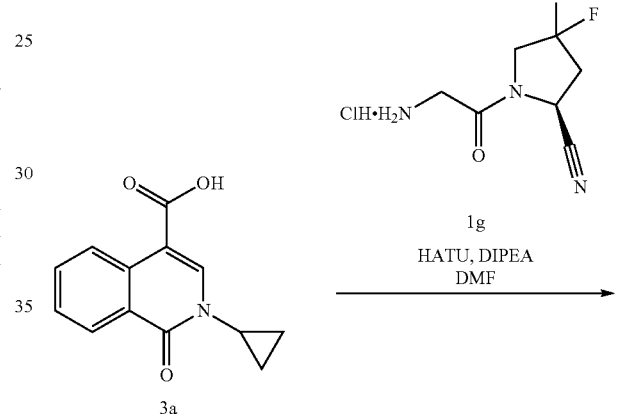

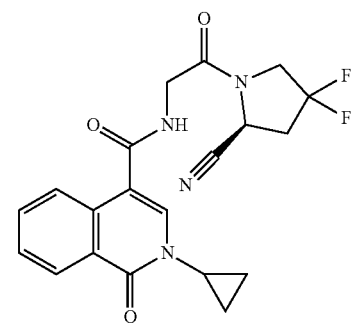

Compound 3

Compound 3a: To a stirred solution of 1-oxo-1,2-dihydroisoquinoline-4-carboxylic acid (1000 mg, 5.2 mmol, 1 equiv) in DCM (15 mL), was added cyclopropylboronic acid (683 mg, 7.9 mmol, 1.5 equiv), copper acetate (4732 mg, 26 mmol, 5 equiv), molecular sieves and Et$_3$N (7.2 mL, 52 mmol, 10 equiv). The reaction mixture was allowed to stir for overnight at RT. Progress of the reaction was monitored by TLC and LCMS. After completion of the reaction, the reaction mixture was passes through the celite bed and the filtrate was concentrated under reduced pressure to obtain crude, which was diluted with water (100 mL) and extracted with ethyl acetate (100 mL). Aqueous layer was acidified with 3N HCl (30 mL) to pH-3 and extracted with ethyl acetate (100 mL×2). Organic layer was dried over anhydrous sodium sulphate and concentrated under reduced pressure to obtain 2-cyclopropyl-1-oxo-1,2-dihydroisoquinoline-4-carboxylic acid (550 mg, 45%) as a light brown solid compound.

LCMS 230 [M+H]+

Compound 3: To a stirred solution of 2-cyclopropyl-1-oxo-1,2-dihydroisoquinoline-4-carboxylic acid (200 mg, 0.87 mmol, 1 equiv) in DMF (5 mL), was added DIPEA (0.6 mL, 3.48 mmol, 4 equiv) and HATU (926 mg, 2.43 mmol, 2.8 equiv). The reaction mixture was allowed to stir for 30 min under nitrogen. (S)-1-(2-aminoacetyl)-4,4-difluoropyrrolidine-2-carbonitrile hydrochloride (236 mg, 1.04 mmol, 1.2 equiv) was added to above mixture and allowed to stir for overnight at RT. Progress of the reaction was monitored by TLC and LCMS. After completion of the reaction, the reaction mixture was diluted with water (30 mL) and extracted with ethyl acetate (100 mL×2). Organic layer was washed with water (100 mL), brine solution (100 mL), dried over anhydrous sodium sulphate and concentrated under reduced pressure to obtain crude compound, which was purified by reversed phase HPLC to obtain (S)—N-(2-(2-cyano-4,4-difluoropyrrolidin-1-yl)-2-oxoethyl)-2-cyclopropyl-1-oxo-1,2-dihydroisoquinoline-4-carboxamide (Free base) (60 mg, 17%) as a white solid compound.

LCMS 437.3 [M+H]+

$^1$HNMR (400 MHz, DMSO-d6) δ 8.75 (t, J=5.9 Hz, 1H), 8.24 (dd, J=19.7, 8.1 Hz, 2H), 7.78-7.66 (m, 2H), 7.55 (t, J=7.5 Hz, 1H), 5.14 (d, J=9.2 Hz, 1H), 4.37-4.24 (m, 1H), 4.14 (qd, J=17.0, 16.5, 7.9 Hz, 3H), 3.35 (s, 1H), 2.88 (dd, J=40.5, 13.1 Hz, 2H), 1.75 (s, 0H), 1.05 (d, J=7.3 Hz, 2H), 0.98 (s, 2H).

Example 4

Synthesis of (S)—N-(2-(2-cyano-4,4-difluoropyrrolidin-1-yl)-2-oxoethyl)quinoline-6-carboxamide

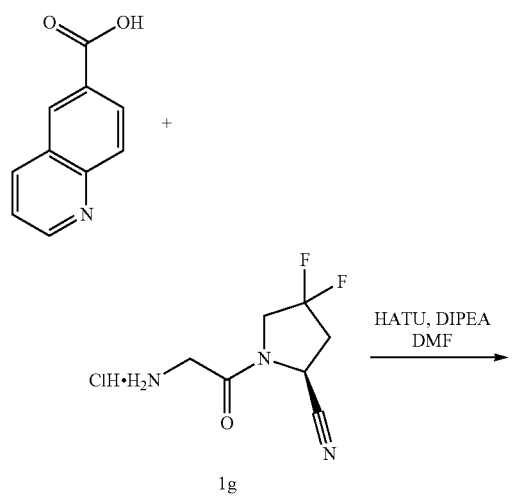

To a stirred solution of quinoline-6-carboxylic acid (230 mg, 1.32 mmol, 1.0 equiv) and HATU (1003 mg, 2.64 mmol, 2.0 equiv) in DMF (15 ml) was added (S)-4,4-difluoro-1-glycylpyrrolidine-2-carbonitrile hydrochloride (250 mg, 1.32 mmol, 1.0 equiv.) and stirred the reaction mixture for 10 min. DIPEA (510 mg, 3.96 mmol, 3.0 equiv) was added and the reaction mixture was allowed to stir at RT for 16 h. The progress of the reaction was monitored by NMR and TLC. The reaction mixture was diluted with water (50 mL) and extracted with ethyl acetate (50 mL×3). Combined organic layer was washed with water (25 mL×4), dried over anhydrous sodium sulphate and concentrated under reduced pressure. The crude material obtained was purified by reversed phase HPLC to obtain (S)—N-(2-(2-cyano-4,4-difluoropyrrolidin-1-yl)-2-oxoethyl)quinoline-6-carboxamide (175 mg, 38% Yield) as an off-white solid.

LCMS 345 [M+H]+

$^1$H NMR (400 MHz, DMSO-d$_6$) δ 11.62 (br. s., 1H), 8.68 (t, J=5.62 Hz, 1H), 8.25 (t, J=8.31 Hz, 2H), 7.75 (t, J=7.09 Hz, 1H), 7.47-7.62 (m, 2H), 5.03-5.18 (m, 1H), 4.22-4.36 (m, 1H), 3.99-4.20 (m, 3H), 2.77-2.98 (m, 2H).

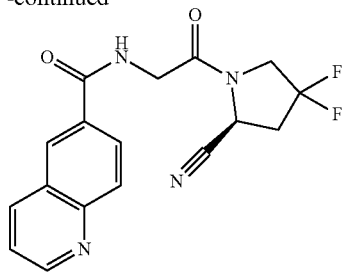

Compound 4

Example 5

Synthesis of (S)—N-(2-(2-cyano-4,4-difluoropyrrolidin-1-yl)-2-oxoethyl)-6,7-dihydro-5H-cyclopenta[d]pyrimidine-4-carboxamide

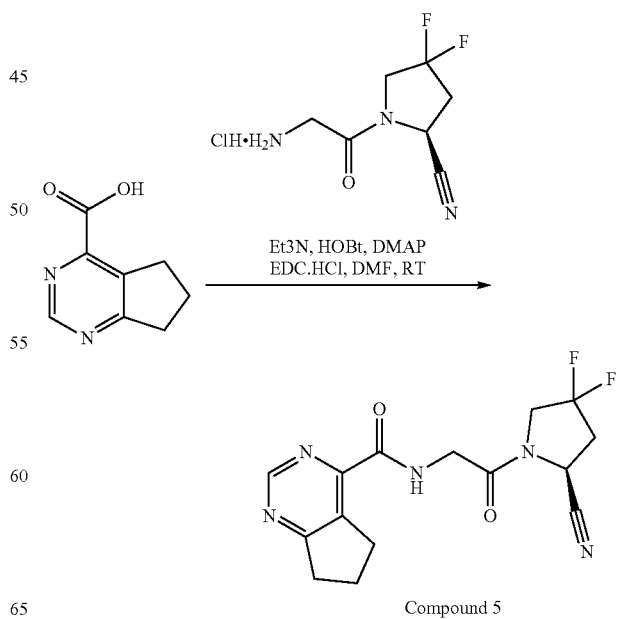

Compound 5

To a stirred solution of (S)-4,4-difluoro-1-glycylpyrrolidine-2-carbonitrile hydrochloride (100 mg, 0.44 mmol, 1 equiv) in DMF (3 mL), was added quinoline-4-carboxylic acid (73 mg, 0.44 mmol, 1 equiv), Et₃N (0.06 mL, 0.48 mmol, 1.1 equiv), HOBt (68 mg, 0.44 mmol, 1 equiv), DMAP (3 mg, 0.02 mmol, 0.05 equiv) and EDC.HCl (93 mg, 0.48 mmol, 1.1 equiv). The reaction mixture was allowed to stir the overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by normal phase combi flash to obtain (S)—N-(2-(2-cyano-4,4-difluoropyrrolidin-1-yl)-2-oxoethyl)-6,7-dihydro-5H-cyclopenta[d]pyrimidine-4-carboxamide (40 mg, 27%) as a white solid compound.

LCMS 336 [M+H]⁺

¹HNMR (400 MHz, DMSO-d6) δ 9.02 (s, 1H), 5.09-5.01 (m, 1H), 4.33-3.92 (m, 4H), 3.24 (t, J=7.7 Hz, 2H), 2.97 (t, J=7.8 Hz, 2H), 2.93-2.70 (m, 2H), 2.06 (p, J=7.7 Hz, 2H).

Example 6

Synthesis of (S)—N-(2-(2-cyano-4, 4-difluoropyrrolidin-1-yl)-2-oxoethyl)-6-oxo-1, 6-dihydropyridine-3-carboxamide

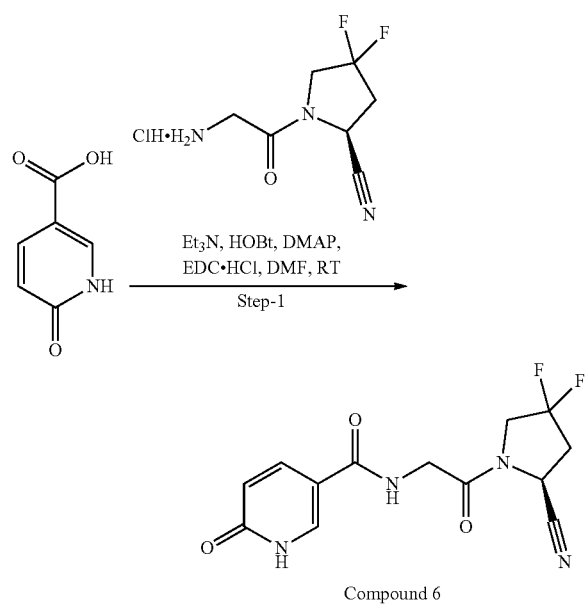

Compound 6

To a stirred solution of 6-oxo-1, 6-dihydropyridine-3-carboxylic acid (50 mg, 0.22 mmol, 1 equiv) in DMF (3 mL), was added Et₃N (0.03 mL, 0.24 mmol, 1.1 equiv), HOBt (34 mg, 0.22 mmol, 1 equiv), DMAP (1.3 mg, 0.01 mmol, 0.05 equiv) and EDC.HCl (47 mg, 0.24 mmol, 1.1 equiv). The reaction mixture was allowed to stir for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by reversed phase HPLC to obtain (S)—N-(2-(2-cyano-4, 4-difluoropyrrolidin-1-yl)-2-oxoethyl)-6-oxo-1, 6-dihydropyridine-3-carboxamide (Free base) (50 mg, 58%) as a white solid compound.

LCMS 311 [M+H]⁺

¹HNMR (400 MHz, DMSO-d6) δ 11.78 (s, 1H), 8.60 (q, J=7.8, 6.0 Hz, 1H), 8.03 (d, J=2.7 Hz, 1H), 7.87 (dd, J=9.6, 2.8 Hz, 1H), 6.37 (d, J=9.6 Hz, 1H), 5.07 (dd, J=9.3, 2.8 Hz, 1H), 4.32-4.20 (m, 1H), 4.07 (qt, J=16.8, 7.9 Hz, 3H), 2.97-2.71 (m, 2H).

Example 7

Synthesis of (S)—N-(2-(2-cyano-4, 4-difluoropyrrolidin-1-yl)-2-oxoethyl)-2, 3-dihydro-1H-indene-2-carboxamide

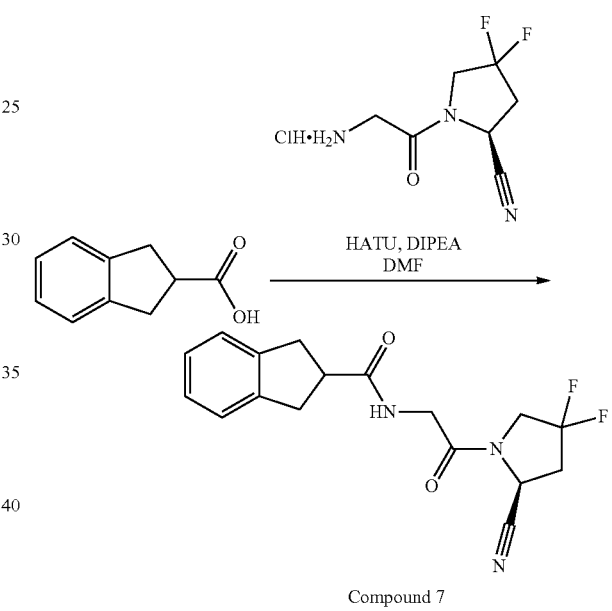

Compound 7

To a stirred solution of 2, 3-dihydro-1H-indene-2-carboxylic acid (100 mg, 0.617 mmol, 1 equiv) in DMF (3 mL), was added DIPEA (0.4 mL, 2.46 mmol, 4 equiv) and HATU (657 mg, 1.72 mmol, 2.8 equiv) and the mixture was allowed to stir for 30 min. (S)-1-(2-aminoacetyl)-4,4-difluoropyrrolidine-2-carbonitrile hydrochloride (167 mg, 0.74 mmol, 1.2 equiv) was added to above mixture and the resulting mixture was allowed to stir for overnight at RT. Progress of the reaction was monitored by LCMS. After completion of the reaction, the reaction mixture was diluted with water (30 mL) and extracted with ethyl acetate (50 mL×2). Organic layer was washed with water (50 mL), brine solution (50 mL). Organic layer was dried over anhydrous sodium sulphate and concentrated under reduced pressure to obtain crude compound, which was purified by reversed phase HPLC to obtain (S)—N-(2-(2-cyano-4,4-difluoropyrrolidin-1-yl)-2-oxoethyl)-2,3-dihydro-1H-indene-2-carboxamide (Free base) (100 mg, 49%) as a white solid compound.

LCMS 334.1 [M+H]⁺

¹HNMR (400 MHz, DMSO-d6) δ 8.29 (t, J=5.8 Hz, 1H), 7.19 (dt, J=7.3, 3.6 Hz, 2H), 7.12 (dd, J=5.5, 3.2 Hz, 2H), 5.07 (dd, J=9.3, 2.8 Hz, 1H), 4.22 (ddd, J=15.8, 11.3, 4.5 Hz, 1H), 4.16-4.00 (m, 1H), 3.97 (t, J=6.0 Hz, 1H), 3.29 (dd, J=17.8, 9.2 Hz, 2H), 3.08 (t, J=6.3 Hz, 4H), 2.96-2.71 (m, 2H).

Example 8

Synthesis of (S)—N-(2-(2-cyano-4, 4-difluoropyrrolidin-1-yl)-2-oxoethyl) isoindoline-2-carboxamide

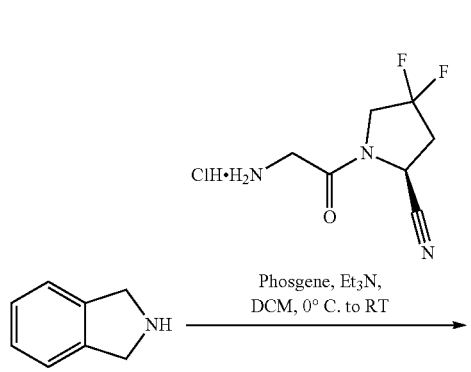

Compound 8

To a stirred solution of (S)-1-(2-aminoacetyl)-4, 4-difluoropyrrolidine-2-carbonitrile hydrochloride (50 mg, 0.22 mmol, 1 equiv) in DCM (3 mL), was added Et$_3$N (0.2 mL, 1.1 mmol, 5 equiv). The reaction mixture was allowed to stir for 15 min under nitrogen. Isoindoline (26 mg, 0.22 mmol, 1.0 equiv) was added to above mixture and cool the reaction mixture to 0° C. Phosgene (20% in Toluene) (0.6 mL) was added to above mixture drop wise. Raise the temperature to RT and allowed to stir for overnight at RT. Progress of the reaction was monitored by LCMS. After completion of reaction, the reaction mixture was diluted with water (30 mL) and extracted with DCM (50 mL×2). Organic layer was washed with water (50 mL), brine solution (50 mL). Organic layer was dried over anhydrous sodium sulphate and concentrated under reduced pressure to obtain crude compound, which was purified by reversed phase HPLC to obtain (S)—N-(2-(2-cyano-4, 4-difluoropyrrolidin-1-yl)-2-oxoethyl) isoindoline-2-carboxamide (Free base) (20 mg, 27%) as a white solid compound.

LCMS 335.1 [M+H]$^+$ $^1$HNMR (400 MHz, DMSO-d6) δ 7.34 (dt, J=7.1, 3.6 Hz, 2H), 7.31-7.25 (m, 2H), 6.70 (t, J=5.8 Hz, 1H), 5.07 (dd, J=9.3, 2.9 Hz, 1H), 4.62 (s, 4H), 4.24 (ddd, J=16.1, 11.5, 4.6 Hz, 1H), 4.15-4.01 (m, 1H), 3.90 (t, J=5.3 Hz, 2H), 0.97-2.71 (m, 2H).

Example 9

Synthesis of (S)—N-(2-(2-cyano-4, 4-difluoropyrrolidin-1-yl)-2-oxoethyl)-2-methyl-1-oxo-1, 2-dihydroisoquinoline-4-carboxamide

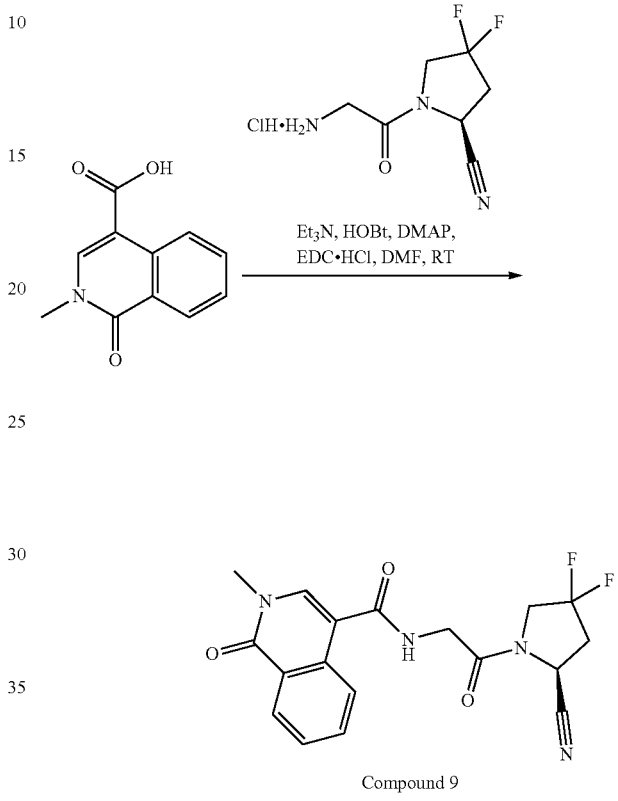

Compound 9

To a stirred solution of (S)-4,4-difluoro-1-glycylpyrrolidine-2-carbonitrile hydrochloride (100 mg, 0.44 mmol, 1 equiv) in DMF (3 mL), was added 2-methyl-1-oxo-1,2-dihydroisoquinoline-4-carboxylic acid (89 mg, 0.44 mmol, 1 equiv), Et$_3$N (0.06 mL, 0.48 mmol, 1.1 equiv), HOBt (68 mg, 0.44 mmol, 1 equiv), DMAP (3 mg, 0.02 mmol, 0.05 equiv) and EDC.HCl (93 mg, 0.48 mmol, 1.1 equiv). The reaction mixture was allowed to stir for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by normal phase combi flash to obtain (S)—N-(2-(2-cyano-4, 4-difluoropyrrolidin-1-yl)-2-oxoethyl)-2-methyl-1-oxo-1,2-dihydroisoquinoline-4-carboxamide (Free base) (80 mg, 48%) as a white solid compound.

LCMS 375 [M+H]$^+$ $^1$HNMR (400 MHz, DMSO-d6) δ 8.69 (t, J=5.7 Hz, 1H), 8.26 (d, J=8.1 Hz, 1H), 8.16 (d, J=8.2 Hz, 1H), 7.83 (s, 1H), 7.79-7.70 (m, 1H), 7.56 (t, J=7.6 Hz, 1H), 5.07 (dd, J=9.5, 2.6 Hz, 1H), 4.29-3.99 (m, 4H), 3.54 (s, 3H), 2.97-2.70 (m, 2H).

Example 10

Synthesis of (S)—N-(2-(2-cyano-4,4-difluoropyrrolidin-1-yl)-2-oxoethyl)-2-hydroxyquinoline-6-carboxamide

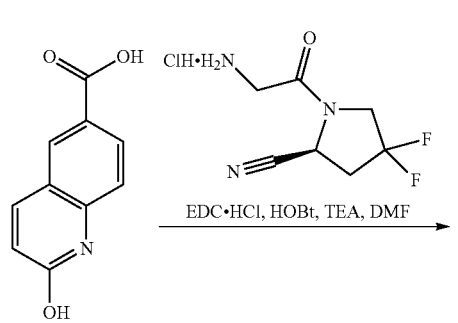

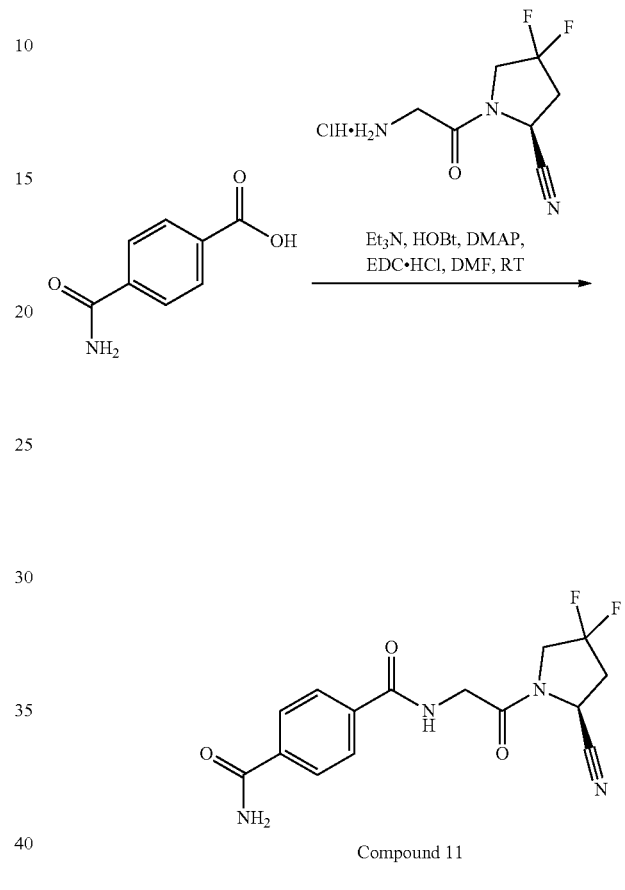

Compound 10

To a stirred solution of 2-hydroxyquinoline-6-carboxylic acid (0.200 g, 1.05 mmol, 1.0 equiv) in DMF (5 mL), was added (S)-4,4-difluoro-1-glycylpyrrolidine-2-carbonitrile hydrochloride (0.261 g, 1.16 mmol, 1.1 equiv), HOBt (0.156 g, 1.16 mmol, 1.1 equiv) and EDC.HCl (0.221 g, 1.16 mmol, 1.1 equiv). The mixture was allowed to stir at RT for 10 min. Triethyl amine (0.73 mL) was added and the mixture was allowed to stir at RT for overnight. Product formation was confirmed by LCMS and TLC. The reaction mixture was diluted with water (50 mL) and extracted with ethyl acetate (50 mL×2). Combined organic layer was washed with water (20 mL×4), dried over anhydrous $Na_2SO_4$ and concentrated. The crude material obtained was purified by reversed phase HPLC to obtain (S)—N-(2-(2-cyano-4,4-difluoropyrrolidin-1-yl)-2-oxoethyl)-2-hydroxyquinoline-6-carboxamide (0.010 g, ~5% Yield) as an off-white solid.

LCMS 361.2 [M+H]$^+$ $^1$H NMR (400 MHz, DMSO-d$_6$) d 11.97 (br. s., 1H), 8.80 (br. s., 1H), 8.23 (br. s., 1H), 7.89-8.04 (m, 2H), 7.35 (d, J=8.33 Hz, 1H), 6.56 (d, J=7.45 Hz, 1H), 5.10 (d, J=10.96 Hz, 1H), 4.30 (br. s., 2H), 4.15 (d, J=10.96 Hz, 2H), 2.85 (br. s., 1H), 2.80 (br. s., 1H).

Example 11

Synthesis of (S)—N-(2-(2-cyano-4,4-difluoropyrrolidin-1-yl)-2-oxoethyl)terephthalamide Compound 11

To a stirred solution of (S)-4,4-difluoro-1-glycylpyrrolidine-2-carbonitrile hydrochloride (136 mg, 0.606 mmol, 1 equiv) in DMF (10 mL), was added 4-carbamoylbenzoic acid (100 mg, 0.606 mmol, 1 equiv), Et$_3$N (0.2 mL, 1.818 mmol, 3 equiv), HOBT (90 mg, 0.666 mmol, 1.1 equiv), EDC.HCL (128 mg, 0.666 mmol, 1.1 equiv). The reaction mixture was allowed to stir for overnight at RT. Progress of the reaction was monitored by TLC and LCMS. After completion of the reaction, the reaction mixture was diluted with water (50 mL) and extracted with ethyl acetate (50 mL×2). Organic layer was washed with water (20 mL×4), brine solution (50 mL). Organic layer was dried over anhydrous sodium sulphate and concentrated under reduced pressure to obtain crude compound, which was purified by normal phase combi flash to obtain (S)—N-(2-(2-cyano-4,4-difluoropyrrolidin-1-yl)-2-oxoethyl)terephthalamide (Free base) (25 mg, 12% Yield) as an off white solid compound.

LCMS 337 [M+H]$^+$ $^1$HNMR (400 MHz, DMSO-d$_6$) ☐ 2.79-3.00 (m, 3H) 4.04-4.22 (m, 3H) 4.24-4.41 (m, 1H) 5.10 (d, J=7.02 Hz, 1H) 7.51 (br. s., 1H) 7.83-8.02 (m, 3H) 8.09 (br. s., 1H) 8.92 (d, J=5.70 Hz, 1H).

Example 12

Synthesis of (S)-4-cyano-N-(2-(2-cyano-4,4-difluoropyrrolidin-1-yl)-2-oxoethyl)-3-(trifluoromethyl)benzamide

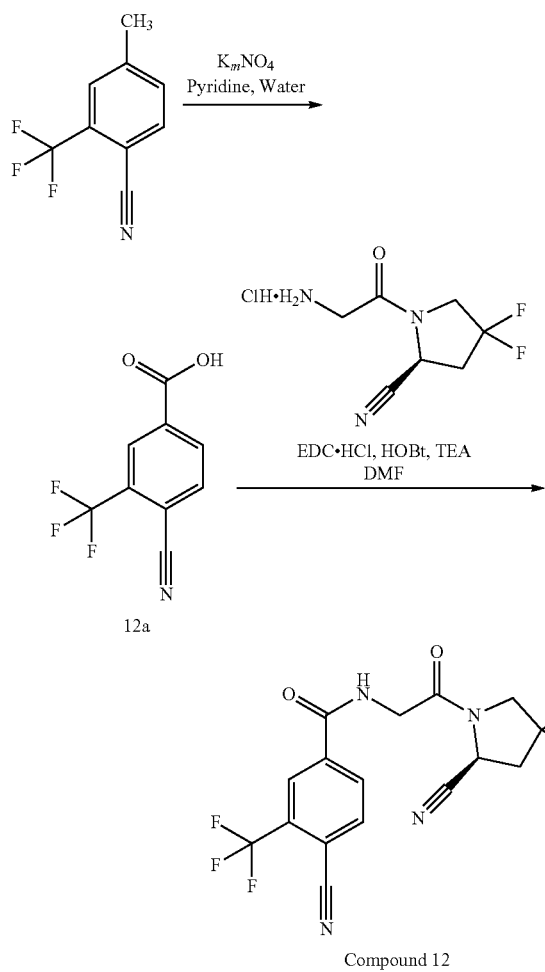

Compound 12

Compound 12a. To a solution of 4-methyl-2-(trifluoromethyl)benzonitrile (0.790 g, 4.270 mmol, 1 equiv) in pyridine (8 mL) and water (2 mL) was added KMnO$_4$ (0.675 g, 4.270 mmol, 1.0 equiv). The resultant reaction mixture was heated at 100° C. in microwave reactor for 1 h. Product formation was confirmed by LCMS (-ve mode mass). After completion of reaction, the mixture was filtered through celite bed and washed with ethyl acetate. Filtrate was acidified with 1 N HCl and extracted with ethyl acetate (50 mL×2). Combined organic layer was dried over anhydrous Na$_2$SO$_4$ and concentrated. The crude product obtained was purified by flash chromatography (0-50% ethyl acetate in hexane as an eluent) to obtain 4-cyano-3-(trifluoromethyl)benzoic acid (0.200 g, 22% Yield) as an off-white solid.

LCMS 214.2 (M−1)

$^1$H NMR (400 MHz, DMSO-d6) δ 8.66 (d, J=4.38 Hz, 1H), 8.32-8.42 (m, 2H).

Compound 12. To a stirred solution of 4-cyano-3-(trifluoromethyl)benzoic acid (0.200 g, 0.930 mmol, 1.0 equiv) in DMF (5 mL), was added (S)-4,4-difluoro-1-glycylpyrrolidine-2-carbonitrile hydrochloride (0.210 g, 0.930 mmol, 1.0 equiv), HOBt (0.151 g, 1.116 mmol, 1.2 equiv) and EDC.HCl (0.212 g, 1.116 mmol, 1.2 equiv). The reaction mixture was allowed to stir at RT for 10 min. Triethyl amine (0.4 mL) was added and the mixture was allowed to stir at RT for overnight. Product formation was confirmed by LCMS and TLC. After completion of reaction, the mixture was diluted with water (30 mL) and extracted with ethyl acetate (50 mL×2). Combined organic layer was washed with water (20 mL×4), dried over anhydrous Na$_2$SO$_4$ and concentrated. The crude product obtained was purified by flash chromatography (0-50% ethyl acetate in hexane as an eluent) to obtain (S)-4-cyano-N-(2-(2-cyano-4,4-difluoropyrrolidin-1-yl)-2-oxoethyl)-3-(trifluoromethyl)benzamide (0.060 g, 17% Yield) as an off-white solid.

LCMS 387.1 [M+H]$^+$ $^1$H NMR (400 MHz, DMSO-d6) d 9.35 (br. s., 1H), 8.41 (s, 1H), 8.35 (s, 2H), 5.10 (d, J=7.89 Hz, 1H), 4.31 (t, J=11.62 Hz, 1H), 4.05-4.22 (m, 2H), 2.77-3.00 (m, 2H), 2.73 (s, 1H).

Example 13

Synthesis of (S)—N-(2-(2-cyano-4,4-difluoropyrrolidin-1-yl)-2-oxoethyl)-3-phenylisonicotinamide

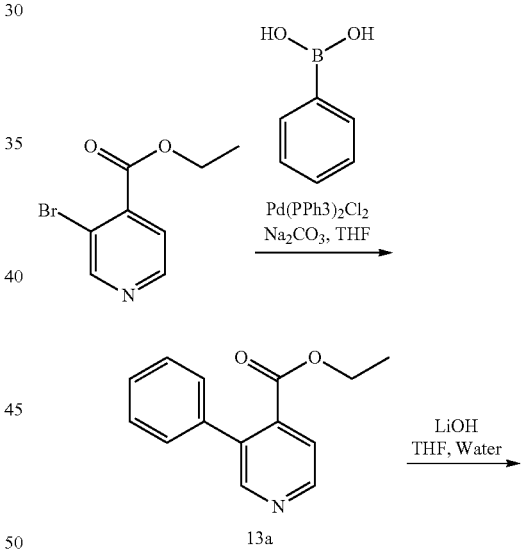

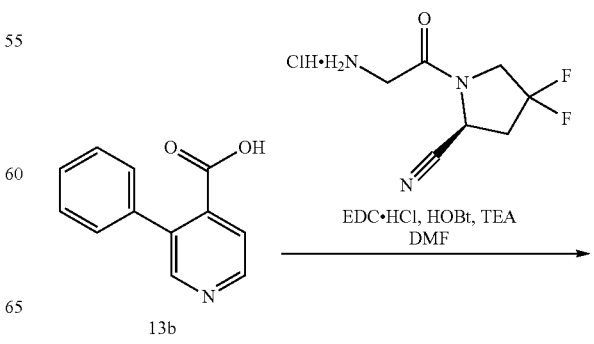

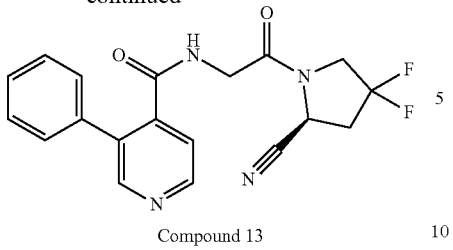

Compound 13

Compound 13a. To a solution of ethyl 3-bromoisonicotinate (1.00 g, 4.34 mmol, 1. equiv) in THF (20 mL) was added phenylboronic acid (0.584 g, 4.78 mmol, 1.1 equiv), Na₂CO₃ (0.922 g, 8.68 mmol, 2.0 equiv) followed by the addition of Pd(PPh₃)₂Cl₂ (0.153 g, 0.217 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-30% ethyl acetate in hexane as an eluent) to obtain ethyl 3-phenylisonicotinate (0.300 g, 31% Yield) as an off-white solid.

LCMS 228.2 [M+H]⁺

¹H NMR (400 MHz, DMSO-d6) δ 8.68-8.76 (m, 2H), 7.67 (d, J=4.82 Hz, 1H), 7.41-7.51 (m, 3H), 7.37 (d, J=6.14 Hz, 2H), 4.11 (q, J=7.02 Hz, 2H), 0.98 (t, J=7.24 Hz, 3H).

Compound 13b. To a stirred solution of ethyl 3-phenylisonicotinate (0.250 g, 1.10 mmol, 1.0 equiv) in THF (5 mL) and water (5 mL), was added LiOH (0.053 g, 2.20 mmol, 2.0 equiv). The mixture was allowed to stir at RT for overnight. Product formation was confirmed by LCMS and ¹H NMR Spectroscopy. The reaction mixture was diluted with water (15 mL) and washed with ethyl acetate (15 mL). Aqueous layer was separated and freeze dried on lyophilyzer to obtain 3-phenylisonicotinic acid (0.300 g, 99% Yield) as an off-white solid.

LCMS 200.1 [M+H]⁺

¹H NMR (400 MHz, DMSO-d₆) δ 8.30-8.47 (m, 2H), 7.58 (d, J=7.02 Hz, 2H), 7.26-7.45 (m, 3H), 7.13 (d, J=4.82 Hz, 1H).

Compound 13. To a stirred solution of 3-phenylisonicotinic acid (0.200 g, 1.00 mmol, 1.0 equiv) in DMF (5 mL), was added (S)-4,4-difluoro-1-glycylpyrrolidine-2-carbonitrile hydrochloride (0.224 g, 1.00 mmol, 1.0 equiv), HOBt (0.163 g, 1.206 mmol, 1.2 equiv) and EDC.HCl (0.230 g, 1.206 mmol, 1.2 equiv). The mixture was allowed to stir at RT for 10 min. Triethyl amine (0.7 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic layer was washed with water (20 mL×4), dried over anhydrous Na₂SO₄ and concentrated. The crude product obtained was purified by flash chromatography (0-50% ethyl acetate in hexane as an eluent) to obtain (S)—N-(2-(2-cyano-4,4-difluoropyrrolidin-1-yl)-2-oxoethyl)-3-phenylisonicotinamide (0.050 g, 14% Yield) as an off-white solid.

LCMS 371.2 [M+H]⁺

1H NMR (400 MHz, DMSO-d6) δ 8.96 (t, J=5.48 Hz, 1H), 8.62-8.70 (m, 1H), 7.54 (d, J=6.58 Hz, 1H), 7.29-7.51 (m, 3H), 5.10 (d, J=7.02 Hz, 1H), 4.21 (br. s., 1H), 3.93-4.12 (m, 2H), 2.80 (d, J=13.59 Hz, 2H).

Example 14

Synthesis of (S)—N-(2-(2-cyano-4, 4-difluoropyrrolidin-1-yl)-2-oxoethyl)-6-oxo-5-phenyl-1, 6-dihydropyridine-3-carboxamide

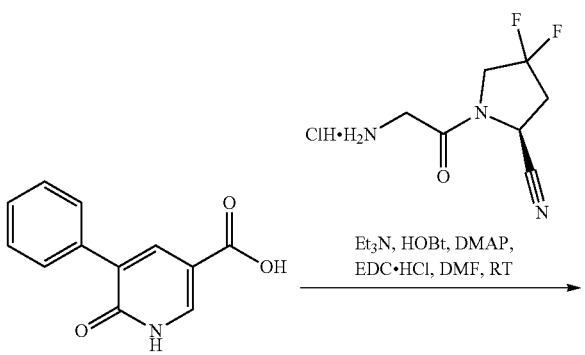

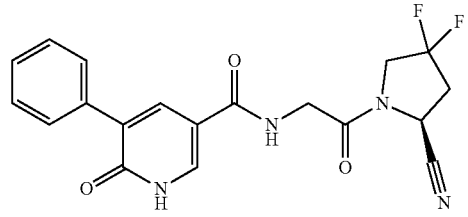

Compound 14

To a stirred solution of (S)-4,4-difluoro-1-glycylpyrrolidine-2-carbonitrile hydrochloride (50 mg, 0.22 mmol, 1 equiv) in DMF (2 mL), was added 6-oxo-5-phenyl-1,6-dihydropyridine-3-carboxylic acid (48 mg, 0.22 mmol, 1 equiv), Et₃N (0.03 mL, 0.24 mmol, 1.1 equiv), HOBt (34 mg, 0.22 mmol, 1 equiv), DMAP (2 mg, 0.01 mmol, 0.05 equiv) and EDC.HCl (46 mg, 0.24 mmol, 1.1 equiv). The reaction mixture was allowed to stir for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by normal phase combi flash to obtain (S)—N-(2-(2-cyano-4,4-difluoropyrrolidin-1-yl)-2-oxoethyl)-6-oxo-5-phenyl-1, 6-dihydropyridine-3-carboxamide (Free base) (30 mg, 35%) as an off white solid compound.

LCMS 387 [M+H]⁺

¹HNMR (400 MHz, DMSO-d6) δ 12.22 (s, 1H), 8.72 (t, J=5.8 Hz, 1H), 8.11 (d, J=2.7 Hz, 1H), 8.04 (s, 1H), 7.74 (d, J=7.5 Hz, 2H), 7.42 (t, J=7.5 Hz, 2H), 7.35 (t, J=7.2 Hz, 1H), 5.09 (dd, J=9.4, 2.8 Hz, 1H), 4.29 (ddd, J=15.9, 11.6, 4.6 Hz, 1H), 4.18-3.93 (m, 3H), 2.98-2.70 (m, 2H).

Example 15

Synthesis of (S)-4-cyano-N-(2-(2-cyano-4, 4-difluoropyrrolidin-1-yl)-2-oxoethyl)-3-fluorobenzamide

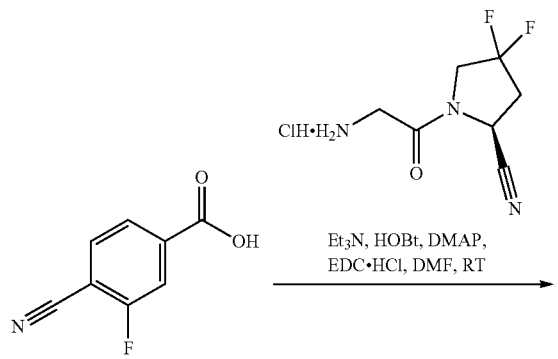

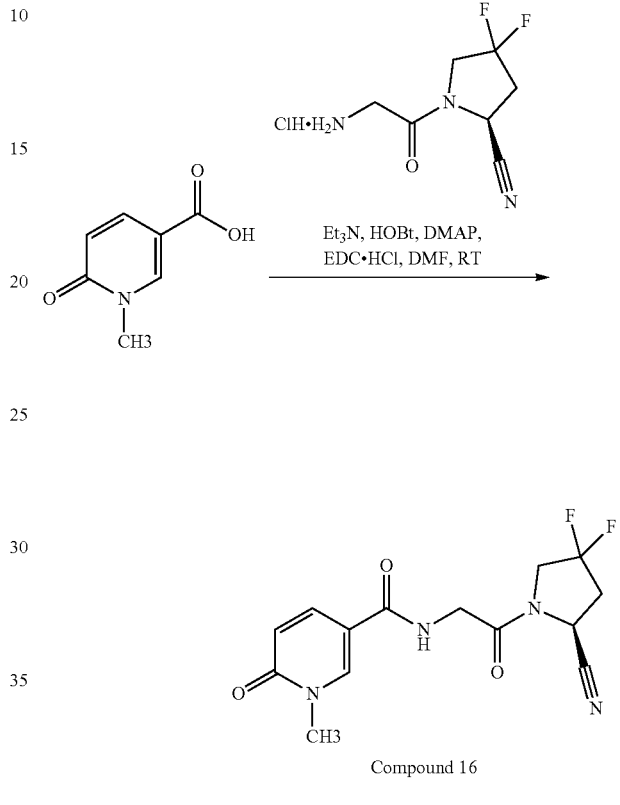

Compound 15

To a stirred solution of (S)-4,4-difluoro-1-glycylpyrrolidine-2-carbonitrile hydrochloride (100 mg, 0.44 mmol, 1 equiv) in DMF (3 mL), was added 4-cyano-3-fluorobenzoic acid (73 mg, 0.44 mmol, 1 equiv), Et$_3$N (0.06 mL, 0.48 mmol, 1.1 equiv), HOBt (67 mg, 0.44 mmol, 1 equiv), DMAP (3 mg, 0.02 mmol, 0.05 equiv) and EDC.HCl (92 mg, 0.48 mmol, 1.1 equiv). The reaction mixture was allowed to stir for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by normal phase combi flash to obtain (S)-4-cyano-N-(2-(2-cyano-4, 4-difluoropyrrolidin-1-yl)-2-oxoethyl)-3-fluorobenzamide (Free base) (45 mg, 30%) as a white solid compound.

LCMS 337 [M+H]$^+$ $^1$HNMR (400 MHz, DMSO-d6) δ 9.18 (q, J=8.4, 5.8 Hz, 1H), 8.10 (t, J=7.3 Hz, 1H), 7.91 (dd, J=18.9, 9.1 Hz, 2H), 5.10 (dd, J=9.3, 2.8 Hz, 1H), 4.31 (ddt, J=16.3, 11.9, 5.9 Hz, 1H), 4.25-4.00 (m, 3H), 2.99-2.74 (m, 2H).

Example 16

Synthesis of (S)—N-(2-(2-cyano-4, 4-difluoropyrrolidin-1-yl)-2-oxoethyl)-1-methyl-6-oxo-1, 6-dihydropyridine-3-carboxamide Compound 16

To a stirred solution of (S)-4,4-difluoro-1-glycylpyrrolidine-2-carbonitrile hydrochloride (100 mg, 0.44 mmol, 1 equiv) in DMF (3 mL), was added 1-methyl-6-oxo-1,6-dihydropyridine-3-carboxylic acid (68 mg, 0.44 mmol, 1 equiv), Et$_3$N (0.06 mL, 0.48 mmol, 1.1 equiv), HOBt (67 mg, 0.44 mmol, 1 equiv), DMAP (3 mg, 0.02 mmol, 0.05 equiv) and EDC.HCl (92 mg, 0.48 mmol, 1.1 equiv). The reaction mixture was allowed to stir for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by normal phase combi flash to obtain (S)—N-(2-(2-cyano-4, 4-difluoropyrrolidin-1-yl)-2-oxoethyl)-1-methyl-6-oxo-1,6-dihydropyridine-3-carboxamide (Free base) (30 mg, 21%) as a white solid compound.

LCMS 325 [M+H]$^+$ $^1$HNMR (400 MHz, DMSO-d6) δ 8.33-8.66 (d, J=2.6 Hz, 2H), 7.98 (dd, J=9.4, 2.7 Hz, 1H), 6.68 (d, J=9.4 Hz, 1H), 5.14 (dd, J=8.4, 4.4 Hz, 1H), 4.26 (dd, J=12.1, 7.1 Hz, 1H), 4.22 (s, 2H), 4.20-4.06 (m, 1H), 3.65 (s, 3H), 3.06-2.82 (m, 2H).

Example 17

Synthesis of (S)-4-cyano-N-(2-(2-cyano-4,4-difluoropyrrolidin-1-yl)-2-oxoethyl)benzamide

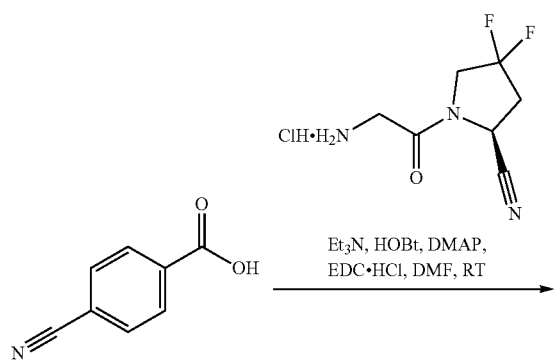

Compound 17

To a stirred solution of (S)-4,4-difluoro-1-glycylpyrrolidine-2-carbonitrile hydrochloride (100 mg, 0.44 mmol, 1 equiv) in DMF (3 mL), was added 4-cyanobenzoic acid (68 mg, 0.44 mmol, 1 equiv), Et₃N (0.06 mL, 0.48 mmol, 1.1 equiv), HOBt (67 mg, 0.44 mmol, 1 equiv), DMAP (3 mg, 0.02 mmol, 0.05 equiv) and EDC.HCl (92 mg, 0.48 mmol, 1.1 equiv). The reaction mixture was allowed to stir for overnight at RT. Progress of the reaction was monitored by TLC and LCMS. After completion of the reaction, the reaction mixture was diluted with water (10 mL) and extracted with ethyl acetate (30 mL×2). Organic layer was washed with water (50 mL), brine solution (50 mL). Organic layer was dried over anhydrous sodium sulphate and concentrated under reduced pressure to obtain crude compound, which was purified by normal phase combi flash to obtain (S)-4-cyano-N-(2-(2-cyano-4,4-difluoropyrrolidin-1-yl)-2-oxoethyl)benzamide (Free base) (35 mg, 25%) as a white solid compound.

LCMS 319 [M+H]⁺

¹HNMR (400 MHz, DMSO-d6) δ 9.10 (q, J=7.5, 5.8 Hz, 1H), 8.01 (q, J=8.0 Hz, 5H), 5.10 (dd, J=9.4, 2.8 Hz, 1H), 4.30 (ddd, J=16.1, 11.8, 4.8 Hz, 1H), 4.14 (qt, J=17.2, 8.4 Hz, 3H), 17.9, 14.3, 9.9 Hz, 2H).

Example 18

Synthesis of (S)-4-cyano-N-(2-(2-cyano-4,4-difluoropyrrolidin-1-yl)-2-oxoethyl)-2-(trifluoromethyl)benzamide

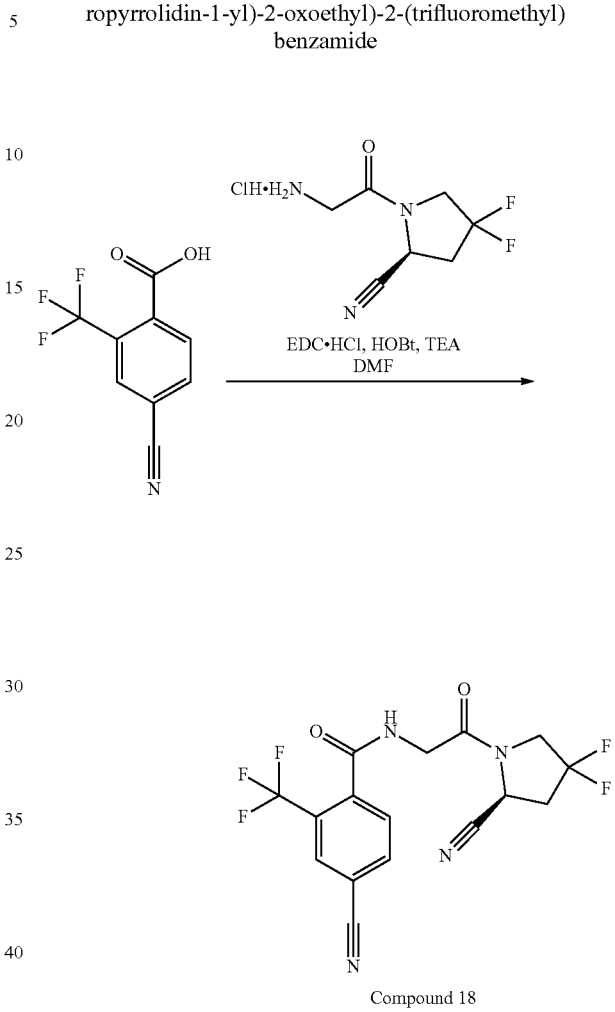

Compound 18

To a stirred solution of 3-phenylisonicotinic acid (0.100 g, 0.46 mmol, 1.0 equiv) in DMF (10 mL), was added (S)-4,4-difluoro-1-glycylpyrrolidine-2-carbonitrile hydrochloride (0.104 g, 0.46 mmol, 1.0 equiv), HOBt (0.068 g, 0.50 mmol, 1.1 equiv) and EDC.HCl (0.96 g, 0.50 mmol, 1.1 equiv). The mixture was allowed to stir at RT for 10 min. Triethyl amine (0.19 mL) was added and the mixture was allowed to stir at RT for overnight. Product formation was confirmed by LCMS and TLC. The reaction mixture was diluted with water and extracted with ethyl acetate (50 mL×2). Combined organic extracts were washed with water (20 mL×4), dried over anhydrous Na₂SO₄ and concentrated. The crude product obtained was purified by reversed phase HPLC to obtain (S)-4-cyano-N-(2-(2-cyano-4,4-difluoropyrrolidin-1-yl)-2-oxoethyl)-2-(trifluoromethyl)benzamide (0.030 g, 17% Yield) as an off-white solid.

LCMS 387.2 [M+H]⁺

¹H NMR (400 MHz, DMSO-d6) δ 9.05 (br. s., 1H), 8.40 (s, 1H), 8.28 (d, J=7.45 Hz, 1H), 7.78 (d, J=7.89 Hz, 1H), 5.12 (d, J=7.02 Hz, 1H), 4.27 (t, J=15.13 Hz, 1H), 4.01-4.21 (m, 3H), 2.72-2.99 (m, 3H).

Example 19

Synthesis of (S)—N-(2-(2-cyano-4,4-difluoropyrrolidin-1-yl)-2-oxoethyl)-4-phenylquinoline-6-carboxamide

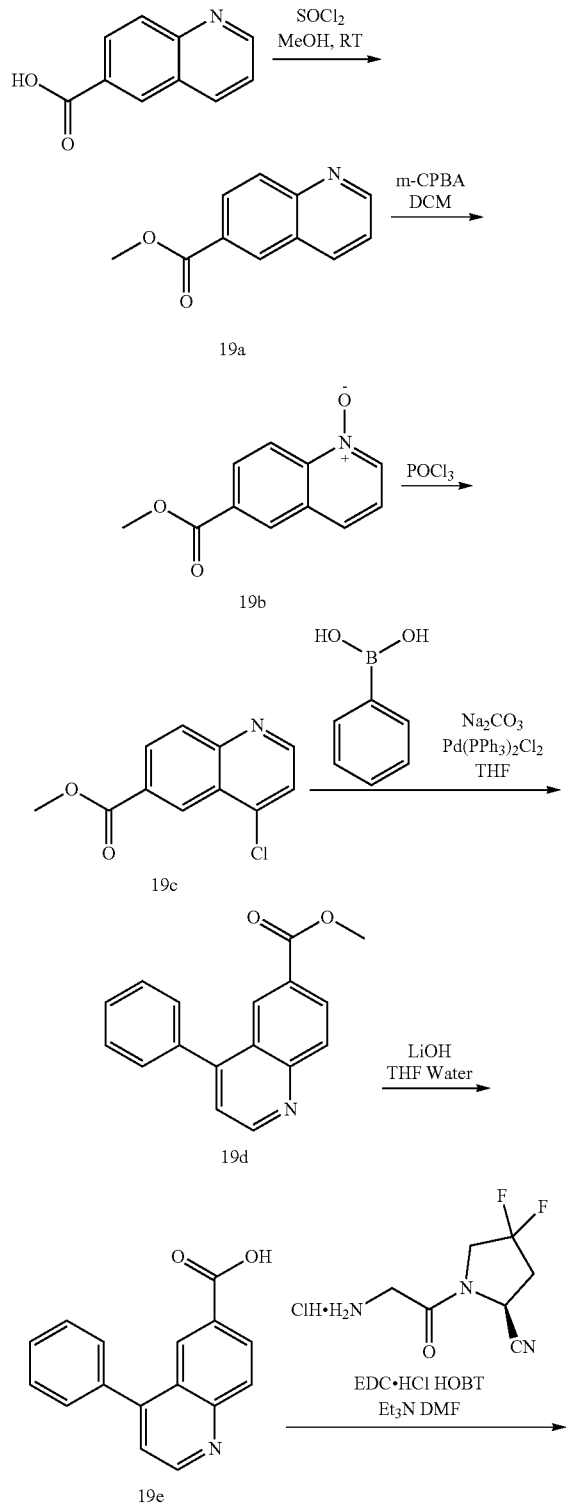

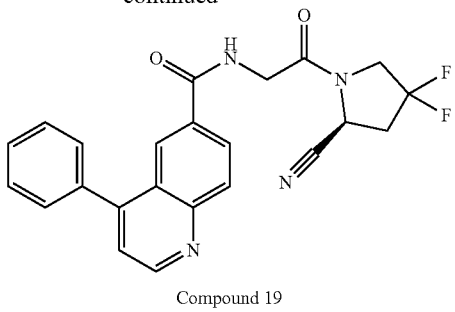

Compound 19

Compound 19a. To a solution of quinoline-6-carboxylic acid (1.00 g, 5.7 mmol, 1 equiv) in MeOH (10 mL) was added $SOCl_2$ (2.06 mL, 17.30 mmol, 3.0 equiv) at 0° C. The reaction mixture was heated at 50° C. for overnight. After completion of reaction (TLC) the mixture was basified with saturated $NaHCO_3$ and extracted with DCM (100 mL×2). Combined organic layer was dried over anhydrous $Na_2SO_4$ and concentrated under reduced pressure to obtain methyl quinoline-6-carboxylate (1.00 g, 98% Yield) as a brown solid.

LCMS 188.2 [M+H]+

Compound 19b. To a solution of methyl quinoline-6-carboxylate (1.00 g, 5.3 mmol, 1 equiv) in DCM (30 mL) was added mCPBA (1.84 g, 10.6 mmol, 2 equiv) and the mixture was allowed to stir at RT for overnight. After completion of reaction (TLC) the mixture was diluted with saturated $NaHCO_3$ (40 mL) and extracted with DCM (100 mL×2). The combined organic layer was dried over anhydrous $Na_2SO_4$ and concentrated under reduced pressure to obtain a residue, which was crystallized in ethyl acetate to obtain 6-(methoxycarbonyl)quinoline 1-oxide (1.00 g, 92% Yield).

LCMS 204.2 [M+H]+

Compound 19c. The 6-(methoxycarbonyl)quinoline 1-oxide (0.900 g, 4.4 mmol 1 equiv) was taken in 50 mL RB under nitrogen atmosphere, to this was added $POCl_3$ (5 mL) and then resulting mixture was stirred for 2 h under nitrogen atmosphere. After completion of reaction (TLC) the mixture was concentrated under reduced pressure. The resulting residue was dissolved in DCM (100 mL) and washed with saturated $NaHCO_3$ (25 mL×3). Organic layer was separated and dried over anhydrous $Na_2SO_4$ and concentrated under reduced pressure to obtain crude material which was purified by flash chromatography (0-20% Ethyl acetate in Hexane as an eluent) to obtain methyl 4-chloroquinoline-6-carboxylate (0.300 g, 30% Yield).

LCMS 222.1 [M+H]+

Compound 19d. To the solution of methyl 4-chloroquinoline-6-carboxylate (300 mg, 1.30 mmol, 1.0 equiv) in THF (5 mL), was added phenylboronic acid (198 mg, 1.60 mmol, 1.2 equiv), $Na_2CO_3$ (287 mg, 2.70 mmol, 2.0 equiv) and a catalytic amount of $Pd(PPh_3)_2Cl_2$ (47 mg, 0.069 mmol, 0.05 equiv). The resulting reaction mixture was heated at 100° C. for overnight. Product formation was confirmed by LCMS. After completion of reaction the reaction mixture was diluted with water (30 mL) and extracted with ethyl acetate (50 mL×2). Combined organic layer was dried over anhydrous Na₂SO₄ and concentrated under reduced pressure to obtain crude material which was purified by flash chromatography (0-20% Ethyl acetate in Hexane as an eluent) to obtain methyl 4-phenylquinoline-6-carboxylate (0.300 g, 84% Yield).

LCMS 264.1 [M+H]+

$^1$H NMR (400 MHz, DMSO-d$_6$) δ 9.08 (d, J=4.38 Hz, 1H), 8.53 (s, 1H), 8.08-8.35 (m, 2H), 7.48-7.69 (m, 5H), 3.86 (s, 3H).

Compound 19e. To a stirred solution of ethyl 3-phenylisonicotinate (0.360 g, 1.30 mmol, 1.0 equiv) in THF (5 mL) and water (5 mL), was added LiOH (0.098 g, 4.10 mmol, 3.0 equiv). The mixture was allowed to stir at RT for overnight. Product formation was confirmed by LCMS and $^1$H NMR. The reaction mixture was concentrated to obtain 4-phenylquinoline-6-carboxylic acid (0.420 g, 100% Yield) as an off-white solid.

LCMS 249.9 [M+H]+

$^1$H NMR (400 MHz, DMSO-d$_6$) δ 8.88 (d, J=4.38 Hz, 1H), 8.37 (s, 1H), 8.27 (d, J=8.77 Hz, 1H), 7.95 (d, J=8.77 Hz, 1H), 7.49-7.65 (m, 4H), 7.39 (d, J=4.38 Hz, 1H).

Compound 19. To a stirred solution of 4-phenylquinoline-6-carboxylic acid (0.200 g, 0.80 mmol, 1.0 equiv) in DMF (5 mL), was added (S)-4,4-difluoro-1-glycylpyrrolidine-2-carbonitrile hydrochloride (0.180 g, 0.80 mmol, 1.0 equiv), HOBt (0.118 g, 0.88 mmol, 1.1 equiv) and EDC.HCl (0.168 g, 0.88 mmol, 1.2 equiv). The mixture was allowed to stir at RT for 10 min. Triethyl amine (0.4 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic extracts were washed with water (20 mL×4), dried over anhydrous Na₂SO₄ and concentrated. The crude product obtained was purified reversed phase HPLC to obtain (S)—N-(2-(2-cyano-4,4-difluoropyrrolidin-1-yl)-2-oxoethyl)-4-phenylquinoline-6-carboxamide (0.030 g, 9% Yield) as an off-white solid.

LCMS 421.2 [M+H]+

$^1$H NMR (400 MHz, DMSO-d$_6$) δ 9.04 (d, J=4.38 Hz, 2H), 8.43 (s, 1H), 8.12-8.28 (m, 2H), 7.61 (s, 3H), 7.55 (d, J=4.38 Hz, 2H), 5.09 (d, J=8.33 Hz, 1H), 4.29 (br. s., 1H), 4.04-4.23 (m, 2H), 2.90 (br. s., 2H), 2.81 (d, J=17.54 Hz, 2H).

Example 20

Synthesis of (2R,3R)—N-(2-((S)-2-cyano-4,4-difluoropyrrolidin-1-yl)-2-oxoethyl)-1-ethyl-6-oxo-2-phenylpiperidine-3-carboxamide

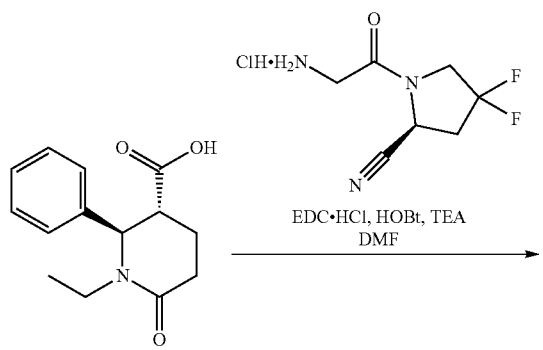

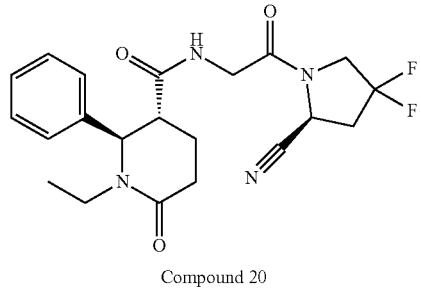

Compound 20

To a stirred solution of (2R,3R)-1-ethyl-6-oxo-2-phenylpiperidine-3-carboxylic acid (0.200 g, 0.809 mmol, 1.0 equiv) in DMF (5 mL), was added (S)-4,4-difluoro-1-glycylpyrrolidine-2-carbonitrile hydrochloride (0.200 g, 0.890 mmol, 1.0 equiv), HOBt (0.163 g, 1.21 mmol, 1.5 equiv) and EDC.HCl (0.230 g, 1.21 mmol, 1.5 equiv). The mixture was allowed to stir at RT for 10 min. Triethyl amine (0.4 mL) was added and the mixture was allowed to stir at RT for overnight. Product formation was confirmed by LCMS and TLC. The reaction mixture was diluted with water and extracted with ethyl acetate (50 mL×2). Combined organic layer was washed with water (20 mL×4), dried over anhydrous Na₂SO₄ and concentrated. The crude product obtained was purified by reversed phase HPLC to obtain (2R,3R)—N-(2-((S)-2-cyano-4,4-difluoropyrrolidin-1-yl)-2-oxoethyl)-1-ethyl-6-oxo-2-phenylpiperidine-3-carboxamide (0.040 g, 12% Yield) as an off-white solid.

LCMS 419.3 [M+H]+

$^1$H NMR (400 MHz, DMSO-d$_6$) δ 8.26 (d, J=4.82 Hz, 1H), 7.17-7.43 (m, 4H), 5.07 (t, J=9.65 Hz, 1H), 4.88 (d, J=5.26 Hz, 1H), 4.17 (t, J=12.06 Hz, 1H), 3.95-4.11 (m, 2H), 3.77-3.90 (m, 1H), 3.58-3.74 (m, 1H), 2.87 (dd, J=5.26, 9.65 Hz, 1H), 2.72-2.83 (m, 2H), 2.27-2.46 (m, 3H), 1.84 (d, J=6.58 Hz, 2H), 0.92 (t, J=6.36 Hz, 3H).

Example 21

Synthesis of (S)—N-(2-(2-cyano-4,4-difluoropyrrolidin-1-yl)-2-oxoethyl)-4-oxo-4,6,7,8,9,10-hexahydropyrido[1,2-a]azepine-1-carboxamide

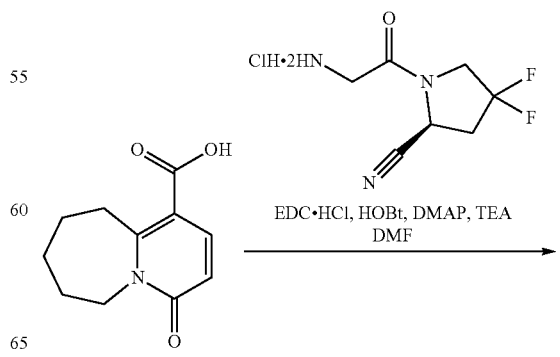

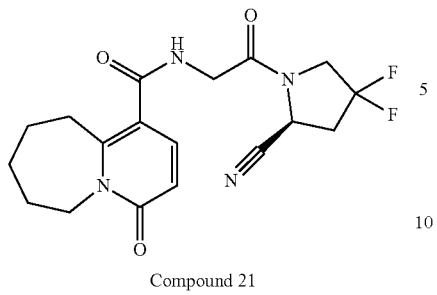

Compound 21

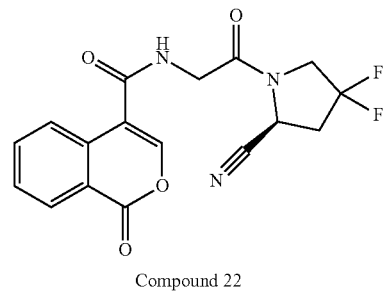

Compound 22

To a stirred solution of 4-oxo-4,6,7,8,9,10-hexahydropyrido[1,2-a]azepine-1-carboxylic acid (0.050 g, 0.241 mmol, 1.0 equiv) in DMF (2 mL), was added (S)-4,4-difluoro-1-glycylpyrrolidine-2-carbonitrile hydrochloride (0.060 g, 0.265 mmol, 1.1 equiv), DMAP (0.002 g, 0.0120 mmol, 0.05 equiv), HOBt (0.050 g, 0.362 mmol, 1.5 equiv) and EDC.HCl (0.070 g, 0.362 mmol, 1.5 equiv). The mixture was allowed to stir at RT for 10 min, Et$_3$N (0.1 mL) was added and the mixture was allowed to stir at RT for overnight. Product formation was confirmed by LCMS and TLC. The reaction mixture was diluted with water and extracted with ethyl acetate (25 mL×2). Combined organic extracts were washed with water (10 mL×4), dried over anhydrous Na$_2$SO$_4$ and concentrated. The crude product obtained was purified by reversed phase HPLC to obtain (S)—N-(2-(2-cyano-4,4-difluoropyrrolidin-1-yl)-2-oxoethyl)-4-oxo-4,6,7, 8,9,10-hexahydropyrido[1,2-a]azepine-1-carboxamide (0.015 g, 17% Yield) as an off-white solid.

LCMS 379.3 [M+H]$^+$ $^1$H NMR (400 MHz, DMSO-d$_6$) δ 8.51 (d, J=5.70 Hz, 1H), 7.37 (d, J=9.21 Hz, 1H), 6.30 (d, J=9.65 Hz, 1H), 5.10 (d, J=7.02 Hz, 1H), 4.34 (br. s., 2H), 4.17-4.31 (m, 2H), 3.96-4.15 (m, 3H), 3.09 (br. s., 2H), 2.72-2.92 (m, 2H), 1.69 (br. s., 3H), 1.59 (br. s., 2H).

Example 22

Synthesis of (S)—N-(2-(2-cyano-4,4-difluoropyrrolidin-1-yl)-2-oxoethyl)-1-oxo-1H-isochromene-4-carboxamide

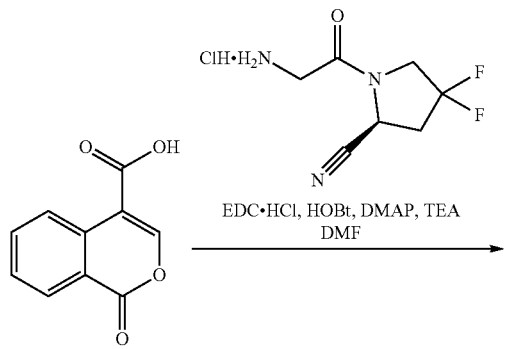

To a stirred solution of 1-oxo-1H-isochromene-4-carboxylic acid (0.200 g, 1.04 mmol, 1.0 equiv) in DMF (5 mL), was added (S)-4,4-difluoro-1-glycylpyrrolidine-2-carbonitrile hydrochloride (0.235 g, 1.04 mmol, 1.0 equiv), HOBt (0.168 g, 1.24 mmol, 1.2 equiv) and EDC.HCl (0.235 g, 1.24 mmol, 1.2 equiv). The mixture was allowed to stir at RT for 10 min. Triethyl amine (0.5 mL) was added and the mixture was allowed to stir at RT for overnight. Product formation was confirmed by LCMS and TLC. The reaction mixture was diluted with water and extracted with ethyl acetate (50 mL×2). Combined organic extracts were washed with water (20 mL×4), dried over anhydrous Na$_2$SO$_4$ and concentrated. The crude product obtained was purified by reversed phase HPLC to obtain (S)—N-(2-(2-cyano-4,4-difluoropyrrolidin-1-yl)-2-oxoethyl)-1-oxo-1H-isochromene-4-carboxamide (0.030 g, 15% Yield) as an off-white solid.

LCMS 362.2 [M+H]$^+$ $^1$H NMR 400 MHz, DMSO-d6) δ 8.90 (br. s., 1H), 8.22 (d, J=7.02 Hz, 1H), 8.05 (d, J=7.89 Hz, 1H), 7.93 (s, 2H), 7.57-7.74 (m, 1H), 5.14 (d, J=6.58 Hz, 1H), 4.01-4.22 (m, 2H), 2.83 (d, J=17.98 Hz, 2H), 1.87 (s, 2H).

Example 23

Synthesis of (S)—N-(1-(2-cyano-4,4-difluoropyrrolidine-1-carbonyl)cyclopropyl)-1-oxo-1,2-dihydroisoquinoline-4-carboxamide

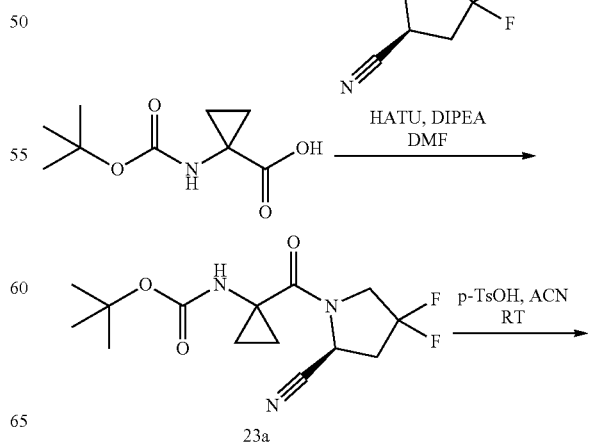

23a

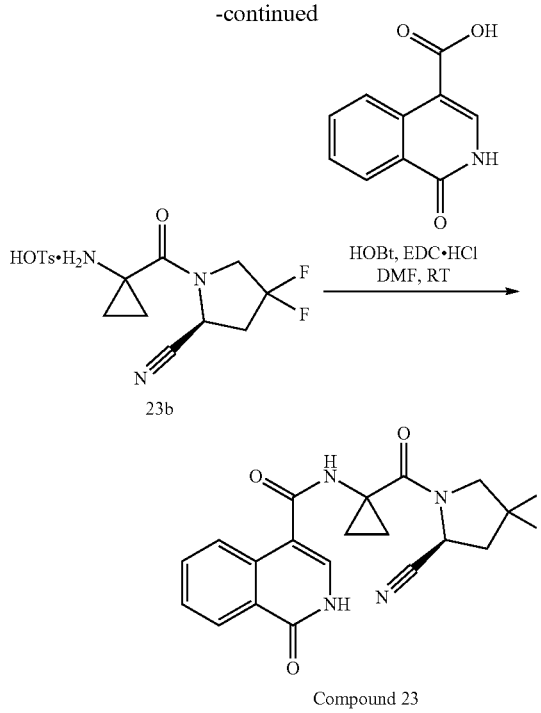

Compound 23

Compound 23a. To a stirred solution of 1-((tert-butoxycarbonyl)amino)cyclopropane-1-carboxylic acid (201 mg, 1.00 mmol, 1 equiv) in DMF (2 mL), was added HATU (760 mg, 2.00 mmol, 2.0 equiv) followed by the addition of (S)-4,4-difluoropyrrolidine-2-carbonitrile hydrochloride (305 mg, 1.00 mmol, 1.0 equiv). The reaction mixture was allowed to stir at RT for 10 min. DIPEA (0.86 mL, 5.00 mmol, 5.0 equiv) was added and the reaction mixture was allowed to stir for overnight at RT. Progress of the reaction was monitored by $^1$H NMR. After completion of the reaction, the reaction mixture was diluted with water (25 mL) and extracted with ethyl acetate (50 mL×2). Combined organic layer was washed with water (25 mL×4), dried over anhydrous sodium sulphate and concentrated under reduced pressure. Crude product obtained was enriched by flash chromatography (0-50% Ethyl acetate in hexane as an eluent) to obtain tert-butyl (S)-(1-(2-cyano-4,4-difluoropyrrolidine-1-carbonyl)cyclopropyl)carbamate (300 mg, 95% Yield) as an off-white solid.

LCMS 315.2 [M+H]$^+$

Compound 23b. To a stirred solution of tert-butyl (S)-(1-(2-cyano-4,4-difluoropyrrolidine-1-carbonyl)cyclopropyl) carbamate (468 mg, 1.48 mmol, 1 equiv) in MeCN (5 mL), was added pTsOH (383 mg, 2.22 mmol, 1.5 equiv). The reaction mixture was allowed to stir for overnight at RT. Progress of the reaction was monitored by NMR. After completion of the reaction, solvent was removed under reduced pressure to obtain (S)-1-(1-aminocyclopropane-1-carbonyl)-4,4-difluoropyrrolidine-2-carbonitrile 4-methylbenzenesulfonate (898 mg, quant.) as a white solid compound.

$^1$H NMR (400 MHz, DMSO-d$_6$) δ 8.66 (br. s., 1H), 7.42-7.54 (m, 2H), 7.09-7.20 (m, J=7.89 Hz, 2H), 5.10-5.28 (m, 1H), 4.14-4.31 (m, 1H), 3.87-4.11 (m, 1H), 2.74-3.03 (m, 1H), 2.29 (s, 3H), 1.42-1.67 (m, 1H), 1.31-1.41 (m, 1H).

Compound 23. To a stirred solution of 1-oxo-1,2-dihydroisoquinoline-4-carboxylic acid (0.398 g, 2.10 mmol, 1.0 equiv) in DMF (5 mL), was added (S)-1-(1-aminocyclopropane-1-carbonyl)-4,4-difluoropyrrolidine-2-carbonitrile 4-methylbenzenesulfonate (0.816 g, 2.10 mmol, 1.0 equiv), HOBt (0.311 g, 2.31 mmol, 1.1 equiv) and EDC.HCl (0.441 g, 2.31 mmol, 1.1 equiv). The mixture was allowed to stir at RT for 10 min. Triethyl amine (0.87 mL) was added and the mixture was allowed to stir at RT for overnight. Product formation was confirmed by LCMS and TLC. The reaction mixture was diluted with water (30 mL) and extracted with ethyl acetate (50 mL×2). Combined organic layer was washed with water (20 mL×4), dried over anhydrous Na$_2$SO$_4$ and concentrated. The crude product obtained was crystallized in MeOH to obtain (S)—N-(1-(2-cyano-4,4-difluoropyrrolidine-1-carbonyl)cyclopropyl)-1-oxo-1,2-dihydroisoquinoline-4-carboxamide (0.140 g, 17% Yield) as an off-white solid.

LCMS 387.2 [M+H]$^+$ $^1$H NMR (400 MHz, DMSO-d$_6$) δ 11.79 (br. s., 1H), 10.72 (br. s., 1H), 8.24 (d, J=7.89 Hz, 1H), 7.76 (t, J=7.67 Hz, 1H), 7.54 (t, J=7.45 Hz, 1H), 5.40 (br. s., 1H), 4.22 (d, J=11.40 Hz, 1H), 3.68 (d, J=11.84 Hz, 1H), 2.87 (br. s., 1H), 2.78 (d, J=14.03 Hz, 1H), 1.65 (br. s., 1H), 1.40 (br. s., 1H), 1.15-1.23 (m, 1H), 1.12 (br. s., 1H).

Example 24

Synthesis of (S)—N-(2-(2-cyano-4,4-difluoropyrrolidin-1-yl)-2-oxoethyl)-3-cyclopropylisonicotinamide

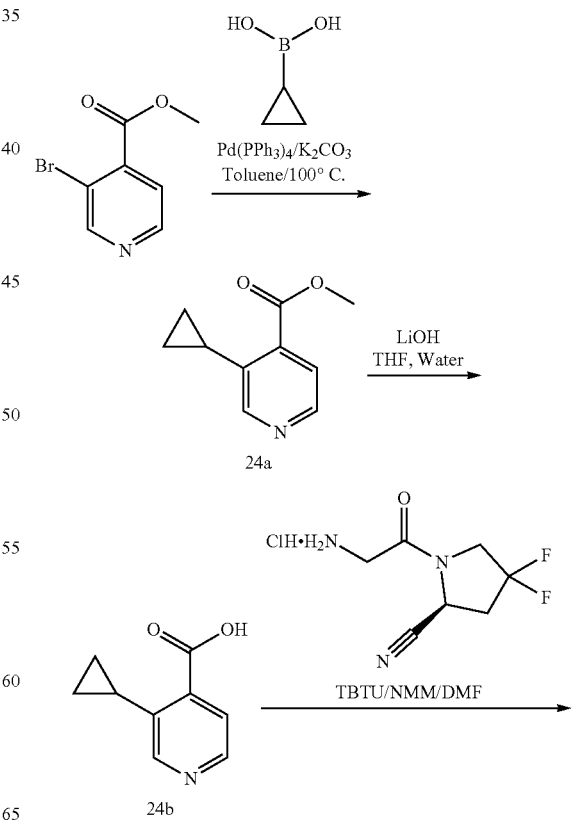

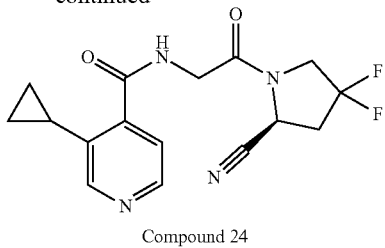

Compound 24

Compound 24a. To a stirred solution of ethyl 3-bromoisonicotinate (0.5 g, 2.32 mmol, 1.0 equiv) in toluene (30 mL) was added cyclopropylboronic acid (0.398 g, 4.63 mmol, 2.0 equiv), $K_2CO_3$ (0.958 g, 6.95 mmol, 3.0 equiv) and resulting reaction mixture purged with $N_2$ gas for 10 min, followed by the addition of $Pd(PPh_3)_4$ (0.133 g, 0.116 mmol, 0.05 equiv). The resulting reaction mixture was heated at 100° C. for overnight. Product formation was confirmed by LCMS. After the completion of reaction, the mixture was filtered through Celite® bed, washed with ethyl acetate (100 mL). Filtrate was concentrated under reduced pressure. The crude product obtained was purified by flash chromatography (0-15% ethyl acetate in hexane as an eluent) to obtain methyl 3-cyclopropylisonicotinate (0.360 g, 87.8% Yield) as a yellow liquid.

LCMS 178.2 [M+H]$^+$ $^1$H NMR (400 MHz, DMSO-d$_6$) δ 8.51 (d, J=5.26 Hz, 1H), 8.37 (s, 1H), 7.56 (d, J=4.82 Hz, 1H), 3.89 (s, 3H), 2.35 (d, J=14.03 Hz, 1H), 0.96-1.04 (m, 2H), 0.80-0.87 (m, 2H).

Compound 24b. To a stirred solution of methyl 3-cyclopropylisonicotinate (0.420 g, 2.37 mmol, 1.0 equiv) in THF (10 mL) and water (5 mL), was added LiOH (0.170 g, 7.11 mmol, and 3.0 equiv). The mixture was allowed to stir at RT for overnight. Product formation was confirmed by LCMS and $^1$H NMR. The reaction mixture was concentrated under reduced pressure and diluted with water (15 mL) and washed with ethyl acetate (15 mL). Aqueous layer was separated and freeze dried on lyophilyzer to obtain 3-cyclopropylisonicotinic acid (0.380 g, 100% Yield) as an off-white solid.

LCMS 164.1 [M+H]$^+$ $^1$H NMR (400 MHz, DMSO-d$_6$) δ 8.54 (d, J=4.82 Hz, 1H), 8.38 (s, 1H), 7.66 (d, J=5.26 Hz, 1H), 2.42-2.46 (m, 1H), 0.99-1.07 (m, 2H), 0.78-0.94 (m, 2H).

Compound 24. To a stirred solution of 3-cyclopropylisonicotinic acid (0.200 g, 1.22 mmol, 1.0 equiv) in DMF (5 mL), was added (S)-4,4-difluoro-1-glycylpyrrolidine-2-carbonitrile hydrochloride (0.33 g, 1.46 mmol, 1.2 equiv) and TBTU (0.587 g, 1.83 mmol, 1.5 equiv) and the mixture was continued to stir at RT for 10 min. N-Methylmorpholine (0.4 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic extracts were washed with water (20 mL×4), dried over anhydrous $Na_2SO_4$ and concentrated. The crude product obtained was purified by flash chromatography (0-50% ethyl acetate in hexane as an eluent) followed by reverse phase purification to obtain (S)—N-(2-(2-cyano-4,4-difluoropyrrolidin-1-yl)-2-oxoethyl)-3-cyclopropylisonicotinamide (0.065 g, 16% Yield) as an white solid.

LCMS 335.2 [M+H]$^+$ $^1$H NMR (400 MHz, DMSO-d$_6$) δ 8.85 (br. s., 1H), 8.44 (d, J=4.82 Hz, 1H), 8.24 (s, 1H), 7.26 (d, J=4.82 Hz, 1H), 5.12 (d, J=8.33 Hz, 1H), 4.27 (d, J=11.84 Hz, 1H), 4.05-4.17 (m, 2H), 2.90 (br. s., 1H), 2.81 (d, J=17.10 Hz, 2H), 2.22 (d, J=5.26 Hz, 1H), 0.97 (d, J=8.33 Hz, 2H), 0.74-0.90 (m, 2H).

Example 25

Synthesis of N-(1-((S)-2-cyano-4,4-difluoropyrrolidin-1-yl)-1-oxopropan-2-yl)-1-oxo-1,2-dihydroisoquinoline-4-carboxamide

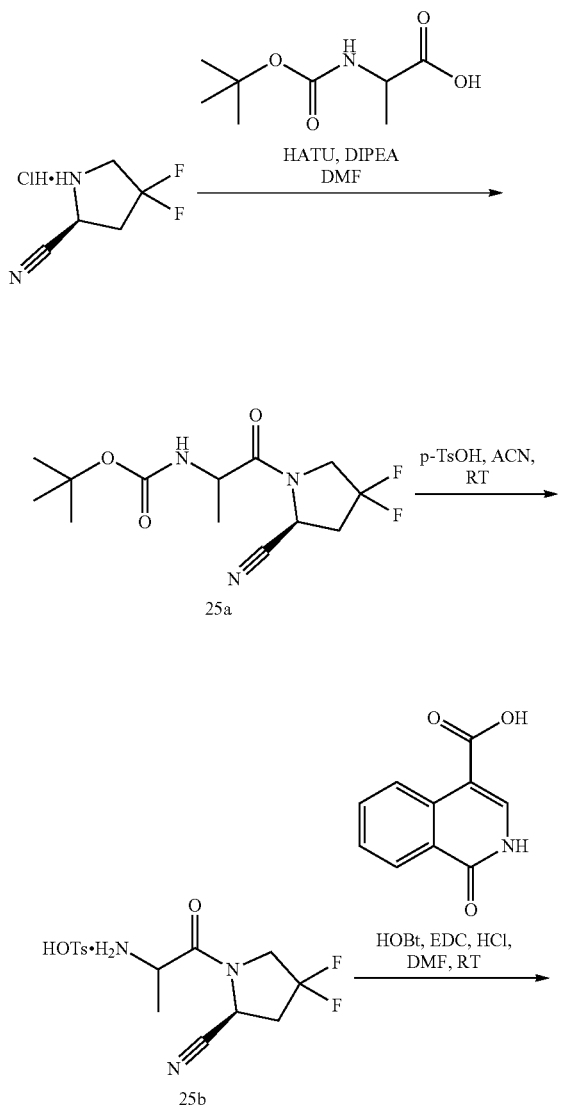

-continued

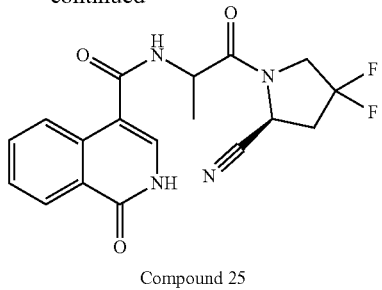

Compound 25

Compound 25a. To a stirred solution of (tert-butoxycarbonyl)alanine (140 mg, 0.73 mmol, 1 equiv) in DMF (3 mL), was added HATU (555 mg, 1.46 mmol, 2.0 equiv) followed by the addition of (S)-4,4-difluoropyrrolidine-2-carbonitrile hydrochloride (225 mg, 0.73 mmol, 1.0 equiv). The reaction mixture was allowed to stir at RT for 10 min. DIPEA (0.63 mL, 3.65 mmol, 5.0 equiv) was added and the reaction mixture was allowed to stir for overnight at RT. Progress of the reaction was monitored by $^1$H NMR. After completion of the reaction, the reaction mixture was diluted with water (25 mL) and extracted with ethyl acetate (50 mL×2). Combined organic layer was washed with water (25 mL×4), dried over anhydrous sodium sulphate and concentrated under reduced pressure. Crude product obtained was enriched by flash chromatography (0-50% Ethyl acetate in hexane as an eluent) to obtain tert-butyl (1-((S)-2-cyano-4,4-difluoropyrrolidin-1-yl)-1-oxopropan-2-yl)carbamate (280 mg, quant.) as an off-white solid.

LCMS 304.2.2 [M+H]$^+$

Compound 25b. To a stirred solution of tert-butyl (1-((S)-2-cyano-4,4-difluoropyrrolidin-1-yl)-1-oxopropan-2-yl)carbamate (500 mg, 1.65 mmol, 1 equiv) in ACN (5 mL), was added PTSA (425 mg, 2.40 mmol, 1.5 equiv). The reaction mixture was allowed to stir the mixture for overnight at RT. Progress of the reaction was monitored by NMR. After completion of the reaction, solvent was removed under reduced pressure to obtain (2S)-1-alanyl-4,4-difluoropyrrolidine-2-carbonitrile 4-methylbenzenesulfonate (630 mg, quant.) as a white solid compound.

$^1$H NMR (400 MHz, DMSO-d$_6$) δ 8.22 (br. s., 2H), 7.44-7.52 (m, 2H), 7.06-7.17 (m, J=7.89 Hz, 2H), 5.12 (d, J=9.21 Hz, 1H), 4.21 (br. s., 1H), 3.61 (d, J=4.38 Hz, 1H), 3.07-3.26 (m, 1H), 2.77-2.96 (m, 1H), 2.29 (s, 3H), 1.20-1.26 (m, 3H).

Compound 25. To a stirred solution of 1-oxo-1,2-dihydroisoquinoline-4-carboxylic acid (0.100 g, 0.53 mmol, 1.0 equiv) in DMF (5 mL), was added (2S)-1-alanyl-4,4-difluoropyrrolidine-2-carbonitrile 4-methylbenzenesulfonate (0.200 g, 0.53 mmol, 1.0 equiv), HOBt (0.078 g, 0.58 mmol, 1.1 equiv) and EDC.HCl (0.111 g, 0.58 mmol, 1.1 equiv). The mixture was allowed to stir at RT for 10 min. Triethyl amine (0.22 mL) was added and the mixture was allowed to stir at RT for overnight. Product formation was confirmed by LCMS and TLC. The reaction mixture was diluted with water and extracted with ethyl acetate (50 mL×2). Combined organic extracts were washed with water (20 mL×4), dried over anhydrous Na$_2$SO$_4$ and concentrated. The crude product obtained was crystallized in pure MeOH to obtain N-(1-((S)-2-cyano-4,4-difluoropyrrolidin-1-yl)-1-oxopropan-2-yl)-1-oxo-1,2-dihydroisoquinoline-4-carboxamide (0.120 g, 60% Yield) as an off-white solid.

LCMS 375.3 [M+H]$^+$ $^1$H NMR (400 MHz, DMSO-d$_6$) δ 11.64 (br. s., 1H), 8.77 (dd, J=6.80, 18.20 Hz, 1H), 8.22 (d, J=7.89 Hz, 2H), 7.73 (br. s., 1H), 7.45-7.65 (m, 2H), 4.98-5.16 (m, 1H), 4.62 (d, J=5.70 Hz, 1H), 4.31 (d, J=17.54 Hz, 2H), 2.92 (br. s., 1H), 2.85 (br. s., 1H), 1.26-1.44 (m, 3H).

Example 26

Synthesis of (S)—N-(2-(2-cyano-4,4-difluoropyrrolidin-1-yl)-2-oxoethyl)-6-fluoro-1-oxo-1,2-dihydroisoquinoline-4-carboxamide

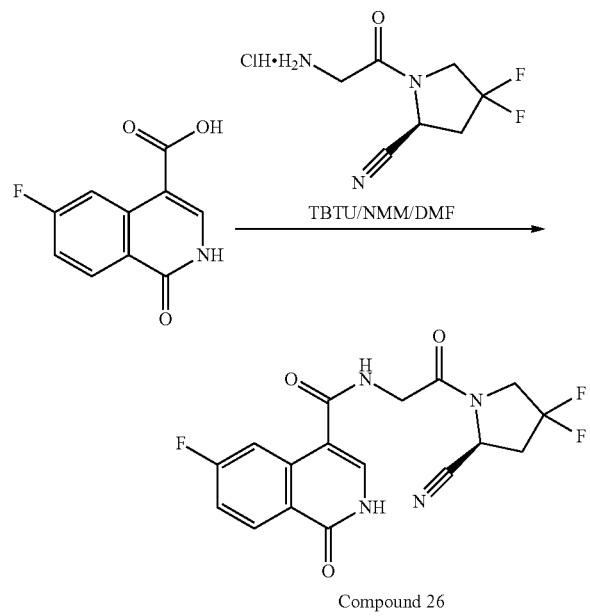

Compound 26

To a stirred solution of 6-fluoro-1-oxo-1,2-dihydroisoquinoline-4-carboxylic acid (0.80 g, 0.386 mmol, 1.0 equiv) in DMF (12 mL), was added (S)-4,4-difluoro-1-glycylpyrrolidine-2-carbonitrile hydrochloride (0.173 g, 0.772 mmol, 2.0 equiv) and TBTU (0.136 g, 0.425 mmol, 1.1 equiv). The mixture was allowed to stir at RT for 10 min. N-methylmorpholine (0.3 mL) was added and the mixture was allowed to stir at RT for overnight. Product formation was confirmed by LCMS and TLC. After completion of reaction, the mixture was diluted with water (15 mL) and extracted with ethyl acetate (15 mL×2). Combined organic layer was washed with water (20 mL×4), dried over anhydrous Na$_2$SO$_4$ and concentrated. The crude product obtained was purified by flash chromatography (0-5% methanol in DCM as an eluent) to obtain (S)—N-(2-(2-cyano-4,4-difluoropyrrolidin-1-yl)-2-oxoethyl)-6-fluoro-1-oxo-1,2-dihydroisoquinoline-4-carboxamide (0.015 g, 10.3% Yield) as an off white solid.

LCMS 379.2 [M+H]$^+$

1H NMR (400 MHz, DMSO-d$_6$) δ 11.74 (br. s., 1H), 8.72 (br. s., 1H), 8.29 (br. s., 1H), 8.07 (d, J=13.16 Hz, 1H), 7.66 (br. s., 1H), 7.41 (d, J=7.89 Hz, 1H), 5.13 (d, J=8.33 Hz, 1H), 4.28 (d, J=16.22 Hz, 1H), 4.05-4.21 (m, 3H), 2.82 (d, J=10.09 Hz, 2H).

Example 27

Synthesis of N-[2-[(2S)-2-cyano-4,4-difluoro-pyrrolidin-1-yl]-2-oxo-ethyl]-3-methoxy-pyridine-4-carboxamide

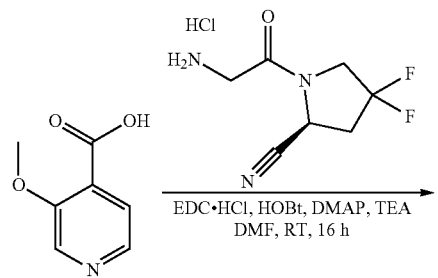

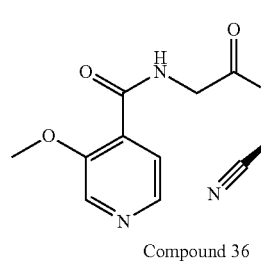

Compound 36

To a stirred solution 3-methoxypyridine-4-carboxylic acid (0.100 g, 0.65 mmol, 1.0 equiv) in DMF (3 mL), was added (2S)-1-(2-aminoacetyl)-4,4-difluoro-pyrrolidine-2-carbonitrile hydrochloride (0.146 g, 0.65 mmol, 1.0 equiv), HOBt (0.105 g, 0.78 mmol, 1.2 equiv) and EDC.HCl (0.149 g, 0.78 mmol, 1.2 equiv). The mixture was allowed to stir at RT for 10 min. Triethyl amine (0.3 mL) was added and the mixture was allowed to stir at RT for overnight. Product formation was confirmed by LCMS and TLC. The reaction mixture was diluted with water and extracted with ethyl acetate (40 mL×2). Combined organic layer was washed with water (15 mL×4), dried over anhydrous Na$_2$SO$_4$ and concentrated. The crude product was washed with hexane and crystallized in diethyl ether to obtain N-[2-[(2S)-2-cyano-4,4-difluoro-pyrrolidin-1-yl]-2-oxo-ethyl]-3-methoxy-pyridine-4-carboxamide (0.060 g, 28% Yield) as an off-white solid.

LCMS 325.2 [M+H]$^+$ $^1$H NMR (DMSO-d$_6$, 400 MHz): δ=8.66-8.72 (m, 1H), 8.59 (s, 1H), 8.35 (d, J=4.8 Hz, 1H), 7.66 (d, J=4.8 Hz, 1H), 5.12 (dd, J=9.0, 2.4 Hz, 1H), 4.15-4.34 (m, 2H), 4.11 (d, J=11.8 Hz, 2H), 3.99 (s, 3H), 2.89 (d, J=3.1 Hz, 1H), 2.82 ppm (d, J=8.8 Hz, 1H).

Example 28

Synthesis of (S)—N-(2-(2-cyano-4,4-difluoropyrrolidin-1-yl)-2-oxoethyl)-3-(trifluoromethyl)isonicotinamide

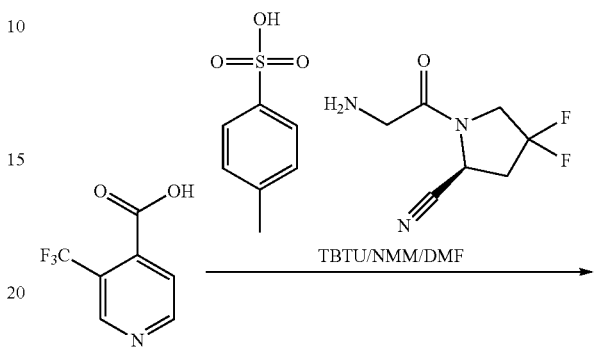

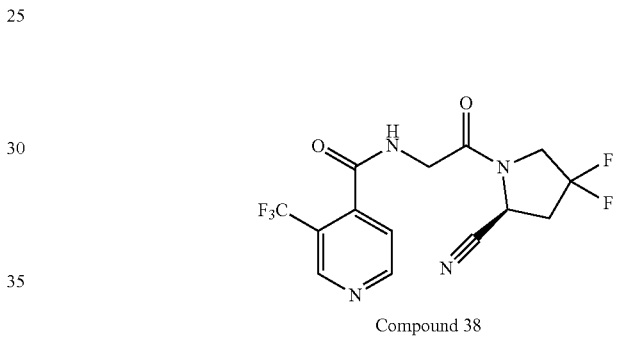

Compound 38

To a stirred solution of 3-(trifluoromethyl)isonicotinic acid (0.100 g, 0.523 mmol, 1.0 equiv) in DMF (7 mL), was added (S)-4,4-difluoro-1-glycylpyrrolidine-2-carbonitrile 4-methylbenzenesulfonate (0.226 g, 0.627 mmol, 1.2 equiv) and TBTU (0.201 g, 0.627 mmol, 1.2 equiv). The mixture was allowed to stir at RT for 10 min. N-Methylmorpholine (0.2 mL) was added and the mixture was allowed to stir at RT for overnight. Product formation was confirmed by LCMS and TLC. After completion of reaction, the mixture was diluted with water (25 mL) and extracted with ethyl acetate (25 mL×2). Combined organic layer was washed with water (20 mL×4), dried over anhydrous Na$_2$SO$_4$ and concentrated. The crude product obtained was crystallized with 20% DCM in hexane to afford (S)—N-(2-(2-cyano-4,4-difluoropyrrolidin-1-yl)-2-oxoethyl)-3-(trifluoromethyl) isonicotinamide (0.070 g, 37% Yield) as an off white solid.

LCMS 363.2 [M+H]$^+$

1H NMR (400 MHz, DMSO-d$_6$) δ 9.09 (br. s., 1H), 9.04 (s, 1H), 8.98 (d, J=4.82 Hz, 1H), 7.61 (d, J=4.82 Hz, 1H), 5.13 (d, J=8.33 Hz, 1H), 4.26 (d, J=15.79 Hz, 1H), 4.18 (br. s., 1H), 4.11 (d, J=11.84 Hz, 2H), 2.82 (d, J=15.35 Hz, 1H), 2.73 (s, 1H).

Example 29

Synthesis of (S)—N-(2-(2-cyano-4,4-difluoropyrrolidin-1-yl)-2-oxoethyl)-3-vinylisonicotinamide

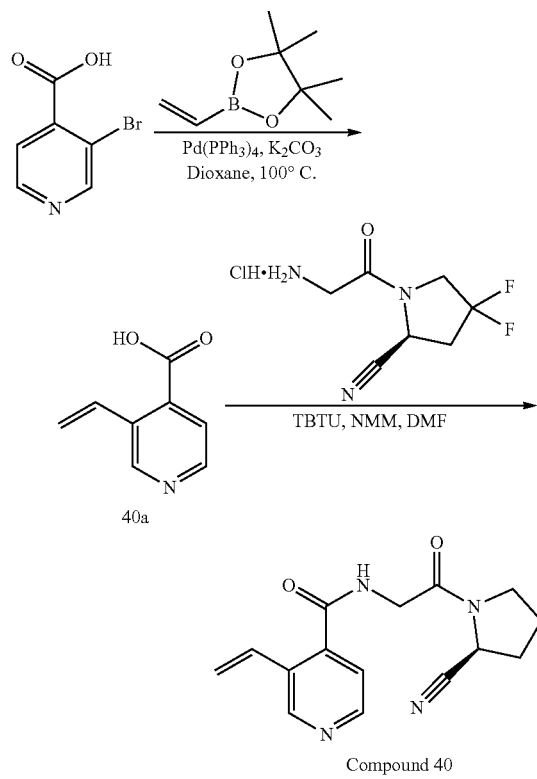

Compound 40a. To a solution of 3-bromoisonicotinic acid (0.300 g, 1.49 mmol, 1.0 equiv) in Dioxane:water (1:1) (12 mL) was added compound 4,4,5,5-tetramethyl-2-vinyl-1,3,2-dioxaborolane (0.34 g, 2.21 mmol, 2.0 equiv), $K_2CO_3$ (0.31 g, 2.23 mmol, 1.5 equiv) and resulting reaction mixture purged with $N_2$ gas for 10 minute, followed by the addition of $Pd(PPh_3)_4$ (0.086 g, 0.074 mmol. 0.05 equiv). The resulting reaction mixture was heated at 100° C. for overnight. Product formation was confirmed by LCMS. The reaction mixture was concentrated and diluted with water (15 mL) and washed with ethyl acetate (10 mL×2). Aqueous layer was separated and freeze dried to obtain 3-vinylisonicotinic acid (Quant. Yield) as a white solid.

LCMS 150.2 [M+H]$^+$

1H NMR (400 MHz, DMSO-$d_6$) δ 8.65 (s, 1H), 8.29 (d, J=4.82 Hz, 1H), 7.26-7.39 (m, 1H), 7.23 (d, J=4.38 Hz, 1H), 5.74 (d, J=17.98 Hz, 1H), 5.19 (d, J=10.96 Hz, 1H).

Compound 40. To a stirred solution of compound 3-vinylisonicotinic acid (0.200 g, 1.342 mmol, 1.0 equiv) in DMF (15 mL), was added (S)-4,4-difluoro-1-glycylpyrrolidine-2-carbonitrile hydrochloride (0.453 g, 2.013 mmol, 1.5 equiv) and TBTU (0.646 g, 2.013 mmol, 1.5 equiv). The mixture was allowed to stir at RT for 10 min. N-Methylmorpholine (0.5 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic extracts were washed with water (20 mL×6), dried over anhydrous $Na_2SO_4$ and concentrated. The crude product obtained was purified by flash chromatography (5% MeOH in DCM as an eluent) followed by reverse phase purification to obtain (S)—N-(2-(2-cyano-4,4-difluoropyrrolidin-1-yl)-2-oxoethyl)-3-vinylisonicotinamide (0.012 g, 3% Yield) as a white solid.

LCMS 320.2 [M+H]$^+$ $^1$H NMR (400 MHz, DMSO-$d_6$) δ 8.85-9.00 (m, 1H), 8.56 (d, J=4.82 Hz, 1H), 7.35 (d, J=4.82 Hz, 1H), 7.02 (dd, J=11.40, 17.54 Hz, 1H), 6.01 (d, J=17.54 Hz, 1H), 5.43 (d, J=10.96 Hz, 1H), 5.14 (d, J=8.33 Hz, 1H), 4.28 (br. s., 1H), 3.99-4.21 (m, 3H), 2.91 (br. s., 1H), 2.82 (d, J=17.54 Hz, 1H), 2.67 (br. s., 1H).

Example 30

Synthesis of N-[2-[(2S)-2-cyano-4,4-difluoro-pyrrolidin-1-yl]-2-oxo-ethyl]-3-(1-piperidyl)pyridine-4-carboxamide To a stirred solution 3-(1-piperidyl)pyridine-4-carboxylic acid (0.100 g, 0.49 mmol, 1.0 equiv) in DMF (3 mL), was added (2S)-1-(2-aminoacetyl)-4,4-difluoro-pyrrolidine-2-carbonitrile hydrochloride (0.110 g, 0.49 mmol, 1.0 equiv), HOBt (0.078 g, 0.58 mmol, 1.2 equiv) and EDC.HCl (0.110 g, 0.58 mmol, 1.2 equiv). The mixture was allowed to stir at RT for 10 min. Triethyl amine (0.21 mL) was added and the mixture was allowed to stir at RT for overnight. Product formation was confirmed by LCMS and TLC. The reaction mixture was diluted with water and extracted with ethyl acetate (40 mL×2). Combined organic layer was washed with water (15 mL×4), dried over anhydrous $Na_2SO_4$ and concentrated. The crude product was purified by column chromatography (2% MeOH in DCM) to obtain N-[2-[(2S)-2-cyano-4,4-difluoro-pyrrolidin-1-yl]-2-oxo-ethyl]-3-(1-piperidyl)pyridine-4-carboxamide (0.050 g, 27.32% Yield) as an off-white solid.

LCMS 378.3 [M+H]$^+$ $^1$H NMR (DMSO-$d_6$, 400 MHz) δ 9.78 (br. s., 1H), 8.58 (br. s., 1H), 8.40 (br. s., 1H), 7.64 (d, J=4.8 Hz, 1H), 5.14 (d, J=9.2 Hz, 1H), 4.17-4.37 (m, 2H), 4.01-4.17 (m, 1H), 2.94-3.07 (m, 3H), 2.90 (br. s., 1H), 2.82 (d, J=9.6 Hz, 1H), 1.72 (br. s., 3H), 1.53 ppm (br. s., 2H).

Example 31

Synthesis of (S)—N-(2-(2-cyano-4,4-difluoropyrrolidin-1-yl)-2-oxoethyl)-3-(3,5-difluorophenyl)isonicotinamide

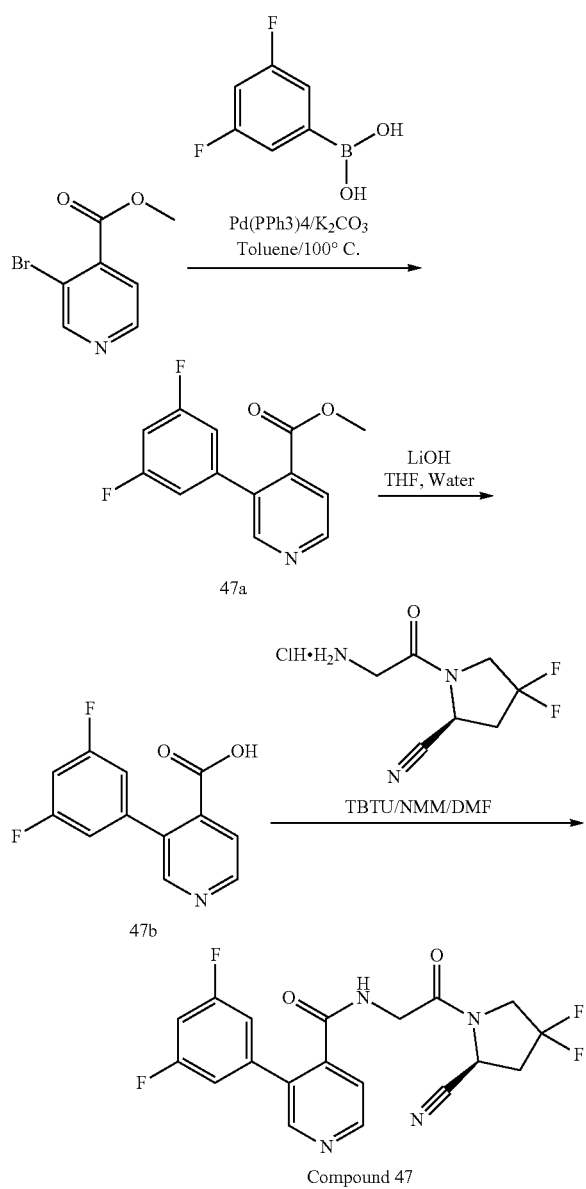

Compound 47

Compound 47a. To a solution of ethyl 3-bromoisonicotinate (0.25 g, 1.16 mmol, 1.0 equiv) in toluene (15 mL) was added (3,5-difluorophenyl)boronic acid (0.366 g, 2.315 mmol, 2.0 equiv), K$_2$CO$_3$ (0.48 g, 3.472 mmol, 3.0 equiv) and resulting reaction mixture purged with N$_2$ gas for 10 minute followed by the addition of Pd(PPh$_3$)$_4$ (0.69 g, 0.058 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-10% ethyl acetate in hexane as an eluent) to obtain methyl 3-(3,5-difluorophenyl)isonicotinate (0.34 g, quant.) as an off white solid.

LCMS 250.2 [M+H]$^+$ $^1$H NMR (400 MHz, DMSO-d$_6$) δ 8.80 (d, J=4.82 Hz, 1H), 8.72 (s, 1H), 8.40 (s, 1H), 7.77 (d, J=5.26 Hz, 1H), 7.27-7.45 (m, 1H), 7.16 (d, J=6.58 Hz, 1H), 3.71 (s, 3H).

Compound 47b. To a stirred solution of methyl 3-(3,5-difluorophenyl)isonicotinate (0.34 g, 1.364 mmol, 1.0 equiv) in THF (10 mL) and water (5 mL), was added LiOH (0.98 g, 4.08 mmol, 3.0 equiv). The mixture was allowed to stir at RT for overnight. Product formation was confirmed by LCMS and $^1$H NMR Spectroscopy. The reaction mixture was concentrated and diluted with water (15 mL) and washed with ethyl acetate (15 mL). Aqueous layer was separated and freeze dried on lyophilyzer to obtain 3-(3,5-difluorophenyl)isonicotinic acid (0.340 g, quant. as an off-white solid).

LCMS 236.2 [M+H]$^+$ $^1$H NMR (400 MHz, DMSO-d$_6$) δ 8.45 (s, 1H), 8.41 (d, J=4.82 Hz, 1H), 7.32 (d, J=7.02 Hz, 2H), 7.05-7.22 (m, 2H).

Compound 47. To a stirred solution of 3-(3,5-difluorophenyl)isonicotinic acid (0.200 g, 0.845 mmol, 1.0 equiv) in DMF (10 mL), was added (S)-4,4-difluoro-1-glycylpyrrolidine-2-carbonitrile hydrochloride (0.38 g, 1.46 mmol, 2.0 equiv) and TBTU (0.587 g, 1.83 mmol, 1.5 equiv). The mixture was allowed to stir at RT for 10 min. N-methylmorpholine (0.4 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic layer was washed with water (20 mL×4), dried over anhydrous Na$_2$SO$_4$ and concentrated. The crude product obtained was purified by flash chromatography (0-50% ethyl acetate in hexane as an eluent) followed by reversed phase purification to obtain (S)—N-(2-(2-cyano-4,4-difluoropyrrolidin-1-yl)-2-oxoethyl)-3-(3,5-difluorophenyl)isonicotinamide (0.020 g, 5.8% Yield) as an white solid.

LCMS 407.3 [M+H]$^+$ $^1$H NMR (DMSO-d$_6$, 400 MHz) δ 9.01 (br. s., 1H), 8.65-8.74 (m, 1H), 7.49 (d, J=4.8 Hz, 1H), 7.22-7.33 (m, 1H), 5.08 (d, J=7.0 Hz, 1H), 4.15-4.33 (m, 1H), 3.92-4.15 (m, 3H), 2.89 (br. s., 1H), 2.79 ppm (d, J=13.2 Hz, 1H).

Example 32

Synthesis of (S)—N-(2-(2-cyano-4,4-difluoropyrrolidin-1-yl)-2-oxoethyl)-3-(4-fluorophenyl)isonicotinamide

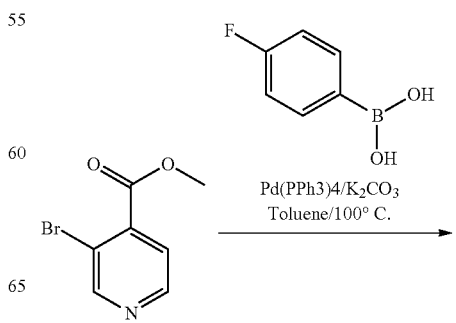

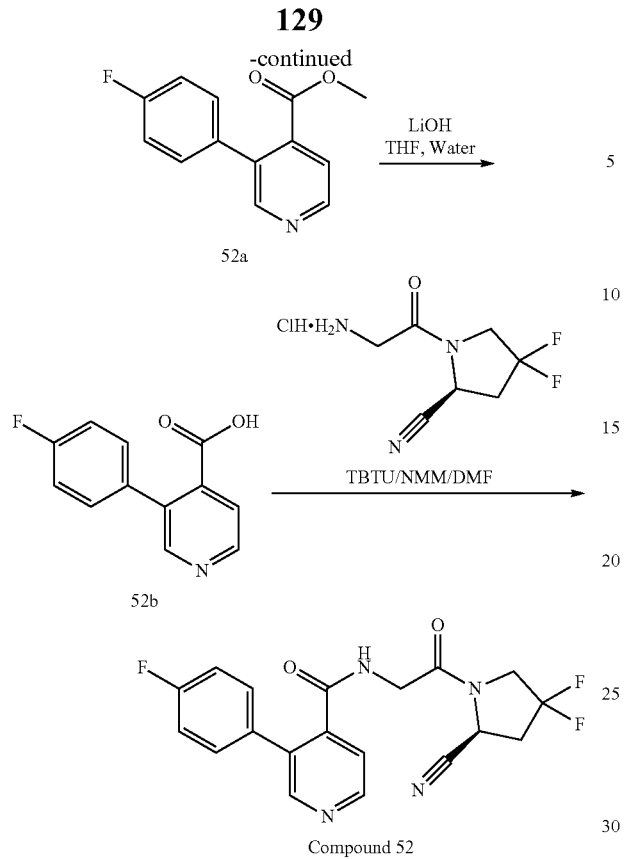

Compound 52a. To a solution of ethyl 3-bromoisonicotinate (0.2 g, 0.93 mmol, 1.0 equiv) in Toluene (15 mL) was added (4-fluorophenyl)boronic acid (0.21 g, 1.85 mmol, 2.0 equiv), $K_2CO_3$ (0.38 g, 2.78 mmol, 3.0 equiv). The resulting reaction mixture purged with $N_2$ gas for 10 minute, followed by the addition of $Pd(PPh_3)_4$ (0.054 g, 0.046 mmol. 0.05 equiv). The reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-20% ethyl acetate in hexane as an eluent) to obtain methyl 3-(4-fluorophenyl)isonicotinate (0.185 g, 83.3%) as an off white solid.

LCMS 232.2 [M+H]$^+$ $^1$H NMR (400 MHz, DMSO-d$_6$) δ 8.74 (d, J=5.26 Hz, 1H), 8.70 (s, 1H), 7.70 (d, J=4.82 Hz, 1H), 7.42 (dd, J=5.70, 8.33 Hz, 2H), 7.31 (t, J=8.77 Hz, 2H), 3.68 (s, 3H).

Compound 52b. To a stirred solution of methyl 3-(4-fluorophenyl)isonicotinate (0.37 g, 1.601 mmol, 1.0 equiv) in THF (20 mL) and water (10 mL), was added LiOH (0.192 g, 8.01 mmol, 5.0 equiv). The mixture was allowed to stir at RT for overnight. Product formation was confirmed by LCMS and $^1$H NMR Spectroscopy. The reaction mixture was concentrated and diluted with water (20 mL), washed with ethyl acetate (15 mL×2). Aqueous layer was separated and freeze dried to obtain 3-(4-fluorophenyl)isonicotinic acid (Quant. Yield) as a white solid

LCMS 218.2 [M+H]$^+$ $^1$H NMR (400 MHz, DMSO-d$_6$) δ 8.38 (s, 1H), 8.36 (d, J=4.82 Hz, 1H), 7.61 (dd, J=5.92, 8.11 Hz, 2H), 7.18 (t, J=8.77 Hz, 2H), 7.13 (d, J=4.82 Hz, 1H).

Compound 52. To a stirred solution of 3-(4-fluorophenyl)isonicotinic acid (0.200 g, 0.92 mmol, 1.0 equiv) in DMF (20 mL), was added (S)-4,4-difluoro-1-glycylpyrrolidine-2-carbonitrile hydrochloride (0.228 g, 1.014 mmol, 1.1 equiv) and TBTU (0.325 g, 1.014 mmol, 1.5 equiv). The mixture was allowed to stir at RT for 10 min. N-Methylmorpholine (0.3 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic extracts were washed with water (20 mL×4), dried over anhydrous $Na_2SO_4$ and concentrated. The crude product obtained was purified by flash chromatography (5% MeOH in DCM as an eluent) followed by reverse phase purification to obtain (S)—N-(2-(2-cyano-4,4-difluoropyrrolidin-1-yl)-2-oxoethyl)-3-(4-fluorophenyl)isonicotinamide (0.005 g, 2% Yield) as a white solid.

LCMS 389.3 [M+H]$^+$

1H NMR (400 MHz, DMSO-d$_6$) δ 8.97 (br. s., 1H), 8.65 (br. s., 2H), 7.57 (br. s., 2H), 7.45 (br. s., 1H), 7.23 (br. s., 2H), 5.08 (br. s., 1H), 4.20 (br. s., 1H), 4.05 (br. s., 2H), 2.87 (br. s., 1H), 2.81 (br. s., 2H).

Example 33

Synthesis of (S)-3-(5-chloro-2-fluorophenyl)-N-(2-(2-cyano-4,4-difluoropyrrolidin-1-yl)-2-oxoethyl) isonicotinamide

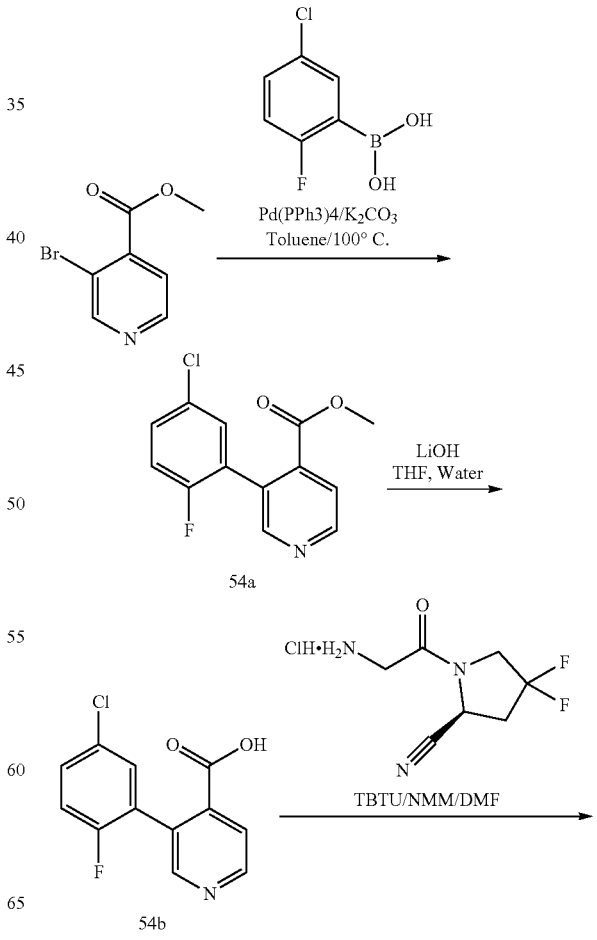

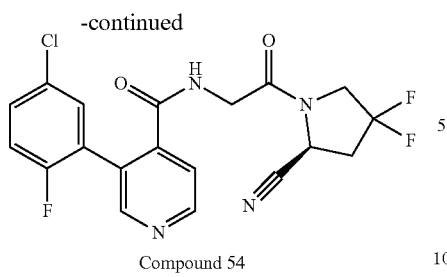

Compound 54

Compound 54a. To a solution of ethyl 3-bromoisonicotinate (0.25 g, 1.16 mmol, 1.0 equiv) in Toluene (15 mL) was added (5-chloro-2-fluorophenyl)boronic acid (0.403 g, 2.315 mmol, 2.0 equiv), $K_2CO_3$ (0.48 g, 3.472 mmol, 3.0 equiv) and resulting reaction mixture purged with $N_2$ gas for 10 minute, followed by the addition of $Pd(PPh_3)_4$ (0.69 g, 0.058 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-10% ethyl acetate in hexane as an eluent) to obtain methyl 3-(5-chloro-2-fluorophenyl)isonicotinate (0.400 g, quant. as an off white solid).

LCMS 266.2 $[M+H]^+$ $^1H$ NMR (400 MHz, DMSO-$d_6$) δ 8.84 (d, J=5.26 Hz, 1H), 8.73 (s, 1H), 7.83 (d, J=5.26 Hz, 1H), 7.49-7.68 (m, 2H), 7.29-7.41 (m, 2H), 3.72 (s, 3H).

Compound 54b. To a stirred solution of compound methyl 3-(5-chloro-2-fluorophenyl)isonicotinate (0.4 g, 1.504 mmol, 1.0 equiv) in THF (20 mL) and water (10 mL), was added LiOH (0.108 g, 4.51 mmol, 3.0 equiv). The mixture was allowed to stir at RT for overnight. Product formation was confirmed by LCMS and $^1H$ NMR Spectroscopy. The reaction mixture was concentrated and diluted with water (15 mL) and washed with ethyl acetate (15 mL). Aqueous layer was separated and freeze dried on lyophilyzer to obtain 3-(5-chloro-2-fluorophenyl)isonicotinic acid (0.400 quant. as a white solid).

LCMS 252.2 $[M+H]^+$ $^1H$ NMR (400 MHz, DMSO-$d_6$) δ 8.46 (d, J=4.82 Hz, 1H), 8.34 (s, 1H), 7.32-7.52 (m, 3H), 7.24 (t, J=9.21 Hz, 1H).

Compound 54. To a stirred solution of compound 3-(5-chloro-2-fluorophenyl)isonicotinic acid (0.200 g, 0.796 mmol, 1.0 equiv) in DMF (20 mL), was added (S)-4,4-difluoro-1-glycylpyrrolidine-2-carbonitrile hydrochloride (0.358 g, 1.59 mmol, 2.0 equiv) and TBTU (0.383 g, 1.19 mmol, 1.5 equiv). The mixture was allowed to stir at RT for 10 min. N-Methylmorpholine (0.3 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic layer was washed with water (20 mL×4), dried over anhydrous $Na_2SO_4$ and concentrated. The crude product obtained was purified by flash chromatography (0-50% ethyl acetate in hexane as an eluent) followed by reverse phase purification to obtain (S)-3-(5-chloro-2-fluorophenyl)-N-(2-(2-cyano-4,4-difluoropyrrolidin-1-yl)-2-oxoethyl)isonicotinamide (0.055 g, 16.41% Yield) as an white solid.

LCMS 423.2 $[M+H]^+$

1H NMR $^1H$ NMR (400 MHz, DMSO-$d_6$) δ 8.92 (br. s., 1H), 8.78 (d, J=4.82 Hz, 1H), 8.64 (s, 1H), 7.61 (d, J=4.82 Hz, 1H), 7.52 (d, J=7.02 Hz, 2H), 7.31 (s, 1H), 5.07 (d, J=9.21 Hz, 1H), 3.93-4.09 (m, 2H), 2.80 (br. s., 2H).

Example 34

Synthesis of N-(2-((S)-2-cyano-4,4-difluoropyrrolidin-1-yl)-2-oxoethyl)-4-oxo-3,4,4a,8a-tetrahydrophthalazine-1-carboxamide

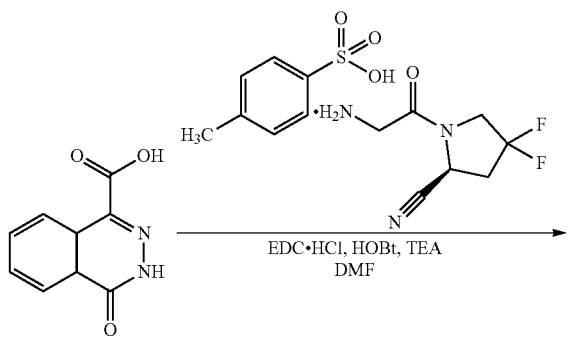

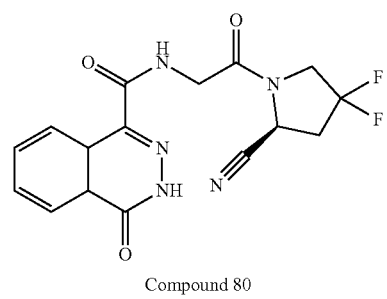

Compound 80

To a stirred solution of 4-oxo-3,4,4a,8a-tetrahydrophthalazine-1-carboxylic acid (0.200 g, 1.05 mmol, 1.0 equiv) in DMF (5 mL), was added (S)-4,4-difluoro-1-glycylpyrrolidine-2-carbonitrile 4-methylbenzenesulfonate (0.380 g, 1.05 mmol, 1.0 equiv), HOBt (0.170 g, 1.26 mmol, 1.2 equiv) and EDC.HCl (0.240 g, 1.26 mmol, 1.2 equiv). The mixture was allowed to stir at RT for 10 min. Triethyl amine (0.3 mL) was added and the mixture was allowed to stir at RT for overnight. Product formation was confirmed by LCMS and TLC. The reaction mixture was diluted with water and extracted with ethyl acetate (50 mL×2). Combined organic layer was washed with water (20 mL×4), dried over anhydrous $Na_2SO_4$ and concentrated. The crude product obtained was purified by reversed phase HPLC to obtain N-(2-((S)-2-cyano-4,4-difluoropyrrolidin-1-yl)-2-oxoethyl)-4-oxo-3,4,4a,8a-tetrahydrophthalazine-1-carboxamide (0.110 g, 29% Yield) as an off-white solid.

LCMS 363 $[M+H]^+$ $^1H$ NMR (400 MHz, DMSO-$d_6$) δ13.04 (s, 1H), 8.84 (br. s., 1H), 8.61 (d, J=7.45 Hz, 1H), 8.30 (d, J=7.89 Hz, 1H), 7.94-7.99 (m, 1H), 7.90 (d, J=7.02 Hz, 1H), 5.14 (d, J=6.58 Hz, 1H), 4.30 (br. s., 1H), 4.12-4.23 (m, 2H), 4.08 (d, J=11.84 Hz, 1H), 2.91 (br. s., 1H), 2.83 (d, J=17.98 Hz, 1H).

Example 35

Synthesis of N-[2-[(2S)-2-cyano-4,4-difluoro-pyrrolidin-1-yl]-2-oxo-ethyl]-3-methyl-4-oxo-phthalazine-1-carboxamide

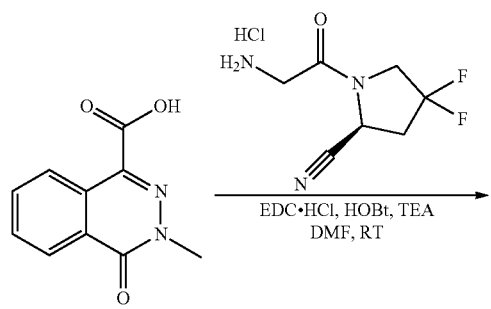

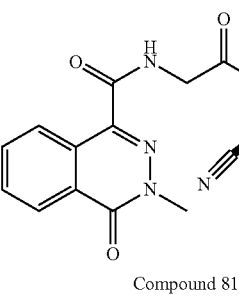

Compound 81

Example 36

Synthesis of (S)—N-(4-(2-cyano-4,4-difluoropyrrolidin-1-yl)-4-oxobutyl)-1-oxo-1,2-dihydroisoquinoline-4-carboxamide

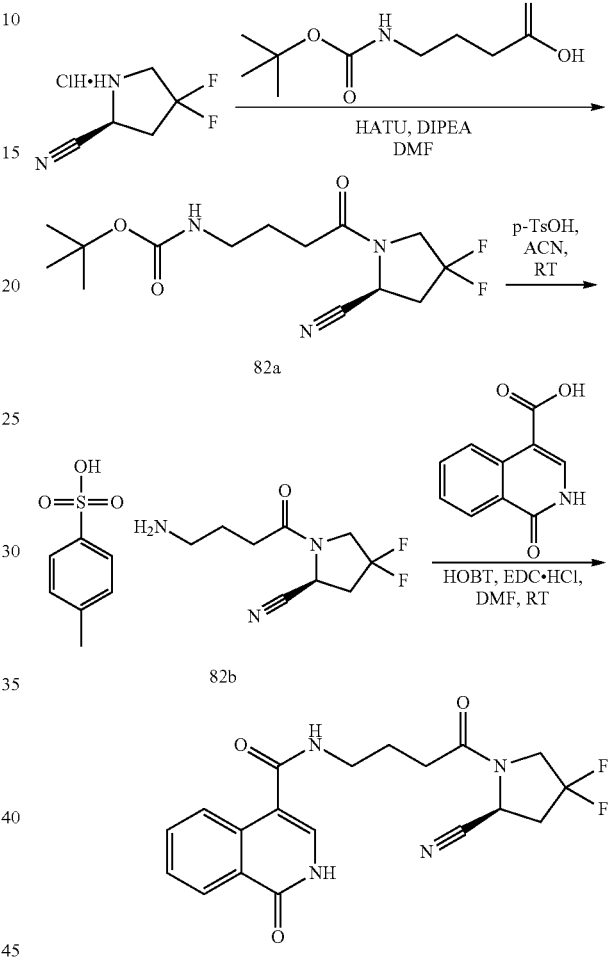

Compound 82

To a stirred solution 3-methyl-4-oxo-phthalazine-1-carboxylic acid (0.100 g, 0.49 mmol, 1.0 equiv) in DMF (3 mL), was added (2S)-1-(2-aminoacetyl)-4,4-difluoro-pyrrolidine-2-carbonitrile hydrochloride (0.110 g, 0.49 mmol, 1.0 equiv), HOBt (0.080 g, 0.59 mmol, 1.2 equiv) and EDC.HCl (0.113 g, 0.59 mmol, 1.2 equiv). The mixture was allowed to stir at RT for 10 min. Triethyl amine (0.21 mL) was added and the mixture was allowed to stir at RT for overnight. Product formation was confirmed by LCMS and TLC. The reaction mixture was diluted with water and extracted with ethyl acetate (30 mL×2). Combined organic layer was washed with water (15 mL×4), dried over anhydrous $Na_2SO_4$ and concentrated. The crude product was washed with hexane and crystallized in diethyl ether to obtain (S)—N-(2-(2-cyano-4,4-difluoropyrrolidin-1-yl)-2-oxo-ethyl)-3-methyl-4-oxo-3,4-dihydrophthalazine-1-carboxamide (0.040 g, 21.7% Yield) as an off-white solid.

LCMS 376.3 [M+H]$^+$ $^1$H NMR (DMSO-$d_6$, 400 MHz): δ=8.93 (t, J=5.7 Hz, 1H), 8.66 (d, J=7.9 Hz, 1H), 8.33 (d, J=7.9 Hz, 1H), 7.86-8.03 (m, 2H), 5.14 (d, J=7.0 Hz, 1H), 4.31 (br. s., 1H), 4.07-4.24 (m, 3H), 2.92 (br. s., 1H), 2.83 ppm (d, J=17.1 Hz, 1H).

Compound 82a. To a stirred solution of 4-((tert-butoxycarbonyl)amino)butanoic acid (200 mg, 0.98 mmol, 1 equiv) in DMF (4 mL), was added HATU (745 mg, 1.96 mmol, 2.0 equiv) followed by the addition of (S)-4,4-difluoropyrrolidine-2-carbonitrile hydrochloride (599 mg, 1.97 mmol, 2.0 equiv). The reaction mixture was allowed to stir at RT for 10 min. DIPEA (0.8 mL, 4.7 mmol, 5.0 equiv) was added and the reaction mixture was allowed to stir for overnight at RT. Progress of the reaction was monitored by LCMS. After completion of the reaction, the reaction mixture was diluted with water (25 mL) and extracted with ethyl acetate (50 mL×2). Combined organic layer was washed with water (25 mL×4), dried over anhydrous sodium sulphate and concentrated under reduced pressure. Crude product obtained was enriched by flash chromatography (0-50% Ethyl acetate in hexane as an eluent) to obtain tert-butyl (S)-(4-(2-cyano-4,4-difluoropyrrolidin-1-yl)-4-oxobutyl)carbamate (267 mg, 85% Yield) as an off-white solid.

LCMS 318.3 [M+H]$^+$

Compound 82b. To a stirred solution of tert-butyl (S)-(4-(2-cyano-4,4-difluoropyrrolidin-1-yl)-4-oxobutyl)carbamate (267 mg, 0.84 mmol, 1 equiv) in ACN (3 mL), was added PTSA (217 mg, 1.26 mmol, 1.5 equiv). The reaction mixture was allowed to stir the mixture for overnight at RT. Progress of the reaction was monitored by NMR. After completion of the reaction, solvent was removed under reduced pressure to obtain (S)-1-(4-aminobutanoyl)-4,4-difluoropyrrolidine-2-carbonitrile 4-methylbenzenesulfonate (425 mg, quant.) as a white solid compound.

$^1$H NMR (DMSO-d$_6$, 400 MHz) δ 7.68 (br. s., 2H), 7.48 (d, J=8.3 Hz, 2H), 7.12 (d, J=7.9 Hz, 2H), 5.04 (d, J=9.2 Hz, 1H), 4.07 (d, J=15.8 Hz, 1H), 3.91-4.02 (m, 1H), 2.77-2.93 (m, 2H), 2.38-2.44 (m, 1H), 2.29 (s, 4H), 1.99-2.12 (m, 2H), 1.69-1.86 ppm (m, 3H).

Compound 82. To a stirred solution of 1-oxo-1,2-dihydroisoquinoline-4-carboxylic acid (206 mg, 1.09 mmol, 1.0 equiv) in DMF (3 mL), was added (S)-1-(4-aminobutanoyl)-4,4-difluoropyrrolidine-2-carbonitrile 4-methylbenzenesulfonate (425 mg, 1.09 mmol, 1.0 equiv), HOBt (160 mg, 1.19 mmol, 1.1 equiv) and EDC.HCl (229 mg, 1.19 mmol, 1.1 equiv). The mixture was allowed to stir at RT for 10 min. Triethyl amine (0.4 mL) was added and the mixture was allowed to stir at RT for overnight. Product formation was confirmed by LCMS and TLC. The reaction mixture was diluted with water and extracted with ethyl acetate (50 mL×2). Combined organic layer was washed with water (20 mL×4), dried over anhydrous Na$_2$SO$_4$ and concentrated. The crude product obtained was crystallized in pure MeOH to obtain (S)—N-(4-(2-cyano-4,4-difluoropyrrolidin-1-yl)-4-oxobutyl)-1-oxo-1,2-dihydroisoquinoline-4-carboxamide (17 mg, 4% Yield) as an off-white solid.

LCMS 389.3 [M+H]$^+$ $^1$H NMR (DMSO-d$_6$, 400 MHz) δ 11.57 (br. s., 1H), 8.34 (br. s., 1H), 8.22 (d, J=7.9 Hz, 2H), 7.73 (t, J=7.5 Hz, 1H), 7.42-7.60 (m, 2H), 5.05 (d, J=8.3 Hz, 1H), 3.90-4.20 (m, 4H), 3.22-3.29 (m, 2H), 2.86 (br. s., 1H), 2.78 (d, J=12.3 Hz, 1H), 2.20-2.40 (m, 2H), 1.69-1.86 ppm (m, 2H).

Example 37

Synthesis of (S)—N-(2-(2-cyano-4,4-difluoropyrrolidin-1-yl)-2-oxoethyl)-H-indazole-5-carboxamide

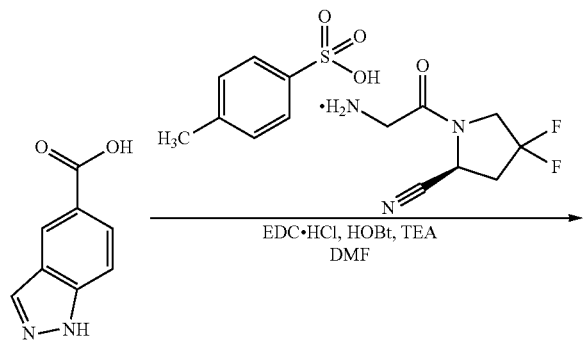

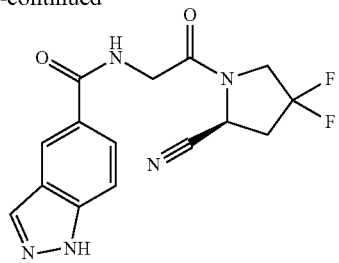

Compound 83

To a stirred solution of 1H-indazole-5-carboxylic acid (0.200 g, 1.2 mmol, 1.0 equiv) in DMF (10 mL), was added (S)-4,4-difluoro-1-glycylpyrrolidine-2-carbonitrile PTSA (0.444 g, 1.2 mmol, 1.0 equiv), HOBt (0.198 g, 1.46 mmol, 1.2 equiv) and EDC.HCl (0.280 g, 1.46 mmol, 1.2 equiv). The mixture was allowed to stir at RT for 10 min. Triethyl amine (0.4 mL) was added and the mixture was allowed to stir at RT for overnight. Product formation was confirmed by LCMS and TLC. The reaction mixture was diluted with water and extracted with ethyl acetate (50 mL×2). Combined organic layer was washed with water (20 mL×4), dried over anhydrous Na$_2$SO$_4$ and concentrated. The crude product obtained was purified by reverse phase HPLC to obtain (S)—N-(2-(2-cyano-4,4-difluoropyrrolidin-1-yl)-2-oxoethyl)-1H-indazole-5-carboxamide (0.020 g, 10% Yield) a white solid.

LCMS 334 [M+H]$^+$ $^1$H NMR (400 MHz, DMSO-d$_6$) δ 13.29 (br. s., 1H), 8.79 (br. s., 1H), 8.38 (s, 1H), 8.23 (s, 1H), 7.88 (d, J=8.77 Hz, 1H), 7.60 (d, J=8.77 Hz, 1H), 5.10 (d, J=8.77 Hz, 1H), 4.31 (br. s., 1H), 4.04-4.21 (m, 3H), 2.90-2.81 (m, 2H).

Example 38

Synthesis of (S)—N-(2-(2-cyano-4,4-difluoropyrrolidin-1-yl)-2-oxoethyl)furo[2,3-c]pyridine-2-carboxamide

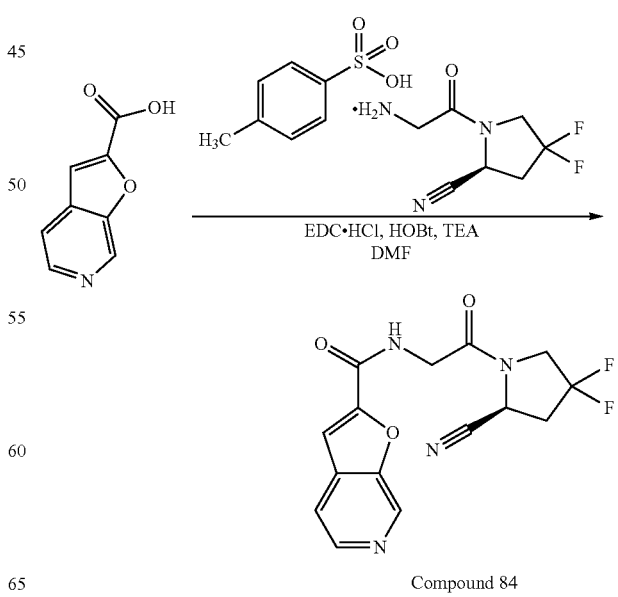

Compound 84

To a stirred solution of furo[2,3-c]pyridine-2-carboxylic acid (0.050 g, 0.30 mmol, 1.0 equiv) in DMF (10 mL), was added (S)-4,4-difluoro-1-glycylpyrrolidine-2-carbonitrile 4-methylbenzenesulfonate (0.110 g, 0.30 mmol, 1.0 equiv), HOBt (0.049 g, 0.36 mmol, 1.2 equiv) and EDC.HCl (0.069 g, 0.36 mmol, 1.2 equiv). The mixture was allowed to stir at RT for 10 min. Triethyl amine (0.1 mL) was added and the mixture was allowed to stir at RT for overnight. Product formation was confirmed by LCMS and TLC. The reaction mixture was diluted with water and extracted with ethyl acetate (50 mL×2). Combined organic extracts were washed with water (20 mL×4), dried over anhydrous $Na_2SO_4$ and concentrated. The crude product obtained was purified by reverse phase HPLC to obtain (S)—N-(2-(2-cyano-4,4-difluoropyrrolidin-1-yl)-2-oxoethyl)furo[2,3-c]pyridine-2-carboxamide (0.020 g, 19% Yield) as a white solid.

LCMS 335 [M+H]$^+$ $^1$H NMR (DMSO-d6, 400 MHz) δ (br. s., 1H), 9.09 (s, 1H), 8.49 (d, J=5.3 Hz, 1H), 7.84 (d, J=5.3 Hz, 1H), 7.69 (s, 1H), 5.11 (d, J=9.6 Hz, 1H), 4.25-4.39 (m, 1H), 4.04-4.22 (m, 3H), 2.72-3.00 ppm (m, 3H).

Example 39

Synthesis of (S)—N-(2-(2-cyano-4,4-difluoropyrrolidin-1-yl)-2-oxoethyl)pyrazolo[1,5-a]pyridine-5-carboxamide

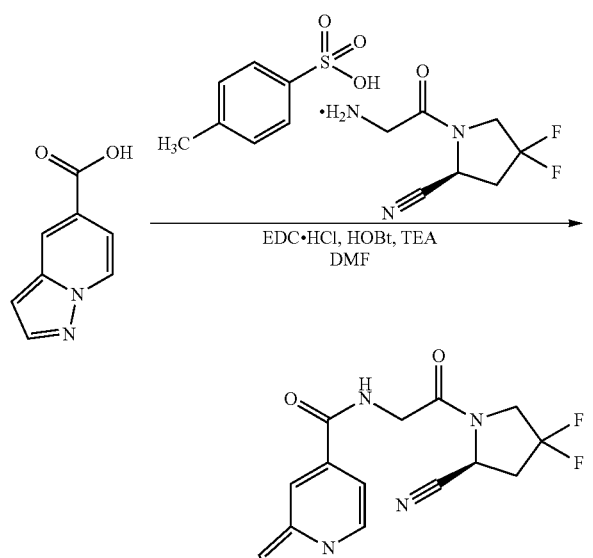

Compound 85

To a stirred solution of pyrazolo[1,5-a]pyridine-5-carboxylic acid (0.100 g, 0.61 mmol, 1.0 equiv) in DMF (2 mL), was added (S)-4,4-difluoro-1-glycylpyrrolidine-2-carbonitrile 4-methylbenzenesulfonate (0.222 g, 0.61 mmol, 1.0 equiv), HOBt (0.93 g, 0.67 mmol, 1.1 equiv) and EDC.HCl (0.129 g, 0.67 mmol, 1.1 equiv). The mixture was allowed to stir at RT for 10 min. Triethyl amine (0.2 mL) was added and the mixture was allowed to stir at RT for overnight. Product formation was confirmed by LCMS and TLC. The reaction mixture was diluted with water and extracted with ethyl acetate (50 mL×2). Combined organic extracts were washed with water (20 mL×4), dried over anhydrous $Na_2SO_4$ and concentrated. The crude product obtained was purified by reverse phase HPLC to obtain (S)—N-(2-(2-cyano-4,4-difluoropyrrolidin-1-yl)-2-oxoethyl)pyrazolo[1,5-a]pyridine-5-carboxamide (0.030 g, 15% Yield) as an off-white solid.

LCMS 334.2 [M+H]$^+$ $^1$H NMR (400 MHz, DMSO-d$_6$) δ 9.02 (br. s., 1H), 8.78 (d, J=7.5 Hz, 1H), 8.29 (br. s., 1H), 8.11 (s, 1H), 7.30 (d, J=7.0 Hz, 1H), 6.85 (br. s., 1H), 5.11 (d, J=7.9 Hz, 1H), 4.42-4.23 (m, 1H), 4.23-4.05 (m, 3H), 3.01-2.72 (m, 3H).

Example 40

Synthesis of (S)—N-(2-(2-cyano-4,4-difluoropyrrolidin-1-yl)-2-oxoethyl)-6-methoxy-2-phenylnicotinamide

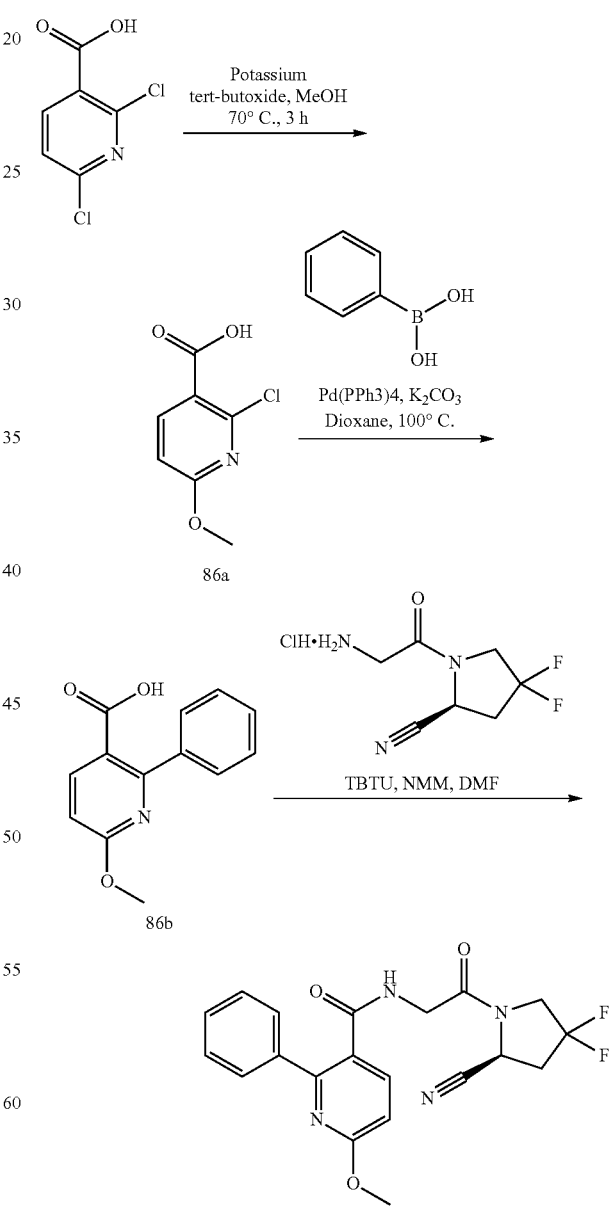

Compound 86

Compound 86a. To a solution of 2,6-dichloronicotinic acid (2.0 g, 10.41 mmol, 1.0 equiv) in MeOH (50 mL) was added compound potassium tert-butoxide (4.7 g, 41.66 mmol, 4.0 equiv), and resulting reaction mixture was heated at 70° C. for 3 h. Product formation was confirmed by LCMS and TLC. After the completion of reaction, the reaction mixture was concentrated and diluted with water (50 ml). Aqueous layer extracted with ethyl acetate (30 mL×3). Combined organic extracts were washed with brine (50 mL), dried over anhydrous Na$_2$SO$_4$ and concentrated. The crude product obtained was purified by flash chromatography (5% MeOH in DCM as an eluent) to obtain 2-chloro-6-methoxynicotinic acid (1.8 g, 96.4%) as white solid

LCMS 188 [M+H]$^+$ $^1$H NMR $^1$H NMR (400 MHz, DMSO-d$_6$) δ 13.33 (br. s., 1H), 8.06-8.24 (m, 1H), 6.92 (d, J=8.77 Hz, 1H), 3.91 (s, 3H).

Compound 86b. To a solution of 2-chloro-6-methoxynicotinic acid (0.200 g, 1.07 mmol, 1.0 equiv) in Dioxane (10 mL) was added phenylboronic acid (0.195 g, 1.604 mmol, 1.5 equiv), Na$_2$CO$_3$ (0.23 g, 2.14 mmol, 2.0 equiv) and resulting reaction mixture purged with N$_2$ gas for 10 minute, followed by the addition of Pd(PPh$_3$)$_4$ (0.062 g, 0.054 mmol. 0.05 equiv). The resulting reaction mixture was heated at 100° C. for overnight. Product formation was confirmed by LCMS and TLC. After the completion of reaction, the mixture was filtered through celite bed, washed with ethyl acetate (100 mL). Filtrate was concentrated under reduced pressure. The crude product obtained was purified by flash chromatography (0-2% MeOH in DCM as an eluent) to obtain 6-methoxy-2-phenylnicotinic acid (0.07 g, 28.6%) as white solid.

LCMS 230 [M+H]$^+$ $^1$H NMR (400 MHz, DMSO-d$_6$) δ 12.89 (br. s., 1H), 8.17 (d, J=6.58 Hz, 3H), 7.67 (d, J=7.45 Hz, 1H), 7.38-7.60 (m, 3H), 4.04 (s, 3H).

Compound 86. To a stirred solution of 6-methoxy-2-phenylnicotinic acid (0.050 g, 0.218 mmol, 1.0 equiv) in DMF (5 mL), was added (S)-4,4-difluoro-1-glycylpyrrolidine-2-carbonitrile hydrochloride (0.073 g, 0.327 mmol, 1.5 equiv) and TBTU (0.104 g, 0.327 mmol, 1.5 equiv). The mixture was allowed to stir at RT for 10 min. N-Methylmorpholine (0.1 mL) was added and the mixture was allowed to stir at RT for overnight. Product formation was confirmed by LCMS and TLC. After completion of reaction, the mixture was diluted with water (15 mL) and extracted with ethyl acetate (10 mL×2). Combined organic extracts were washed with water (10 mL×4), dried over anhydrous Na$_2$SO$_4$ and concentrated. The crude product obtained was purified by flash chromatography (5% MeOH in DCM as an eluent) followed by reverse phase purification to obtain (S)—N-(2-(2-cyano-4,4-difluoropyrrolidin-1-yl)-2-oxo-ethyl)-6-methoxy-2-phenylnicotinamide (0.015 g, 17.2% Yield) as a white solid.

LCMS 401.2 [M+H]$^+$ $^1$H NMR (400 MHz, DMSO-d$_6$) δ 8.76 (br. s., 1H), 8.48 (s, 2H), 7.79 (d, J=8.33 Hz, 2H), 7.39 (br.s., 2H), 6.86 (d, J=8.33 Hz, 1H), 5.10 (d, J=7.45 Hz, 1H), 4.23 (br. s., 1H), 3.98-4.12 (m, 2H), 3.94 (s, 3H), 2.90 (d, J=8.33 Hz, 1H), 2.70-2.86 (m, 1H), 2.67 (br. s., 1H).

Example 41

Synthesis of (S)—N-(2-(2-cyano-4,4-difluoropyrrolidin-1-yl)-2-oxoethyl)-3-(1-methyl-1H-indazol-4-yl)isonicotinamide

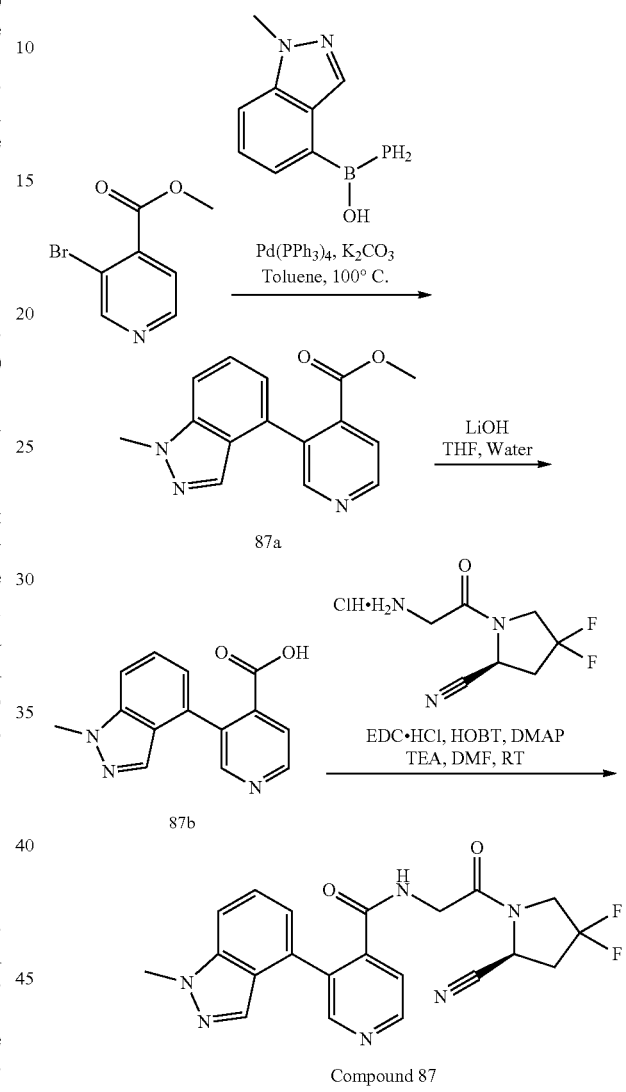

Compound 87a. To a solution of ethyl 3-bromoisonicotinate (0.2 g, 0.93 mmol, 1.0 equiv) in Toluene (15 mL) was added (1-methyl-1H-indazol-4-yl)boronic acid (0.325 g, 1.85 mmol, 2.0 equiv), K$_2$CO$_3$ (0.38 g, 2.78 mmol, 3.0 equiv) and resulting reaction mixture purged with N$_2$ gas for 10 minute, followed by the addition of Pd(PPh$_3$)$_4$ (0.054 g, 0.046 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-30% ethyl acetate in hexane as an eluent) to obtain methyl 3-(1-methyl-1H-indazol-4-yl)isonicotinate (0.150 g, 60.7%) as brown liquid.

LCMS 268.2 [M+H]$^+$

¹H NMR (400 MHz, DMSO-d₆) δ 8.72-8.87 (m, 2H), 7.79 (d, J=5.26 Hz, 1H), 7.64-7.76 (m, 2H), 7.49 (s, 1H), 7.07 (d, J=7.02 Hz, 1H), 4.10 (s, 3H), 3.53 (s, 3H).

Compound 87b. To a stirred solution of methyl 3-(1-methyl-1H-indazol-4-yl)isonicotinate (0.27 g, 1.011 mmol, 1.0 equiv) in THF (10 mL) and water (10 mL), was added LiOH (0.072 g, 3.03 mmol, 3.0 equiv). The mixture was allowed to stir at RT for overnight. Product formation was confirmed by LCMS and ¹H NMR Spectroscopy. The reaction mixture was concentrated and diluted with water (20 mL) and washed with ethyl acetate (15 mL×2). Aqueous layer was separated and freeze dried to obtain 3-(1-methyl-1H-indazol-4-yl)isonicotinic acid (Quant. Yield) as a white solid.

LCMS 254.2 [M+H]⁺

¹H NMR (400 MHz, DMSO-d₆) δ 8.34-8.52 (m, 2H), 7.90 (s, 1H), 7.56 (d, J=8.77 Hz, 1H), 7.39 (s, 1H), 7.16-7.31 (m, 2H), 4.06 (s, 3H).

Compound 87. To a stirred solution of 3-(1-methyl-1H-indazol-4-yl)isonicotinic acid (0.100 g, 0.395 mmol, 1.0 equiv) in DMF (5 mL), was added (S)-4,4-difluoro-1-glycylpyrrolidine-2-carbonitrile hydrochloride (0.088 g, 0.395 mmol, 1.0 equiv), EDC.HCl (0.075 g, 0.395 mmol, 1.0 equiv), HOBt (0.060 g, 0.395 mmol, 1.0 equiv) and DMAP (0.003 g, 0.019 mmol, 0.05 equiv). The mixture was allowed to stir at RT for 10 min. TEA (0.5 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic extracts were washed with water (20 mL×4), dried over anhydrous Na₂SO₄ and concentrated. The crude product obtained was purified by flash chromatography (5% MeOH in DCM as an eluent) followed by reverse phase purification to obtain (S)—N-(2-(2-cyano-4,4-difluoropyrrolidin-1-yl)-2-oxoethyl)-3-(1-methyl-1H-indazol-4-yl)isonicotinamide (0.010 g, 6% Yield) as a white solid.

LCMS 425.3 [M+H]⁺

1H NMR (400 MHz, DMSO-d₆) δ 8.92 (br. s., 1H), 8.62-8.80 (m, 2H), 7.86 (s, 1H), 7.64 (d, J=8.33 Hz, 1H), 7.56 (d, J=4.82 Hz, 1H), 7.35-7.45 (m, 1H), 7.18 (d, J=7.02 Hz, 1H), 5.05 (d, J=6.58 Hz, 1H), 4.13 (br. s., 1H), 4.06 (s, 3H), 3.83-3.99 (m, 3H), 2.75 (d, J=11.84 Hz, 2H), 2.65 (br. s., 1H).

Example 42

Synthesis of N-[2-[(2S)-2-cyano-4,4-difluoro-pyrrolidin-1-yl]-2-oxo-ethyl]-3-morpholino-pyridine-4-carboxamide

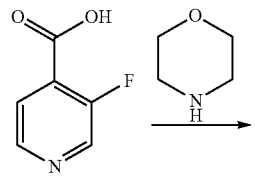

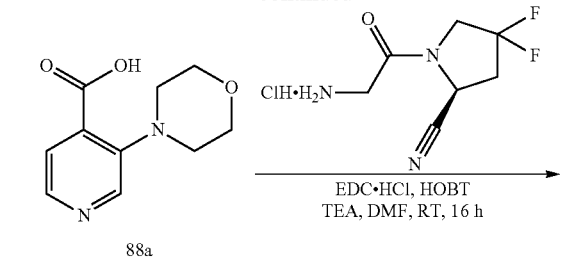

Compound 88

Compound 88a. In a 25 mL bottle, 3-fluoropyridine-4-carboxylic acid (0.500 g, 3.54 mmol, 1.0 equiv) and morpholine (0.616 g, 7.08 mmol, 2.0 equiv) were added and the reaction mixture was heated at 120° C. for 1 h. Reaction progress was monitored by NMR and LCMS. After completion of reaction, reaction mixture was concentrated under reduced pressure and the crude compound was purified by normal phase flash chromatography (2-10% MeOH in DCM as an eluent) to obtain 3-morpholinopyridine-4-carboxylic acid (100 mg, 13% Yield) as a yellow solid.

LCMS 209.3 [M+H]⁺

¹H NMR (400 MHz, DMSO-d₆) δ 14.16 (br. s., 1H), 8.55 (s, 1H), 8.34 (d, J=4.8 Hz, 1H), 7.53 (d, J=4.8 Hz, 1H), 3.82-3.63 (m, 4H), 3.19-3.01 (m, 4H).

Compound 88. To a stirred solution 3-morpholinopyridine-4-carboxylic acid (0.100 g, 0.48 mmol, 1.0 equiv) in DMF (3 mL), was added (2S)-1-(2-aminoacetyl)-4,4-difluoro-pyrrolidine-2-carbonitrile hydrochloride (0.108 g, 0.48 mmol, 1.0 equiv), HOBt (0.078 g, 0.58 mmol, 1.2 equiv) and EDC.HCl (0.111 g, 0.58 mmol, 1.2 equiv). The mixture was allowed to stir at RT for 10 min. Triethyl amine (0.21 mL) was added and the reaction mixture was allowed to stir at RT for overnight. Product formation was confirmed by LCMS. The reaction mixture was diluted with water and extracted with ethyl acetate (40 mL×2). Combined organic extracts were washed with water (15 mL×4), dried over anhydrous Na₂SO₄ and concentrated. The crude product obtained was purified by reverse phase HPLC to obtain (S)—N-(2-(2-cyano-4,4-difluoropyrrolidin-1-yl)-2-oxo-ethyl)-3-morpholinoisonicotinamide (0.020 g, 11% Yield) as an off-white solid.

LCMS 380.5 [M+H]⁺

¹H NMR (400 MHz, DMSO-d₆) δ 9.48 (br. s., 1H), 8.55 (s, 1H), 8.40 (d, J=4.8 Hz, 1H), 7.57 (d, J=4.8 Hz, 1H), 4.37-4.09 (m, 4H), 3.78 (br. s., 4H), 3.08 (br. s., 4H), 2.90 (br. s., 2H), 2.08 (s, 1H).

Example 43

Synthesis of (S)-3-benzyl-N-(2-(2-cyano-4,4-difluoropyrrolidin-1-yl)-2-oxoethyl)isonicotinamide

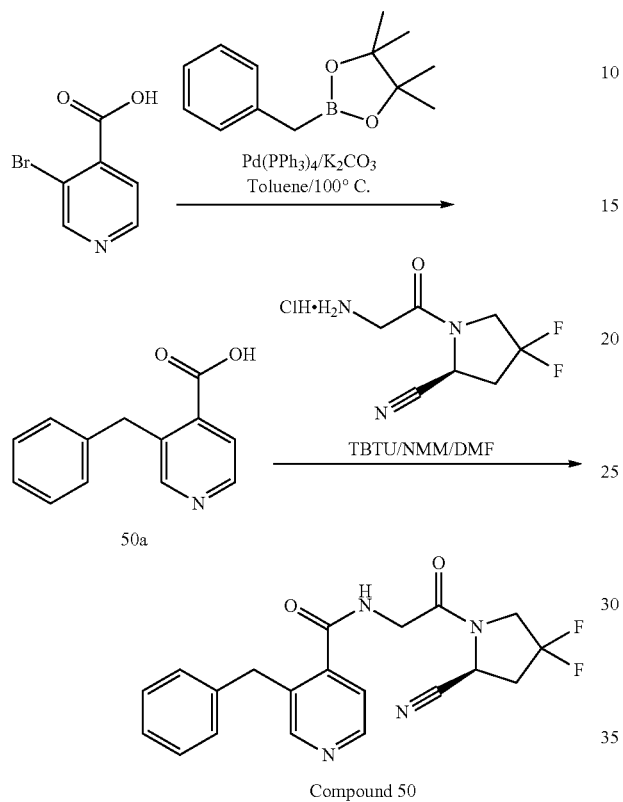

Compound 50a. To a solution of 3-bromoisonicotinic acid (0.5 g, 2.475 mmol, 1.0 equiv) in dioxane (6 mL) and water (12 mL) was added 2-benzyl-4,4,5,5-tetramethyl-1,3,2-dioxaborolane (1.1 g, 4.95 mmol, 2.0 equiv), K$_2$CO$_3$ (1.1 g, 7.45 mmol, 3.0 equiv) and resulting reaction mixture was purged with N$_2$ gas for 10 min. Pd(PPh$_3$)$_4$ (0.143 g, 0.124 mmol. 0.05 equiv) was added and the resulting reaction mixture was heated at 100° C. for overnight. Product formation was confirmed by LCMS. After the completion of reaction, the reaction mixture was concentrated and diluted with water (10 mL). Aqueous layer washed with EtOAc (10 mL×2) and acidify with 6N HCl (pH~3.0), extracted with EtOAc (10 mL×3). Combined organic extracts were washed with water (30 mL), dried over anhydrous Na$_2$SO$_4$ and concentrated. The crude product obtained was purified by flash chromatography (0-10% Methanol in DCM as an eluent) to obtain 3-benzylisonicotinic acid (0.100 g, 19%) as an off white solid.

LCMS 214.2 [M+H]$^+$

Compound 50. To a stirred solution of 3-benzylisonicotinic acid (0.100 g, 0.467 mmol, 1.0 equiv) in DMF (8 mL), was added (S)-4,4-difluoro-1-glycylpyrrolidine-2-carbonitrile hydrochloride (0.105 g, 0.467 mmol, 1.0 equiv) and TBTU (0.164 g, 0.514 mmol, 1.1 equiv). The mixture was allowed to stir at RT for 10 min. N-methylmorpholine (0.4 mL) was added and the mixture was allowed to stir at RT for overnight. Product formation was confirmed by LCMS and TLC. After completion of reaction, the reaction mixture was diluted with water (20 mL) and extracted with ethyl acetate (20 mL×2). Combined organic extracts were washed with water (20 mL×4), dried over anhydrous Na$_2$SO$_4$ and concentrated. The crude product obtained was purified by flash chromatography (5% MeOH in DCM as an eluent) followed by reversed phase purification to obtain (S)-3-benzyl-N-(2-(2-cyano-4,4-difluoropyrrolidin-1-yl)-2-oxoethyl)isonicotinamide (0.025 g, 14% Yield) as an white solid.

LCMS 385.2 [M+H]$^+$ $^1$H NMR (400 MHz, DMSO-d$_6$) δ 8.94 (br. s., 1H), 8.61-8.42 (m, 2H), 7.34 (d, J=4.8 Hz, 1H), 7.30-7.21 (m, 3H), 7.18 (d, J=7.0 Hz, 2H), 5.13 (d, J=7.0 Hz, 1H), 4.27 (d, J=15.3 Hz, 2H), 4.23-4.01 (m, 4H), 2.90 (br. s., 1H), 2.82 (d, J=17.5 Hz, 1H).

Example 44

Synthesis of N-(2-((S)-2-cyano-4,4-difluoropyrrolidin-1-yl)-2-oxoethyl)-3-(cyclohex-1-en-1-yl)isonicotinamide

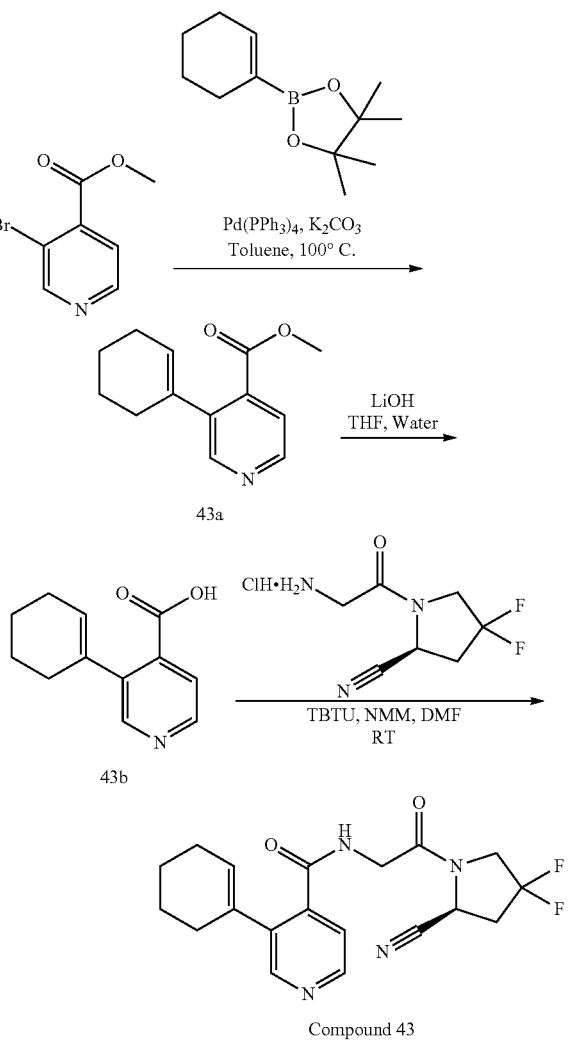

Compound 43a. To a solution of ethyl 3-bromoisonicotinate (0.4 g, 1.85 mmol, 1.0 equiv) in toluene (20 mL) was added 2-(cyclohex-1-en-1-yl)-4,4,5,5-tetramethyl-1,3,2-dioxaborolane (0.58 g, 2.77 mmol, 1.5 equiv), $K_2CO_3$ (0.51 g, 3.78 mmol, 2.0 equiv) and resulting reaction mixture purged with $N_2$ gas for 10 min. followed by the addition of $Pd(PPh_3)_4$ (0.065 g, 0.093 mmol. 0.05 equiv). The resulting reaction mixture was heated at 100° C. for overnight. Product formation was confirmed by LCMS. After the completion of reaction, the reaction mixture was filtered through Celite® bed, washed with ethyl acetate (100 mL). Filtrate was concentrated under reduced pressure. The crude product obtained was purified by flash chromatography (0-10% ethyl acetate in hexane as an eluent) to obtain methyl 3-(cyclohex-1-en-1-yl)isonicotinate (0.170 g, 42.4%) as colorless oil.

LCMS 218.2 $[M+H]^+$ $^1$H NMR (400 MHz, DMSO-$d_6$) δ 8.60 (d, J=5.3 Hz, 1H), 8.52 (s, 1H), 7.56 (d, J=5.3 Hz, 1H), 5.62 (br. s., 1H), 2.24-2.06 (m, 4H), 1.77-1.54 (m, 4H).

Compound 43b. To a stirred solution of methyl 3-(cyclohex-1-en-1-yl)isonicotinate (0.17 g, 0.779 mmol, 1.0 equiv) in THF (5 mL) and water (5 mL), was added LiOH (0.037 g, 1.56 mmol, 2.0 equiv). The mixture was allowed to stir at RT for overnight. Product formation was confirmed by LCMS and $^1$H NMR. The reaction mixture was concentrated and diluted with water (20 mL) and washed with ethyl acetate (15 mL×2). Aqueous layer was separated and lyophilized to obtain 3-(cyclohex-1-en-1-yl)isonicotinic acid (Quant. Yield) as a white solid.

LCMS 204.2 $[M+H]^+$ $^1$H NMR (400 MHz, DMSO-$d_6$) δ 8.25 (d, J=4.8 Hz, 1H), 8.17 (s, 1H), 7.10 (d, J=4.8 Hz, 1H), 5.66 (br. s., 1H), 2.29 (br. s., 2H), 2.12-2.05 (m, 2H), 1.72-1.53 (m, 4H).

Compound 43. To a stirred solution of 3-(cyclohex-1-en-1-yl)isonicotinic acid (0.100 g, 0.493 mmol, 1.0 equiv) in DMF (5 mL), was added (S)-4,4-difluoro-1-glycylpyrrolidine-2-carbonitrile hydrochloride (0.110 g, 0.493 mmol, 1.0 equiv), TBTU (0.174 g, 0.542 mmol, 1.1 equiv). The mixture was allowed to stir at RT for 10 min. N-Methylmorpholine (0.4 mL) was added and the mixture was allowed to stir at RT for overnight. Product formation was confirmed by LCMS and TLC. After completion of reaction, the reaction mixture was diluted with water (20 mL) and extracted with ethyl acetate (20 mL×2). Combined organic extracts were washed with water (20 mL×4), dried over anhydrous $Na_2SO_4$ and concentrated. The crude product obtained was purified by flash chromatography (5% MeOH in DCM as an eluent) followed by reverse phase purification to obtain N-(2-((S)-2-cyano-4,4-difluoropyrrolidin-1-yl)-2-oxoethyl)-3-(cyclohex-1-en-1-yl)isonicotinamide (0.004 g, 2.4% Yield) as an white solid.

LCMS 375.3 $[M+H]^+$ $^1$H NMR (500 MHz, DMSO-d6) δ 8.69 (t, J=5.8 Hz, 1H), 8.53 (d, J=4.9 Hz, 1H), 8.46 (s, 1H), 7.33 (d, J=4.9 Hz, 1H), 5.79 (d, J=3.9 Hz, 1H), 5.10 (dd, J=9.3, 2.7 Hz, 1H), 4.33-4.23 (m, 1H), 4.15-4.03 (m, 3H), 2.95-2.74 (m, 2H), 2.25 (s, 2H), 2.12 (d, J=6.4 Hz, 2H), 1.70-1.61 (m, 2H), 1.58 (q, J=6.0, 5.5 Hz, 2H).

Example 45

Synthesis of (S)—N-(2-(2-cyano-4,4-difluoropyrrolidin-1-yl)-2-oxoethyl)-3-(1-methyl-1H-indol-4-yl)isonicotinamide

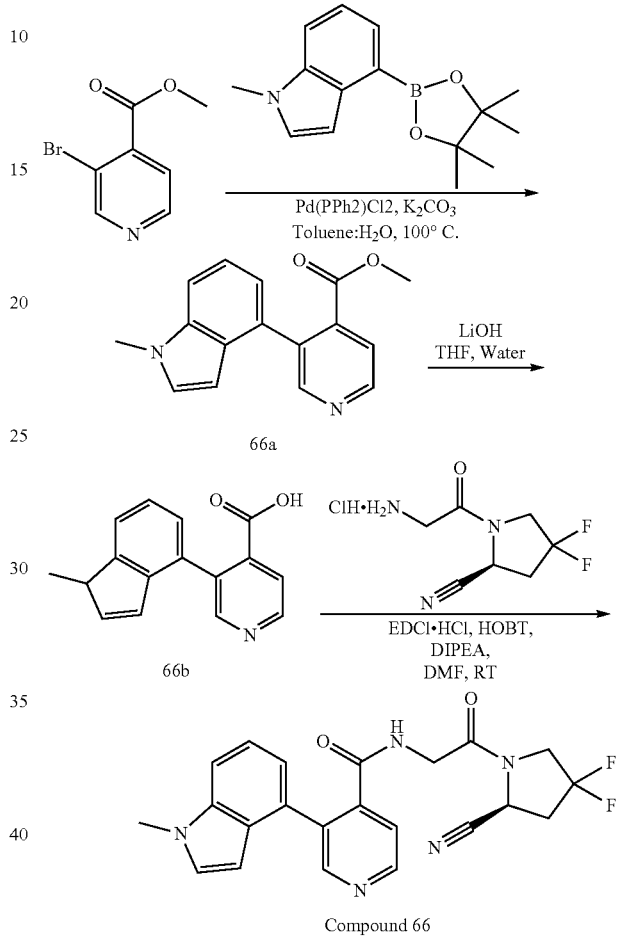

Compound 66a. To a solution of ethyl 3-bromoisonicotinate (0.2 g, 0.93 mmol, 1.0 equiv) in mixture of toluene (16 mL) & water (4 mL) was added 1-methyl-4-(4,4,5,5-tetramethyl-1,3,2-dioxaborolan-2-yl)-1H-indole (0.48 g, 1.85 mmol, 2.0 equiv), $K_2CO_3$ (0.382 g, 2.78 mmol, 3.0 equiv) and resulting reaction mixture purged with $N_2$ gas for 10 min. followed by the addition of $Pd(PPh_3)_2Cl_2$ (0.033 g, 0.046 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-20% ethyl acetate in hexane as an eluent) to obtain methyl 3-(1-methyl-1H-indol-4-yl)isonicotinate (0.180 g, 73.4%) as a yellow oil.

LCMS 267.2 $[M+H]^+$ $^1$H NMR (400 MHz, DMSO-$d_6$) δ 8.74 (s, 1H), 8.67 (d, J=4.8 Hz, 1H), 7.67-7.49 (m, 3H), 7.40 (d, J=3.1 Hz, 1H), 7.12 (d, J=8.8 Hz, 1H), 6.49 (d, J=3.1 Hz, 1H), 3.92 (s, 3H), 3.63 (s, 3H).

Compound 66b. To a stirred solution of methyl-1H-indol-4-yl)isonicotinate (0.18 g, 0.67 mmol, 1.0 equiv) in THF (5 mL) and water (5 mL), was added LiOH.H₂O (0.085 g, 2.63 mmol, 3.0 equiv). The mixture was allowed to stir at RT for overnight. Product formation was confirmed by LCMS. The reaction mixture was concentrated and diluted with water (20 mL) and washed with ethyl acetate (15 mL×2). Aqueous layer was separated and lyophilized to obtain 3-(1-methyl-1H-indol-4-yl)isonicotinic acid (Quant. Yield) as a white solid.

LCMS 253.2 [M+H]⁺

Compound 66. To a stirred solution of 3-(1-methyl-1H-indol-4-yl)isonicotinic acid (0.050 g, 0.198 mmol, 1.0 equiv) in DMF (2 mL), was added (S)-4,4-difluoro-1-glycylpyrrolidine-2-carbonitrile hydrochloride (0.044 g, 0.198 mmol, 1.0 equiv), EDCI.HCl (0.057 g, 0.297 mmol, 1.5 equiv), HOBt (0.04 g, 0.297 mmol, 1.5 equiv). The resulting reaction mixture was allowed to stir at RT for 10 min. Et₃N (0.2 mL) was added and the mixture was allowed to stir at RT for overnight. Product formation was confirmed by LCMS and TLC. After completion of reaction, the mixture was diluted with water (10 mL) and extracted with ethyl acetate (10 mL×2). Combined organic extracts were washed with water (10 mL×4), dried over anhydrous Na₂SO₄ and concentrated. The crude product obtained was purified by flash chromatography (5% MeOH in DCM as an eluent) to obtain (S)—N-(2-(2-cyano-4,4-difluoropyrrolidin-1-yl)-2-oxoethyl)-3-(1-methyl-1H-indol-4-yl)isonicotinamide (0.013 g, 15.5% Yield) as a white solid.

LCMS 424.3 [M+H]⁺

¹H NMR (500 MHz, DMSO-d6) δ 8.91 (t, J=6.0 Hz, 1H), 8.69 (s, 1H), 8.61 (d, J=4.9 Hz, 1H), 8.19 (t, J=5.8 Hz, 1H), 7.74 (d, J=1.8 Hz, 1H), 7.49-7.40 (m, 2H), 7.40-7.29 (m, 2H), 6.47 (d, J=3.1 Hz, 1H), 5.08 (ddd, J=15.6, 9.3, 2.8 Hz, 2H), 4.18 (t, J=13.4 Hz, 2H), 4.10-3.89 (m, 6H), 3.81 (s, 4H), 2.91-2.72 (m, 4H), 1.88 (s, 2H), 1.32-1.21 (m, 5H), 0.84 (q, J=10.7, 8.5 Hz, 1H).

Example 46

Synthesis of (S)—N-(2-(2-cyano-4,4-difluoropyrrolidin-1-yl)-2-oxoethyl)-3-(indolin-5-yl)isonicotinamide

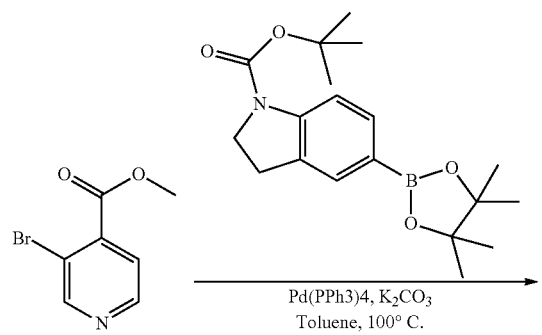

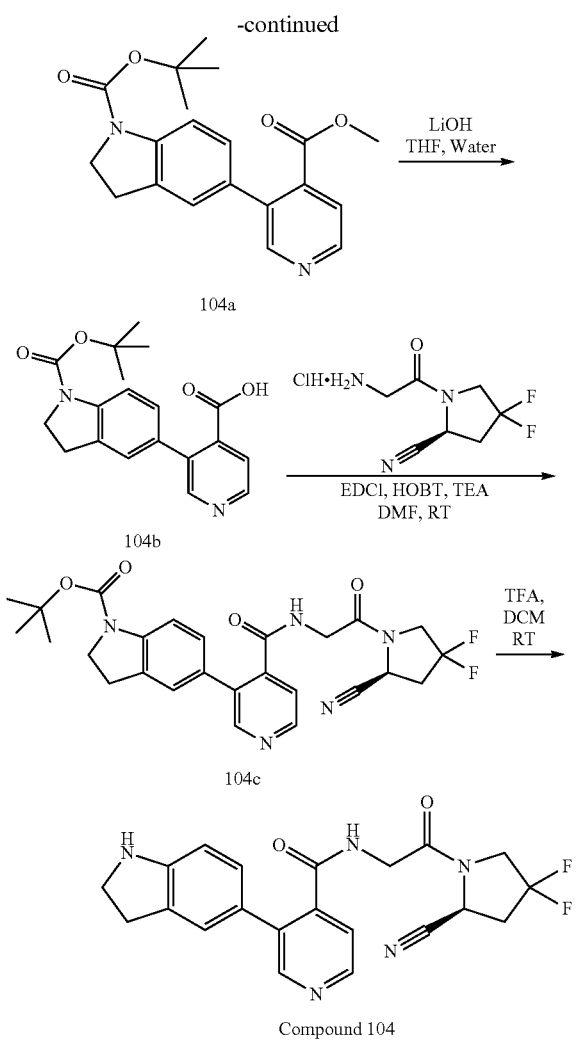

Compound 104

Compound 104a. To a solution of ethyl 3-bromoisonicotinate (0.2 g, 0.922 mmol, 1.0 equiv) in toluene (8 mL) and water (2 mL) was added tert-butyl 5-(4,4,5,5-tetramethyl-1,3,2-dioxaborolan-2-yl)indoline-1-carboxylate (0.381 g, 1.106 mmol, 1.2 equiv), K₂CO₃ (0.38 g, 2.764 mmol, 3.0 equiv) and resulting reaction mixture purged with N₂ gas for 10 min, followed by the addition of Pd(PPh₃)₄ (0.033 g, 0.046 mmol. 0.05 equiv). The resulting reaction mixture was heated at 100° C. for overnight. Product formation was confirmed by LCMS. After the completion of reaction, the mixture was filtered through Celite® bed, washed with ethyl acetate (100 mL). Filtrate was concentrated under reduced pressure. The crude product obtained was purified by flash chromatography (0-20% ethyl acetate in hexane as an eluent) to obtain compound of tert-butyl 5-(4-(methoxycarbonyl)pyridin-3-yl)indoline-1-carboxylate (0.200 g, 61.34%) as a yellow oil.

LCMS 355.4 [M+H]⁺

Compound 104b. To a stirred solution of compound tert-butyl 5-(4-(methoxycarbonyl)pyridin-3-yl)indoline-1-carboxylate (0.200 g, 0.565 mmol, 1.0 equiv) in THF (8 mL) and water (8 mL), was added LiOH (0.028 g, 1.29 mmol, 2.0 equiv). The mixture was allowed to stir at RT for overnight. Product formation was confirmed by LCMS. The reaction mixture was concentrated and diluted with water (10 mL) and washed with ethyl acetate (10 mL×2). Aqueous layer was separated and freeze dried on lyophilyzer to obtain compound 3-(1-(tert-butoxycarbonyl)indolin-5-yl)isonicotinic acid (Quant. Yield) as a white solid.

LCMS 341.4 [M+H]+

Compound 104c. To a stirred solution of compound 3-(1-(tert-butoxycarbonyl)indolin-5-yl)isonicotinic acid (0.050 g, 0.147 mmol, 1.0 equiv) in DMF (3 mL), was added (S)-4,4-difluoro-1-glycylpyrrolidine-2-carbonitrile hydrochloride (0.034 g, 0.147 mmol, 1.0 equiv), EDCI.HCl (0.042 g, 0.225 mmol, 1.5 equiv), HOBT (0.03 g, 0.225 mmol, 1.5 equiv). The mixture was allowed to stir at RT for 30 min. Triethylamine (0.2 mL) was added and the mixture was allowed to stir at RT for overnight. Product formation was confirmed by LCMS. After completion of reaction, the mixture was diluted with water (0 1 mL) and extracted with ethyl acetate (10 mL×2). Combined organic extracts were washed with water (10 mL×4), dried over anhydrous $Na_2SO_4$ and concentrated to obtained tert-butyl (S)-5-(4-((2-(2-cyano-4,4-difluoropyrrolidin-1-yl)-2-oxoethyl)carbamoyl)pyridin-3-yl)indoline-1-carboxylate (0.035 g, 46% Yield) as an yellow solid.

LCMS 512.4 [M+H]+

Compound 104. To a stirred solution of tert-butyl (S)-5-(4-((2-(2-cyano-4,4-difluoropyrrolidin-1-yl)-2-oxoethyl)carbamoyl)pyridin-3-yl)indoline-1-carboxylate (0.07 g, 0.14 mmol, 1.0 equiv) in DCM (5 mL), was added trifloroacetic acid (0.5 mL). The mixture was allowed to stir at RT overnight. Product formation was confirmed by LCMS. The reaction mixture concentrated and the crude was purified by reverse phase purification to obtain (S)—N-(2-(2-cyano-4,4-difluoropyrrolidin-1-yl)-2-oxoethyl)-3-(indolin-5-yl)isonicotinamide (0.022 g, 40% Yield) as a white solid.

LCMS 512.3 [M+H]+

$^1$H NMR (400 MHz, DMSO-$d_6$) δ 8.83 (br. s., 1H), 8.58 (s, 1H), 8.52 (d, J=4.8 Hz, 1H), 7.33 (d, J=4.8 Hz, 1H), 7.26 (s, 1H), 7.08 (d, J=6.6 Hz, 1H), 6.50 (d, J=7.9 Hz, 1H), 5.68 (br. s., 1H), 5.09 (d, J=7.5 Hz, 1H), 4.21 (br. s., 1H), 4.06 (br. s., 1H), 4.00 (br. s., 3H), 3.45 (t, J=8.6 Hz, 2H), 2.96 (d, J=9.2 Hz, 2H), 2.80 (d, J=17.5 Hz, 1H).

Example 47

Synthesis of (S)-3-(6-chloronaphthalen-2-yl)-N-(2-(2-cyano-4,4-difluoropyrrolidin-1-yl)-2-oxoethyl) isonicotinamide

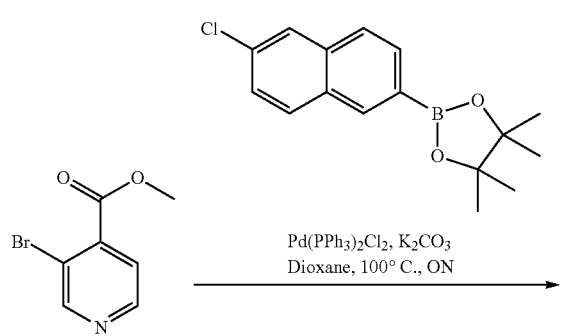

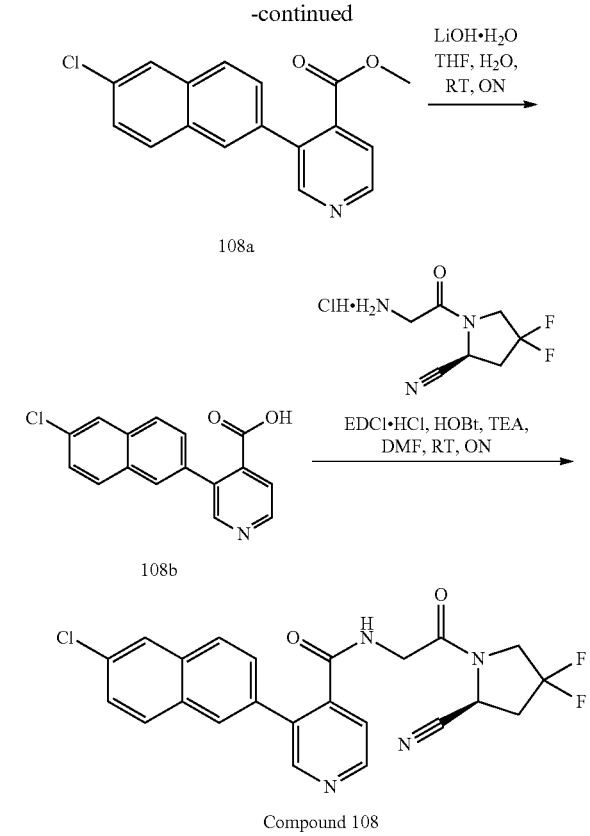

Compound 108

Compound 108a. To a solution of methyl 3-bromoisonicotinate (0.150 g, 0.694 mmol, 1.0 equiv) in Dioxan (4 mL) was added 2-(6-chloronaphthalen-2-yl)-4,4,5,5-tetramethyl-1,3,2-dioxaborolane (0.300 g, 1.04 mmol, 1.5 equiv), $K_2CO_3$ (0.192 g, 1.38 mmol, 2.0 equiv) and resulting reaction mixture purged with $N_2$ gas for 10 minute, followed by the addition of Pd(PPh$_3$)Cl$_2$ (0.024 g, 0.0347 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-20% ethyl acetate in hexane as an eluent) to methyl 3-(6-chloronaphthalen-2-yl)isonicotinate (0.200 g, 97.43% yield) as an yellow solid.

LCMS 298.1 [M+H]+

Compound 108b. To a stirred solution of methyl 3-(6-chloronaphthalen-2-yl)isonicotinate (0.200 g, 0.673 mmol, 1.0 equiv) in THF (4 mL) and water (4 mL), was added LiOH.H$_2$O (0.043 g, 1.011 mmol, 1.5 equiv). The mixture was allowed to stir at RT for overnight. Product formation was confirmed by LCMS and $^1$H NMR Spectroscopy. The reaction mixture was concentrated and diluted with water (20 mL) and washed with ethyl acetate (10 mL×2). Aqueous layer was separated and freeze dried on lyophilyzer to obtain 3-(6-chloronaphthalen-2-yl)isonicotinic acid (Quant. Yield) as an yellow solid.

LCMS 284.2 [M+H]+

Compound 108. To a stirred solution of 3-(6-chloronaphthalen-2-yl)isonicotinic acid (0.130 g, 0.459 mmol, 1.0 equiv) in DMF (5 mL), was added (S)-4,4-difluoro-1-glycylpyrrolidine-2-carbonitrile hydrochloride (0.103 g, 0.459 mmol, 1.0 equiv), EDCI.HCl (0.133 g, 0.688 mmol, 1.5 equiv) & HOBt (0.094 g, 0.688 mmol, 1.5 equiv). The mixture was allowed to stir at RT for 10 min. TEA (0.3 mL) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous Na$_2$SO$_4$ and concentrated. The crude product obtained was purified by flash chromatography (5% MeOH in DCM as an eluent) to obtain (S)-3-(6-chloronaphthalen-2-yl)-N-(2-(2-cyano-4,4-difluoropyrrolidin-1-yl)-2-oxoethyl)isonicotinamide (0.100 g, 48% Yield) as an off-white solid.

LCMS 455.2 [M+H]$^+$ $^1$H NMR (400 MHz, DMSO-d$_6$) δ 9.12 (t, J=5.9 Hz, 1H), 8.82 (s, 1H), 8.72 (d, J=4.8 Hz, 1H), 8.23 (s, 1H), 8.12-8.00 (m, 2H), 7.95 (d, J=8.3 Hz, 1H), 7.75 (dd, J=1.8, 8.3 Hz, 1H), 7.61-7.45 (m, 2H), 5.12 (dd, J=2.9, 9.0 Hz, 1H), 4.27-3.97 (m, 3H), 2.95-2.76 (m, 2H).

Example 48

Synthesis of (S)—N-(2-(2-cyano-4,4-difluoropyrrolidin-1-yl)-2-oxoethyl)-6-hydroxy-2-phenylnicotinamide

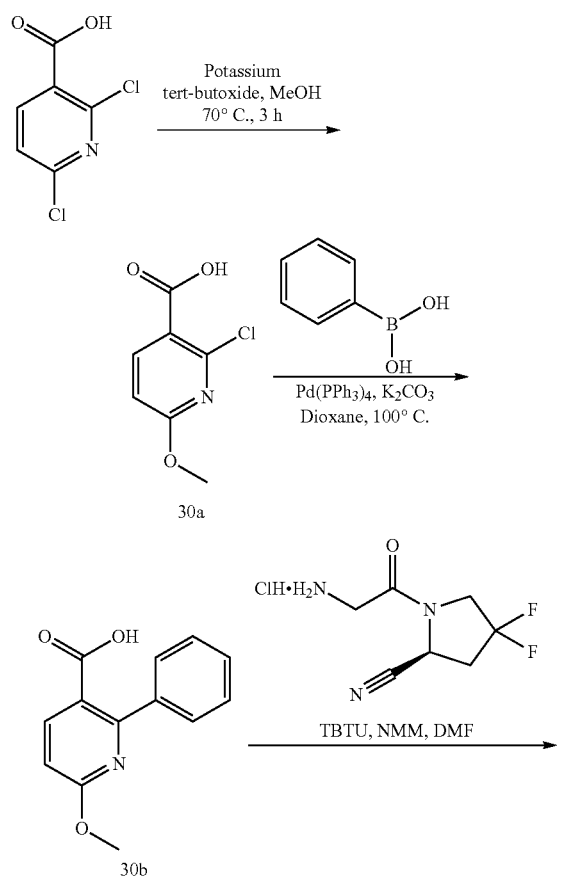

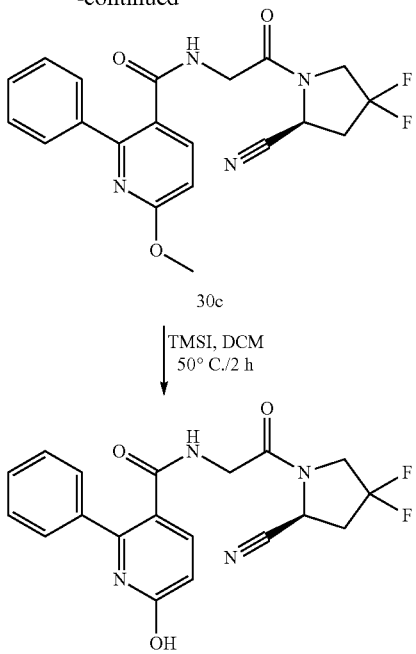

Compound 30a. To a solution of 2,6-dichloronicotinic acid (2.0 g, 10.41 mmol, 1.0 equiv) in MeOH (50 mL) was added compound potassium tert-butoxide (4.7 g, 41.66 mmol, 4.0 equiv), and resulting reaction mixture was heated at 70° C. for 3 hour. Product formation was confirmed by LCMS and TLC. After the completion of reaction, the reaction mixture was concentrated up to maximum and diluted with water (50 ml). Aqueous layer extracted with ethyl acetate (30 mL×3). Filtrate was concentrated under reduced pressure. Combined organic extracts were washed with brine (50 mL), dried over anhydrous Na$_2$SO$_4$ and concentrated. The crude product obtained was purified by flash chromatography (5% MeOH in DCM as an eluent) to obtain 2-chloro-6-methoxynicotinic acid (1.8 g, 96.4%) as a white solid

LCMS 188 [M+H]$^+$ $^1$H NMR (400 MHz, DMSO-d$_6$) δ 13.33 (br. s., 1H), 8.06-8.24 (m, 1H), 6.92 (d, J=8.77 Hz, 1H), 3.91 (s, 3H).

Compound 30b. To a solution of 2-chloro-6-methoxynicotinic acid (0.200 g, 1.07 mmol, 1.0 equiv) in Dioxane (10 mL) was added compound (0.195 g, 1.604 mmol, 1.5 equiv), Na$_2$CO$_3$ (0.23 g, 2.14 mmol, 2.0 equiv) and resulting reaction mixture purged with N$_2$ gas for 10 minute, followed by the addition of Pd(PPh$_3$)$_4$ (0.062 g, 0.054 mmol. 0.05 equiv). The resulting reaction mixture was heated at 100° C. for overnight. Product formation was confirmed by LCMS and TLC. After the completion of reaction, the mixture was filtered through celite bed, washed with ethyl acetate (100 mL). Filtrate was concentrated under reduced pressure. The crude product obtained was purified by flash chromatography (0-2% MeOH in DCM as an eluent) to obtain 6-methoxy-2-phenylnicotinic acid (0.07 g, 28.6% Yield) as a white solid.

LCMS 230 [M+H]$^+$ $^1$H NMR (400 MHz, DMSO-d$_6$) δ 12.89 (br. s., 1H), 8.17 (d, J=6.58 Hz, 3H), 7.67 (d, J=7.45 Hz, 1H), 7.38-7.60 (m, 3H), 4.04 (s, 3H).

Compound 30c. To a stirred solution of 6-methoxy-2-phenylnicotinic acid (0.050 g, 0.218 mmol, 1.0 equiv) in DMF (5 mL), was added (S)-4,4-difluoro-1-glycylpyrrolidine-2-carbonitrile hydrochloride (0.073 g, 0.327 mmol, 1.5 equiv) and TBTU (0.104 g, 0.327 mmol, 1.5 equiv). The mixture was allowed to stir at RT for 10 min. N-Methylmorpholine (0.1 mL) was added and the mixture was allowed to stir at RT for overnight. Product formation was confirmed by LCMS and TLC. After completion of reaction, the mixture was diluted with water (15 mL) and extracted with ethyl acetate (10 mL×2). Combined organic extracts were washed with water (10 mL×4), dried over anhydrous $Na_2SO_4$ and concentrated. The crude product obtained was purified by flash chromatography (5% MeOH in DCM as an eluent) followed by reverse phase purification to obtain (S)—N-(2-(2-cyano-4,4-difluoropyrrolidin-1-yl)-2-oxoethyl)-6-methoxy-2 phenylnicotinamide (0.015 g, 17.2% Yield) as an white solid.

LCMS 401.2 [M+H]$^+$ $^1$H NMR (400 MHz, DMSO-d$_6$) δ 8.76 (br. s., 1H), 8.48 (s, 2H), 7.79 (d, J=8.33 Hz, 2H), 7.39 (br.s., 2H), 6.86 (d, J=8.33 Hz, 1H), 5.10 (d, J=7.45 Hz, 1H), 4.23 (br. s., 1H), 3.98-4.12 (m, 2H), 3.94 (s, 3H), 2.90 (d, J=8.33 Hz, 1H), 2.70-2.86 (m, 1H), 2.67 (br. s., 1H).

Compound 30. To a stirred solution of (S)—N-(2-(2-cyano-4,4-difluoropyrrolidin-1-yl)-2-oxoethyl)-6-methoxy-2 phenylnicotinamide (0.035 g, 0.087 mmol, 1.0 equiv) in DCM (5 mL), was added TMSI (1 ml) dissolved in DCM (5 ml) drop wise. The mixture was allowed to stir at RT for 10 min and then stir at 50° C. for 2 h. Product formation was confirmed by LCMS and TLC. After completion of reaction, the mixture was concentrated up to dry, residue diluted with Ethyl acetate (15 mL) and washed with water (10 mL×2), dried over anhydrous $Na_2SO_4$ and concentrated. The crude product obtained was purified by reverse phase purification to obtain (S)—N-(2-(2-cyano-4,4-difluoropyrrolidin-1-yl)-2-oxoethyl)-6-hydroxy-2-phenylnicotinamide (0.003 g, 8.9% Yield) as an off white solid.

LCMS 387.2 [M+H]$^+$ $^1$H NMR (400 MHz, DMSO-d$_6$) δ 10.18 (s, 1H), 8.37 (d, J=7.9 Hz, 1H), 7.82 (br. s., 2H), 7.54 (br. s., 2H), 6.81 (d, J=7.0 Hz, 1H), 5.12 (d, J=8.8 Hz, 1H), 4.37-4.18 (m, 2H), 4.18-3.95 (m, 1H), 2.89 (s, 1H), 2.81 (d, J=8.8 Hz, 2H).

Example 49

Synthesis of (S)—N-(2-(2-cyano-4,4-difluoropyrrolidin-1-yl)-2-oxoethyl)-3-(o-tolyl)isonicotinamide

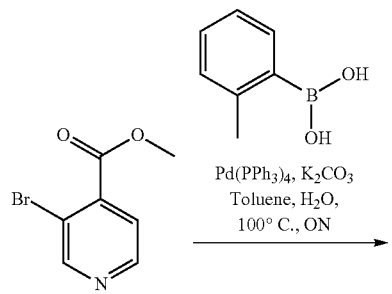

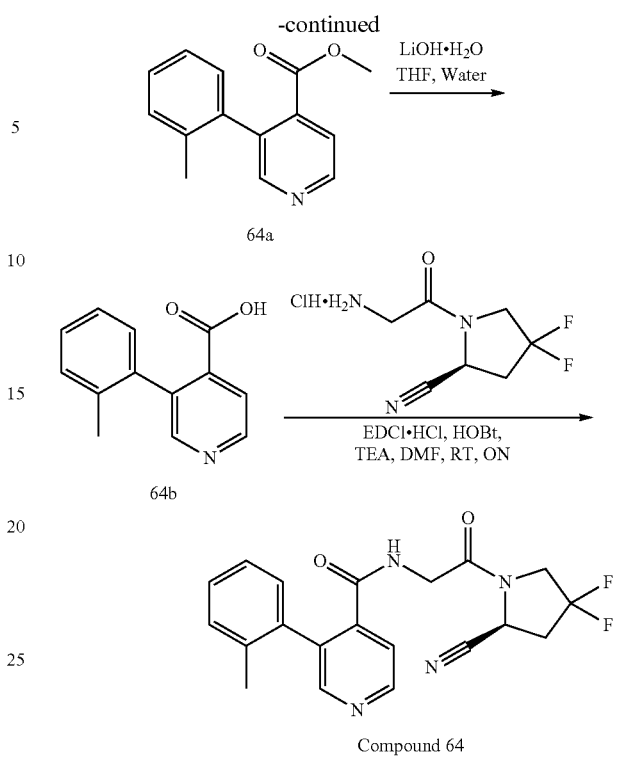

Compound 64

Compound 64a. To a solution of ethyl 3-bromoisonicotinate (0.3 g, 1.38 mmol, 1.0 equiv) in Toluene (15 mL) and water (2 mL) was added o-tolylboronic acid (0.288 g, 1.66 mmol, 1.2 equiv), $K_2CO_3$ (0.571 g, 4.14 mmol, 3.0 equiv) and resulting reaction mixture purged with $N_2$ gas for 10 minute, followed by the addition of Pd(PPh$_3$)$_4$ (0.08 g, 0.007 mmol. 0.05 equiv). The resulting reaction mixture was heated at 90° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-20% ethyl acetate in hexane as an eluent) to obtain methyl 3-(o-tolyl)isonicotinate (0.300 g, 95%) as yellow liquid.

LCMS 228.3 [M+H]$^+$ $^1$H NMR (400 MHz, DMSO-d$_6$) δ 8.76 (d, J=5.3 Hz, 1H), 8.55 (s, 1H), 7.77 (d, J=4.8 Hz, 1H), 7.39-7.14 (m, 3H), 7.08 (d, J=7.5 Hz, 1H), 3.33 (s, 3H), 2.02 (s, 3H)

Compound 64b. To a stirred solution of methyl 3-(o-tolyl)isonicotinate (0.4 g, 1.762 mmol, 1.0 equiv) in THF (5 mL) and water (5 mL), was added LiOH.H$_2$O (0.148 g, 3.524 mmol, 2.0 equiv). The mixture was allowed to stir at RT for overnight. Product formation was confirmed by LCMS. The reaction mixture was concentrated and diluted with water (20 mL) and washed with ethyl acetate (10 mL×2). Aqueous layer was separated and freeze dried on lyophilyzer to obtain 3-(o-tolyl)isonicotinic acid (Quant. Yield) as a white solid.

LCMS 214.2 [M+H]$^+$

Compound 64. To a stirred solution of 3-(o-tolyl)isonicotinic acid (0.100 g, 0.469 mmol, 1.0 equiv) in DMF (4 mL), was added (S)-4,4-difluoro-1-glycylpyrrolidine-2-carbonitrile hydrochloride (0.105 g, 0.469 mmol, 1.0 equiv), EDCI.HCl (0.135 g, 0.704 mmol, 1.5 equiv) & HOBt (0.096 g, 0.704 mmol, 1.5 equiv). The mixture was allowed to stir at RT for 10 min. Triethylamine (0.5 mL) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous $Na_2SO_4$ and concentrated. The crude product obtained was purified by flash chromatography (3% MeOH in DCM as an eluent) to obtain (S)—N-(2-(2-cyano-4,4-difluoropyrrolidin-1-yl)-2-oxoethyl)-3-(o-tolyl)isonicotinamide (0.1 g, 55.5% Yield) as a white solid.

LCMS 315.2 $[M+H]^+$ $^1$H NMR (400 MHz, DMSO-$d_6$) δ 8.79-8.62 (m, 2H), 8.46 (s, 1H), 7.52 (d, J=4.4 Hz, 1H), 7.25 (br. s., 2H), 7.22-7.03 (m, 2H), 5.06 (d, J=8.8 Hz, 1H), 4.14 (d, J=12.7 Hz, 1H), 4.03-3.83 (m, 2H), 2.87 (d, J=16.7 Hz, 1H), 2.81-2.69 (m, 2H), 2.09 (s, 3H).

Example 50

Synthesis of (R)—N-(2-(2-cyano-4,4-difluoropyrrolidin-1-yl)-2-oxoethyl)-3-cyclopropylisonicotinamide

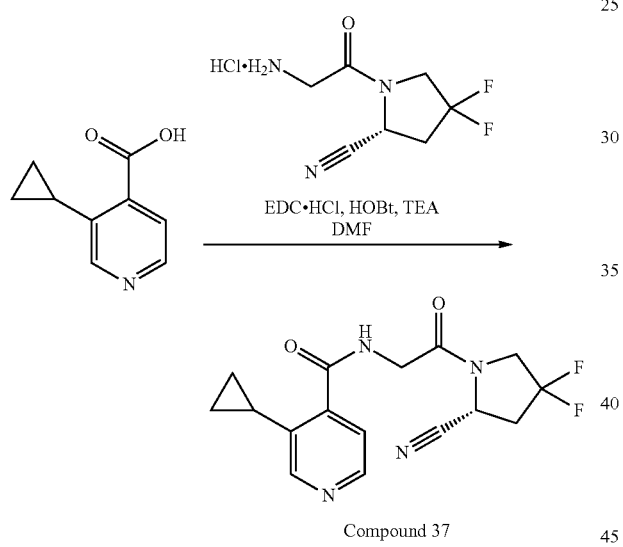

Compound 37

Compound 37. To a stirred solution of 3-cyclopropylisonicotinic acid (0.100 g, 060 mmol, 1.0 eq) in DMF (05 mL), was added (R)-4,4-difluoro-1-glycylpyrrolidine-2-carbonitrile.HCl (0.138 g, 0.60 mmol, 1.0 eq), HOBt (0.098 g, 0.72 mmol, 1.2 eq) and EDC.HCl (0.138 g, 0.72 mmol, 1.2 eq). The mixture was allowed to stir at RT for 10 min. Triethyl amine (0.2 mL) was added and the mixture was allowed to stir at RT for overnight. Product formation was confirmed by LCMS and TLC. The reaction mixture was diluted with water and extracted with ethyl acetate (50 mL×2). Combined organic extracts were washed with water (20 mL×4), dried over anhydrous $Na_2SO_4$ and concentrated. The crude product obtained was purified by reverse phase HPLC to obtain (R)—N-(2-(2-cyano-4,4-difluoropyrrolidin-1-yl)-2-oxoethyl)-3-cyclopropylisonicotinamide (0.005 g, 03% Yield) a white solid.

LCMS 335 $[M+H]^+$ $^1$H NMR (400 MHz, DMSO-δ 8.85 (br. s., 1H), 8.44 (d, J=4.4 Hz, 1H), 8.24 (s, 1H), 7.26 (d, J=4.8 Hz, 1H), 5.12 (d, J=7.5 Hz, 1H), 4.27 (d, J=12.3 Hz, 2H), 4.21-3.99 (m, 2H), 2.98-2.86 (m, 1H), 2.81 (d, J=17.1 Hz, 1H), 2.73 (s, 1H), 2.21 (br. s., 2H), 1.24 (br. s., 2H).

Example 51

Synthesis of (S)—N-(2-(2-cyano-4,4-difluoropyrrolidin-1-yl)-2-oxoethyl)-6-oxo-4-phenyl-1,6-dihydropyridine-3-carboxamide

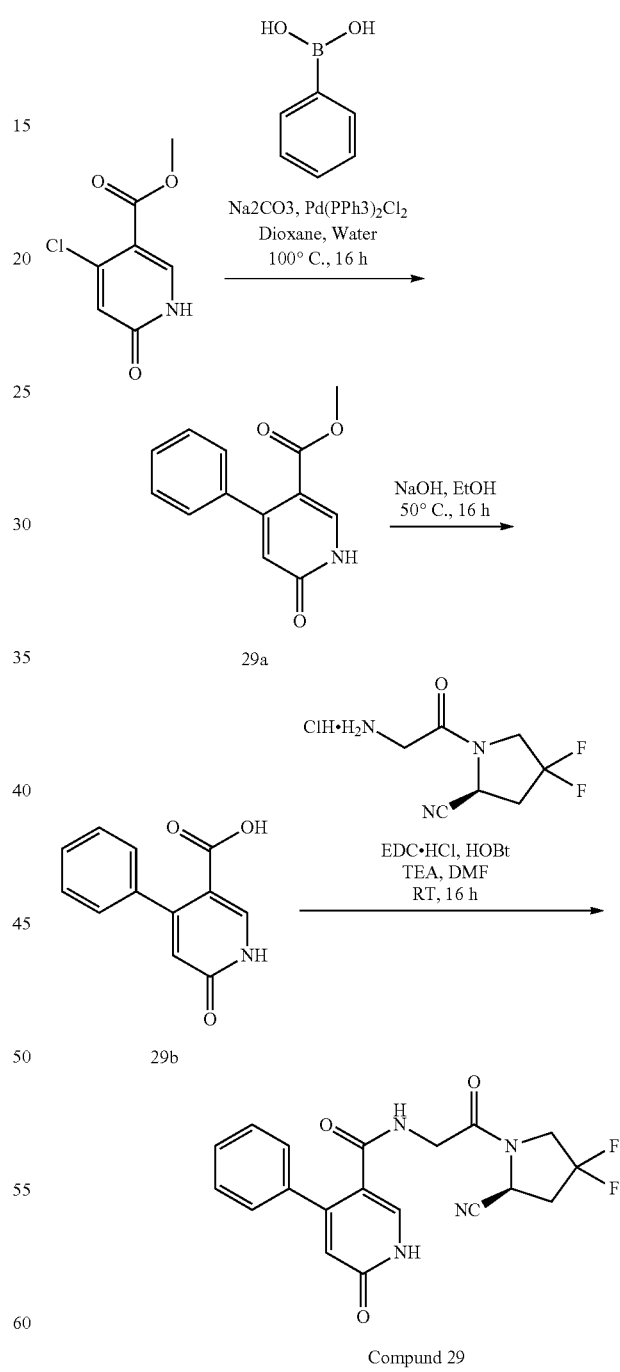

Compund 29

Compound 29a. To a stirred solution of methyl 4-chloro-6-oxo-1,6-dihydropyridine-3-carboxylate (0.200 g, 1.07 mmol, 1 equiv) in Dioxan (4 mL) and water (1 mL), was added $Na_2CO_3$ (0.227 g, 2.14 mmol, 2 equiv) and phenylboronic acid (0.196 g, 1.61 mmol, 1.5 equiv). Aerated the reaction mixture with nitrogen gas for 15 min. Pd(PPh3)$_2$Cl$_2$ (0.078 g, 0.11 mmol, 0.1 equiv) was added to the reaction mixture. Reaction mixture was again aerated with nitrogen gas for 15 min. The reaction mixture was allowed to stirrer for 16 h at 100° C. Progress of the reaction was monitored by LCMS. After completion of the reaction, the reaction mixture was diluted with water (15 mL) and extracted with ethyl acetate (25 mL×2). Combined organic extracts were washed with brine (25 mL), dried over anhydrous Na2SO4 and concentrated under reduced pressure to obtain methyl 6-oxo-4-phenyl-1,6-dihydropyridine-3-carboxylate (0.170 g, 69% Yield) as an off-white solid

LCMS 230.3 [M+H]$^+$

Compound 29b. To a stirred solution of methyl 6-oxo-4-phenyl-1,6-dihydropyridine-3-carboxylate (0.170 g, 0.74 mmol, 1 equiv) in EtOH and water (1:1)(6 mL), was added NaOH (0.059 g, 1.48 mmol, 2 equiv). The mixture was allowed to stir at 50° C. for 16 h. Progress of the reaction was monitored by LCMS. After completion of the reaction, the reaction mixture was diluted 1 M HCl (10 mL) and extracted with ethyl acetate (20 mL×3). Combined organic extracts were washed with brine (25 mL), dried over anhydrous Na2SO4 and concentrated under reduced pressure. Crude product was purified by flash chromatography (0-10% MeOH in DCM as an eluent) to obtain 6-oxo-4-phenyl-1,6-dihydropyridine-3-carboxylic acid (0.090 g, 56% Yield) as an off-white solid.

LCMS 216.2 [M+H]$^+$

Compound 29. To a stirred solution of 6-oxo-4-phenyl-1,6-dihydropyridine-3-carboxylic acid (0.080 g, 0.37 mmol, 1 equiv) in DMF (3 mL), was added (S)-4,4-difluoro-1-glycylpyrrolidine-2-carbonitrile hydrochloride (0.083 g, 0.37 mmol, 1.0 equiv), HOBt (0.059 g, 0.44 mmol, 1.2 equiv) and EDC.HCl (0.085 g, 0.44 mmol, 1.2 equiv). The mixture was allowed to stir at RT for 10 min. Triethylamine (0.112 g, 1.11 mmol, 3.0 equiv) was added and the mixture was allowed to stir at RT for overnight. Product formation was confirmed by LCMS. The reaction mixture was diluted with water and extracted with ethyl acetate (40 mL×2). Combined organic extracts were washed with water (15 mL×4), dried over anhydrous Na2SO4 and concentrated. The crude product obtained was purified by normal phase combi-flash chromatography to obtain (S)—N-(2-(2-cyano-4,4-difluoropyrrolidin-1-yl)-2-oxoethyl)-6-oxo-4-phenyl-1,6-dihydropyridine-3-carboxamide (0.045 g, 31.25% Yield) as an off-white solid.

LCMS 387.3 [M+H]$^+$ $^1$H NMR (400 MHz, DMSO-d6) δ 12.39-11.70 (m, 1H), 8.66 (t, J=5.9 Hz, 1H), 7.64 (s, 1H), 7.44-7.32 (m, 5H), 6.29 (s, 1H), 5.08 (dd, J=9.3, 2.9 Hz, 1H), 4.20 (ddd, J=16.0, 11.6, 4.4 Hz, 1H), 4.01 (dd, J=19.7, 8.6 Hz, 3H), 2.96-2.70 (m, 2H), 1.38-1.21 (m, 3H), 1.16 (s, 1H).

Example 52

Synthesis of (S)—N-(2-(2-cyano-4,4-difluoropyrrolidin-1-yl)-2-oxoethyl)-3-phenoxyisonicotinamide

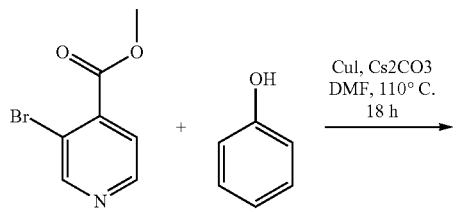

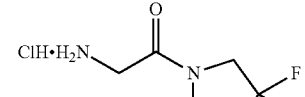

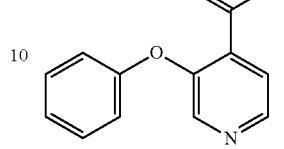

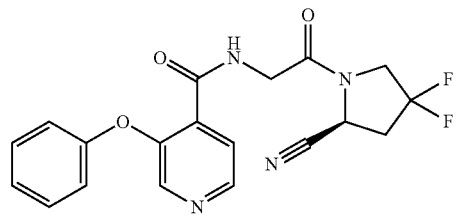

Compound 97a. To a stirred solution of methyl 3-bromoisonicotinate (1.0 g, 4.65 mmol, 1 equiv) in DMF (10 mL), was added phenol (0.437 g, 4.65 mmol, 1 equiv), CuI (1.762 g, 9.3 mmol, 2 equiv) and Cs$_2$CO$_3$ (3.03 g, 10.0 mmol, 2 equiv). Heated the reaction mixture at 110° C. for 18 h. Reaction progress was checked by LCMS. The reaction mixture was diluted with water (20 mL) and added few drops of dil. HCl till pH was slightly acidic. Aqueous layer was extracted with ethyl acetate (50 mL×2). Combined organic extracts were washed with brine (50 mL), dried over anhydrous Na$_2$SO$_4$, filtered and concentrated under reduced pressure to obtain 3-phenoxyisonicotinic acid (0.200 g, 20% Yield) as an off-white solid.

LCMS: 216.1 [M+H]$^+$

Compound 97. To a stirred solution of 3-phenoxyisonicotinic acid (0.140 g, 0.65 mmol, 1 equiv) in DMF (3 mL), was added (S)-4,4-difluoro-1-glycylpyrrolidine-2-carbonitrile hydrochloride (0.146 g, 0.65 mmol, 1.0 equiv), HOBt (0.105 g, 0.78 mmol, 1.2 equiv) and EDC.HCl (0.149 g, 0.78 mmol, 1.2 equiv). The mixture was allowed to stir at RT for 10 min. Triethyl amine (0.197 g, 1.95 mmol, 3 equiv) was added and the mixture was allowed to stir at ambient temperature for 16 h. Product formation was confirmed by LCMS. The reaction mixture was diluted with water (10 mL) and extracted with ethyl acetate (40 mL×2). Combined organic extracts were washed with water (25 mL×5). Organic extract was dried over anhydrous Na$_2$SO$_4$, filtered and concentrated under reduced pressure to obtain crude product. The crude product obtained was purified by normal phase combi-flash chromatography to obtain (S)—N-(2-(2-cyano-4,4-difluoropyrrolidin-1-yl)-2-oxoethyl)-3-phenoxyisonicotinamide (0.050 g, 19.9% Yield) as an off-white solid.

LCMS 387.2 [M+H]$^+$ $^1$H NMR (400 MHz, DMSO-d6) δ 8.80 (t, J=5.2 Hz, 1H), 8.49 (d, J=4.9 Hz, 1H), 8.25 (s, 1H), 7.67 (d, J=4.9 Hz, 1H), 7.43 (t, J=7.9 Hz, 2H), 7.21 (t, J=7.5 Hz, 1H), 7.11 (d, J=8.0 Hz, 2H), 5.10 (dd, J=9.3, 3.0 Hz, 1H), 4.29-3.98 (m, 4H), 2.93-2.73 (m, 2H), 1.23 (d, J=3.6 Hz, 1H).

Example 53

Synthesis of N-(2-((2R)-2-cyano-4,4-difluorocyclopentyl)-2-oxoethyl)-3-(phenylamino)isonicotinamide

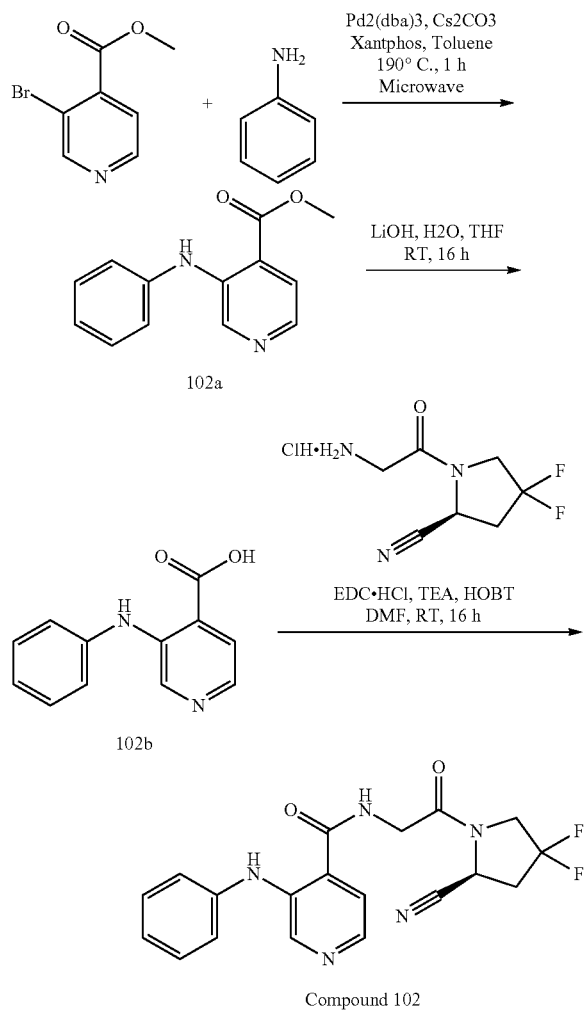

Compound 102a. To a stirred solution of methyl 3-bromoisonicotinate (1.0 g, 4.65 mmol, 1 equiv) in toluene (6 mL), was added aniline (0.476 g, 5.12 mmol, 1.1 equiv), Tris(dibenzylideneacetone)dipalladium(0) (0.431 g, 0.47 mmol, 0.1 equiv), xantphos (0.539 g, 0.93 mmol, 0.2 equiv) and Cs₂CO₃ (2.28 g, 6.98 mmol, 1.5 equiv). The resulting reaction mixture was heated at 190° C. for 1 h in microwave. Reaction progress was checked by LCMS. The reaction mixture was diluted with water (15 mL) and extracted with ethyl acetate (30 mL×2). Combined organic extracts were washed with brine (30 mL), dried organic extract over anhydrous Na₂SO₄, filtered and concentrated under reduced pressure. Crude compound was purified by normal phase combi-flash chromatography to obtain methyl-3-(phenylamino)isonicotinate (0.300 g, 28% Yield) as yellow semisolid.

LCMS: 229.2 [M+H]⁺

Compound 102b. To a stirred solution of methyl-3-(phenylamino)isonicotinate (0.300 g, 1.31 mmol, 1 equiv) in THF and water (1:1)(4 mL), was added LiOH.H₂O (0.083 g, 1.97 mmol, 1.5 equiv). The mixture was allowed to stir at ambient temperature for 16 h. Product formation was confirmed by LCMS. The reaction mixture was diluted with water (20 mL), extracted with ethyl acetate and concentrated the aqueous layer under reduced pressure and lyophilized to obtain 3-(phenylamino)isonicotinic acid (0.260 g.) as an off-white solid

LCMS 215.2 [M+H]+

Compound 102. To a stirred solution of 3-(phenylamino)isonicotinic acid (0.260 g, 1.21 mmol, 1 equiv) in DMF (3 mL), was added (1R)-4,4-difluoro-2-glycylcyclopentane-1-carbonitrile hydrochloride (0.272 g, 1.21 mmol, 1.0 equiv), HOBt (0.196 g, 1.45 mmol, 1.2 equiv) and EDC.HCl (0.278 g, 1.45 mmol, 1.2 equiv). and triethyl amine (0.366 g, 3.63 mmol, 3 equiv) was added and the mixture was allowed to stir at ambient temperature for 16 h. Product formation was confirmed by LCMS. The reaction mixture was diluted with water (15 mL) and extracted with ethyl acetate (40 mL×3). Combined organic extracts were washed with water (25 mL×5), dried over anhydrous Na₂SO₄, filtered and concentrated under reduced pressure to obtain crude product which was purified by reverse phase HPLC N-(2-((2R)-2-cyano-4,4-difluorocyclopentyl)-2-oxoethyl)-3-(phenylamino)isonicotinamide (0.004 g, 0.8% Yield).

LCMS 386.2 [M+H]+

¹H NMR (400 MHz, DMSO-d6) δ 9.22-9.07 (m, 2H), 8.64 (s, 1H), 8.12 (d, J=5.0 Hz, 1H), 7.58 (d, J=5.0 Hz, 1H), 7.34 (t, J=7.7 Hz, 2H), 7.22 (d, J=7.8 Hz, 2H), 7.03 (t, J=7.4 Hz, 1H), 5.13 (dd, J=9.4, 2.9 Hz, 1H), 4.36-4.25 (m, 1H), 4.25-4.04 (m, 3H), 3.00-2.74 (m, 2H), 2.09 (s, 3H), 1.24 (s, 1H).

Example 54

Synthesis of (S)—N-(2-(2-cyano-4,4-difluoropyrrolidin-1-yl)-2-oxoethyl)-1',2',3',6'-tetrahydro-[3,4'-bipyridine]-4-carboxamide 2,2,2-trifluoroacetate

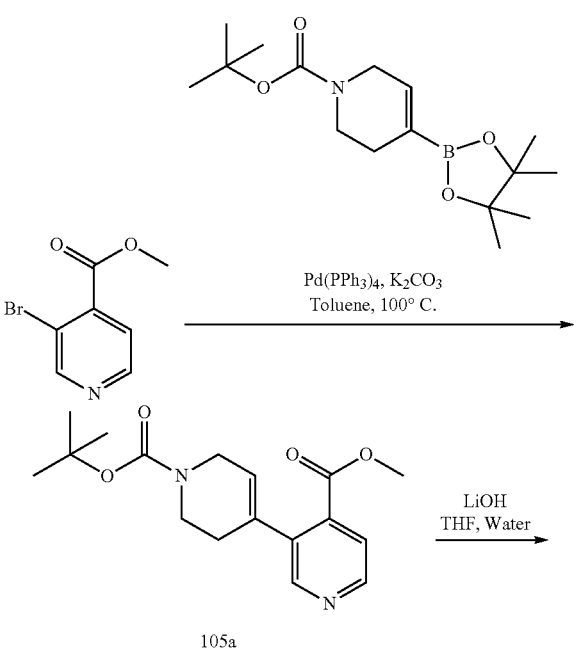

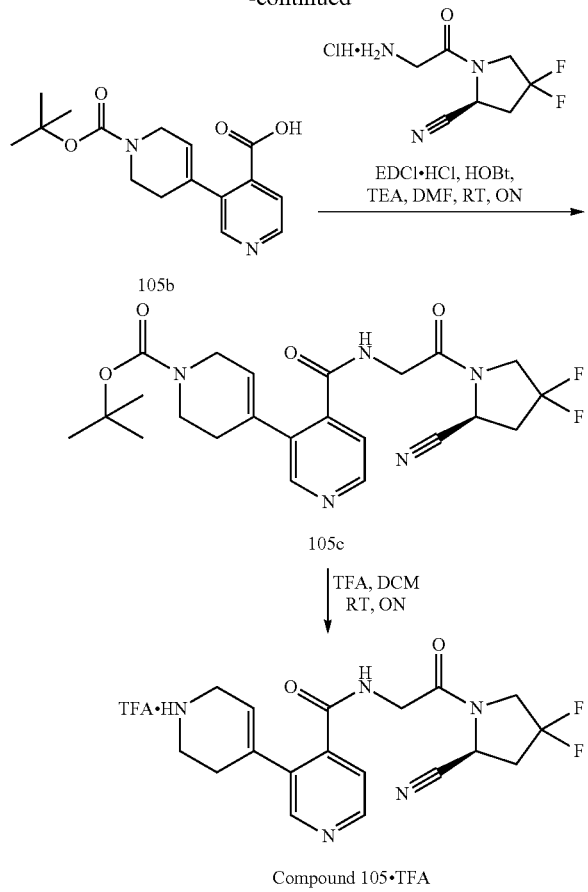

Compound 105a. To a solution of ethyl 3-bromoisonicotinate (0.2 g, 0.925 mmol, 1.0 equiv) in Toluene (8 mL) and water (2 mL) was added tert-butyl 4-(4,4,5,5-tetramethyl-1,3,2-dioxaborolan-2-yl)-3,6-dihydropyridine-1(2H)-carboxylate (0.429 g, 1.39 mmol, 1.5 equiv), $K_2CO_3$ (0.255 g, 1.85 mmol, 2.0 equiv) and resulting reaction mixture purged with $N_2$ gas for 10 minute, followed by the addition of Pd(PPh$_2$)Cl$_2$ (0.033 g, 0.046 mmol. 0.05 equiv). The resulting reaction mixture was heated at 90° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-20% ethyl acetate in hexane as an eluent) to obtain 1'-(tert-butyl) 4-methyl 3',6'-dihydro-[3,4'-bipyridine]-1',4(2'H)-dicarboxylate (0.130 g, 44.4% Yield) as an yellow oil.

LCMS 319.2 [M+H]$^+$ $^1$H NMR (400 MHz, DMSO-d$_6$) δ 8.65 (d, J=4.8 Hz, 1H), 8.59-8.52 (m, 1H), 7.63 (d, J=4.8 Hz, 1H), 5.68 (br. s., 1H), 3.96 (br. s., 2H), 3.87-3.69 (m, 3H), 3.52 (br. s., 2H), 2.27 (br. s., 2H), 1.53-1.25 (m, 9H), 1.07 (s, 3H).

Compound 105b. To a stirred solution of 1'-(tert-butyl) 4-methyl 3',6'-dihydro-[3,4'-bipyridine]-1',4(2'H)-dicarboxylate (0.13 g, 0.408 mmol, 1.0 equiv) in THF (5 mL) and water (5 mL), was added LiOH (0.020 g, 0.817 mmol, 2.0 equiv). The mixture was allowed to stir at RT for overnight. Product formation was confirmed by LCMS and $^1$H NMR Spectroscopy. The reaction mixture was concentrated and diluted with water (20 mL) and washed with ethyl acetate (15 mL×2). Aqueous layer was separated and freeze dried on lyophilyzer to obtain 1'-(tert-butoxycarbonyl)-1',2',3',6'-tetrahydro-[3,4'-bipyridine]-4-carboxylic acid (Quantative Yield) as white solid.

LCMS 305.2 [M+H]$^+$ $^1$H NMR (400 MHz, DMSO-d$_6$) δ 8.30 (d, J=4.8 Hz, 2H), 8.22 (s, 1H), 7.17 (d, J=4.8 Hz, 1H), 3.92 (br. s., 2H), 2.38 (br. s., 2H), 2.06 (s, 1H), 2.04-1.92 (m, 1H), 1.43 (s, 9H), 1.06 (s, 2H)

Compound 105c. To a stirred solution of 1'-(tert-butoxycarbonyl)-1',2',3',6'-tetrahydro-[3,4'-bipyridine]-4-carboxylic acid (0.100 g, 0.32 mmol, 1.0 equiv) in DMF (5 mL), was added (S)-4,4-difluoro-1-glycylpyrrolidine-2-carbonitrile hydrochloride (0.074 g, 0.32 mmol, 1.0 equiv), EDCI.HCl (0.092 g, 0.48 mmol, 1.5 equiv) & HOBt (0.065 g, 0.48 mmol, 1.5 equiv). The mixture was allowed to stir at RT for 10 min. Triethylamine (0.5 mL) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous $Na_2SO_4$ and concentrated. The crude product obtained was purified by flash chromatography (5% MeOH in DCM as an eluent) followed by reverse phase purification to obtain tert-butyl (S)-4-((2-(2-cyano-4,4-difluoropyrrolidin-1-yl)-2-oxoethyl)carbamoyl)-3',6'-dihydro-[3,4'-bipyridine]-1'(2'H)-carboxylate (0.020 g, 13.15% Yield) as a white solid.

LCMS 476.3 [M+H]$^+$

1H NMR (400 MHz, DMSO-d$_6$) δ 8.83 (br. s., 1H), 8.57 (d, J=4.8 Hz, 1H), 8.52 (s, 1H), 7.36 (d, J=5.3 Hz, 1H), 5.83 (br. s., 1H), 5.09 (br. s., 1H), 4.25 (d, J=13.6 Hz, 2H), 4.11 (d, J=5.3 Hz, 2H), 3.94 (br. s., 2H), 3.48 (br. s., 2H), 2.81 (d, J=17.5 Hz, 3H), 2.67 (br. s., 2H), 2.35 (d, J=14.5 Hz, 3H), 1.43 (s, 9H).

Compound 105•TFA. To a stirred solution of N-(2-((S)-2-cyano-4,4-difluoropyrrolidin-1-yl)-2-oxoethyl)-3-(cyclohex-2-en-1-yl)isonicotinamide (0.020 g, 0.042 mmol, 1.0 equiv) in DCM (2 mL), was added TFA (0.02 mL, 0.126 mmol, 3.0 equiv) at room temperature and the mixture was allowed to stir at RT for overnight. Product formation was confirmed by LCMS. After completion of reaction, the mixture concentrated up to dried to obtained crude. The crude product obtained was purified by reverse phase purification to obtain (S)—N-(2-(2-cyano-4,4-difluoropyrrolidin-1-yl)-2-oxoethyl)-1',2',3',6'-tetrahydro-[3,4'-bipyridine]-4-carboxamide 2,2,2-trifluoroacetate (0.005 g, 31.72% Yield) as off white solid.

LCMS 376.3 [M+H]$^+$ $^1$H NMR (400 MHz, DMSO-d$_6$) δ 8.71 (br. s., 1H), 8.54 (d, J=4.4 Hz, 1H), 8.47 (s, 1H), 7.33 (d, J=4.4 Hz, 2H), 5.85 (br. s., 1H), 5.11 (d, J=8.3 Hz, 1H), 4.26 (d, J=12.3 Hz, 1H), 4.15-4.00 (m, 2H), 3.31 (br. s., 4H), 2.98-2.82 (m, 3H), 2.79 (br. s., 1H), 2.24 (br. s., 2H), 1.80 (br. s., 3H), 1.75 (s, 2H).

Example 55

Synthesis of (S)—N-(2-(2-cyano-4,4-difluoropyrrolidin-1-yl)-2-oxoethyl)-3-(5-methylfuran-2-yl)isonicotinamide

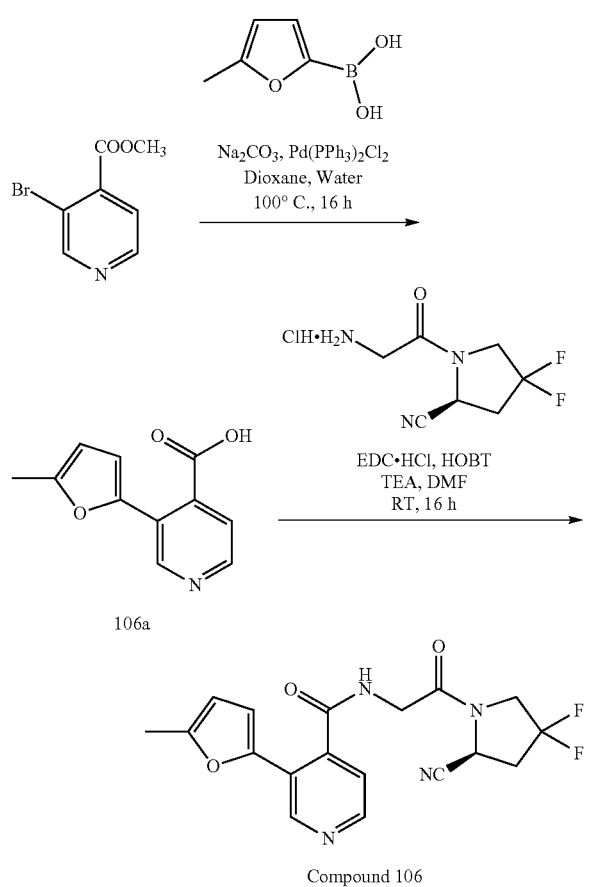

Compound 106

Compound 106a. To a stirred solution methyl 3-bromoisonicotinate (0.300 g, 1.4 mmol, 1.0 equiv) in Dioxan (5 mL) and water (5 mL), was added (5-methylfuran-2-yl) boronic acid (0.212 g, 1.68 mmol, 1.2 equiv), $Na_2CO_3$ (0.297 g, 2.8 mmol, 2.0 equiv) and aerated the reaction mixture with nitrogen for 15 min and added Dichlorobis(triphenylphosphine)palladium(II) (0.098 g, 0.14 mmol, 0.1 equiv). Aerated the reaction mixture again with nitrogen for 15 min. The mixture was allowed to stir at 100° C. for 2 h. Product formation was confirmed by LCMS. The reaction mixture was diluted with water (50 mL) and washed with ethyl acetate (20 mL×2). Aqueous layer was separated and freeze dried over lyophilizer to obtain 3-(5-methylfuran-2-yl)isonicotinic acid (0.250 g).

LCMS 204.2 [M+H]+

Compound 106. To a stirred solution 3-(5-methylfuran-2-yl)isonicotinic acid (0.100 g, 0.5 mmol, 1.0 equiv) in DMF (3 mL), was added (S)-4,4-difluoro-1-glycylpyrrolidine-2-carbonitrile hydrochloride (0.112 g, 0.5 mmol, 1.0 equiv), HOBt (0.081 g, 0.6 mmol, 1.2 equiv) and EDC.HCl (0.115 g, 0.6 mmol, 1.2 equiv). The mixture was allowed to stir at RT for 10 min. Triethyl amine (0.151 g, 1.5 mmol, 3.0 equiv) was added and the mixture was allowed to stir at RT for overnight. Product formation was confirmed by LCMS. The reaction mixture was diluted with water and extracted with ethyl acetate (40 mL×2). Combined organic extracts were washed with water (25 mL×6), dried over anhydrous $Na_2SO_4$ and concentrated. The crude product obtained was purified by reversed phase HPLC to obtain (S)—N-(2-(2-cyano-4,4-difluoropyrrolidin-1-yl)-2-oxoethyl)-3-(5-methylfuran-2-yl)isonicotinamide (0.010 g, 5.04% Yield) as an off-white solid.

LCMS 375.3 [M+H]+

1H NMR (400 MHz, DMSO-d6) δ 8.97 (t, J=5.8 Hz, 1H), 8.92 (s, 1H), 8.52 (d, J=4.9 Hz, 1H), 7.32 (d, J=4.9 Hz, 1H), 6.90 (d, J=3.4 Hz, 1H), 6.21 (d, J=3.4 Hz, 1H), 5.13 (dd, J=9.3, 2.8 Hz, 1H), 4.29 (ddd, J=16.0, 11.2, 4.1 Hz, 1H), 4.16 (d, J=5.8 Hz, 2H), 4.12-4.03 (m, 1H), 2.97-2.74 (m, 2H), 2.34 (s, 3H), 1.24 (s, 1H).

Example 56

Synthesis of (S)-6'-amino-N-(2-(2-cyano-4,4-difluoropyrrolidin-1-yl)-2-oxoethyl)-[3,3'-bipyridine]-4-carboxamide Formate

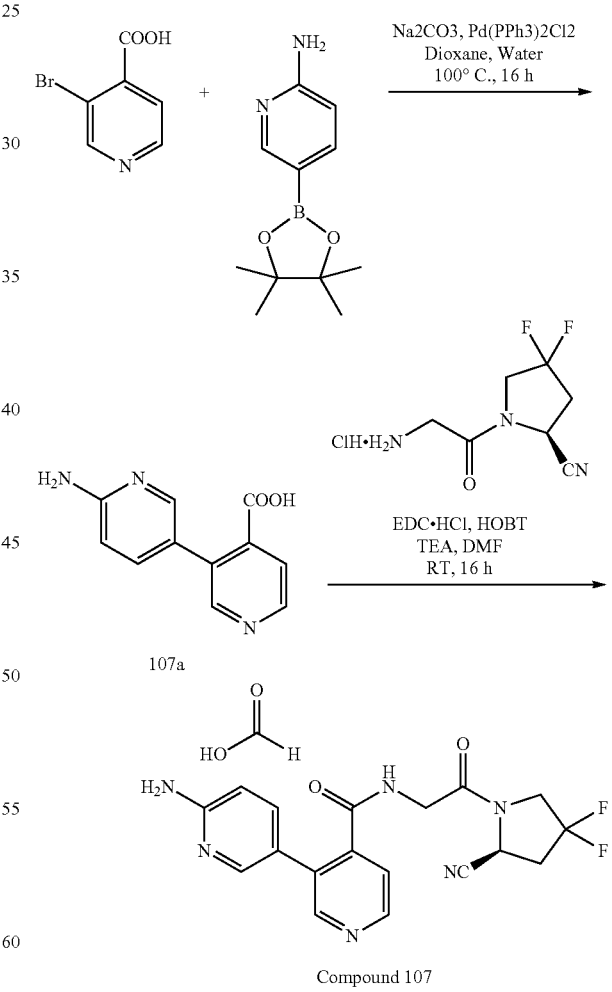

Compound 107

Compound 107a. To a stirred solution of 3-bromoisonicotinic acid (0.500 g, 2.34 mmol, 1 equiv) in Dioxan (5 mL) and water (5 mL), was added $Na_2CO_3$ (0.496 g, 4.68 mmol, 2 equiv) and 5-(4,4,5,5-tetramethyl-1,3,2-dioxaborolan-2- yl)pyridin-2-amine (0.618 g, 2.81 mmol, 1.2 equiv). Aerated the reaction mixture with nitrogen gas for 15 min. Bis (triphenylphosphine)palladium chloride (0.164 g, 0.234 mmol, 0.1 equiv) was added to the reaction mixture. Reaction mixture was again aerated with nitrogen gas for 15 min. The reaction mixture was allowed to heat at 120° C. for 16 h. Progress of the reaction was monitored by LCMS. After completion of the reaction, the reaction mixture was diluted with water (35 mL). Aqueous phase was washed with ethyl acetate (20 mL×2) and freeze dried on Lyophilizer to obtain 6'-amino-[3,3'-bipyridine]-4-carboxylic acid (0.600 g, Quant. Yield).

LCMS 216.2 [M+H]$^+$

Compound 107. To a stirred solution of 6'-amino-[3,3'-bipyridine]-4-carboxylic acid (0.200 g, 0.93 mmol, 1 equiv) in DMF (4 mL), was added (S)-4,4-difluoro-1-glycylpyrrolidine-2-carbonitrile hydrochloride (0.208 g, 0.93 mmol, 1.0 equiv), HOBt (0.151 g, 1.12 mmol, 1.2 equiv) and EDC.HCl (0.214 g, 1.12 mmol, 1.2 equiv). The mixture was allowed to stir at RT for 10 min. Triethylamine (0.282 g, 2.79 mmol, 3.0 equiv) was added and the mixture was allowed to stir at RT for overnight. Product formation was confirmed by LCMS. The reaction mixture was diluted with water and extracted with ethyl acetate (40 mL×2). Combined organic extracts were washed with water (15 mL×4), dried over anhydrous Na2SO4 and concentrated. The crude product was purified by reversed phase HPLC to obtain (S)-6'-amino-N-(2-(2-cyano-4,4-difluoropyrrolidin-1-yl)-2-oxoethyl)-[3,3'-bipyridine]-4-carboxamide formate (0.003 g, 0.8% Yield).

LCMS 387.3 [M+H]$^+$ $^1$H NMR (400 MHz, DMSO-d6) δ 8.88 (t, J=5.8 Hz, 1H), 8.64-8.55 (m, 2H), 8.18 (s, 1H), 8.03 (s, 1H), 7.55 (d, J=8.6 Hz, 1H), 7.38 (d, J=4.9 Hz, 1H), 6.46 (d, J=8.6 Hz, 1H), 6.11 (s, 2H), 5.13-5.03 (m, 1H), 4.30-4.17 (m, 1H), 4.05 (dt, J=21.0, 8.8 Hz, 3H), 3.95-3.80 (m, 1H), 3.26 (s, 3H), 2.94-2.72 (m, 2H), 2.13 (d, J=16.6 Hz, 1H), 1.23 (s, 1H), 1.12 (d, J=16.9 Hz, 1H).

Example 57

Synthesis of (S)—N-(2-(2-cyano-4,4-difluoropyrrolidin-1-yl)-2-oxoethyl)-3-(quinolin-4-yl)isonicotinamide

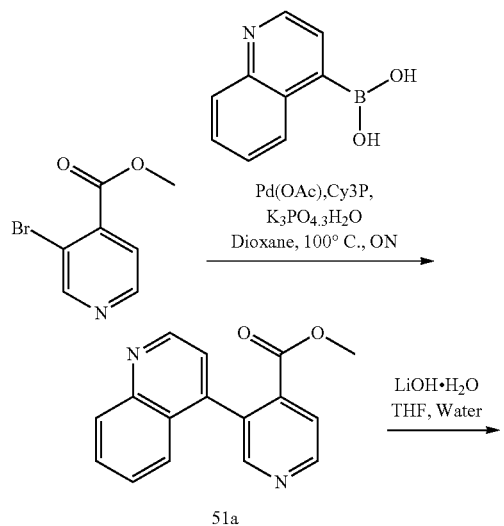

51a

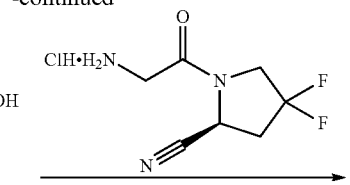

51b

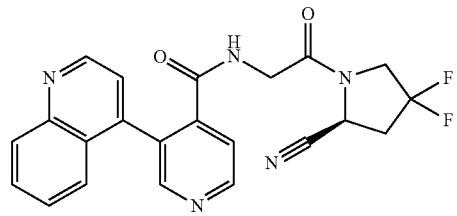

Compound 51

Compound 51a. To a solution of ethyl 3-bromoisonicotinate (0.3 g, 1.38 mmol, 1.0 equiv) in Toluene (15 mL) and water (2 mL) was added quinolin-4-ylboronic acid (0.288 g, 1.66 mmol, 1.2 equiv), K$_3$PO$_4$.3H$_2$O (0.887 g, 4.14 mmol, 3.0 equiv) and resulting reaction mixture purged with N$_2$ gas for 10 minute, followed by the addition of Pd(OAc) (0.032 g, 0.139 mmol. 0.1 equiv) and tricyclohexylphosphine (0.053 g, 0.139 mmol. 0.1 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (100% ethyl acetate as an eluent) to obtain methyl 3-(quinolin-4-yl)isonicotinate (0.230 g, 62.7% Yield) as white solid.

LCMS 265.3 [M+H]$^+$

Compound 51b. To a stirred solution of methyl 3-(quinolin-4-yl)isonicotinate (0.21 g, 0.795 mmol, 1.0 equiv) in THF (7 mL) and water (7 mL), was added LiOH.H$_2$O (0.067 g, 1.59 mmol, 2.0 equiv). The mixture was allowed to stir at RT for overnight. Product formation was confirmed by LCMS. The reaction mixture was concentrated and diluted with water (20 mL) and washed with ethyl acetate (10 mL×2). Aqueous layer was separated and freeze dried on lyophilyzer to obtain 3-(quinolin-4-yl)isonicotinic acid (Quant. Yield) as white solid.

LCMS 251.2 [M+H]$^+$

Compound 51. To a stirred solution of 3-(quinolin-4-yl) isonicotinic acid (0.12 g, 0.48 mmol, 1.0 equiv) in DMF (5 mL), was added (S)-4,4-difluoro-1-glycylpyrrolidine-2-carbonitrile hydrochloride (0.108 g, 0.48 mmol, 1.0 equiv), EDCI.HCl (0.138 g, 0.72 mmol, 1.5 equiv) & HOBt (0.097 g, 0.72 mmol, 1.5 equiv). The mixture was allowed to stir at RT for 10 min. Triethylamine (1 mL) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous Na$_2$SO$_4$ and concentrated. The crude product obtained was purified by flash chromatography (5% MeOH in DCM as an eluent) to obtain (S)—N-(2-(2-cyano- 4,4-difluoropyrrolidin-1-yl)-2-oxoethyl)-3-(quinolin-4-yl) isonicotinamide (0.040 g, 19.8% Yield) as an white solid. LCMS 422.2 [M+H]+

¹H NMR (400 MHz, DMSO-d₆) δ 9.00 (br. s., 1H), 8.92-8.81 (m, 2H), 8.65 (s, 1H), 8.08 (d, J=8.3 Hz, 1H), 7.78 (d, J=4.8 Hz, 1H), 7.70 (d, J=4.8 Hz, 1H), 7.55 (br. s., 2H), 7.47 (d, J=4.4 Hz, 1H), 5.03 (d, J=8.3 Hz, 1H), 4.11 (br. s., 1H), 3.96-3.74 (m, 3H), 2.82 (br. s., 1H), 2.74 (d, J=9.2 Hz, 1H)

Example 58

Synthesis of (S)—N-(2-(2-cyano-4, 4-difluoropyrrolidin-1-yl)-2-oxoethyl)-4-(4-fluorophenyl)-6-oxo-1,6-dihydropyridine-3-carboxamide

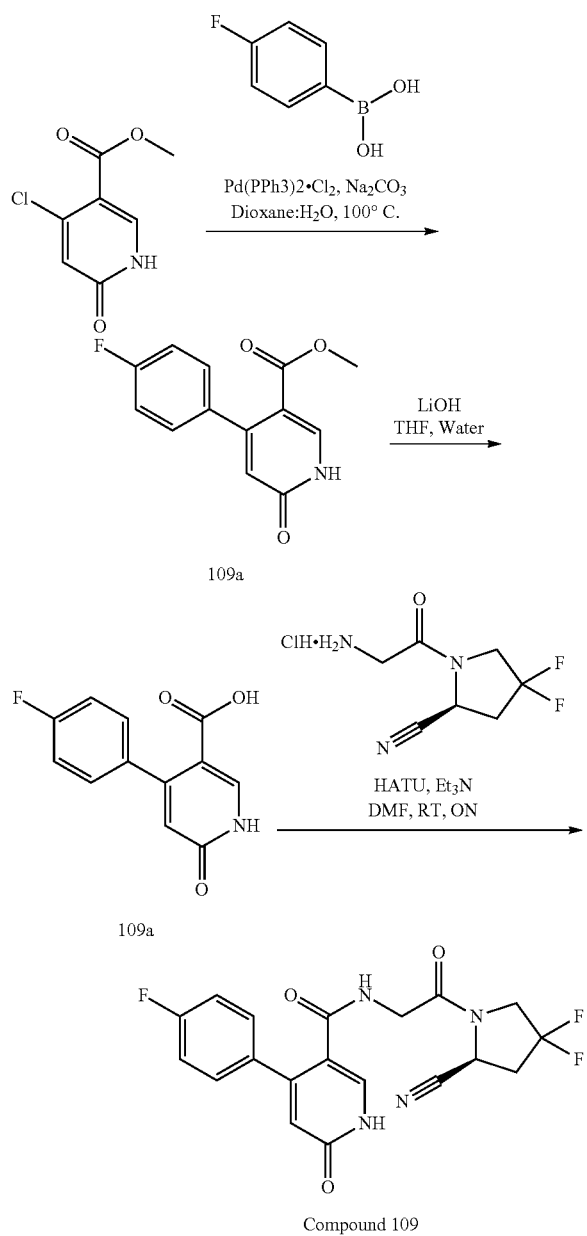

Compound 109

Compound 109a. To a solution of methyl 4-chloro-6-oxo-1,6-dihydropyridine-3-carboxylate (1 g, 5.3191 mmol, 1.0 equiv) in Dioxan (30 mL):water (10 mL) was added compound 4-fluorophenyl)boronic acid (0.82 g, 5.8510 mmol, 1.1 equiv), Na₂CO₃ (1.12 g, 10.63 mmol, 2.0 equiv) and resulting reaction mixture purged with N₂ gas for 10 minute, followed by the addition of Pd(PPh₃)₂Cl₂ (0.187 g, 0.2659 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. Diluted with water & extracted with EtOAc (3×50 mL), organic layer was dried over Na₂SO₄ & concentrated under reduced pressure. The crude product obtained was purified by flash chromatography (0-50% ethyl acetate in hexane as an eluent) to obtain compound of methyl 4-(4-fluorophenyl)-6-oxo-1,6-dihydropyridine-3-carboxylate. (1.2 g, 81.34%) as a white solid.

LCMS 247.8 [M+H]+

¹H NMR (400 MHz, DMSO-d₆) δ 12.22 (br. s., 1H), 8.05 (s, 1H), 7.65-7.58 (m, 1H), 7.56 (d, J=6.6 Hz, 1H), 7.35-7.26 (m, 1H), 7.22-7.14 (m, 1H), 6.21 (s, 1H), 3.61-3.52 (m, 3H)

Compound 109b. To a stirred solution of compound methyl 4-(4-fluorophenyl)-6-oxo-1,6-dihydropyridine-3-carboxylate (1.2 g, 4.8582 mmol, 1.0 equiv) in THF (30 mL) and water (10 mL), was added LiOH (0.225 g, 9.7165 mmol, 2.0 equiv). The mixture was allowed to stir at 80° C. for overnight. Product formation was confirmed by LCMS. The reaction mixture was concentrated and diluted with water (30 mL) and washed with ethyl acetate (10 mL×2). Aqueous layer was separated and freeze dried on lyophilyzer to obtain compound 4-(4-fluorophenyl)-6-oxo-1,6-dihydropyridine-3-carboxylic acid (1 gm, 88%) as a white solid.

LCMS: 234.0 [M+H]+

¹H NMR (400 MHz, DMSO-d₆) δ11.07 (s, 1H) 7.63 (s, 1H), 7.34 (dd, J=5.7, 8.3 Hz, 2H), 7.11 (t, J=9.0 Hz, 2H), 6.03 (s, 1H), 3.53 (s, 1H).

Compound 109. To a stirred solution of 4-(4-fluorophenyl)-6-oxo-1,6-dihydropyridine-3-carboxylic acid (0.4 gm, 1.7167 mmol, 1.0 equiv), HATU (0.278 gm, 2.064 mmol, 1.2 equiv) in DMF (10 ml) after 10 min was added a (S)-4,4-difluoro-1-glycylpyrrolidine-2-carbonitrile hydrochloride (0.464 gm, 2.06 mmol, 1.2 equiv) and stirred the reaction mixture for 10 min, followed by drop wise addition of Et₃N (0.5 ml, 3.4334 mmol, 3 equiv) allowed the reaction for 16 h stirring at rt. reaction progress was monitored by LCMS and TLC, workup done by addition of chilled water (50 mL) to the reaction mass and extracted by ethyl acetate (3×50 ml) and collected all the organic layers, washed by water by three times and once by sodium bicarbonate and once by brine solution. Organic layer was dried over anhydrous Na₂SO₄, concentrated on reduced pressure crude was purified by reverse phase chromatography to afford the desired product (S)—N-(2-(2-cyano-4,4-difluoropyrrolidin-1-yl)-2-oxoethyl)-4-(4-fluorophenyl)-6-oxo-1,6-dihydropyridine-3-carboxamide (100 mg, 20%).

LCMS: 405.2 [M+H]+

¹H NMR (400 MHz, DMSO-d₆) δ11.93 (br. s., 1H), 8.69 (br. s., 1H), 7.64 (s, 1H), 7.44 (br. s., 2H), 7.17 (t, J=8.8 Hz, 2H), 6.30 (s, 1H), 5.08 (br. s., 1H), 4.20 (d, J=11.0 Hz, 2H), 3.99-3.89 (m, 2H), 2.80 (d, J=13.6 Hz, 2H).

Example 59

Synthesis of (S)—N-(2-(2-cyano-4,4-difluoropyrrolidin-1-yl)-2-oxoethyl)-3-(3,5-dimethylisoxazol-4-yl)isonicotinamide

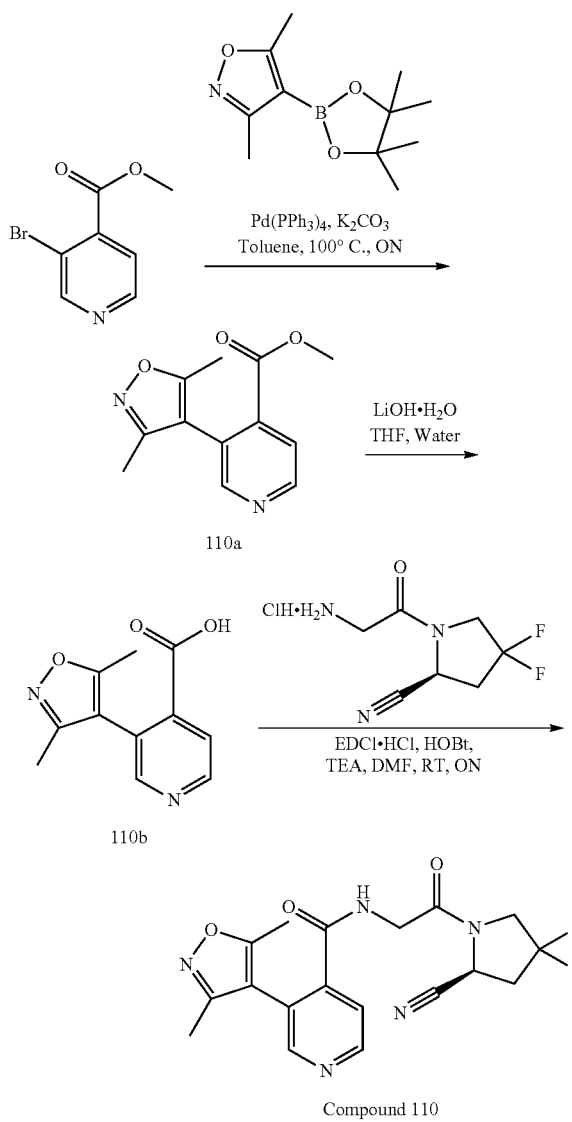

Compound 110

Compound 110a. To a solution of ethyl 3-bromoisonicotinate (0.1 g, 0.463 mmol, 1.0 equiv) in Toluene (5 mL) was added 3,5-dimethyl-4-(4,4,5,5-tetramethyl-1,3,2-dioxaborolan-2-yl)isoxazole (0.126 g, 0.926 mmol, 2 equiv), $K_2CO_3$ (0.192 g, 1.39 mmol, 3.0 equiv) and resulting reaction mixture purged with $N_2$ gas for 10 minute, followed by the addition of $Pd(PPh_3)_4$ (0.027 g, 0.023 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-30% ethyl acetate in hexane as an eluent) to obtain methyl 3-(3,5-dimethylisoxazol-4-yl)isonicotinate (0.105 g, 97.2% Yield) as an yellow liquid.

LCMS 233.2 [M+H]$^+$ $^1$H NMR (400 MHz, DMSO-d$_6$) δ 8.81 (d, J=4.8 Hz, 1H), 8.65 (s, 1H), 7.85 (d, J=5.3 Hz, 1H), 3.32 (s, 3H), 2.23 (s, 3H), 2.09-1.90 (m, 3H).

Compound 110b. To a stirred solution of 3-(3,5-dimethylisoxazol-4-yl)isonicotinate (0.120 g, 0.518 mmol, 1.0 equiv) in THF (5 mL) and water (5 mL), was added LiOH.2H$_2$O (0.043 g, 1.034 mmol, 2.0 equiv). The mixture was allowed to stir at RT for overnight. Product formation was confirmed by LCMS. The reaction mixture was concentrated and diluted with water (20 mL) and washed with ethyl acetate (10 mL×2). Aqueous layer was separated and freeze dried on lyophilyzer to obtain 3-(3,5-dimethylisoxazol-4-yl)isonicotinic acid (Quant. Yield) as a white solid.

LCMS 219.2 [M+H]$^+$

Compound 110. To a stirred solution of 3-(3,5-dimethylisoxazol-4-yl)isonicotinic acid (0.1 g, 0.46 mmol, 1.0 equiv) in DMF (4 mL), was added (S)-4,4-difluoro-1-glycylpyrrolidine-2-carbonitrile hydrochloride (0.103 g, 0.46 mmol, 1.0 equiv), EDCI.HCl (0.132 g, 0.69 mmol, 1.5 equiv) & HOBt (0.093 g, 0.69 mmol, 1.5 equiv). The mixture was allowed to stir at RT for 10 min. Triethylamine (0.5 mL) was added and the mixture was allowed to stir at RT for overnight. Product formation was confirmed by LCMS and TLC. After completion of reaction, the mixture was diluted with water (20 mL) and extracted with ethyl acetate (50 mL×3). Combined organic extracts were washed with water (50 mL×5), dried over anhydrous Na$_2$SO$_4$ and concentrated. The crude product obtained was purified by flash chromatography (5% MeOH in DCM as an eluent to obtain (S)—N-(2-(2-cyano-4,4-difluoropyrrolidin-1-yl)-2-oxoethyl)-3-(3,5-dimethylisoxazol-4-yl)isonicotinamide (0.055 g, 30.7% Yield) as an white solid.

LCMS 390.2 [M+H]$^+$ $^1$H NMR (400 MHz, DMSO-d$_6$) δ 8.85 (d, J=5.7 Hz, 1H), 8.75 (d, J=4.8 Hz, 1H), 8.56 (s, 1H), 7.56 (d, J=4.8 Hz, 1H), 5.10-4.98 (m, 1H), 4.27-4.18 (m, 1H), 4.11-3.95 (m, 2H), 2.95-2.74 (m, 3H), 2.25 (s, 3H), 2.06 (s, 3H).

Example 60

Synthesis of (S)-3-(4-chloro-3-fluorophenyl)-N-(2-(2-cyano-4,4-difluoropyrrolidin-1-yl)-2-oxoethyl) isonicotinamide

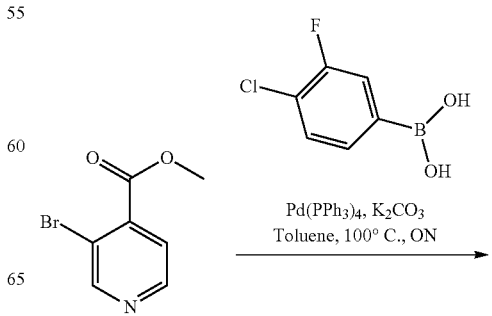

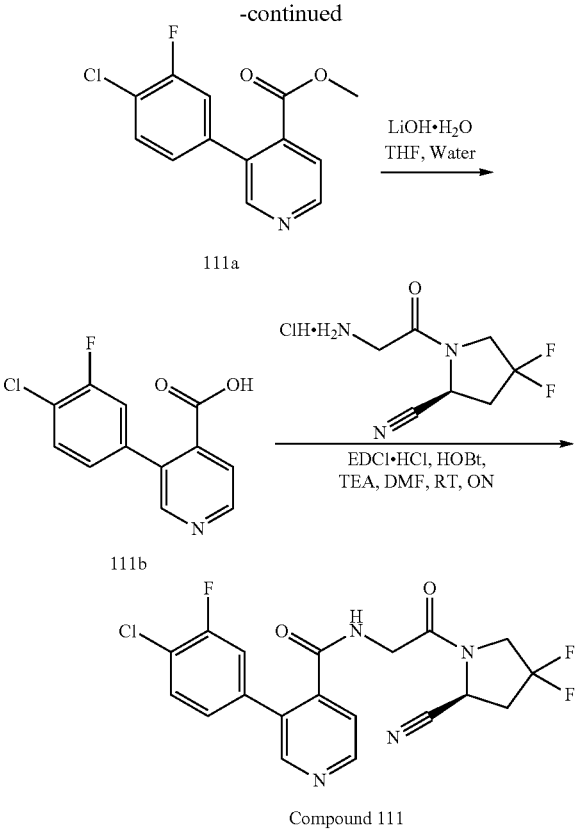

Compound 111

Compound 111a. To a solution of ethyl 3-bromoisonicotinate (1) (0.2 g, 0.926 mmol, 1.0 equiv) in Toluene (10 mL) was added 3,5-dimethyl-4-(4,4,5,5-tetramethyl-1,3,2-dioxaborolan-2-yl)isoxazole (2) (0.242 g, 1.39 mmol, 1.5 equiv), K₂CO₃ (0.383 g, 2.79 mmol, 3.0 equiv) and resulting reaction mixture purged with N₂ gas for 10 minute, followed by the addition of Pd(PPh₃)₄ (0.053 g, 0.046 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-20% ethyl acetate in hexane as an eluent) to obtain methyl 3-(3,5-dimethylisoxazol-4-yl)isonicotinate (3) (0.250 g, 98% Yield) as an off-white solid.

LCMS 266.1 [M+H]⁺

Compound 111b. To a stirred solution of methyl 3-(4-chloro-3-fluorophenyl)isonicotinic acid (0.25 g, 0.94 mmol, 1.0 equiv) in THF (8 mL) and water (8 mL), was added LiOH.H₂O (0.080 g, 1.89 mmol, 2.0 equiv). The mixture was allowed to stir at RT for overnight. Product formation was confirmed by LCMS. The reaction mixture was concentrated and diluted with water (20 mL) and washed with ethyl acetate (10 mL×2). Aqueous layer was separated and freeze dried on lyophilyzer to obtain 3-(4-chloro-3-fluorophenyl)isonicotinic acid (Quant. Yield) as a white solid.

LCMS 252.1 [M+H]⁺

$^1$H NMR (400 MHz, DMSO-d₆) δ 8.47-8.35 (m, 2H), 7.67-7.51 (m, 2H), 7.42 (d, J=8.3 Hz, 1H), 7.19 (d, J=4.8 Hz, 1H).

Compound 111. To a stirred solution of 3-(4-chloro-3-fluorophenyl)isonicotinic acid (0.12 g, 0.48 mmol, 1.0 equiv) in DMF (5 mL), was added (S)-4,4-difluoro-1-glycylpyrrolidine-2-carbonitrile hydrochloride (0.108 g, 0.48 mmol, 1.0 equiv), EDCI.HCl (0.138 g, 0.717 mmol, 1.5 equiv) & HOBt (0.097 g, 0.717 mmol, 1.5 equiv). The mixture was allowed to stir at RT for 10 min. Triethylamine (1 mL) was added and the mixture was allowed to stir at RT for overnight. Product formation was confirmed by LCMS and TLC. After completion of reaction, the mixture was diluted with water (20 mL) and extracted with ethyl acetate (50 mL×3). Combined organic extracts were washed with water (50 mL×5), dried over anhydrous Na₂SO₄ and concentrated. The crude product obtained was purified by flash chromatography (5% MeOH in DCM as an eluent) to obtain (S)-3-(4-chloro-3-fluorophenyl)-N-(2-(2-cyano-4,4-difluoropyrrolidin-1-yl)-2-oxoethyl)isonicotinamide (0.120 g, 59.1% Yield) as an white solid.

LCMS 423.5 [M+H]⁺

$^1$H NMR (400 MHz, DMSO-d₆) δ 9.04 (t, J=5.9 Hz, 1H), 8.76-8.63 (m, 2H), 7.65-7.54 (m, 2H), 7.49 (d, J=4.8 Hz, 1H), 7.41 (d, J=7.0 Hz, 1H), 5.09 (br. s., 1H), 4.22 (d, J=11.8 Hz, 1H), 4.12-3.96 (m, 2H), 3.92 (d, J=5.3 Hz, 1H), 2.97-2.76 (m, 2H).

Example 61

Synthesis of (S)-3-(3-(tert-butyl)phenyl)-N-(2-(2-cyano-4,4-difluoropyrrolidin-1-yl)-2-oxoethyl)isonicotinamide

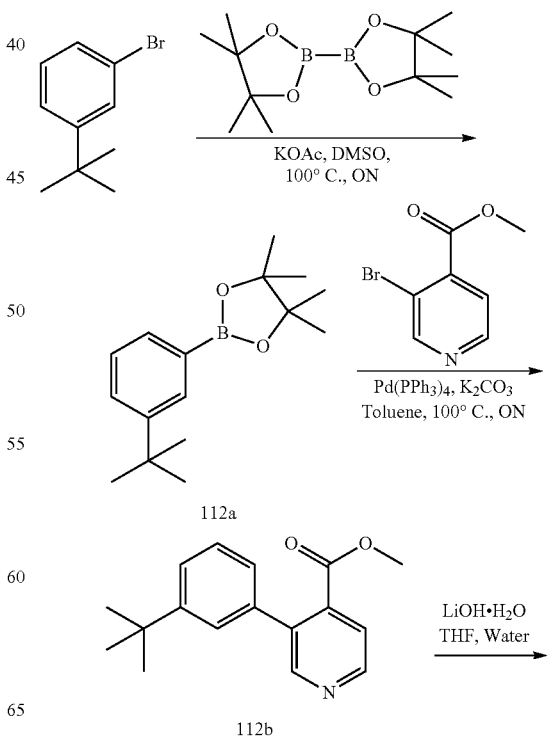

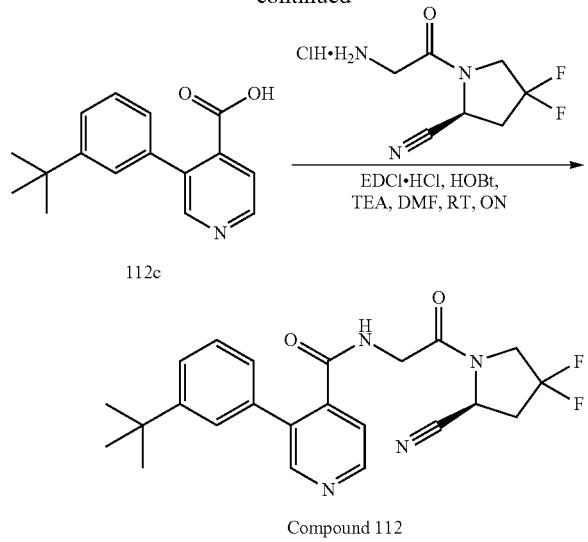

Compound 112

Compound 112a. To a solution of 1-bromo-3-(tert-butyl) benzene (0.2 g, 0.938 mmol, 1.0 equiv) in DMSO (10 mL) was added 4,4,4',4',5,5,5',5'-octamethyl-2,2'-bi(1,3,2-dioxaborolane) (0.356 g, 1.41 mmol, 1.5 equiv), KOAc (0.184 g, 1.876 mmol, 2.0 equiv) and resulting reaction mixture purged with $N_2$ gas for 10 minute, followed by the addition of Pd(PPh$_3$)$_4$ (0.055 g, 0.047 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (hexane as an eluent) to obtain 2-(3-(tert-butyl)phenyl)-4,4,5,5-tetramethyl-1,3,2-dioxaborolane (0.230 g, 94.26% Yield) as an off-white solid.

LCMS 261.3 [M+H]$^+$ $^1$H NMR (400 MHz, DMSO-d$_6$) δ7.67 (s, 1H), 7.57-7.45 (m, 2H), 7.32 (t, J=7.5 Hz, 1H), 1.44 (d, J=6.6 Hz, 1H), 1.39-1.23 (m, 9H), 1.23-1.04 (m, 12H)

Compound 112b. To a solution of 2-(3-(tert-butyl)phenyl)-4,4,5,5-tetramethyl-1,3,2-dioxaborolane (0.216 g, 0.833 mmol, 1.2 equiv) in Toluene (15 mL) was added ethyl 3-bromoisonicotinate (0.150 g, 0.649 mmol, 1.0 equiv), K$_2$CO$_3$ (0.287 g, 2.08 mmol, 3.0 equiv) and resulting reaction mixture purged with $N_2$ gas for 10 minute, followed by the addition of Pd(PPh$_3$)$_4$ (0.040 g, 0.035 mmol. 0.05 equiv). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-20% ethyl acetate in hexane as an eluent) to obtain methyl 3-(3-(tert-butyl)phenyl) isonicotinate (0.150 g, 80.6%) as yellow semi solid.

LCMS 270.5 [M+H]$^+$ $^1$H NMR (400 MHz, DMSO-d$_6$) δ 8.75-8.66 (m, 2H), 7.74 (d, J=4.8 Hz, 1H), 7.66 (d, J=4.8 Hz, 1H), 7.51-7.39 (m, 2H), 7.24 (d, J=7.5 Hz, 1H), 3.66 (s, 3H), 1.30 (s, 9H).

Compound 112c. To a stirred solution of methyl 3-(3-(tert-butyl)phenyl)isonicotinate (0.150 g, 0.555 mmol, 1.0 equiv) in THF (4 mL) and water (4 mL), was added LiOH.H$_2$O (0.047 g, 1.11 mmol, 2.0 equiv). The mixture was allowed to stir at RT for overnight. Product formation was confirmed by LCMS. The reaction mixture was concentrated and diluted with water (20 mL) and washed with ethyl acetate (10 mL×2). Aqueous layer was separated and freeze dried on lyophilyzer to obtain 3-(3-(tert-butyl)phenyl) isonicotinic acid (Quant. Yield) as a white solid.

LCMS 256.3 [M+H]$^+$

Compound 112. To a stirred solution of 3-(3-(tert-butyl) phenyl)isonicotinic acid (0.1 g, 0.392 mmol, 1.0 equiv) in DMF (5 mL), was added (S)-4,4-difluoro-1-glycylpyrrolidine-2-carbonitrile hydrochloride (0.89 g, 0.392 mmol, 1.0 equiv), EDCI.HCl (0.113 g, 0.59 mmol, 1.5 equiv) & HOBt (0.080 g, 0.59 mmol, 1.5 equiv). The mixture was allowed to stir at RT for 10 min. Triethylamine (0.5 mL) was added and the mixture was allowed to stir at RT for overnight. Product formation was confirmed by LCMS and TLC. After completion of reaction, the mixture was diluted with water (20 mL) and extracted with ethyl acetate (50 mL×3). Combined organic extracts were washed with water (50 mL×5), dried over anhydrous Na$_2$SO$_4$ and concentrated. The crude product obtained was purified by flash chromatography (5% MeOH in DCM as an eluent) followed by prep purification to obtain (S)-3-(3-(tert-butyl)phenyl)-N-(2-(2-cyano-4,4-difluoropyrrolidin-1-yl)-2-oxoethyl)isonicotinamide (0.028 g, 16.86% Yield) as an white solid.

LCMS 427.3 [M+H]$^+$ $^1$H NMR (400 MHz, DMSO-d$_6$) δ 8.92 (br. s., 1H), 8.76-8.56 (m, 2H), 7.50 (s, 1H), 7.48-7.40 (m, 2H), 7.40-7.29 (m, 2H), 5.14-5.04 (m, 1H), 4.21 (br. s., 1H), 4.03 (d, J=2.6 Hz, 2H), 2.87 (br. s., 1H), 2.79 (d, J=14.5 Hz, 1H), 2.67 (br. s., 1H).

Example 62

Synthesis of (S)—N-(2-(2-cyano-4,4-difluoropyrrolidin-1-yl)-2-oxoethyl)-3-ethoxyisonicotinamide

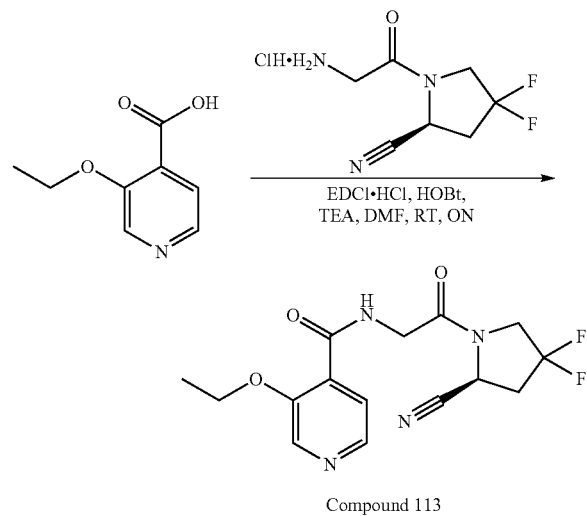

Compound 113

Compound 113. To a stirred solution of 3-ethoxyisonicotinic acid (0.05 g, 0.299 mmol, 1.0 equiv) in DMF (3 mL), was added (S)-4,4-difluoro-1-glycylpyrrolidine-2-carbonitrile hydrochloride (0.067 g, 0.299 mmol, 1.0 equiv), EDCI.HCl (0.086 g, 0.488 mmol, 1.5 equiv) & HOBt (0.06 g, 0.488 mmol, 1.5 equiv). The mixture was allowed to stir at RT for 10 min. Triethylamine (0.5 mL) was added and the mixture was allowed to stir at RT for overnight. Product formation was confirmed by LCMS and TLC. After completion of reaction, the mixture was diluted with water (20 mL) and extracted with ethyl acetate (50 mL×3). Combined organic extracts were washed with water (50 mL×5), dried over anhydrous $Na_2SO_4$ and concentrated. The crude product obtained was purified by flash chromatography (5% MeOH in DCM as an eluent to obtain (S)—N-(2-(2-cyano-4,4-difluoropyrrolidin-1-yl)-2-oxoethyl)-3-ethoxyisonicotinamide (0.07 g, 30.7% Yield) as an off-white solid.

LCMS 339.2 $[M+H]^+$ $^1$H NMR (400 MHz, DMSO-$d_6$) δ 8.71 (br. s., 1H), 8.59 (s, 1H), 8.34 (d, J=4.8 Hz, 1H), 7.70 (d, J=4.8 Hz, 1H), 5.15 (dd, J=2.9, 9.0 Hz, 1H), 4.36 (q, J=7.0 Hz, 2H), 4.30-4.12 (m, 3H), 4.12-3.98 (m, 1H), 2.90-2.68 (m, 2H), 1.46 (t, J=6.8 Hz, 3H).

Example 63

Synthesis of (S)—N-(2-(2-cyano-4,4-difluoropyrrolidin-1-yl)-2-oxoethyl)-3-((4-fluorophenyl)amino)isonicotinamide 2,2,2-trifluoroacetate

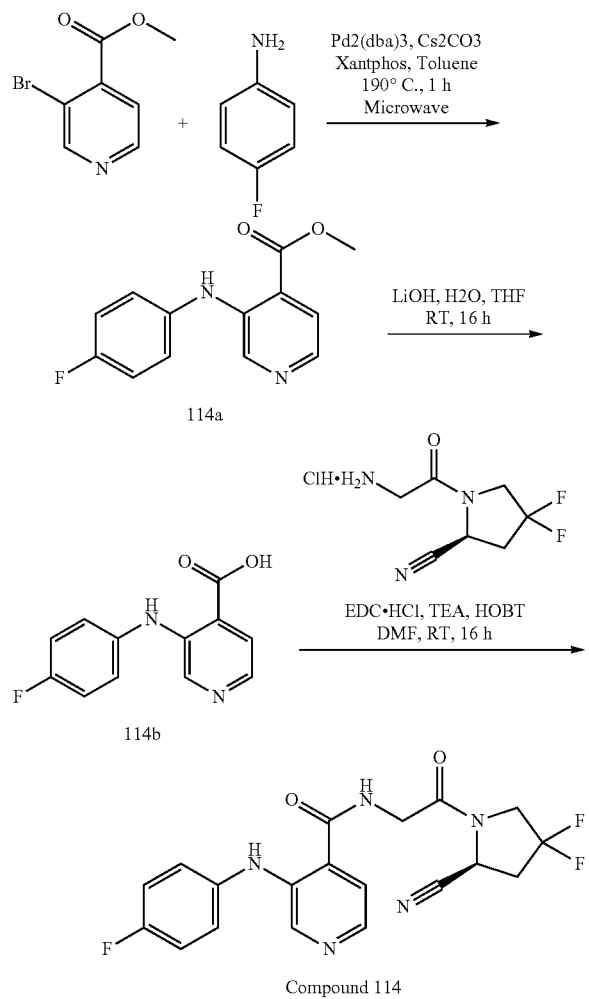

Compound 114a. To a stirred solution of methyl 3-bromoisonicotinate (0.200 g, 0.93 mmol, 1 equiv) in toluene (3 mL), was added 4-fluoroaniline (0.103 g, 0.93 mmol, 1.0 equiv), Tris(dibenzylideneacetone)dipalladium(0) (0.043 g, 0.046 mmol, 0.05 equiv), xantphos (0.053 g, 0.093 mmol, 0.1 equiv) and $Cs_2CO_3$ (0.456 g, 1.4 mmol, 1.5 equiv). The resulting reaction mixture was heated at 190° C. for 1 h in microwave. Reaction progress was checked by LCMS. The reaction mixture was diluted with water (15 mL) and extracted with ethyl acetate (30 mL×2). Combined organic extracts were washed with brine (30 mL), dried organic extract over anhydrous $Na_2SO_4$, filtered and concentrated under reduced pressure. Crude compound was purified by normal phase combi-flash chromatography to obtain methyl 3-((4-fluorophenyl)amino)isonicotinate (0.120 g, 53% Yield) as an off-white solid.

LCMS: 246.8 $[M+H]^+$

Compound 114b. To a stirred solution of methyl 3-((4-fluorophenyl)amino)isonicotinate (0.350 g, 1.4 mmol, 1 equiv) in THF and water (1:1)(6 mL), was added LiOH.$H_2O$ (0.089 g, 2.1 mmol, 1.5 equiv). The mixture was allowed to stir at ambient temperature for 16 h. Product formation was confirmed by LCMS. The reaction mixture was diluted with water (20 mL), extracted with ethyl acetate and concentrated the aqueous layer under reduced pressure and lyophilized to obtain 3-((4-fluorophenyl)amino)isonicotinic acid (0.350 g. Quant Yield) as an off-white solid

LCMS 233.2 $[M+H]+$

Compound 114. To a stirred solution of 3-((4-fluorophenyl)amino)isonicotinic acid (0.350 g, 1.5 mmol, 1 equiv) in DMF (4 mL), was added (1R)-4,4-difluoro-2-glycylcyclopentane-1-carbonitrile hydrochloride (0.337 g, 1.5 mmol, 1.0 equiv), HOBt (0.243 g, 1.8 mmol, 1.2 equiv), EDC.HCl (0.343 g, 1.8 mmol, 1.2 equiv) and triethyl amine (0.455 g, 4.5 mmol, 3 equiv) was added and the mixture was allowed to stir at ambient temperature for 16 h. Product formation was confirmed by LCMS. The reaction mixture was diluted with water (15 mL) and extracted with ethyl acetate (40 mL×3). Combined organic extracts were washed with water (25 mL×5), dried over anhydrous $Na_2SO_4$, filtered and concentrated under reduced pressure to obtain crude product which was purified by reverse phase HPLC to obtain (S)—N-(2-(2-cyano-4,4-difluoropyrrolidin-1-yl)-2-oxoethyl)-3-((4-fluorophenyl)amino)isonicotinamide as a TFA salt (0.003 g, 0.5% Yield).

LCMS 404.2 $[M+H]^+$ $^1$H NMR (400 MHz, DMSO-d6) δ 9.22 (t, J=6.0 Hz, 1H), 9.12 (s, 1H), 8.58 (s, 1H), 8.50 (q, J=15.7 Hz, 1H), 8.15 (s, 1H), 7.68-7.63 (m, 1H), 7.32-7.14 (m, 4H), 5.12 (dd, J=9.3, 2.9 Hz, 1H), 4.30 (ddd, J=15.9, 11.5, 4.6 Hz, 1H), 4.20-4.06 (m, 3H), 2.92-2.73 (m, 2H), 2.33-2.25 (m, 1H), 1.56-1.49 (m, 1H), 1.23 (s, 1H), 0.87 (d, J=12.4 Hz, 1H).

Example 64

Synthesis of (S)—N-(2-(2-cyano-4,4-difluoropyrrolidin-1-yl)-2-oxoethyl)-3-(4-fluorophenoxy)isonicotinamide

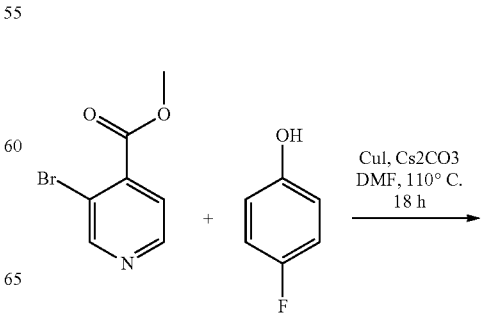

177

-continued

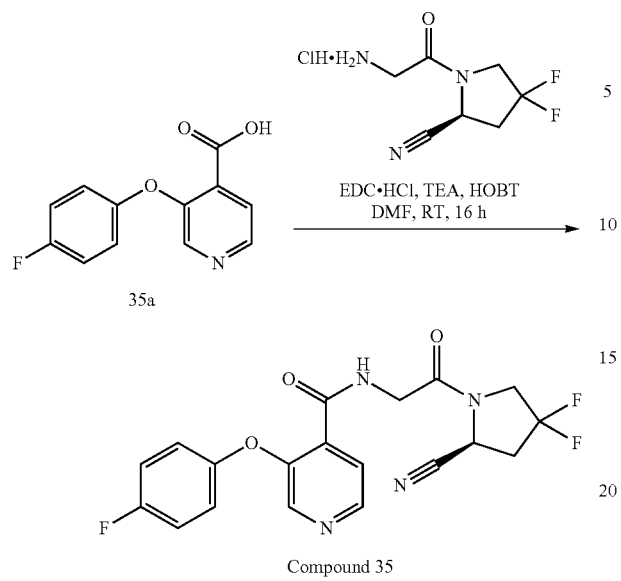

Compound 35

Compound 35a. To a stirred solution of 3-bromopyridine-4-carboxylic acid (1.0 g, 5.0 mmol, 1 equiv) in DMF (10 mL), was added 4-fluorophenol (0.560 g, 5.0 mmol, 1 equiv), CuI (1.90 g, 10.0 mmol, 2 equiv) and $Cs_2CO_3$ (3.260 g, 10.0 mmol, 2 equiv). Heated the reaction mixture at 110° C. for 18 h. Reaction progress was checked by LCMS. The reaction mixture was diluted with water (20 mL) and added few drops of dil. HCl till pH was slightly acidic. The aqueous layer was extracted with ethyl acetate (50 mL×2). Combined organic extracts were washed with brine (50 mL), dried over anhydrous $Na_2SO_4$, filtered and concentrated under reduced pressure to obtain 3-(4-fluorophenoxy)pyridine-4-carboxylic acid (0.200 g, 18% Yield)

LCMS: 234.2 $[M+H]^+$

Compound 35. To a stirred solution of 3-(4-fluorophenoxy)pyridine-4-carboxylic acid (0.200 g, 0.86 mmol, 1 equiv) in DMF (3 mL), was added (S)-4,4-difluoro-1-glycylpyrrolidine-2-carbonitrile hydrochloride (0.194 g, 0.86 mmol, 1.0 equiv), HOBt (0.140 g, 1.03 mmol, 1.2 equiv) and EDC.HCl (0.197 g, 1.03 mmol, 1.2 equiv). The mixture was allowed to stir at RT for 10 min. Triethyl amine (0.260 g, 2.58 mmol, 3 equiv) was added and the mixture was allowed to stir at ambient temperature for 16 h. Product formation was confirmed by LCMS. The reaction mixture was diluted with water (10 mL) and extracted with ethyl acetate (40 mL×2). Combined organic extracts were washed with water (25 mL×5). Organic layer was dried over anhydrous $Na_2SO_4$, filtered and concentrated under reduced pressure to obtain crude product. The crude product obtained was purified by reversed phase HPLC to obtain (S)—N-(2-(2-cyano-4,4-difluoropyrrolidin-1-yl)-2-oxoethyl)-3-(4-fluorophenoxy)isonicotinamide (0.040 g, 11.5% Yield) as an off-white solid.

LCMS 405.2 [M+H]+

$^1$H NMR (400 MHz, DMSO-d6) δ 8.80 (t, J=5.6 Hz, 1H), 8.48 (d, J=4.8 Hz, 1H), 8.24 (s, 1H), 7.65 (d, J=5.0 Hz, 1H), 7.26 (t, J=8.7 Hz, 2H), 7.18 (dd, J=9.0, 4.5 Hz, 2H), 5.10 (dd, J=8.9, 3.0 Hz, 1H), 4.30-3.98 (m, 4H), 2.93-2.72 (m, 2H).

178

Example 65

Synthesis of (S)—N-(2-(2-cyano-4,4-difluoropyrrolidin-1-yl)-2-oxoethyl)-3-(phenylthio)isonicotinamide

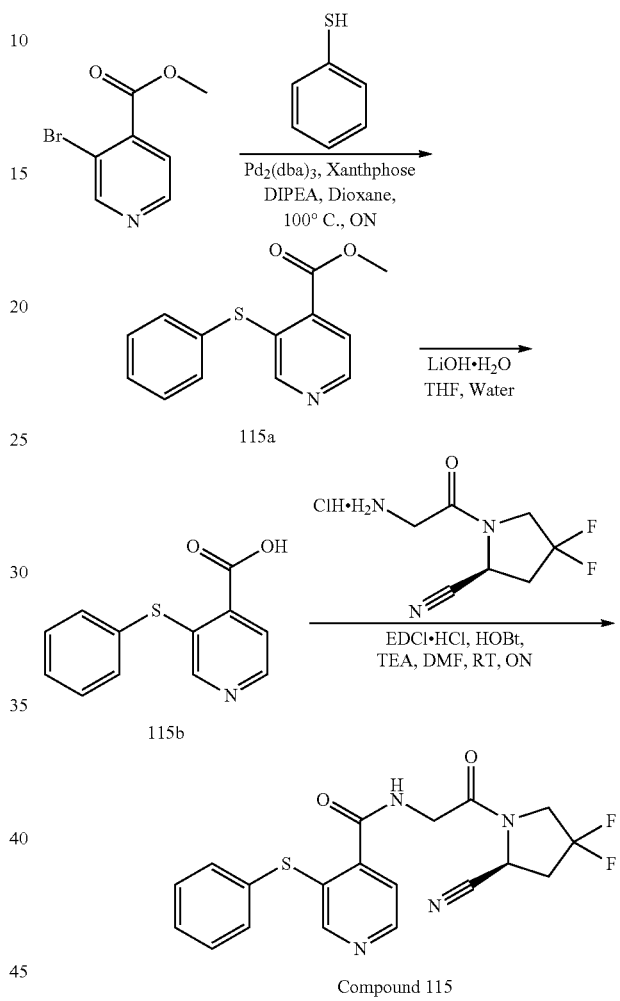

Compound 115

Compound 115a. To a solution of methyl 3-bromoisonicotinate (0.2 g, 0.93 mmol, 1.0 equiv) in Dioxane (10 mL) was added benzenethiol (0.204 g, 1.85 mmol, 2.0 equiv), KOAc (0.184 g, 1.876 mmol, 2.0 equiv) and resulting reaction mixture purged with $N_2$ gas for 10 minute, followed by the addition of $Pd_2(dba)_3$ (0.042 g, 0.046 mmol. 0.05 equiv), Xanthphose (0.026 g, 0.046 mmol, 0.05 equiv) and resulting reaction mixture). The resulting reaction mixture was heated at 90° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (20% ethyl acetate hexane as an eluent) to obtain methyl 3-(phenylthio)isonicotinate (0.100 g, 44.4% Yield) as yellow oil.

LCMS 246.1 $[M+H]^+$ $^1$H NMR (400 MHz, DMSO-d$_6$) δ 8.92 (br. s., 1H), 8.76-8.56 (m, 2H), 7.50 (s, 1H), 7.48-7.40 (m, 2H), 7.40-

7.29 (m, 2H), 5.14-5.04 (m, 1H), 4.21 (br. s., 1H), 4.03 (d, J=2.6 Hz, 2H), 2.87 (br. s., 1H), 2.79 (d, J=14.5 Hz, 1H), 2.67 (br. s., 1H).

Compound 115b. To a stirred solution of obtain methyl 3-(phenylthio)isonicotinate (0.150 g, 0.614 mmol, 1.0 equiv) in THF (5 mL) and water (5 mL), was added LiOH.H$_2$O (0.052 g, 1.23 mmol, 2.0 equiv). The mixture was allowed to stir at RT for overnight. Product formation was confirmed by LCMS. The reaction mixture was concentrated and diluted with water (20 mL) and washed with ethyl acetate (10 mL×2). Aqueous layer was separated and freeze dried on lyophilyzer to obtain 3-(phenylthio)isonicotinate (Quant. Yield) as white solid.

LCMS 232.3 [M+H]$^+$

Compound 115. To a stirred solution of 3-(phenylthio) isonicotinate (0.15 g, 0.65 mmol, 1.0 equiv) in DMF (5 mL), was added (S)-4,4-difluoro-1-glycylpyrrolidine-2-carbonitrile hydrochloride (0.146 g, 0.65 mmol, 1.0 equiv), EDCI.HCl (0.190 g, 0.97 mmol, 1.5 equiv) & HOBt (0.132 g, 0.97 mmol, 1.5 equiv). The mixture was allowed to stir at RT for 10 min. Triethylamine (0.3 mL) was added and the mixture was allowed to stir at RT for overnight. Product formation was confirmed by LCMS and TLC. After completion of reaction, the mixture was diluted with water (20 mL) and extracted with ethyl acetate (50 mL×3). Combined organic extracts were washed with water (50 mL×5), dried over anhydrous Na$_2$SO$_4$ and concentrated. The crude product obtained was purified by flash chromatography (5% MeOH in DCM as an eluent) followed by prep purification to obtain (S)—N-(2-(2-cyano-4,4-difluoropyrrolidin-1-yl)-2-oxoethyl)-3-(phenylthio)isonicotinamide (0.010 g, 3.8% Yield) as a white solid.

LCMS 403.2 [M+H]$^+$ $^1$H NMR (400 MHz, DMSO-d$_6$) δ 9.03 (br. s., 1H), 8.52 (d, J=4.8 Hz, 1H), 8.18 (s, 1H), 7.56-7.32 (m, 6H), 5.13 (d, J=7.5 Hz, 1H), 4.29 (br. s., 1H), 4.24-4.05 (m, 2H), 2.82 (d, J=14.9 Hz, 3H).

Example 66

Synthesis of (S)—N-(2-(2-cyano-4,4-difluoropyrrolidin-1-yl)-2-oxoethyl)-6-oxo-4-(quinolin-4-yl)-1,6-dihydropyridine-3-carboxamide

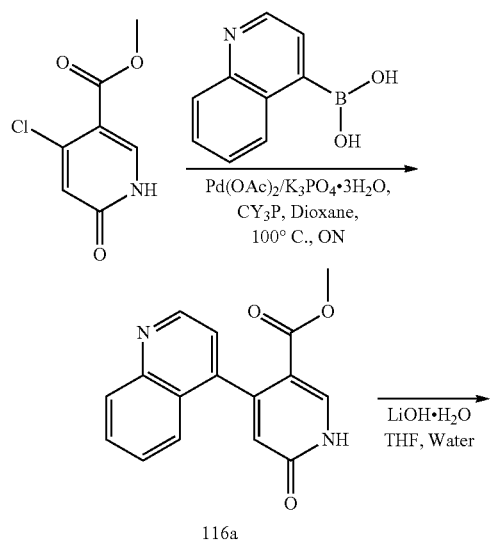

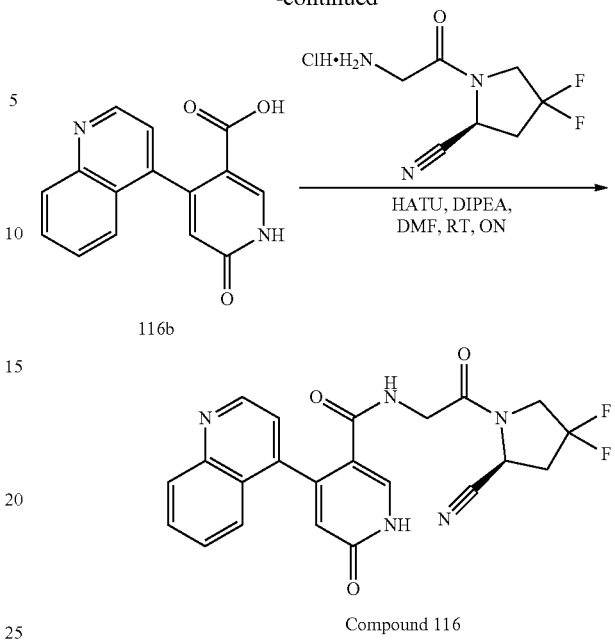

Compound 116

Compound 116a. To a solution of methyl 4-chloro-6-oxo-1,6-dihydropyridine-3-carboxylate (0.2 g, 1.07 mmol, 1.0 equiv) in Dioxane (10 mL) was added quinolin-4-ylboronic acid (0.22 g, 1.26 mmol, 2.0 equiv), K$_3$PO$_4$.3H$_2$O (0.455 g, 2.14 mmol, 2.0 equiv) and resulting reaction mixture purged with N$_2$ gas for 10 minute, followed by the addition of Pd$_2$(dba)$_3$ (0.024 g, 0.11 mmol. 0.1 equiv), tricyclohexylphosphine (0.030 g, 0.11 mmol, 0.1 equiv). The resulting reaction mixture was heated at 140° C. for overnight. Product formation was confirmed by LCMS. After the completion of reaction, the mixture was filtered through celite bed, washed with 10% methanol in DCM (100 mL). Filtrate was concentrated under reduced pressure. The crude product obtained was purified by flash chromatography (5 methanol in DCM as an eluent) to obtain methyl 6-oxo-4-(quinolin-4-yl)-1,6-dihydropyridine-3-carboxylate (3) (0.058 g, 19.4%) as off white solid.

LCMS 281.3 [M+H]$^+$ $^1$H NMR (400 MHz, DMSO-d$_6$) δ 12.47 (br. s., 1H), 8.91 (d, J=4.4 Hz, 1H), 8.23 (s, 1H), 8.11-7.96 (m, 1H), 7.84-7.70 (m, 1H), 7.64-7.43 (m, 2H), 7.35 (d, J=4.4 Hz, 1H), 6.30 (s, 1H), 3.35 (s, 3H).

Compound 116b. To a stirred solution of obtain methyl 6-oxo-4-(quinolin-4-yl)-1,6-dihydropyridine-3-carboxylate (0.115 g, 0.412 mmol, 1.0 equiv) in THF (4 mL) and water (4 mL), was added LiOH.H$_2$O (0.026 g, 0.616 mmol, 1.5 equiv). The mixture was allowed to stir at RT for overnight. Product formation was confirmed by LCMS. The reaction mixture was concentrated and diluted with water (20 mL) and washed with ethyl acetate (10 mL×2). Aqueous layer was separated and freeze dried on lyophilyzer to obtain 6-oxo-4-(quinolin-4-yl)-1,6-dihydropyridine-3-carboxylate (Quant. Yield) as white solid.

LCMS 267.2 [M+H]$^+$ $^1$H NMR (400 MHz, DMSO-d$_6$) δ 11.54 (d, J=17.1 Hz, 1H), 8.80 (d, J=4.4 Hz, 1H), 8.05-7.86 (m, 2H), 7.67 (t, J=7.2 Hz, 1H), 7.58 (d, J=8.3 Hz, 1H), 7.21 (d, J=4.4 Hz, 1H), 5.98 (s, 1H)

Compound 116. To a stirred solution of 6-oxo-4-(quinolin-4-yl)-1,6-dihydropyridine-3-carboxylate (0.1 g, 0.38 mmol, 1.0 equiv) in DMF (5 mL), was added (S)-4,4-difluoro-1-glycylpyrrolidine-2-carbonitrile hydrochloride (0.085 g, 0.38 mmol, 1.0 equiv), HATU (0.286 g, 0.754 mmol, 2.0 equiv). The mixture was allowed to stir at RT for 10 min. DIPEA (0.3 mL) was added and the mixture was allowed to stir at RT for overnight. Product formation was confirmed by LCMS and TLC. After completion of reaction, the mixture was diluted with water (20 mL) and extracted with ethyl acetate (50 mL×3). Combined organic extracts were washed with water (50 mL×5), dried over anhydrous $Na_2SO_4$ and concentrated. The crude product obtained was purified prep purification to obtain (S)—N-(2-(2-cyano-4,4-difluoropyrrolidin-1-yl)-2-oxoethyl)-6-oxo-4-(quinolin-4-yl)-1,6-dihydropyridine-3-carboxamide (0.045 g, 27.12% Yield) as an white solid.

LCMS 438.2 $[M+H]^+$ $^1$H NMR (400 MHz, DMSO-$d_6$) δ 12.24 (br. s., 1H), 8.86 (br. s., 1H), 8.59 (br. s., 1H), 8.03 (d, J=8.3 Hz, 1H), 7.94 (br. s., 1H), 7.74 (br. s., 1H), 7.67 (d, J=7.9 Hz, 1H), 7.60-7.45 (m, 1H), 7.33 (d, J=4.4 Hz, 1H), 6.29 (br. s., 1H), 4.98 (br. s., 1H), 4.05 (d, J=14.9 Hz, 1H), 3.89-3.73 (m, 2H), 2.83-2.60 (m, 3H).

Example 67

Synthesis of (S)—N-(2-(2-cyano-4,4-difluoropyrrolidin-1-yl)-2-oxoethyl)-3-(pyridin-3-ylamino)isonicotinamide

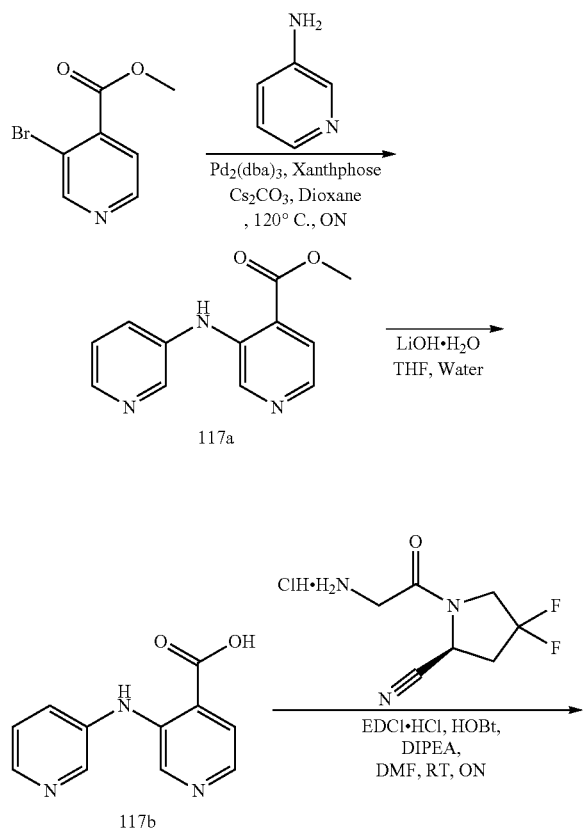

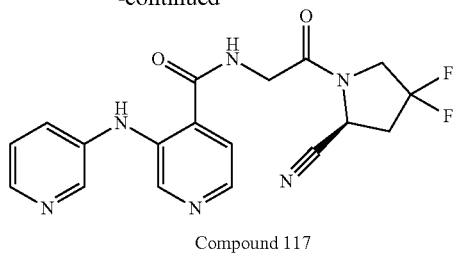

Compound 117

Compound 117a. To a solution of methyl 3-bromoisonicotinate (0.5 g, 2.315 mmol, 1.0 equiv) in Dioxane (10 mL) and water (4 mL), was added pyridin-3-amine (0.218 g, 2.315 mmol, 1.0 equiv), $Cs_2CO_3$ (1.5 g, 4.63 mmol, 2.0 equiv) and resulting reaction mixture purged with $N_2$ gas for 10 minute, followed by the addition of $Pd_2(dba)_3$ (0.106 g, 0.116 mmol. 0.05 equiv), Xanthphose (0.134 g, 0.232 mmol, 0.1 equiv) and resulting reaction mixture). The resulting reaction mixture was heated at 120° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (3% methanol in DCM as an eluent) to obtain methyl 3-(pyridin-3-ylamino)isonicotinate (0.170 g, 32.07%) as dark brown liquid.

LCMS 230.1 $[M+H]^+$ $^1$H NMR (400 MHz, DMSO-$d_6$) δ 8.88 (s, 1H), 8.57-8.44 (m, 2H), 8.29 (d, J=3.5 Hz, 1H), 8.13 (d, J=5.3 Hz, 1H), 7.79-7.62 (m, 2H), 7.39-7.29 (m, 1H), 3.88 (s, 3H).

Compound 117b. To a stirred solution of obtain methyl 3-(pyridin-3-ylamino)isonicotinate (0.170 g, 0.742 mmol, 1.0 equiv) in THF (4 mL) and water (4 mL), was added $LiOH \cdot H_2O$ (0.048 g, 1.114 mmol, 1.5 equiv). The mixture was allowed to stir at RT for overnight. Product formation was confirmed by LCMS. The reaction mixture was concentrated and diluted with water (20 mL) and washed with ethyl acetate (10 mL×2). Aqueous layer was separated and freeze dried on lyophilyzer to obtain 3-(pyridin-3-ylamino) isonicotinate (Quantitative Yield) as white solid.

LCMS 216.1 $[M+H]^+$ $^1$H NMR (400 MHz, DMSO-$d_6$) δ 11.84 (s, 1H), 8.55 (s, 1H), 8.39 (d, J=2.6 Hz, 1H), 8.10 (d, J=3.9 Hz, 1H), 7.96 (d, J=4.8 Hz, 1H), 7.70 (d, J=4.8 Hz, 1H), 7.65-7.55 (m, 1H), 7.28 (dd, J=4.8, 8.3 Hz, 1H).

Compound 117. To a stirred solution of 3-(pyridin-3-ylamino)isonicotinate (0.10 g, 0.465 mmol, 1.0 equiv) in DMF (5 mL), was added (S)-4,4-difluoro-1-glycylpyrrolidine-2-carbonitrile hydrochloride (0.104 g, 0.465 mmol, 1.0 equiv), HATU (0.353 g, 0.93 mmol, 2.0 equiv). The mixture was allowed to stir at RT for 10 min. DIPEA (0.35 mL) was added and the mixture was allowed to stir at RT for overnight. Product formation was confirmed by LCMS and TLC. After completion of reaction, the mixture was diluted with water (20 mL) and extracted with ethyl acetate (50 mL×3). Combined organic extracts were washed with water (50 mL×5), dried over anhydrous $Na_2SO_4$ and concentrated. The crude product obtained was purified by flash chromatography (10% MeOH in DCM as an eluent) followed by prep purification to obtain (S)—N-(2-(2-cyano-4,4-difluoropyrrolidin-1-yl)-2-oxoethyl)-3-(pyridin-3-ylamino)isonicotinamide (0.072 g, 40% Yield) as an off white solid.

LCMS 387.2 $[M+H]^+$ $^1$H NMR (400 MHz, DMSO-d$_6$) δ 9.17 (br. s., 1H), 9.09 (s, 1H), 8.62 (s, 1H), 8.45 (br. s., 1H), 8.19 (br. s., 2H), 7.64 (d, J=7.5 Hz, 1H), 7.58 (d, J=4.8 Hz, 1H), 7.38-7.22 (m, 1H), 5.12 (d, J=7.0 Hz, 1H), 4.31 (d, J=11.4 Hz, 1H), 4.18-3.98 (m, 2H), 2.90 (br. s., 1H), 2.82 (d, J=15.3 Hz, 2H).

Example 68

Synthesis of (S)—N-(2-(2-cyano-4,4-difluoropyrrolidin-1-yl)-2-oxoethyl)-3-(piperidin-4-ylamino)isonicotinamide

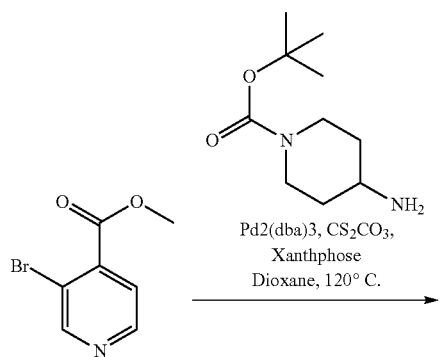

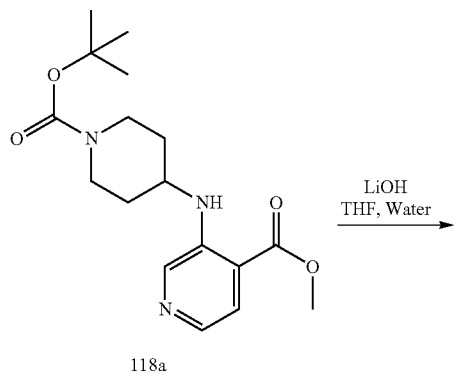

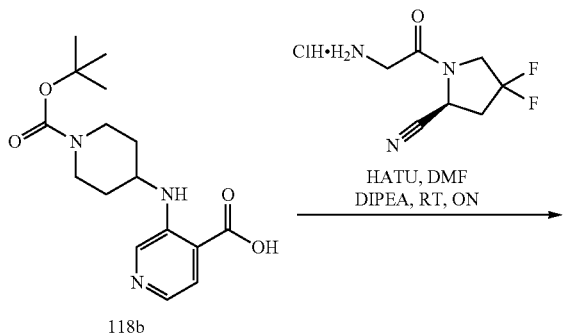

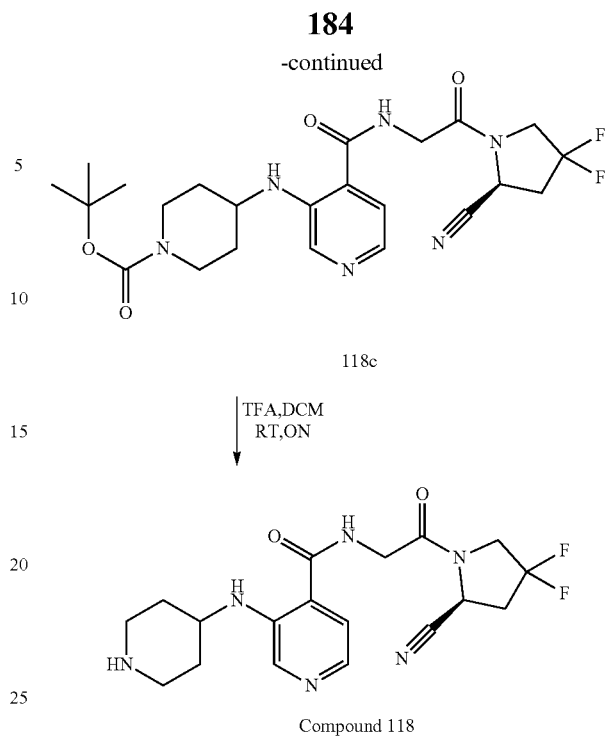

Compound 118

Compound 118a. To a stirred solution of methyl 3-bromoisonicotinate (0.500 gm, 2.3148 mmol, 1 equiv) & tert-butyl 4-aminopiperidine-1-carboxylate (0.463 gm, 2.3148 mmol, 1 equiv) and CS$_2$CO$_3$ (1.5 gm, 4.6296 mmol, 2 equiv) in dioxane (15 mL). The resulting mixture was purged with nitrogen for 10 min followed by addition of Pd$_2$(dba)$_3$ (0.106 gm, 0.1157 mmol, 0.05 equiv) and xantphos (0.134 gm, 0.2314 mmol, 0.1 equiv), again purged with nitrogen for 10 min. The reaction mixture was heated at 120° C. for overnight. The progress of reaction was monitored by LCMS. The reaction mixture was diluted with water (30 mL), extracted with EtOAc (2×50 mL). The combined organic layers were washed with water (30 mL), with brine (30 mL), dried over Na$_2$SO$_4$, concentrated to afford the crude which was purified by flash chromatography to obtain methyl 3-((1-(tert-butoxycarbonyl)piperidin-4-yl)amino)isonicotinate (400 mg, 51.49%) as a white solid.

LCMS: 336.3 [M+H]$^+$ $^1$H NMR: (400 MHz, DMSO-d$_6$) δ 8.41 (s, 1H), 7.60-7.51 (m, 2H), 7.27 (d, J=7.9 Hz, 1H), 3.00 (m., 4H), 2.04-1.88 (s, 3H), 1.44-1.35 (s, 9H), 1.31-1.12 (m, 4H).

Compound 118b. To a stirred solution of compound methyl 3-((1-(tert-butoxycarbonyl) piperidin-4-yl) amino) isonicotinate (0.400 gm, 1.1904 mmol, 1 equiv) in THF (8 mL) and water (4 mL), was added LiOH (0.058 gm, 2.3809 mmol, 2 equiv). The mixture was allowed to stir at 80° C. for overnight. Product formation was confirmed by LCMS. The reaction mixture was concentrated and diluted with water (10 mL) and washed with ethyl acetate (10 mL×2). Aqueous layer was separated and freeze dried on lyophilyzer to obtain compound 3-((1-(tert-butoxycarbonyl) piperidin-4-yl) amino)isonicotinic acid (330 mg, 78% Yield) as a white solid.

LCMS: 322.2 [M+H]$^+$ $^1$H NMR: (400 MHz, DMSO-d$_6$) δ 11.70 (s, 1H), 8.41 (s, 1H), 7.60-7.51 (m, 2H), 7.27 (d, J=7.9 Hz, 1H), 3.00 (m., 4H), 1.44-1.35 (s, 9H), 1.31-1.12 (m, 4H).

Compound 118c. To a stirred solution of 3-((1-(tert-butoxycarbonyl)piperidin-4-yl)amino)isonicotinic acid (0.200 gm, 0.6211 mmol, 1 equiv), HATU (0354 gm, 0.9316 mmol, 1.5 equiv) in DMF (10 ml) after 10 min was added a (S)-4,4-difluoro-1-glycylpyrrolidine-2-carbonitrile hydrochloride (0.168 gm, 0.7453 mmol, 1.2 equiv) and stirred the reaction mixture for 10 min, followed by drop wise addition of DIPEA (0.2 ml, 0.9316 mmol, 1.5 equiv) allowed the reaction for 16 h stirring at rt. reaction progress was monitored by LCMS and TLC, workup done by addition of water (30 ml) and extracted by ethyl acetate (3×50 mL). Combined organic layer was washed with water (4×20 mL), dried over anhydrous $Na_2SO_4$, concentrated under reduced pressure to obtain tert-butyl (S)-4-((4-((2-(2-cyano-4,4-difluoropyrrolidin-1-yl)-2-oxoethyl)carbamoyl)pyridin-3-yl)amino)piperidine-1-carboxylate (220 mg, 71.89% Yield) as a brown solid

LCMS: 493.3 $[M+H]^+$ $^1$H NMR: (400 MHz, DMSO-$d_6$) δ 8.95 (br. s., 1H), 8.28 (s, 1H), 7.86 (d, J=5.3 Hz, 1H), 7.51-7.38 (m, 2H), 5.76 (s, 1H), 4.12-4.02 (m, 4H), 3.81 (d, J=13.2 Hz, 2H), 3.50 (m, 1H), 2.05-1.93 (m, 4H), 1.40 (s, 9H), 1.28-1.10 (m, 4H).

Compound 118. To a stirred solution of tert-butyl (S)-4-((4-((2-(2-cyano-4,4-difluoropyrrolidin-1-yl)-2-oxoethyl)carbamoyl)pyridin-3-yl)amino)piperidine-1-carboxylate (0.190 gm, 0.3861 mmol, 1 equiv) in DCM (5 mL), was added trifloroacetic acid (1.5 mL). The mixture was allowed to stir at RT overnight. Product formation was confirmed by LCMS. The reaction mixture concentrated and the crude was purified by reversed phase HPLC to obtain (S)—N-(2-(2-cyano-4,4-difluoropyrrolidin-1-yl)-2-oxoethyl)-3-(piperidin-4-ylamino)isonicotinamide (60 mg, 39.73% Yield) as a white solid.

LCMS: 393.3 $[M+H]^+$ $^1$H NMR: (400 MHz, DMSO-$d_6$) δ=8.95 (br. s., 1H), 8.28 (s, 1H), 7.86 (d, J=5.3 Hz, 1H), 7.51-7.38 (m, 2H), 5.76 (s, 1H), 4.12-4.02 (m, 4H), 3.81 (d, J=13.2 Hz, 2H), 3.50 (m, 1H), 2.05-1.93 (m, 4H), 1.28-1.10 (m, 4H).

Example 69

Synthesis of (S)—N-(2-(2-cyano-4,4-difluoropyrrolidin-1-yl)-2-oxoethyl)-3-(quinolin-4-ylamino)isonicotinamide

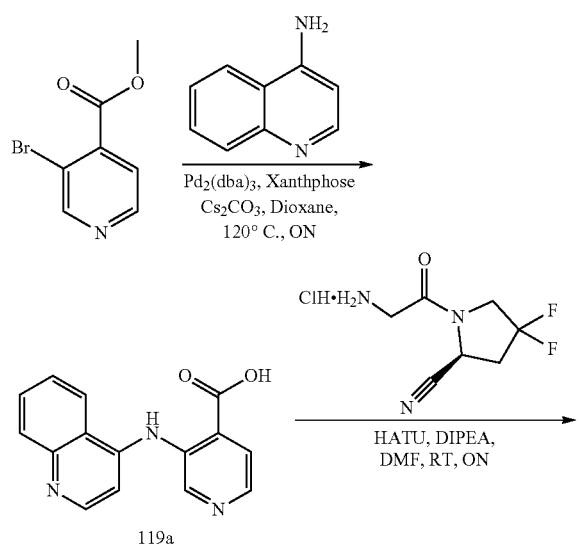

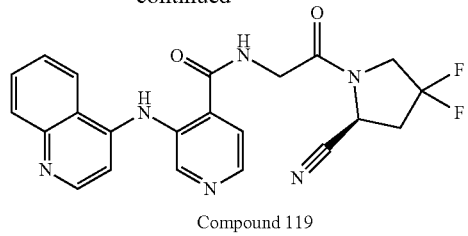

Compound 119

Compound 119a. To a solution of methyl 3-bromoisonicotinate (0.5 g, 2.315 mmol, 1.0 equiv) in Dioxane (10 mL) was added pyridin-3-amine (0.334 g, 2.315 mmol, 1.0 equiv), $Cs_2CO_3$ (1.5 g, 4.63 mmol, 2.0 equiv) and resulting reaction mixture purged with $N_2$ gas for 10 minute, followed by the addition of $Pd_2(dba)_3$ (0.106 g, 0.116 mmol. 0.05 equiv), Xanthphose (0.134 g, 0.232 mmol, 0.1 equiv) and resulting reaction mixture). The resulting reaction mixture was heated at 120° C. for overnight. Product formation was confirmed by LCMS. After the completion of reaction, the mixture diluted with water (30 mL) washed with ethyl acetate (50 mL). Aqueous layer was separated and freeze dried on lyophilyzer to obtain 3-(quinolin-4-ylamino)isonicotinic acid (Quant. Yield) as a white solid.

LCMS 266.1 $[M+H]^+$ $^1$H NMR (400 MHz, DMSO-$d_6$) δ 13.66 (s, 1H), 8.93 (s, 1H), 8.58 (d, J=5.3 Hz, 1H), 8.28-8.18 (m, 1H), 8.14 (d, J=4.8 Hz, 1H), 7.91 (d, J=8.8 Hz, 1H), 7.79 (d, J=4.8 Hz, 1H), 7.72 (t, J=7.0 Hz, 1H), 7.58 (t, J=7.2 Hz, 1H), 7.45-7.33 (m, 1H), 6.76 (br. s., 1H).

Compound 119. To a stirred solution of 3-(quinolin-4-ylamino)isonicotinic acid (0.10 g, 0.377 mmol, 1.0 equiv) in DMF (5 mL), was added (S)-4,4-difluoro-1-glycylpyrrolidine-2-carbonitrile hydrochloride (0.085 g, 0.377 mmol, 1.0 equiv), HATU (0.286 g, 0.754 mmol, 2.0 equiv). The mixture was allowed to stir at RT for 10 min. DIPEA (0.2 mL) was added and the mixture was allowed to stir at RT for overnight. Product formation was confirmed by LCMS and TLC. After completion of reaction, the mixture was diluted with water (20 mL) and extracted with ethyl acetate (50 mL×3). Combined organic extracts were washed with water (50 mL×5), dried over anhydrous $Na_2SO_4$ and concentrated. The crude product obtained was purified prep purification to obtain (S)—N-(2-(2-cyano-4,4-difluoropyrrolidin-1-yl)-2-oxoethyl)-3-(quinolin-4-ylamino)isonicotinamide (0.004 g, 2.4% Yield) as an off white solid.

LCMS 437.2 $[M+H]^+$ $^1$H NMR (400 MHz, DMSO-$d_6$) δ 8.76 (br. s., 1H), 8.48 (s, 2H), 7.79 (d, J=8.33 Hz, 2H), 7.39 (br.s., 2H), 6.86 (d, J=8.33 Hz, 1H), 5.10 (d, J=7.45 Hz, 1H), 4.23 (br. s., 1H), 3.98-4.12 (m, 2H), 3.94 (s, 3H), 2.90 (d, J=8.33 Hz, 1H), 2.70-2.86 (m, 1H), 2.67 (br. s., 1H).

Example 70

Synthesis of (S)-3-(4-aminopiperidin-1-yl)-N-(2-(2-cyano-4,4-difluoropyrrolidin-1-yl)-2-oxoethyl)isonicotinamide 2,2,2-trifluoroacetate

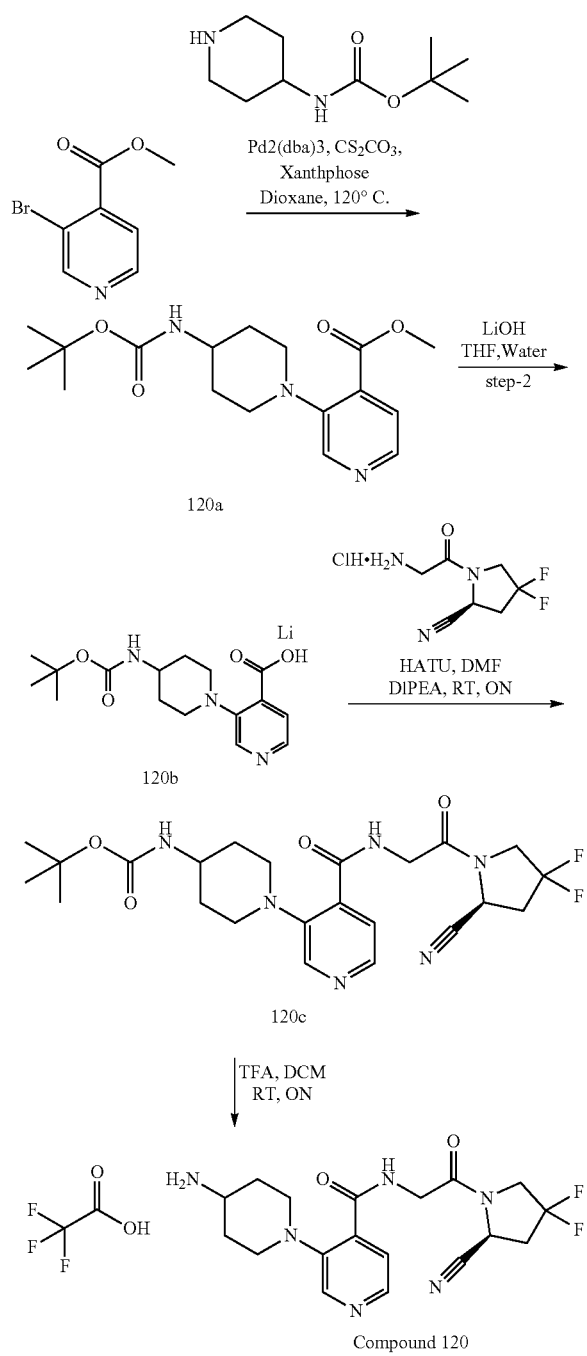

Compound 120a. To a stirred solution of methyl 3-bromoisonicotinate (0.200 gm, 0.925 mmol, 1.0 equiv) & tert-butyl piperidin-4-ylcarbamate (0.185 gm, 0.925 mmol, 1.0 equiv) and $CS_2CO_3$ (0.601 gm, 1.85 mmol, 2.0 equiv) in Dioxan (5 mL). The resulting mixture was purged with nitrogen for 10 min followed by addition of $Pd_2(dba)_3$ (0.042 gm, 0.046 mmol, 0.05 equiv) and xantphos (0.053 gm, 0.092 mmol, 0.1 equiv), again purged with nitrogen for 10 min. The reaction mixture was heated at 120° C. for overnight. The progress of reaction was monitored by LCMS. The reaction mixture was diluted with water (30 mL), extracted with EtOAc (2×50 mL). The combined organic layers were washed with water (30 mL), with brine (30 mL), dried over $Na_2SO_4$, concentrated to afford the crude which was purified by column chromatography to obtain methyl 3-(4-((tert-butoxycarbonyl)amino)piperidin-1-yl)isonicotinate (0.120 g, 38% Yield) as an yellow semi solid.

LCMS: 336.5 $[M+H]^+$

Compound 120b. To a stirred solution of compound methyl 3-(4-((tert-butoxycarbonyl)amino)piperidin-1-yl)isonicotinate (0.100 gm, 0.298 mmol, 1.0 equiv) in THF (3 mL) and water (2 mL), was added LiOH (0.014 gm, 0.597 mmol, 2.0 equiv). The mixture was allowed to stir at RT for overnight. Product formation was confirmed by LCMS. The reaction mixture was concentrated and diluted with water (10 mL) and washed with ethyl acetate (10 mL×2). Aqueous layer was separated and freeze dried on lyophilyzer to obtain 3-(4-((tert-butoxycarbonyl)amino)piperidin-1-yl)isonicotinic acid, lithium salt (0.120 g, Quant. Yield) as a white solid.

LCMS: 322.2 $[M+H]^+$

Compound 120c. To a stirred solution of 3-(4-((tert-butoxycarbonyl)amino)piperidin-1-yl)isonicotinic acid, lithium salt (0.070 gm, 0.213 mmol, 1.0 equiv), HATU (0.162 gm, 0.426 mmol, 2.0 equiv) in DMF (3 ml) after 10 min was added a (S)-4,4-difluoro-1-glycylpyrrolidine-2-carbonitrile hydrochloride (0.048 gm, 0.213 mmol, 1.0 equiv) and stirred the reaction mixture for 10 min, followed by drop wise addition of DIPEA (0.082 g, 0.640 mmol, 3.0 equiv) allowed the reaction for 16 h stirring at RT. Reaction progress was monitored by LCMS and TLC, workup done by addition of water (30 ml) and extracted with ethyl acetate (2×50 ml). Combined organic layer was washed with water (4×20 mL), dried over anhydrous $Na_2SO_4$, concentrated under reduced pressure to obtain (S)-(1-(4-((2-(2-cyano-4,4-difluoropyrrolidin-1-yl)-2-oxoethyl)carbamoyl)pyridin-3-yl)piperidin-4-yl)carbamate (0.110 g) as a crude product which was directly used for next step.

LCMS: 493.3 $[M+H]^+$

Compound 120•TFA. To a stirred solution of (S)-(1-(4-((2-(2-cyano-4,4-difluoropyrrolidin-1-yl)-2-oxoethyl)carbamoyl)pyridin-3-yl)piperidin-4-yl)carbamate (0.110 gm, 0.223 mmol, 1.0 equiv) in DCM (3 mL), was added trifloroacetic acid (1.0 mL). The mixture was allowed to stir at RT overnight. Product formation was confirmed by LCMS. The reaction mixture concentrated and the crude was purified by reverse phase HPLC to obtain (S)-3-(4-aminopiperidin-1-yl)-N-(2-(2-cyano-4,4-difluoropyrrolidin-1-yl)-2-oxoethyl)isonicotinamide 2,2,2-trifluoroacetate (0.015 g) as an off-white solid.

LCMS: 393.3 $[M+H]^+$ $^1$H NMR (400 MHz, DMSO-$d_6$) δ9.25 (d, J=5.7 Hz, 1H), 8.50 (br. s., 1H), 8.34 (d, J=4.8 Hz, 1H), 7.93 (br. s., 2H), 7.49 (d, J=4.8 Hz, 1H), 7.11 (s, 1H), 5.10 (d, J=6.6 Hz, 1H), 4.22-4.11 (m, 2H), 3.51-3.35 (m, 3H), 3.19 (br. s., 1H), 3.04-2.75 (m, 4H), 1.97 (d, J=11.8 Hz, 2H), 1.71 (d, J=11.4 Hz, 2H), 1.55 (br. s., 1H), 0.94-0.77 (m, 2H)

Example 71

Synthesis of (S)-4-benzyl-N-(2-(2-cyano-4,4-difluoropyrrolidin-1-yl)-2-oxoethyl)-6-oxo-1,6-dihydropyridine-3-carboxamide

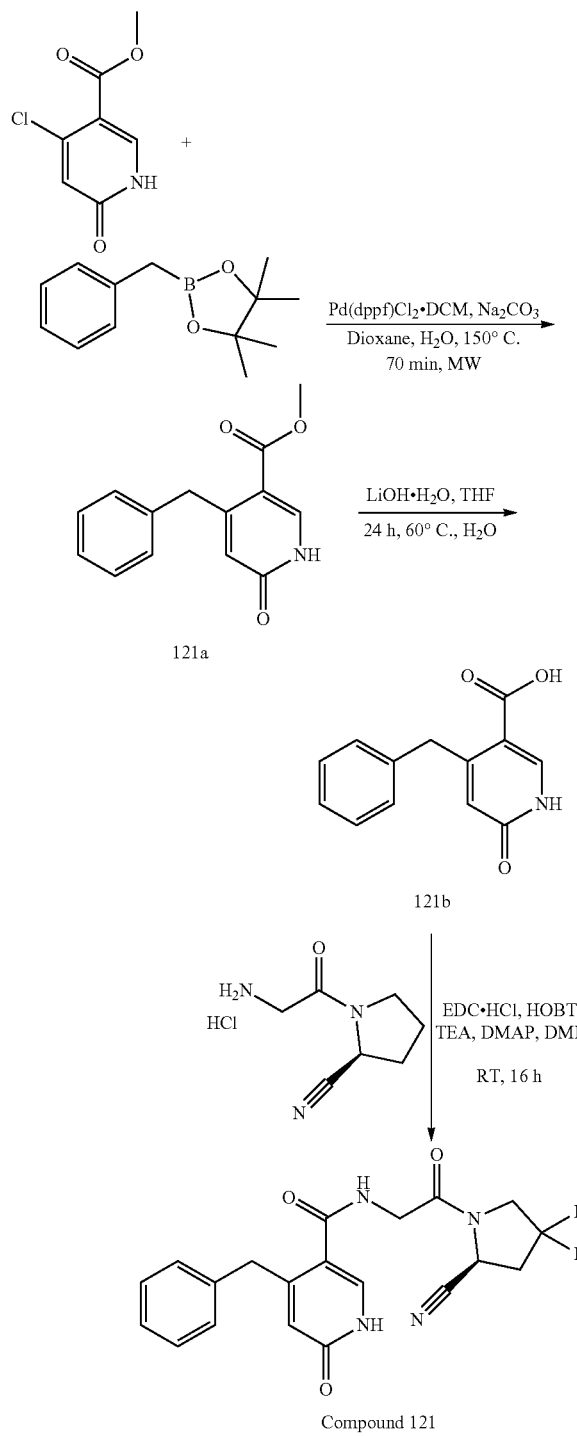

Compound 121a. To a stirring solution of methyl 4-chloro-6-oxo-1,6-dihydropyridine-3-carboxylate (0.250 g, 1.34 mmol, 1.0 equiv) in Dioxan (4 ml) and water (4 ml) were added $Na_2CO_3$ (0.284 g, 2.68 mmol, 2.0 equiv), 2-benzyl-4,4,5,5-tetramethyl-1,3,2-dioxaborolane (0.584 g, 2.68 mmol, 2.0 equiv) and Pd(dppf)$Cl_2$.DCM complex (0.058 g, 0.07 mmol, 0.05 equiv). The reaction mixture was allowed to heat at 150° C. for 70 min in microwave. Product formation was confirmed by TLC and LCMS. The reaction mixture was diluted with water (15 mL) and extracted with ethyl acetate (20 mL×3). Combined organic layer was washed with brine (30 mL). Organic layer was dried over anhydrous sodium sulphate, filtered and concentrated under reduced pressure. Purified the compound by normal phase combi-flash chromatography to obtain methyl 4-benzyl-6-oxo-1,6-dihydropyridine-3-carboxylate (0.030 g).

LCMS 244.0 [M+H]$^+$

Compound 121b. To a stirred solution of methyl 4-benzyl-6-oxo-1,6-dihydropyridine-3-carboxylate (0.300 g, 1.23 mmol, 1 equiv) in THF and water (1:1)(6 mL), was added LiOH.$H_2O$ (0.104 g, 2.47 mmol, 2.0 equiv). The mixture was allowed to stir at 60° C. for 16 h. Product formation was confirmed by LCMS. The reaction mixture was diluted with water (25 mL), extracted with ethyl acetate (20 mL) and concentrated the aqueous layer under reduced pressure and lyophilized to obtain 4-benzyl-6-oxo-1,6-dihydropyridine-3-carboxylic acid (0.260 g).

LCMS 230.0 [M+H]$^+$

Compound 121. To a stirring solution of 4-benzyl-6-oxo-1,6-dihydropyridine-3-carboxylic acid (0.500 g, 2.18 mmol, 1.0 equiv) in DMF (17 ml) were added (S)-4,4-difluoro-1-glycylpyrrolidine-2-carbonitrile hydrochloride (0.590 g, 2.62 mmol, 1.2 equiv), EDC.HCl (0.503 g, 2.62 mmol, 1.2 equiv), HOBT (0.354 g, 2.62 mmol, 1.2 equiv), DMAP (0.001 g) and stirred the reaction mixture at RT for 10 min followed by addition of TEA (0.661 g, 6.54 mmol, 3.0 equiv). The reaction mixture was allowed to stir at RT for 16 h. Product formation was confirmed by LCMS. The reaction mixture was diluted with water (35 mL) and extracted with ethyl acetate (60 mL×3). Combined organic layer was washed with water (40 mL×6) and brine (60 mL). Organic layer was dried over anhydrous sodium sulphate, filtered and concentrated under reduced pressure. Purified the compound by reverse phase HPLC to obtain pure (S)-4-benzyl-N-(2-(2-cyano-4,4-difluoropyrrolidin-1-yl)-2-oxoethyl)-6-oxo-1,6-dihydropyridine-3-carboxamide (0.070 g 8.5%) as an off-white solid.

LCMS 401.1 [M+H]$^+$ $^1$H NMR (400 MHz, DMSO-$d_6$) δ 11.74 (s, 1H), 8.55 (t, J=5.9 Hz, 1H), 7.58 (s, 1H), 7.33-7.15 (m, 5H), 6.05 (s, 1H), 5.09 (dd, J=9.1, 2.8 Hz, 1H), 4.26 (dd, J=14.5, 9.9 Hz, 1H), 4.16-3.95 (m, 5H), 2.98-2.72 (m, 2H).

Example 72

Synthesis of (S)—N-(2-(2-cyano-4,4-difluoropyrrolidin-1-yl)-2-oxoethyl)-3-(1-phenylvinyl)isonicotinamide

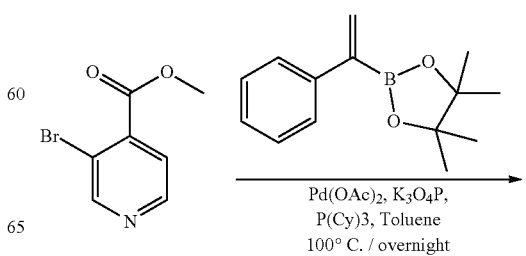

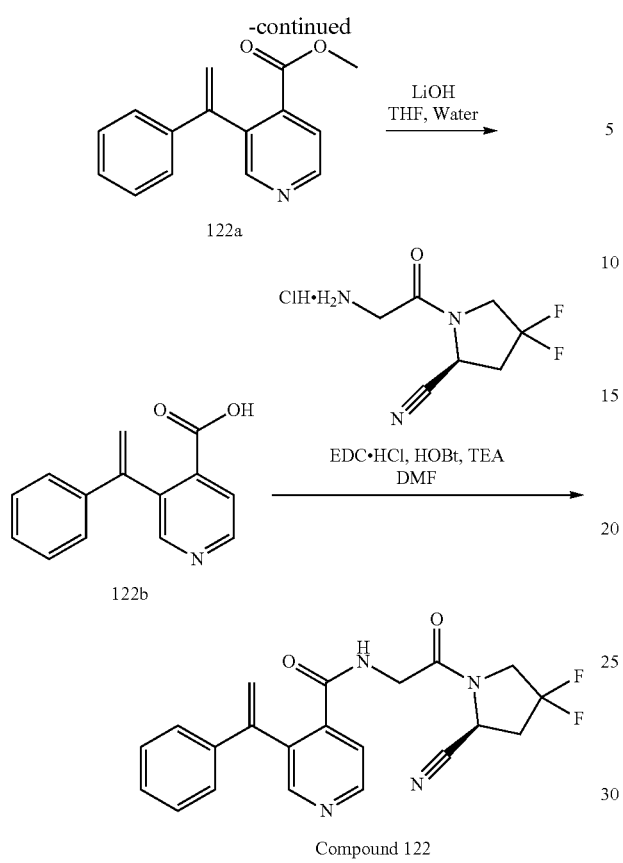

Compound 122

Compound 122a. To a solution of methyl 3-bromoisonicotinate (1.0 g, 4.6 mmol, 1.0 equiv) in toluene (10 mL) was added 4,4,5,5-tetramethyl-2-(1-phenylvinyl)-1,3,2-dioxaborolane (1.06 g, 4.6 mmol, 1.0 equiv), $K_3O_4P$ (1.96 g, 9.2 mmol, 2.0 equiv) followed by the addition of Palladium(II) acetate (0.104 g, 0.46 mmol. 0.1 equiv), and Tricyclohexylphosphine (0.130 g, 0.46 mmol. 0.1 equiv) The resulting reaction mixture was heated at 100° C. for overnight. Product formation was confirmed by LCMS. After completion of reaction, the mixture was diluted with water (200 mL) and extracted with ethyl acetate (150 mL×2). Combined organic extracts were washed with water (20 mL×2), dried over anhydrous $Na_2SO_4$ and concentrated. The crude product obtained was purified by flash chromatography (0-20% ethyl acetate in hexane as an eluent) to obtain methyl 3-(1-phenylvinyl)isonicotinate (0.560 g, 50% Yield) as brown semi solid.

LCMS 240 [M+H]+

Compound 122b. To a stirred solution of methyl 3-(1-phenylvinyl)isonicotinate (0.100 g, 0.41 mmol, 1.0 equiv) in THF (5 mL) and water (5 mL), was added LiOH (0.020 g, 0.82 mmol, 2.0 equiv). The mixture was allowed to stir at RT for overnight. Product formation was confirmed by LCMS and $^1$H NMR Spectroscopy. The reaction mixture was diluted with water (15 mL) and washed with ethyl acetate (15 mL). Aqueous layer was separated and freeze dried on lyophilyzer to obtain 3-(1-phenylvinyl)isonicotinic acid (0.140 g, Quant. Yield) as a brown solid.

LCMS 225.9 [M+H]+

Compound 122. To a stirred solution of 3-(1-phenylvinyl) isonicotinic acid (0.140 g, 0.44 mmol, 1.0 equiv) in DMF (5 mL), was added (S)-4,4-difluoro-1-glycylpyrrolidine-2-carbonitrile hydrochloride (0.100 g, 0.44 mmol, 1.0 equiv), HOBt (0.072 g, 0.53 mmol, 1.2 equiv) and EDC.HCl (0.102 g, 0.53 mmol, 1.2 equiv). The mixture was allowed to stir at RT for 10 min. Triethyl amine (0.2 mL) was added and the mixture was allowed to stir at RT for overnight. Product formation was confirmed by LCMS. After completion of reaction, the mixture was diluted with water (50 mL) and extracted with ethyl acetate (50 mL×2). Combined organic extracts were washed with water (20 mL×4), dried over anhydrous $Na_2SO_4$ and concentrated. The crude product was purified by reversed phase HPLC to obtain (S)—N-(2-(2-cyano-4,4-difluoropyrrolidin-1-yl)-2-oxoethyl)-3-(1-phenylvinyl)isonicotinamide (0.010 g, 07% Yield) as a white solid.

LCMS 397 [M+H]+

$^1$H NMR (400 MHz, DMSO-$d_6$) δ8.66 (t, J=5.9 Hz, 2H), 8.43 (s, 1H), 7.46 (d, J=4.8 Hz, 1H), 7.29 (br. s., 2H), 7.25 (br. s., 2H), 5.77 (s, 1H), 5.38 (s, 1H), 5.07 (d, J=6.6 Hz, 1H), 4.16 (br. s., 1H), 3.97 (d, J=9.2 Hz, 1H), 3.86 (br. s., 2H), 2.78 (d, J=10.5 Hz, 2H), 2.67 (br. s., 1H).

Example 73

Synthesis of N-(2-((S)-2-cyano-4,4-difluoropyrrolidin-1-yl)-2-oxoethyl)-3-(1-phenylethyl)isonicotinamide

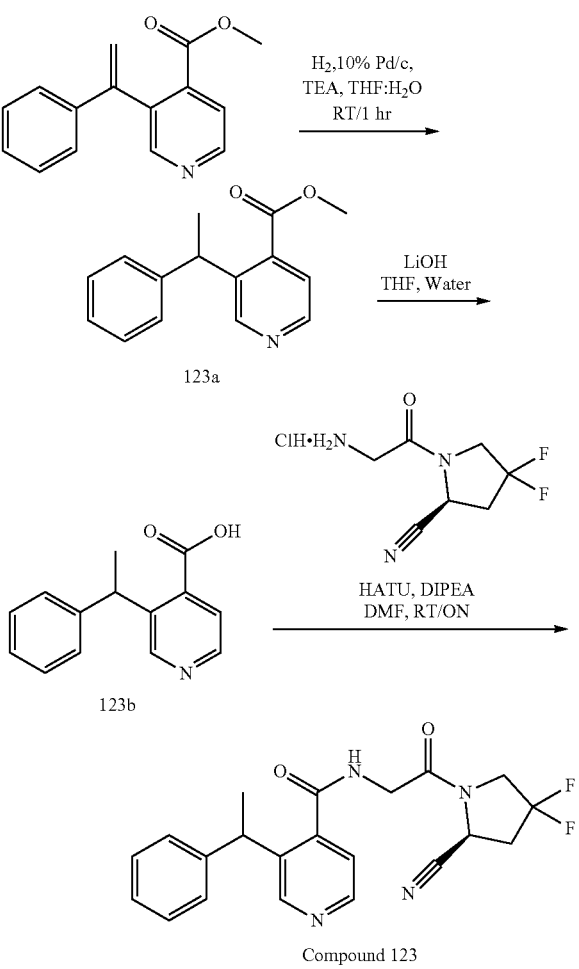

Compound 123

Compound 123a. To a stirred solution of methyl 3-(1-phenylvinyl)isonicotinate (0.200 g, 0.83 mmol, 1.0 equiv) in THF:Methanol (10:04 mL) was added TEA (0.425 g, 4.16 mmol, 5.0 equiv) under nitrogen and Palladium on Carbon [Pd/C] (0.045 g, 0.41 mmol, 0.5 equiv) was added. Purge the reaction mixture with $H_2$ gas for 1 h. Product formation was confirmed by LCMS. After the completion of reaction, reaction mixture was filtered through Celite bed & Filtrate was concentrated under reduced pressure to obtain methyl 3-(1-phenylethyl)isonicotinate (0.180 g, 89% Yield) as a brown semisolid.

LCMS 241.28 $[M+H]^+$

Compound 123b. To a stirred solution of methyl 3-(1-phenylethyl)isonicotinate (0.180 g, 0.74 mmol, 1.0 equiv) in THF (15 mL) and water (10 mL), was added LiOH (0.036 g, 1.48 mmol, 2.0 equiv). The mixture was allowed to stir at RT for overnight. Product formation was confirmed by LCMS and $^1H$ NMR Spectroscopy. The reaction mixture was diluted with water (15 mL) and washed with ethyl acetate (15 mL). Aqueous layer was separated and freeze dried on lyophilyzer to obtain 3-(1-phenylethyl)isonicotinic acid (0.210 g, Quant. Yield) as a brown solid.

LCMS 227.9 $[M+H]^+$ which was purified by reversed phase HPLC to obtain N-(2-((S)-2-cyano-4,4-difluoropyrrolidin-1-yl)-2-oxoethyl)-3-(1-phenylethyl)isonicotinamide (Free base) (0.005 g, 03% Yield) as a white solid.

LCMS 399 $[M+H]^+$ $^1H$ NMR (400 MHz, DMSO-$d_6$) δ 8.97 (d, J=8.8 Hz, 1H), 8.56-8.38 (m, 2H), 7.46-7.33 (m, 2H), 7.29 (t, J=7.2 Hz, 3H), 7.18 (t, J=7.0 Hz, 1H), 5.14 (d, J=9.6 Hz, 1H), 4.69-4.59 (m, 1H), 4.29 (br. s., 1H), 4.22-3.99 (m, 3H), 2.82 (d, J=18.4 Hz, 2H), 1.63 (t, J=7.0 Hz, 3H).

Example 74

Synthesis of N-(2-((S)-2-cyano-4,4-difluoropyrrolidin-1-yl)-2-oxoethyl)-3-((R)-1-phenylethyl)isonicotinamide and N-(2-((S)-2-cyano-4,4-difluoropyrrolidin-1-yl)-2-oxoethyl)-3-((S)-1-phenylethyl)isonicotinamide

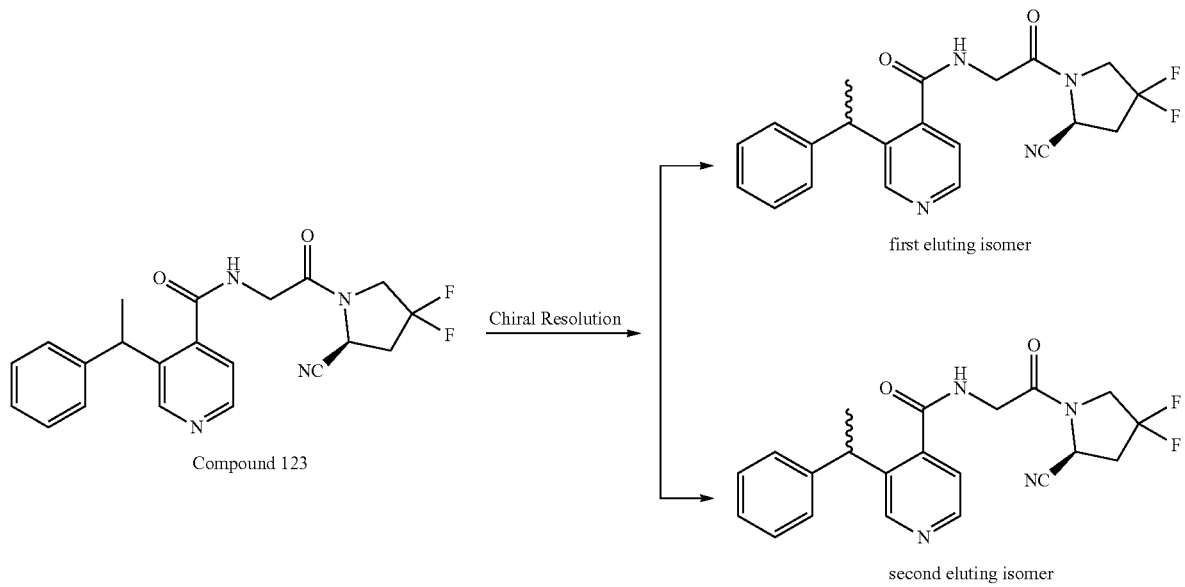

Compound 123. To a stirred solution of 3-(1-phenylethyl)isonicotinic acid (0.100 g, 0.43 mmol, 1.0 equiv) in DMF (5 mL), was added DIPEA (0.3 mL, 1.29 mmol, 3.0 equiv) and HATU (0.327 g, 0.86 mmol, 2.0 equiv). Allow to stir the mixture for 30 min. under nitrogen Atm. (S)-4,4-difluoro-1-glycylpyrrolidine-2-carbonitrile hydrochloride (0.099 g, 0.43 mmol, 1.0 equiv) was added to above mixture and allowed to stir for overnight at RT. Progress of the reaction was monitored by TLC and LCMS. After completion of the reaction, the reaction mixture was diluted with water (30 mL) and extracted with ethyl acetate (100 mL×2). Organic layer was washed with water (100 mL), brine solution (100 mL), dried over anhydrous sodium sulphate and concentrated under reduced pressure to obtain crude compound, Chiral resolution method: The enantiomers were separated by chiral SFC (Chiralpak-IC, 250×20 mm, 5μ). Isocratic Program with analytical grade liquid carbon dioxide with HPLC grade 0.2% DEA in Hexane and Isopropyl alcohol.

LCMS 399.3 $[M+H]^+$ $^1H$ NMR (400 MHz, DMSO-$d_6$) δ 8.97 (d, J=8.8 Hz, 1H), 8.56-8.38 (m, 2H), 7.46-7.33 (m, 2H), 7.29 (t, J=7.2 Hz, 3H), 7.18 (t, J=7.0 Hz, 1H), 5.14 (d, J=9.6 Hz, 1H), 4.69-4.59 (m, 1H), 4.29 (br. s., 1H), 4.22-3.99 (m, 3H), 2.82 (d, J=18.4 Hz, 2H), 1.63 (t, J=7.0 Hz, 3H).

Example 75

Synthesis of (S,E)-N-(2-(2-cyano-4,4-difluoropyrrolidin-1-yl)-2-oxoethyl)-3-styrylisonicotinamide

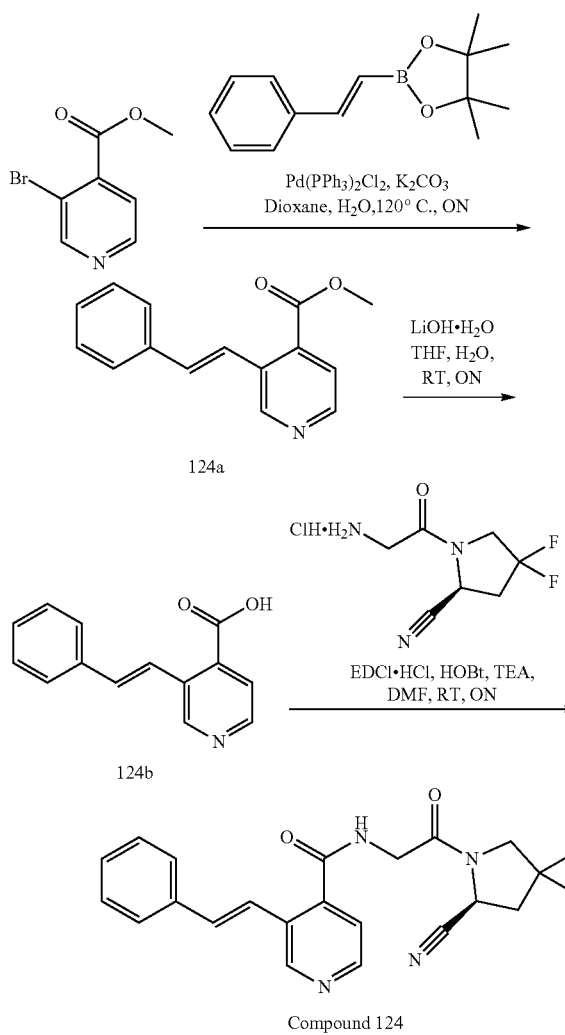

Compound 124a. To a solution of ethyl 3-bromoisonicotinate (0.2 g, 0.925 mmol, 1.0 equiv) in dioxane (10 mL) and water (1 mL) was added (E)-4,4,5,5-tetramethyl-2-styryl-1,3,2-dioxaborolane (0.319 g, 1.39 mmol, 1.5 equiv), $K_2CO_3$ (0.26 g, 1.852 mmol, 2.0 equiv) and resulting reaction mixture purged with $N_2$ gas for 10 minute, followed by the addition of $Pd(PPh_3)Cl_2$ (0.033 g, 0.046 mmol. 0.05 equiv). The resulting reaction mixture was heated at 120° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-30% ethyl acetate in hexane as an eluent) to obtained methyl (E)-3-styrylisonicotinate (0.150 g, 67.87% yield) as a pale yellow solid.

LCMS 240.1 $[M+H]^+$ $^1H$ NMR (DMSO-$d_6$, 400 MHz) δ 9.12 (s, 1H), 8.63 (d, J=5.4 Hz, 1H), 7.65-7.77 (m, 2H), 7.61 (d, J=7.3 Hz, 2H), 7.38-7.49 (m, 2H), 7.26-7.38 (m, 2H), 3.83-3.96 ppm (m, 3H).

Compound 124b. To a stirred solution of methyl (E)-3-styrylisonicotinate (0.1 g, 0.418 mmol, 1.0 equiv) in THF (2 mL) and water (2 mL), was added $LiOH \cdot H_2O$ (0.021 g, 0.0.502 mmol, 1.2 equiv). The mixture was allowed to stir at RT for overnight. Product formation was confirmed by LCMS and $^1H$ NMR Spectroscopy. The reaction mixture was concentrated and diluted with water (10 mL) and washed with ethyl acetate (10 mL×2). Aqueous layer was separated and freeze dried on lyophilyzer to obtain (E)-3-styrylisonicotinic acid (Quant. Yield) as off white solid.

LCMS 226.2 $[M+H]^+$ $^1H$ NMR (DMSO-$d_6$, 400 MHz) δ 8.83 (s, 1H), 8.30 (d, J=4.9 Hz, 1H), 7.86 (d, J=17.1 Hz, 1H), 7.52 (d, J=7.3 Hz, 2H), 7.38 (t, J=7.6 Hz, 2H), 7.20-7.29 (m, 2H), 7.18 ppm (s, 1H).

Compound 124. To a stirred solution of (E)-3-styrylisonicotinic acid (0.06 g, 0.266 mmol, 1.0 equiv) in DMF (2 mL), was added (S)-4,4-difluoro-1-glycylpyrrolidine-2-carbonitrile hydrochloride (0.06 g, 0.266 mmol, 1.0 equiv), EDCI.HCl (0.077 g, 0.39 mmol, 1.5 equiv) & HOBt (0.054 g, 0.39 mmol, 1.5 equiv). The mixture was allowed to stir at RT for 10 min. Triethylamine (0.2 mL) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous $Na_2SO_4$ and concentrated. The crude product obtained was purified by flash chromatography (5% Methanol in DCM as an eluent) to obtain (S,E)-N-(2-(2-cyano-4,4-difluoropyrrolidin-1-yl)-2-oxoethyl)-3-styrylisonicotinamide (0.046 g, 43.8% Yield) as an off white solid.

LCMS 397.2 $[M+H]^+$ $^1H$ NMR (DMSO-$d_6$, 400 MHz) δ 9.14 (s, 1H), 8.99 (t, J=5.9 Hz, 1H), 8.53 (d, J=4.4 Hz, 1H), 7.69 (d, J=7.3 Hz, 2H), 7.63 (s, 1H), 7.47 (d, J=16.1 Hz, 1H), 7.33-7.44 (m, 3H), 7.24-7.33 (m, 1H), 5.10-5.24 (m, 1H), 4.32 (br. s., 1H), 4.05-4.23 (m, 3H), 2.94 (br. s., 1H), 2.80-2.91 ppm (m, 1H).

Example 76

Synthesis of (S)—N-(2-(2-cyano-4,4-difluoropyrrolidin-1-yl)-2-oxoethyl)-3-phenethylisonicotinamide

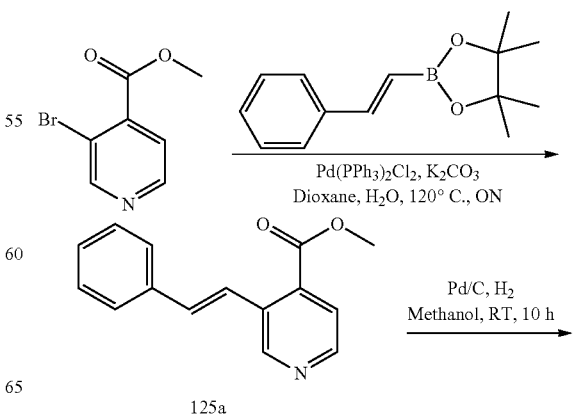

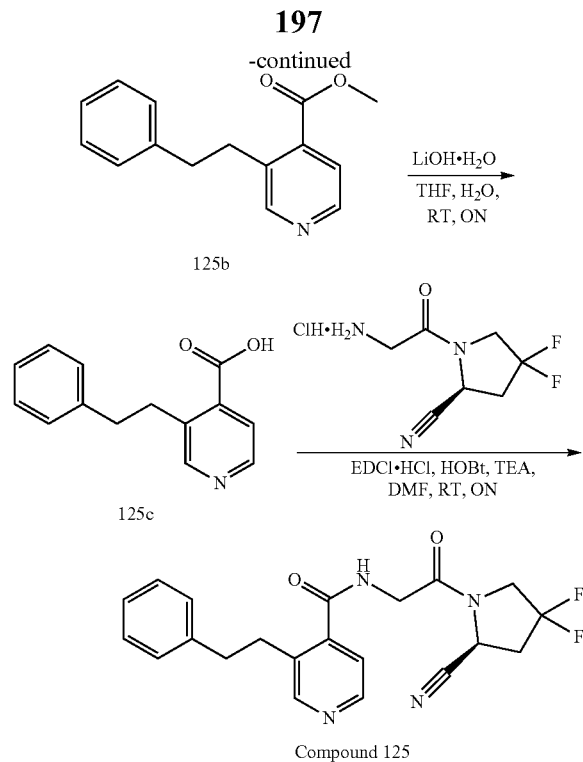

Compound 125

Compound 125a. To a solution of ethyl 3-bromoisonicotinate (0.2 g, 0.925 mmol, 1.0 equiv) in dioxane (10 mL) and water (1 mL) was added (E)-4,4,5,5-tetramethyl-2-styryl-1,3,2-dioxaborolane (0.319 g, 1.39 mmol, 1.5 equiv), $K_2CO_3$ (0.26 g, 1.852 mmol, 2.0 equiv) and resulting reaction mixture purged with $N_2$ gas for 10 minute, followed by the addition of $Pd(PPh_3)Cl_2$ (0.033 g, 0.046 mmol. 0.05 equiv). The resulting reaction mixture was heated at 120° C. for overnight. Product formation was confirmed by LCMS. After the completion of reaction, the mixture was filtered through celite bed, washed with ethyl acetate (100 mL). Filtrate was concentrated under reduced pressure. The crude product obtained was purified by flash chromatography (0-30% ethyl acetate in hexane as an eluent) to methyl (E)-3-styrylisonicotinate (0.150 g, 67.87% yield) as pale yellow solid.

LCMS 240.1 [M+H]$^+$ $^1$H NMR (DMSO-d$_6$, 400 MHz) δ 9.12 (s, 1H), 8.63 (d, J=5.4 Hz, 1H), 7.65-7.77 (m, 2H), 7.61 (d, J=7.3 Hz, 2H), 7.38-7.49 (m, 2H), 7.26-7.38 (m, 2H), 3.83-3.96 ppm (m, 3H).

Compound 125b. To a solution of methyl (E)-3-styrylisonicotinate (0.13 g, 0.544 mmol, 1.0 equiv) in methanol (9 mL) was purged with $N_2$ gas for 10 minute, followed by the addition of Pd/C (0.065 g). Then resulting reaction mixture was purged with $H_2$ gas for 6 h. Product formation was confirmed by LCMS and NMR. After the completion of reaction, the mixture was filtered through celite bed, washed with methanol (30 mL). Filtrate was concentrated under reduced pressure to obtain methyl 3-phenethylisonicotinate (0.1 g, 76.33% yield) as a transparent oil.

LCMS 242.2 [M+H]$^+$ $^1$H NMR (DMSO-d$_6$, 400 MHz) δ 8.57 (s, 2H), 7.27 (d, J=6.8 Hz, 1H), 7.19 (d, J=6.8 Hz, 2H), 3.88 (s, 3H), 3.15 (d, J=8.8 Hz, 2H), 2.83 ppm (br. s., 2H).

Compound 125c. To a stirred solution of methyl 3-phenethylisonicotinate (0.1 g, 0.415 mmol, 1.0 equiv) in THF (4 mL) and water (4 mL), was added LiOH.H$_2$O (0.021 g, 0.5 mmol, and 1.2 equiv). The mixture was allowed to stir at RT for overnight. Product formation was confirmed by LCMS and $^1$H NMR Spectroscopy. The reaction mixture was concentrated and diluted with water (10 mL) and washed with ethyl acetate (10 mL×2). Aqueous layer was separated and freeze dried on lyophilyzer to obtain 3-phenethylisonicotinic acid (Quant. Yield) as off white solid.

LCMS 228.2 [M+H]$^+$ $^1$H NMR (DMSO-d$_6$, 400 MHz) δ 8.22 (d, J=4.9 Hz, 1H), 7.18-7.33 (m, 5H), 7.08-7.18 (m, 1H), 2.96-3.11 (m, 2H), 2.74-2.87 ppm (m, 2H).

Compound 125. To a stirred solution of (E)-3-styrylisonicotinic acid (0.05 g, 0.22 mmol, 1.0 equiv) in DMF (3 mL), was added (S)-4,4-difluoro-1-glycylpyrrolidine-2-carbonitrile hydrochloride (0.05 g, 0.22 mmol, 1.0 equiv), EDCI.HCl (0.063 g, 0.33 mmol, 1.5 equiv) & HOBt (0.046 g, 0.33 mmol, 1.5 equiv). The mixture was allowed to stir at RT for 10 min. Triethylamine (0.2 mL) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous $Na_2SO_4$ and concentrated. The crude product obtained was purified by flash chromatography (5% Methanol in DCM as an eluent) to obtain (S)—N-(2-(2-cyano-4,4-difluoropyrrolidin-1-yl)-2-oxoethyl)-3-phenethylisonicotinamide (0.050 g, 57.12% Yield) as a white solid.

LCMS 399.2 [M+H]$^+$ $^1$H NMR (DMSO-d$_6$, 400 MHz) δ 8.92 (br. s., 1H), 8.40-8.53 (m, 2H), 7.34 (d, J=4.4 Hz, 1H), 7.21-7.29 (m, 4H), 7.17 (d, J=6.4 Hz, 1H), 5.12 (d, J=7.3 Hz, 1H), 4.31 (br. s., 1H), 4.02-4.22 (m, 3H), 2.96-3.08 (m, 2H), 2.77-2.95 ppm (m, 4H).

Example 77

Synthesis of N-(1-((S)-2-cyano-4,4-difluoropyrrolidin-1-yl)-1-oxopropan-2-yl)-3-phenylisonicotinamide

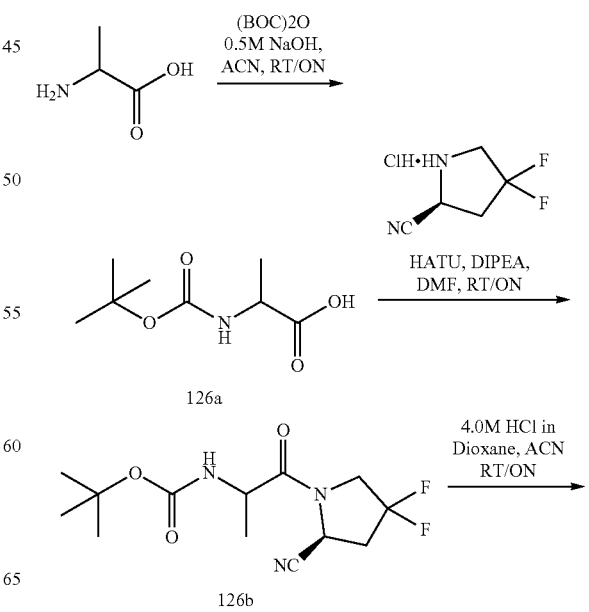

-continued

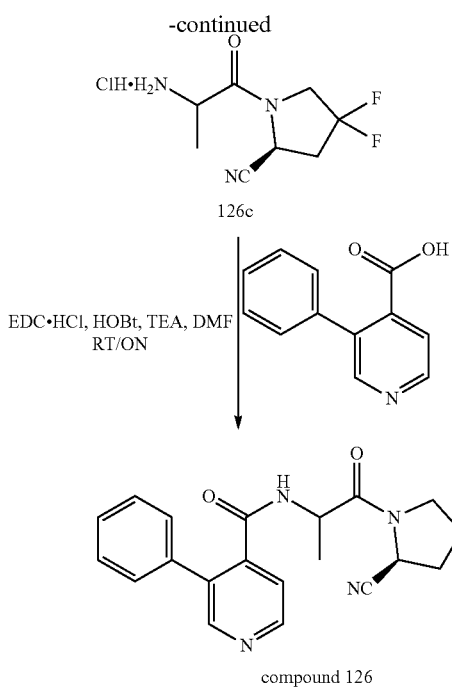

126c compound 126

Compound 126a. To a stirred solution of alanine (2.0 g, 22.2 mmol, 1.0 equiv.) in ACN (20 mL) was added Di-tert-butyl dicarbonate (5.35 g, 24.4 mmol, 1.1 equiv) and stirred for 10 min. 0.5M NaOH solution (20 mL) was added and the reaction mixture was allowed to stir for overnight at RT. reaction progress was monitored by NMR. The reaction was acidify with diluted HCl (PH=2.5) and extracted with ethyl acetate (100 mL), and dried over anhydrous sodium sulphate and concentrated under reduced pressure to obtain (tert-butoxycarbonyl)alanine. (2.100 g, a white solid).

Compound 126b. To a stirred solution of (tert-butoxycarbonyl)alanine (0.623 g, 3.2 mmol, 1.1 equiv.) and HATU (2.20 g, 5.8 mmol, 2.0 equiv.) in DMF (05 mL was added (S)-4,4-difluoropyrrolidine-2-carbonitrile hydrochloride (0.500 g, 2.9 mmol, 1.0 equiv) and stirred for 10 min. DIPEA (1.5 mL, 8.7 mmol, 3.0 equiv.) was added and the reaction mixture was allowed to stir for overnight at RT. reaction progress was monitored by NMR and TLC. The reaction was diluted with cold water (200 mL) and extracted with ethyl acetate (200 mL×2). Combined organic extracts were washed with water (200 mL×3), dried over anhydrous sodium sulphate and concentrated under reduced pressure to obtain tert-butyl (1-((S)-2-cyano-4,4-difluoropyrrolidin-1-yl)-1-oxopropan-2-yl)carbamate (0.700 g, as a brownish solid).

Compound 126c. To a stirred solution of tert-butyl (1-((S)-2-cyano-4,4-difluoropyrrolidin-1-yl)-1-oxopropan-2-yl)carbamate (0.700 g, 2.31 mmol, 1.0 equiv) in acetonitrile (10 mL ) was added dropwise at 0° C. 4.0 M HCl in Dioxan (5.0 ml) over a period of 10 min. the mixture was allowed to stir at RT for overnight. The reaction progress was monitored by NMR. The solvent was evaporated under reduced pressure to obtain residue which was washed with 20 mL ethyl acetate and hexane (1:1) to obtain (2S)-1-alanyl-4,4-difluoropyrrolidine-2-carbonitrile hydrochloride (0.900 g) as an yellow semi solid.

Compound 126. To a stirred solution of 3-phenylisonicotinic acid (0.753 g, 3.7 mmol, 1.0 equiv.) in DMF (5 mL) was added (2S)-1-alanyl-4,4-difluoropyrrolidine-2-carbonitrile hydrochloride (0.900 g, 3.7 mmol, 1.0 equiv.) HOBT (0.594 g, 4.4 mmol, 1.2 equiv.) EDC.HCl (0.848 g, 4.4 mmol, 1.2 equiv.) and stirred for 10 min. TEA (1.0 mL, 7.4 mmol, 2.0 equiv.) was added and the mixture was allowed to stir at RT for 16 h. The reaction progress was monitored by NMR and TLC. The reaction mixture was diluted with cold water (50 mL) and extracted with ethyl acetate (150×2 mL). Combined organic extracts were washed with water by (50 mL×4), dried over anhydrous sodium sulphate and concentrated under reduced pressure. The crude product obtained was purified by reversed phase chromatography to obtain N-(1-((S)-2-cyano-4,4-difluoropyrrolidin-1-yl)-1-oxopropan-2-yl)-3-phenylisonicotinamide (35 mg, 03% Yield) as an off-white solid.

LCMS 385 [M+H]$^+$ $^1$H NMR (400 MHz, DMSO-d$_6$) δ 9.06 (d, J=7.45 Hz, 1H) 8.66 (br. s., 2H) 7.32-7.52 (m, 5H) 5.05 (d, J=7.02 Hz, 1H) 4.56 (br. s., 1H) 4.07 (d, J=9.21 Hz, 1H) 4.01 (br. s., 1H) 2.82 (br. s., 2H) 1.09-1.20 (m, 3H).

Biological Examples

Example B1

Inhibition of FAPα by Test Compounds was Assessed by In Vitro Enzymatic Activity Assays FAPα enzymatic exopeptidase (dipeptidase) activity assay. To assay baseline FAPα enzymatic exopeptidase activity, 40 ng of recombinant human FAPα (rhFAPα, R&S system, #3715-SE) or 40 ng of recombinant mouse FAPα (rmFAPα, R&S system, #8647-SE) was incubated with 100 μM of Z-Gly-Pro-AMC peptide (BACHEM, #L-1145) in a FAPα assay buffer (50 mM Tris pH 7.4, 100 mM NaCl, 0.1 mg/ml bovine serum albumin) for 1 h at 37° C. protected from light in 96-well black plates (Nunc, #237108). To assay FAPα enzymatic exopeptidase activity inhibition by test compounds, all test compounds were pre-incubated with the enzyme for 15 min at 37° C. before starting the reaction by substrate addition in 96-well black plates (Nunc, #237108). 7-Amino-4-Methylcoumarin (AMC) release was detected by measuring fluorescence at Ex/Em 380/460 nm using a Multifunction Microplate Reader (Synergy 4, Biotek). All measurements were carried out in duplicate. Val-boroPro, a non-specific prolyl peptidase inhibitor, was used as a positive control. Percent inhibition of rmFAPα or rhFAPα enzymatic exopeptidase activity at 1 μM was determined for certain compounds, as shown in Table 2. For the calculations, the average measurements from reactions containing only vehicle and substrate, without enzyme, were used as a blank and were subtracted from the rest of the measurements. Percent inhibition was calculated using the average measurements from reactions containing vehicle, enzyme, and substrate as the maximum of enzymatic activity. Additionally, IC$_{50}$ for the rmFAPα or rhFAPα enzymatic exopeptidase activity of certain compounds are also shown in Table 2. Measurements were performed as a single point.

FAPα enzymatic endopeptidase (collagenase) activity assay. To assay baseline FAPα enzymatic exopeptidase activity, 50 ng of recombinant human FAPα (rhFAPα) (R&S system, #3715-SE) diluted in FAPα assay buffer (50 mM Tris pH 7.4, 100 mM NaCl, 0.1 mg/ml bovine serum albumin) was incubated with 5 μg of substrate DQ collagen solution (Molecular Probes #D-12060) with for 5 h at 37° C. and protected from light in 384-well optiplates (Perkin Elmer, #384-F). To assay FAPα enzymatic endopeptidase activity inhibition by test compounds, all test compounds were pre-incubated with the enzyme for 30 min at 37° C. before starting the reaction by substrate addition in 384-well OptiPlates (Perkin Elmer, #384-F). Collagen hydrolysis was determined by measuring fluorescence at Ex/Em 495/515 nm using a multifunction Microplate Reader (Synergy 4, Biotek). All measurements were performed as a single point. Val-boroPro, a non-specific prolyl peptidase inhibitor, was used as a positive control. $IC_{50}$ for the rhFAPα enzymatic endopeptidase activity (as determined by the collagenase assay) of certain compounds are also shown in Table 2.

TABLE 2

Exopeptidase or Endopeptidase inhibition of rmFAPα or rhFAPα by Test Compounds

| Compound No. | rmFAPα (% exo inh @ 1 μM) | rhFAPα (% exo inh @ 1 μM) | rmFAPα (exo $IC_{50}$, μM) | rhFAPα (exo $IC_{50}$, μM) | rhFAPα (endo $IC_{50}$, μM) |
|---|---|---|---|---|---|
| Val-boroPro | ++ | — | ++ | ++ | ++ |
| Ref. Comp. | +++ | +++ | +++ | +++ | +++ |
| 1 | +++ | — | +++ | +++ | +++ |
| 2 | ++ | — | — | — | — |
| 3 | ++ | — | — | — | — |
| 4 | +++ | — | +++ | +++ | — |
| 5 | + | — | — | — | — |
| 6 | +++ | — | +++ | +++ | — |
| 7 | + | — | — | — | — |
| 8 | + | — | — | — | — |
| 9 | +++ | — | +++ | +++ | — |
| 10 | ++ | — | — | — | — |
| 11 | ++ | — | — | — | — |
| 12 | ++ | — | — | — | — |
| 13 | — | +++ | +++ | +++ | +++ |
| 14 | — | +++ | — | +++ | +++ |
| 15 | — | ++ | — | — | — |
| 16 | — | +++ | — | +++ | — |
| 17 | — | ++ | — | — | — |
| 18 | — | ++ | — | — | — |
| 19 | — | +++ | — | +++ | — |
| 20 | — | ++ | — | — | — |
| 21 | — | +++ | — | +++ | — |
| 22 | — | +++ | — | +++ | — |
| 23 | — | + | — | — | — |
| 24 | — | +++ | +++ | +++ | +++ |
| 25 | — | + | — | — | — |
| 26 | — | +++ | — | +++ | — |
| 36 | — | +++ | — | +++ | — |
| 38 | — | +++ | — | +++ | — |
| 40 | — | +++ | — | +++ | — |
| 42 | — | +++ | — | +++ | — |
| 43 | — | +++ | — | +++ | — |
| 47 | — | +++ | — | +++ | — |
| 50 | — | +++ | — | +++ | — |
| 52 | — | +++ | +++ | +++ | — |
| 54 | — | +++ | — | +++ | — |
| 66 | — | +++ | — | +++ | — |
| 80 | — | +++ | — | +++ | — |
| 81 | — | + | — | — | — |
| 82 | — | + | — | — | — |
| 83 | — | ++ | — | — | — |
| 84 | — | ++ | — | — | — |
| 85 | — | +++ | — | — | — |
| 86 | — | ++ | — | — | — |
| 87 | — | +++ | — | +++ | — |
| 88 | — | +++ | — | +++ | — |
| 101 | — | + | — | — | — |
| 104 | — | +++ | — | +++ | — |
| 105 | — | +++ | — | +++ | +++ |
| 30 | — | + | — | — | — |
| 64 | — | +++ | — | +++ | — |
| 37 | — | +++ | — | — | — |
| 106 | — | +++ | — | +++ | — |
| 107 | — | +++ | — | +++ | — |
| 29 | — | +++ | — | +++ | — |
| 51 | — | +++ | — | +++ | — |
| 109 | — | +++ | — | +++ | +++ |
| 110 | — | +++ | — | +++ | — |
| 111 | — | +++ | — | +++ | — |
| 112 | — | +++ | — | +++ | — |
| 113 | — | +++ | — | +++ | — |
| 97 | — | +++ | — | +++ | — |
| 114 | — | +++ | — | +++ | — |
| 35 | — | +++ | — | +++ | — |
| 102 | — | +++ | — | +++ | — |
| 115 | — | +++ | — | +++ | — |
| 116 | — | +++ | — | +++ | — |
| 117 | — | +++ | — | +++ | — |
| 118 | — | +++ | — | +++ | — |
| 119 | — | +++ | — | +++ | — |
| 120 | — | +++ | — | +++ | — |
| 121 | — | +++ | — | +++ | — |
| 122 | — | +++ | — | +++ | — |
| 123 | — | +++ | — | +++ | — |
| First eluting isomer of example 74 | — | +++ | — | +++ | — |
| Second eluting isomer of example 74 | — | +++ | — | ++ | — |
| 124 | — | +++ | — | +++ | — |
| 125 | — | +++ | — | +++ | — |

Ref. Comp.: Compound 60 as described in Jansen, K., et at., J Med Chem, 2014. 57(7): p. 3053-74;
for % of inhibition: +++ refers to > 50% inhibition at 1 μM test compound;
++ refers to 25% < % inhibition < 50% at 1 μM test compound;
+ refers to < 25% inhibition at 1 μM;
for $IC_{50}$: +++ refers to $IC_{50}$ < 1 μM;
++ refers to 1 μM < $IC_{50}$ < 10 μM;
+ refers to $IC_{50}$ > 10 μM;
— represents compound not tested;
rmFAPα: recombinant mouse fibroblast activation protein alpha;
rhFAPα: recombinant human fibroblast activation protein alpha;
endo: endopeptidase;
exo: exopeptidase;
inh: inhibition.

Example B2

Selectivity of the Inhibition of FAPα by Test Compounds was Assessed Compared to Other Prolyl Oligopeptidase Family S9 Members: DPPIV, PREP, and DPP9

DPPIV Enzymatic Activity Assay

To assay baseline dipeptidyl peptidase-4 (DPPIV) activity, 40 ng of recombinant human DPPIV (rhDPPIV) (R&S system, #1180-SE) or 40 ng of recombinant mouse DPPIV (rmDPPIV) (R&S system, #954-SE) was incubated with 400 μM of H-Gly-Pro-pNA substrate (BACHEM, #L-1880) in a DPPIV assay buffer (25 mM Tris, pH 8.3) for 30 min at 37° C. protected from the light in 96-well black plates (Nunc, #237108). To assay DPPIV inhibition by test compounds, test compounds were pre-incubated with the enzyme for 15 min at 37° C. before starting the reaction by substrate addition in 96-well black plates (Nunc, #237108). Para-nitroaniline (pNA) release was detected by measuring absorbance at 405 nm using a Multifunction Microplate Reader (Synergy 4, Biotek). All measurements were carried out in triplicate. Val-boroPro, a non-specific prolyl peptidase inhibitor, was used as a positive control.

PREP Enzymatic Activity Assay

To assay baseline prolyl endopeptidase (PREP) activity, 20 ng of recombinant human PREP (rhPREP) (R&S system, #4308-SE) or 20 ng of recombinant mouse PREP (rmPREP) (R&S system, #6339-SE) was incubated with 100 μM of Z-Gly-Pro-AMC peptide (BACHEM, #L-1145) in a PREP assay buffer (25 mM Tris, 250 mM NaCl, 10 mM DTT, pH 7.5) for 30 min at 37° C. protected from light in 96-well black plates (Nunc, #237108). To assay PREP activity inhibition by test compounds, test compounds were pre-incubated with the enzyme for 15 min at 37° C. before starting the reaction by substrate addition in 96-well black plates (Nunc, #237108). 7-Amino-4-Methylcoumarin (AMC) release was detected by measuring fluorescence at Ex/Em 380/460 nm using a Multifunction Microplate Reader (Synergy 4, Biotek). All measurements were carried out in triplicate. Val-boroPro, a non-specific prolyl peptidase inhibitor, was used as a positive control.

DPP9 Enzymatic Activity Assay

To assay baseline dipeptidyl peptidase 9 (DPP9) activity, 40 ng of recombinant human DPP9 (rhDPP9) (R&S system, #5419-SE) was incubated with 100 μM of H-Gly-Pro-AMC peptide (BACHEM, #L-1215) in a DDP9 assay buffer (50 mM HEPES, pH 8) for 30 min at 37° C. in 96-well black plates (Nunc, #237108). To assay rhDPP9 activity inhibition by test compounds, test compounds were pre-incubated with the enzyme for 15 min at 37° C. before starting the reaction by substrate addition in 96-well black plates (Nunc, #237108). 7-Amino-4-Methylcoumarin (AMC) release was detected by measuring fluorescence at Ex/Em 380/460 nm using a Multifunction Microplate Reader (Synergy 4, Biotek). All measurements were carried out in triplicate. Val-boroPro, a non-specific prolyl peptidase inhibitor, was used as a positive control.

To determine if new FAPα inhibitors were selective or if they also inhibited other prolyl peptidases, the $IC_{50}$ for rmDPPIV, rhDPPIV, rmPREP, and/or DPP9 of certain test compounds, a reference compound (compound 60 as described in Jansen, K., et al., J Med Chem, 2014. 57(7): p. 3053-74), and Val-boroPro were determined, as shown in Table 3.

TABLE 3

Selectivity of FAPα Inhibition by Test Compounds

| Compound No. | rmFAPα (exo $IC_{50}$, μM) | rhFAPα (exo $IC_{50}$, μM) | rmDPPIV ($IC_{50}$, μM) | rhDPPIV ($IC_{50}$, μM) | rmPREP ($IC_{50}$, μM) | rhPREP ($IC_{50}$, μM) | rhDPP9 ($IC_{50}$, μM) |
|---|---|---|---|---|---|---|---|
| Val-boroPro | + | ++ | +++ | +++ | ++ | ++ | +++ |
| Ref. Comp. | +++ | +++ | + | + | + | ++ | ++ |
| 1 | +++ | +++ | ++ | ++ | ++ | ++ | ++ |
| 4 | +++ | − | ++ | + | + | + | − |
| 6 | +++ | − | + | + | − | − | − |
| 9 | +++ | +++ | + | − | +++ | − | + |
| 13 | +++ | +++ | + | + | + | + | ++ |
| 14 | − | +++ | + | + | + | + | ++ |
| 16 | − | +++ | + | − | + | − | − |
| 19 | − | +++ | − | + | − | + | − |
| 21 | − | +++ | − | + | − | ++ | + |
| 22 | − | +++ | − | + | − | ++ | − |
| 24 | +++ | +++ | − | + | − | ++ | ++ |
| 26 | − | +++ | − | ++ | − | ++ | ++ |
| 36 | − | +++ | − | + | − | − | − |
| 38 | − | +++ | − | ++ | − | + | ++ |
| 40 | − | +++ | − | + | − | ++ | + |
| 42 | − | +++ | − | + | − | + | + |
| 43 | − | +++ | − | + | − | + | ++ |
| 47 | − | +++ | − | + | − | + | + |
| 50 | − | +++ | − | + | − | ++ | +++ |
| 52 | +++ | +++ | − | + | − | + | + |
| 54 | − | +++ | − | + | − | + | + |
| 66 | − | +++ | − | + | − | + | + |
| 80 | − | +++ | − | + | − | − | − |
| 87 | − | +++ | − | + | − | + | + |
| 88 | +++ | +++ | − | ++ | − | + | ++ |
| 104 | − | +++ | − | + | − | + | + |
| 105 | − | +++ | − | + | − | + | + |
| 30 | − | − | − | − | − | − | − |
| 64 | − | +++ | − | + | − | + | + |
| 37 | − | − | − | − | − | − | − |
| 106 | − | +++ | − | + | − | + | + |
| 107 | − | +++ | − | ++ | − | + | ++ |
| 29 | − | +++ | − | ++ | − | + | + |
| 51 | − | +++ | − | ++ | − | + | + |
| 109 | − | +++ | − | ++ | − | + | ++ |
| 110 | − | +++ | − | + | − | + | + |
| 111 | − | +++ | − | ++ | − | + | + |
| 112 | − | +++ | − | + | − | + | + |
| 113 | − | +++ | − | + | − | + | + |
| 97 | − | +++ | − | + | − | + | + |
| 114 | − | +++ | − | + | − | + | + |
| 35 | − | +++ | − | + | − | + | + |
| 102 | − | +++ | − | + | − | + | + |
| 115 | − | +++ | − | + | − | ++ | + |

TABLE 3-continued

Selectivity of FAPα Inhibition by Test Compounds

| Compound No. | rmFAPα (exo IC$_{50}$, μM) | rhFAPα (exo IC$_{50}$, μM) | rmDPPIV (IC$_{50}$, μM) | rhDPPIV (IC$_{50}$, μM) | rmPREP (IC$_{50}$, μM) | rhPREP (IC$_{50}$, μM) | rhDPP9 (IC$_{50}$, μM) |
|---|---|---|---|---|---|---|---|
| 116 | – | +++ | – | ++ | – | + | + |
| 117 | – | +++ | – | + | – | ++ | + |
| 118 | – | +++ | – | + | – | + | + |
| 119 | – | +++ | – | + | – | + | + |
| 120 | – | +++ | – | ++ | – | + | + |
| 121 | – | +++ | – | + | – | ++ | ++ |
| 122 | – | +++ | – | + | – | + | + |
| 123 | – | +++ | – | + | – | ++ | ++ |
| First eluting isomer of example 74 | – | +++ | – | – | – | – | ++ |
| Second eluting isomer of example 74 | – | ++ | – | – | – | – | ++ |
| 124 | – | +++ | – | – | – | – | ++ |
| 125 | – | +++ | – | – | – | – | ++ |

Ref. Comp.: Compound 60 as described in Jansen, K., et al., *J Med Chem*, 2014. 57(7): p. 3053-74; for IC$_{50}$: +++ refers to IC$_{50}$ < 1 μM; ++ refers to 1 μM < IC$_{50}$ < 10 μM; + refers to IC$_{50}$ > 10 μM; – represents compound not tested; rmFAPα: recombinant mouse fibroblast activation protein alpha; rhFAPα: recombinant human fibroblast activation protein alpha; rmDPPIV: recombinant mouse dipeptidyl peptidase-4; rhDPPIV: recombinant human dipeptidyl peptidase-4; rmPREP: recombinant mouse prolyl endopeptidase; rhDPP9: recombinant human dipeptidase 9; exo: exopeptidase.

Example B3

Validation of Selective PRXS-AMC Substrate for FAPα Activity Measurements

FAPα activity can be measured by a general fluorescence intensity assay for dipeptidyl-peptidases using a peptide substrate attached to a chemically quenched dye, such as Ala-Pro-7-amino-4-trifluoromethyl-coumarin (AFC) or a substrate containing the consensus Gly-Pro dipeptide such as Z-Gly-Pro-AMC (Levy, M. T., et al., Hepatology, 1999, 29(6): 1768-78; Santos, A. M., et al., J Clin Invest, 2009, 119(12): 3613-25; Park, J. E., et al., J Biol Chem, 1999, 274(51): 36505-12; Niedermeyer, J., et al., Mol Cell Biol, 2000, 20(3): 1089-94; Narra, K., et al., Cancer Biol Ther, 2007, 6(11): 1691-9; Lee, K. N., et al., J Thromb Haemost, 2011, 9(5): 987-96; Li, J., et al., Bioconjug Chem, 2012, 23(8): 1704-11). These substrates are likely targeted also by other circulating proline-specific endopeptidases such as PREP that could be present in the reaction. By contrast, a proprietary substrate reagent, named PRXS-AMC, can specifically monitor FAPα activity.

To validate the high selectivity of this proprietary substrate, enzymatic activity assays for FAP, DPPIV, PREP and DPP9 were carried out using Z-Gly-Pro-AMC or PRXS-AMC as described in Examples B1 and B2.

Figure 1B:
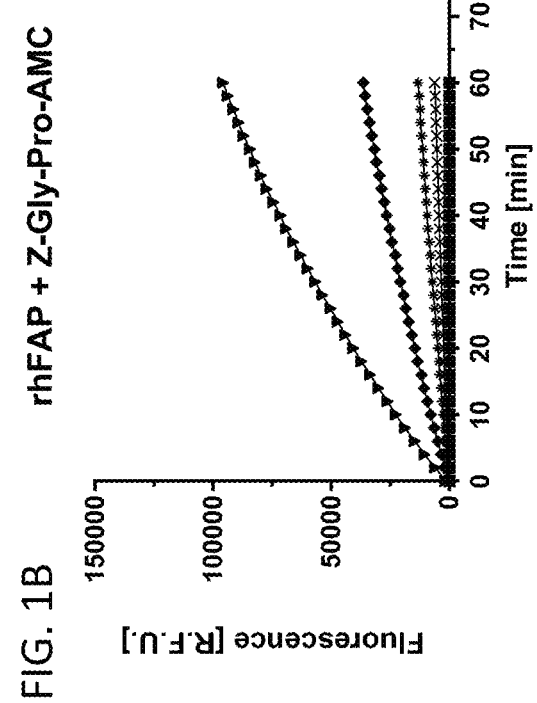
FIG. 1B shows Z-Gly-Pro-AMC degradation over time by rhFAP.

To assay FAPα, DPPIV, DPP9 and PREP enzymatic activities, human recombinant enzymes were used at 5, 2.5, 2.5 and 5 nM final concentrations, respectively. Z-Gly-Pro-AMC or PRXS-AMC were used at 25, 50, 100 and 200 μM final concentrations. Reactions were carried out for 60 min at 37° C. and were protected from light. AMC release was detected by measuring fluorescence at Ex/Em 380/460 nm using a Multifunction Microplate Reader in kinetic mode. Measurements were performed as a single point. Resulting fluorescence over time for PRXS-AMC and Z-gly-pro-AMC in the presence of rhFAPα is shown in FIG. 1A and FIG. 1B, respectively; resulting fluorescence over time for PRXS-AMC and Z-gly-pro-AMC in the presence of rhPREP is shown in FIG. 2A and FIG. 2B, respectively; and resulting fluorescence over time for PRXS-AMC in the presence of rhDPPIV or rhDPP9 is shown in FIG. 3A and FIG. 3B, respectively.

PRXS-AMC is processed to a lesser extent than Z-Gly-Pro-AMC by the closely related prolyl oligopeptidase PREP at similar concentrations (see FIGS. 2A-2B). PRXS-AMC is not processed by DPPIV or DPP9 (FIGS. 3A-3B). In addition, PRXS-AMC showed an improved solubility in aqueous buffers.

Example B4

Enzymatic Activity in Plasma

FAPα Enzymatic Activity in Mouse Plasma

Approximately 500 μL of whole blood from one C57BL/6 mouse was harvested into BD Microtainer® tubes (K2) EDTA (#365974, Becton Dickinson and Co.) via terminal cardiac puncture. The blood sample was immediately centrifuged at approximately 9000 g at 4° C. for 5 minutes. Plasma was separated and stored at −80° C. in aliquots of 300 μL. To assay baseline FAPα enzymatic exopeptidase activity, 5 μL of thawed, plasma was diluted (1:5) with cFAP buffer (100 mM Tris-HCl, 400 mM NaCl, 50 mM salicylic acid, 1 mM EDTA, pH 7.5) and mixed with 35 μL of the same buffer before being pre-incubated with different concentrations of 10 μL of test compounds or DMSO vehicle for 15 minutes at 37° C. in 96-well black plates (Nunc, #237108). After pre-incubation, 50 μL of 200 μM dipeptide substrate Z-Gly-Pro-AMC (Bachem, #L-1145) or PRXS-AMC were added to the mixture. The assay was performed for 1 hour at 37° C. protected from light. 7-Amino-4-Methylcoumarin (AMC) release was detected measuring fluorescence at an excitation wavelength of 380 nm and an emission wavelength of 460 nm using a Multifunction Microplate Reader (Synergy 4, Biotek). All measurements were carried out at least as a single point. Results are shown in Table 4.

DPPIV Enzymatic Activity in Mouse Plasma

Approximately 500 μL of whole blood from one C57BL/6 mouse was harvested into BD Microtainer® tubes (K2)

EDTA (#365974, Becton Dickinson and Co.) via terminal cardiac puncture. The blood sample was immediately centrifuged at approximately 9000 g at 4° C. for 5 minutes. Plasma was separated and stored at −80° C. in aliquots of 300 μL. To assay baseline DPPIV enzymatic exopeptidase activity, 5 μL of thawed, mouse plasma was diluted (1:5) in buffer (100 mM Tris-HCl, 400 mM NaCl, 50 mM salicylic acid, 1 mM EDTA, pH 7.5) and mixed with 35 L of the same buffer before being pre-incubated with different concentrations of 10 μL of test compounds or DMSO vehicle for 15 minutes at 37° C. in 96-well black plates (Nunc, #237108). After pre-incubation, 50 μL of 200 μM dipeptide substrate H-Gly-Pro-AMC (Bachem, #L-1225) was added to the mixture. The assay was performed for 1 hour at 37° C. 7-Amino-4-Methylcoumarin (AMC) release was detected measuring fluorescence at an excitation wavelength of 360 nm and an emission wavelength of 460 nm using a Multifunction Microplate Reader (Synergy 4, Biotek). All measurements were carried out at least in duplicate. Results are shown in Table 4.

TABLE 4

Inhibition and Specificity of Test Compounds in Biological Samples

| Compound Number | mouse plasma FAPα (Z-Gly-Pro-AMC) (exo $IC_{50}$, μM) | mouse plasma FAPα (PRXS-AMC) (exo $IC_{50}$, μM) | mouse plasma DPPIV ($IC_{50}$, μM) |
|---|---|---|---|
| Ref. Comp. | +++ | — | + |
| 1 | +++ | — | +++ |
| 13 | +++ | +++ | + |
| 14 | +++ | +++ | ++ |
| 24 | +++ | +++ | + |
| 26 | +++ | +++ | +++ |
| 38 | +++ | +++ | ++ |
| 40 | +++ | +++ | + |
| 47 | +++ | +++ | + |
| 52 | +++ | +++ | + |
| 54 | +++ | +++ | + |
| 87 | +++ | +++ | ++ |
| 88 | +++ | +++ | ++ |
| 50 | +++ | +++ | — |
| 105 | — | +++ | + |
| 109 | — | +++ | ++ |
| 111 | — | +++ | ++ |
| 121 | — | +++ | + |
| 122 | — | +++ | + |
| 123 | — | — | + |

Ref. Comp.: Compound 60 as described in Jansen, K, et at., J Med Chem, 2014. 57(7): p. 3053-74;
$IC_{50}$: +++ refers to $IC_{50}$ < 1 μM;
++ refers to 1 μM < $IC_{50}$ < 10 μM;
+ refers to $IC_{50}$ > 10 μM;
exo: exopeptidase.

Example B5

FAPα Enzymatic Activity in Human Plasma

Human plasma is diluted 1/10 in PBS. To assay baseline FAPα enzymatic exopeptidase activity, the diluted plasma is incubated with 100 μM Z-Gly-Pro-AMC peptide (BACHEM, #L-1145) for 1 h at 37° C. in 96-well black plates (Nunc, #237108). Test compounds are pre-incubated with the diluted plasma for 15 min at 37° C. before starting the reaction by substrate addition in 96-well black plates (Nunc, #237108). 7-Amino-4-Methylcoumarin (AMC) release is detected measuring fluorescence at Ex/Em 380/460 nm using a Multifunction Microplate Reader (Synergy 4, Biotek). All measurements are carried out in triplicate.

Example B6

Ex Vivo Inhibition of Circulating FAPα Activity from Plasma of Different Species Human Plasma Human blood was obtained from healthy young volunteers. Blood samples were collected in tubes coated with EDTA-K2 by venipuncture method, mixed gently, then kept on ice and centrifuged at 2,500×g for 15 minutes at 4° C. After plasma separation, samples were stored at −80° C. in aliquots of 300 μL.

To determinate the inhibitory potency of exemplary test compounds over circulating FAPα activity from human plasma, 20 μL of thawed plasma were mixed with 20 μL of cFAP buffer (100 mM Tris-HCl, 400 mM NaCl, 50 mM salicylic acid, 1 mM EDTA, pH 7.5) and 10 μL different concentrations of exemplary test compounds or vehicle (DMSO).

Exemplary compounds were allowed to interact with the enzyme for 15 minutes at 37° C. After pre-incubation, 50 μl of 200 μM PRXS-AMC substrate were added to the all mixtures. All reactions were carried out for 1 h at 37° C. protected from light. AMC release was detected measuring fluorescence at an excitation/emission wavelength of 380/460 nm using a Multifunction Microplate Reader. All measurements were carried out as single point.

Results of $IC_{50}$ of exemplary test compounds over circulating FAPα from human are shown in Table 5.

Hamster Plasma

Male Golden Syrian hamsters were provided by National Laboratory Animal Center (NLAC) in Taiwan. The animals were maintained in a hygienic environment under controlled temperature (20-24° C.) and humidity (50%-80%) with 12 hours light/dark cycles. Free access to standard lab diet [MFG (Oriental Yeast Co., Ltd. Japan)] and autoclaved tap water were granted. All aspects of this work including housing, experimentation and disposal of animals were performed in general accordance with the "Guide for the Care and Use of Laboratory Animals: Eighth Edition" (National Academies Press, Washington, D.C., 2011). In addition, the animal care and use protocol was reviewed and approved by the IACUC at Pharmacology Discovery Services Taiwan, Ltd. Immediately after the sacrifice of hamsters, blood samples were collected via terminal cardiac puncture in tubes coated with EDTA-K2, mixed gently, then kept on ice and centrifuged at 2,500×g for 15 minutes at 4° C. After plasma separation, samples were stored at −80° C. in aliquots of 300 μL.

To assay exemplary compounds in hamster plasma, a similar protocol as described for human plasma was performed diluting thawed plasma 1:2 in cFAP buffer. In a 96-well black plate, 5 μl of diluted hamster plasma were mixed with 35 μl of the same buffer and 10 μl of exemplary test compounds at different concentrations or vehicle (DMSO).

Exemplary test compounds were allowed to interact with the enzyme for 15 minutes at 37° C. After pre-incubation, 50 μl of 200 μM PRXS-AMC substrate were added to the all mixtures. All reactions were carried out for 1 h at 37° C. protected from light. AMC release was detected measuring fluorescence at an excitation/emission wavelength of 380/460 nm using a Multifunction Microplate Reader. All measurements were carried out as single point.

Results of $IC_{50}$ of exemplary test compounds over circulating FAPα from hamster plasma are shown in Table 5.

TABLE 5

Inhibition ex-vivo by exemplary compounds of circulating FAPα activity from human and hamster plasma.

| Compound No. | FAPα activity in human plasma (PRXS-AMC) IC$_{50}$, µM | FAPα activity in hamster plasma (PRXS-AMC) IC$_{50}$, µM |
|---|---|---|
| 1 | +++ | — |
| 13 | +++ | +++ |
| 14 | +++ | — |
| 24 | +++ | +++ |
| 26 | +++ | — |
| 38 | +++ | — |
| 47 | +++ | — |
| 54 | +++ | — |
| 52 | +++ | +++ |
| 40 | +++ | — |
| 87 | +++ | — |
| 88 | +++ | — |
| 50 | +++ | — |
| 105 | +++ | +++ |
| 109 | +++ | +++ |
| 122 | — | +++ |
| First eluting isomer of example 74 | +++ | — |

For IC$_{50}$: +++ refers to IC$_{50}$ < 1 µM;
++ refers to 1 µM < IC$_{50}$ < 10 µM;
+ refers to IC$_{50}$ > 10 µM.

Example B7

Intravenous and Oral Bioavailability

The pharmacokinetic properties of exemplary test compounds were assayed after administration of an intravenous (IV) 2 mg/kg or oral (PO) 10 mg/kg single dose in mice. Exemplary test compounds were formulated at 0.4 and 1 mg/ml in a vehicle containing Poly-Ethylene Glycol 200 (PEG200; Cat. No. #P3015, Sigma Aldrich) and distilled water (dH$_2$O) (50/50, v/v) as dosing solutions for intravenous and oral administration, respectively.

C57BL/6j and Balb/c mice, approximately 8-10 weeks old, were obtained from the vivarium Fundación Ciencia & Vida Chile (Santiago, Chile) and maintained in a temperature-controlled room with 12/12 hr light/dark schedule with food and water ad libitum. Animals were acclimated for a minimum period of 4 days upon arrival at the testing facility.

On the day of study, mice were weighed and identified by marking the tail with numbers using a non-toxic permanent marker for designation into the experimental groups (n=3 per group). Each mouse in the IV dosing groups received a systemic bolus of 2 mg/kg dosing solution via the caudal vein. Each mouse of PO dosing groups received an intra-gastric bolus of 10 mg/kg via feeding tubes 20G (Cat. No.: FTP-2038; Instech Salomon Inc.).

Blood samples were harvested by terminal cardiac puncture at 5, 10, 15, 30, 60, 120, 240, 360 and 480 min after dosing. Non-dosed mice were used to collect samples of zero time points. Whole blood was collected into microtainer tubes with (K2) EDTA (Cat. No. #365974, Becton Dickinson & Co.). Blood samples were centrifuged immediately at 9,000 g at 4° C. for 5 min and the plasma was separated. Plasma samples were placed into individually labeled cryovials (Cat. No. #366656, Thermo Fisher Scientific, Inc.) and stored in a −80° C. freezer until LC/MS/MS bioanalysis.

The plasma samples were analyzed by QTRAP 4500 triple quadrupole mass spectrometer (Applied Biosystems SCIEX) in positive or negative ion mode depending on the tested compound and interfaced with an ekspert ultraLC 100-XL UPLC System (eksigent) to determine the concentration of the exemplary test compound. Calibration standards (0.001 to 10 µM) and QCs (0.02, 0.2 and 2 µM) were prepared from naïve mouse plasma in parallel with mouse plasma study samples (60 µl) by precipitation with three volumes of ice cold internal standard solution (acetonitrile containing 20 µM of theophylline). The precipitated samples were centrifuged at 6,100 g for 30 min at 4° C. Following centrifugation, an aliquot of each supernatant was transferred into a clean sample vial and diluted with two volumes of aqueous mobile phase (0.2% formic acid in water). Samples were injected onto a reverse phase analytical column (YMC Triart C18; 2.0×50 mm; 1.9 µm; YMC CO) and eluted with a gradient of 0.1 or 0.2% formic acid in Acetonitrile. Test compound and internal standard were monitored by a multiple reaction monitoring (MRM) experiment using Analyst software (v1.6.2, Applied Biosystems SCIEX). Quantitation was conducted using MultiQuant software (v2.1, Applied Biosystems SCIEX) and the resulting calibration curve was fitted with a linear or quadratic regression and 1/x weighting. The lower limit of quantitation were between 0.003-0.01 µM.

IV and PO PK parameters were calculated from the concentration-time data using Phoenix WinNonlin software (v6.4, Certara, Princeton, N.J.) by noncompartmental analysis. Area under the concentration-time curve (AUClast) was estimated using a log-linear trapezoidal method, from the dosing time to the last measurable concentration. Results for AUC of exemplary compounds in mouse plasma are shown in Table 6.

TABLE 6

AUC and bioavailability of exemplary compounds after oral administration in mice.

| Compound No. | AUC$_{last}$ (hr · ng/ml) | F (%) |
|---|---|---|
| Ref Comp. | 1120 | 39.7 |
| 1 | 327 | 6.3 |
| 13 | 760 | 27.9 |
| 24 | 910 | 54 |
| 50 | 1090 | 79.6 |
| 52 | 721 | 30.3 |
| 105 | 18.3 | 3.0 |
| 109 | 2144 | 9.0 |

Ref Comp.: Compound 60 as described in Jansen, K., et at., J Med Chem, 2014. 57(7): p. 3053-74

Example B8

In Vivo Pharmacokinetics and Pharmacodynamics of Test Compound 13

Solutions of test compound 13 were prepared at 1 mg/mL in a vehicle containing 50% polyethylene glycol 200 (PEG200, #P3015-1KG: Sigma-Aldrich, Inc.) in distilled water for oral administration.

Female C57BL/6 mice (approximately 9-10 weeks old; 20-21 grams) obtained from a vivarium (Fundación Ciencia & Vida, Santiago, Chile) were weighed and divided into cohorts described in Table 7.

TABLE 7

Mice Cohorts for Test Compound 13 Administration.

| Cohort # | Mouse ID # | Dosing | Post-dosing harvesting time (hr) | Body Weight (gr) |
|---|---|---|---|---|
| 1 | 1 | Test Compound 13 (10 mg/kg) | 0.5 | 21 |
|   | 2 |   |   | 21 |
|   | 3 |   |   | 21 |
| 2 | 4 |   | 1 | 21 |
|   | 5 |   |   | 21 |
|   | 6 |   |   | 21 |
| 3 | 7 |   | 2 | 22 |
|   | 8 |   |   | 22 |
|   | 9 |   |   | 22 |
| 4 | 10 |   | 4 | 20 |
|   | 11 |   |   | 20 |
|   | 12 |   |   | 20 |
| 5 | 13 |   | 8 | 21 |
|   | 14 |   |   | 21 |
|   | 15 |   |   | 21 |
| 6 | 16 |   | 12 | 21 |
|   | 17 |   |   | 21 |
|   | 18 |   |   | 21 |
| 7 | 19 |   | 24 | 20 |
|   | 20 |   |   | 20 |
|   | 21 |   |   | 20 |

100 µL of whole blood was sampled from the tail vein of each mouse 24 hours prior to dosing. On the day of dosing, mice of all cohorts orally received a single dose (10 mg/kg) of test compound 13 using feeding needles (#FTP-2038/050312, Instech Laboratories, Inc.).

Depending on each cohort, approximately 500 µL of whole blood from each mouse was collected into BD Microtainer® tubes (K2) EDTA (#365974, Becton Dickinson and Co.) via terminal cardiac puncture at the harvesting time point (Table 5). The blood sample was immediately centrifuged at approximately 9000 g at 4° C. for 5 minutes. Plasma was separated and placed into individually labeled cryotube vials (#366656; Thermo Fisher Scientific, Inc.) and stored at −80° C. prior to being assayed for enzymatic activity or LC/MS/MS analysis.

All plasma samples were thawed and diluted with assay buffer (1 part plasma for 5 parts buffer). The assay buffer contained 100 mM Tris-HCl, 400 mM NaCl, 50 mM salicylic acid, 1 mM EDTA, pH 7.5. All plasmas were assayed for FAP and DPPIV activity. To assay the plasma for FAPα or DPPIV enzymatic activity, 5 µL of each diluted plasma sample was loaded into a well of a 96-well black plate (Nunc, #237108), which contained 45 µL of additional assay buffer. The plates were warmed at 37° C. for 15 minutes before the assay began. To start the assay, 50 µL of 200 µM dipeptide substrate Z-Gly-Pro-AMC (Bachem, #L-1145) (FAPα enzymatic activity assay) or 50 µL of 200 µM dipeptide substrate H-Gly-Pro-AMC (Bachem, #L-1225) (DPPIV enzymatic activity assay) was added to each well. 7-Amino-4-Methylcoumarin (AMC) release was detected measuring fluorescence at an excitation wavelength of 360 nm and an emission wavelength of 460 nm using a Multi-function Microplate Reader (Synergy 4, Biotek). All measurements were carried out at least in duplicate.

Figure 4:
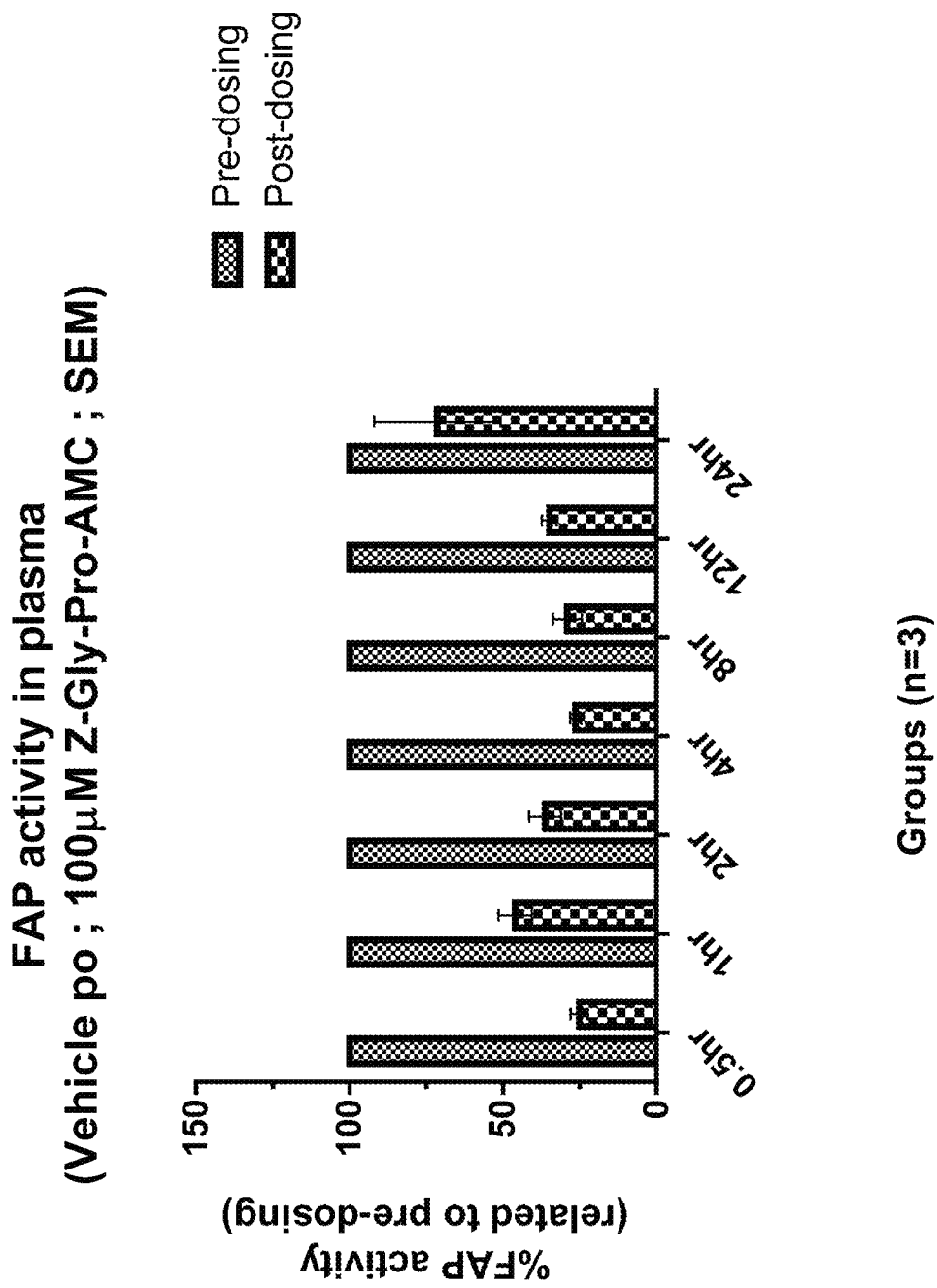
FIG. 4 shows FAPα activity in plasma of mice dosed with compound 13 after various time points post-administration.
Figure 5:
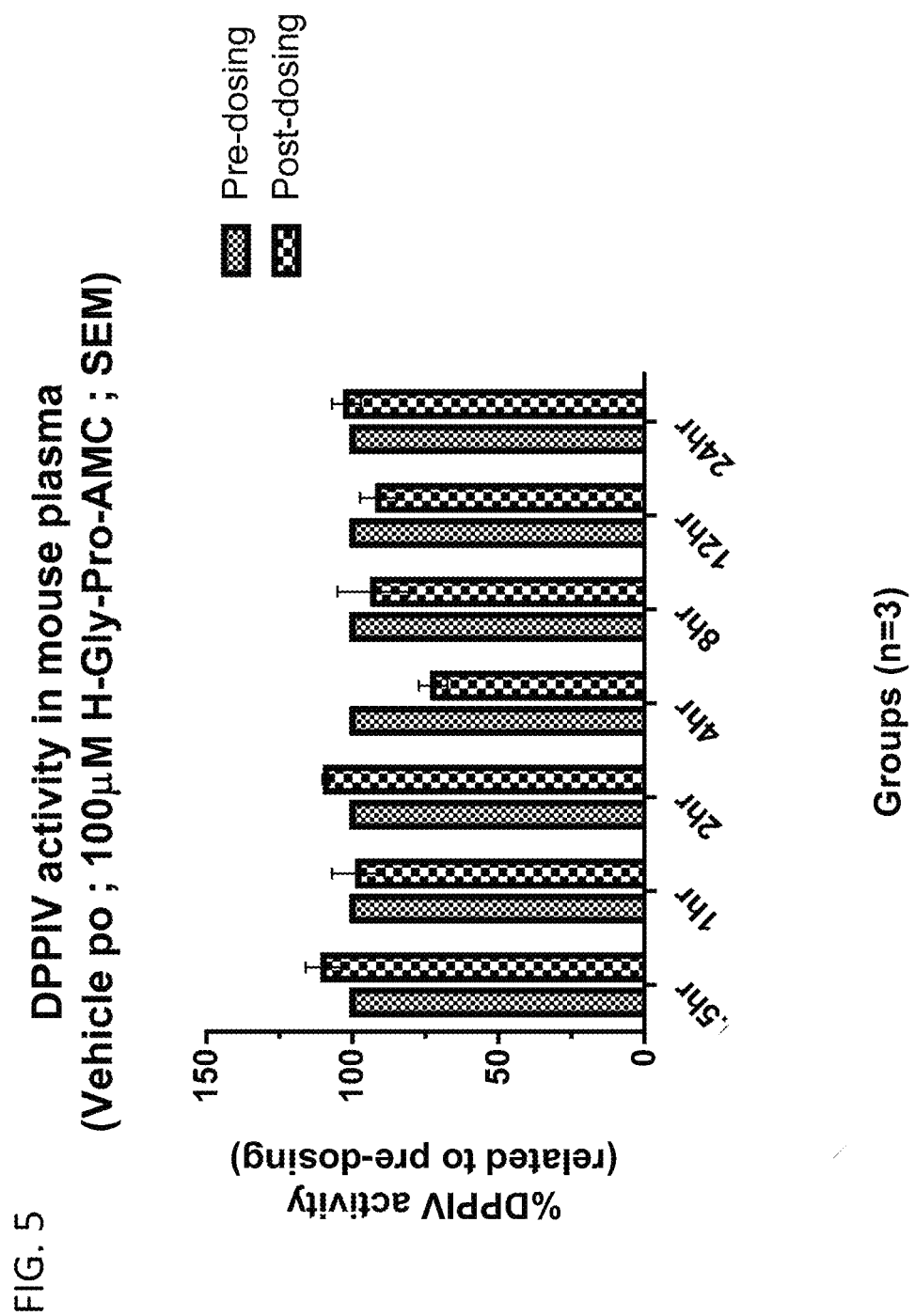
FIG. 5 shows DPPIV activity in plasma of mice dosed with compound 13 after various time points post-administration.

For each animal orally dosed with compound 13, the activities of FAP and DPPIV found in the plasma sample collected post-dosing were normalized as percentage to the respective activity found in pre-dosing plasma samples. Percentage of FAP activities found in plasma of mice orally dosed with compound 13 are summarized in FIG. 4. Percentages of DPPIV activity are summarized in FIG. 5.

Example B9

Oral Pharmacokinetics (PK) and Pharmacodynamics (PD) Studies in Mice

To determine the PK/PD of exemplary test compounds, groups of mice were orally dosed with compound 13 (an exemplary compound) and then plasma samples collected at different time point were subjected to bioanalysis for concentrations of compound and FAP activity. Female c57BL/6 mice, approximately 8-10 weeks old (19-21 gr), obtained from the Vivarium Fundación Ciencia & Vida were acclimated for a minimum period of 4 days upon arrival at the testing facility. On the day of dosing, animals were weighed and identified by marking the tail with numbers using a non-toxic permanent marker for designation into the treatment groups described in Table 8.

TABLE 8

Experimental groups for PK/PD study.

| Group No. | Treatment | N p/group | Route | Dose [mg/Kg] | Dosing sol. [mg/mL] | Dosing [mL/Kg] |
|---|---|---|---|---|---|---|
| 1 | Vehicle - 1 hr | 3 | Oral | — | — | 10 |
| 2 | Vehicle - 2 hr | 3 |   |   |   |   |
| 3 | Vehicle - 4 hr | 3 |   |   |   |   |
| 4 | Vehicle - 12 hr | 3 |   |   |   |   |
| 5 | Vehicle - 16 hr | 3 |   |   |   |   |
| 6 | Vehicle - 24 hr | 3 |   |   |   |   |
| 7 | Compound - 1 hr | 3 | Oral | 50 | 5 | 10 |
| 8 | Compound - 2 hr | 3 |   |   |   |   |
| 9 | Compound - 4 hr | 3 |   |   |   |   |
| 10 | Compound - 12 hr | 3 |   |   |   |   |
| 11 | Compound - 16 hr | 3 |   |   |   |   |
| 12 | Compound - 24 hr | 3 |   |   |   |   |
| 13 | Control | 3 | Non-dose | — | — | — |

The compound 13 (an exemplary compound) was formulated at 5 mg/ml in a vehicle containing Poly-Ethylene Glycol 200 (PEG200; Cat. No. #P3015, Sigma Aldrich) and distilled water (dH$_2$O) (50/50, v/v) as dosing solution for oral administration.

For oral administration, mice from groups 1 up to 6 received a single oral dose at 10 mL/Kg of vehicle PEG200/dH$_2$O (50/50, v/v). Mice from groups 7-12 received a single oral dose of compound 13 (an exemplary compound) formulated freshly at 5 mg/mL in vehicle.

Whole blood was collected via cardiac puncture at 1, 4, 8, 12, 16 and 24 h after administration of vehicle or compound 13 (an exemplary compound). Mice of group 13 were not dosed and were used to collect samples of the zero time point. Blood samples were immediately centrifuged at approximately 9000 g at 4° C. for 5 minutes. Plasma was separated and placed into individually labeled cryotube vials and stored at −80° C. prior to being assayed for enzymatic activity or bioanalysis.

All plasma samples were thawed and diluted 1:5 with assay buffer (100 mM Tris-HCl, 400 mM NaCl, 50 mM salicylic acid, 1 mM EDTA, pH 7.5). All plasma was assayed for FAP and DPPIV activity. To assay the plasma for FAPc or DPPIV enzymatic activity, 5 µL of each diluted plasma sample was loaded into a well of a 96-well black plate, which contained 45 µL of additional assay buffer. The plates were warmed at 37° C. for 15 minutes before the assay began. To start the reactions, 50 µL of 400 µM dipeptide substrate Z-Gly-Pro-AMC (FAPα enzymatic activity assay) or 50 µL of 200 µM dipeptide substrate H-Gly-Pro-AMC (DPPIV enzymatic activity assay) diluted in assay buffer were added to each well. AMC release was detected measuring fluorescence at an excitation wavelength of 360 nm and an emission wavelength of 460 nm using a Multifunction Microplate Reader. All measurements were carried out at least in duplicate.

Figure 6A:
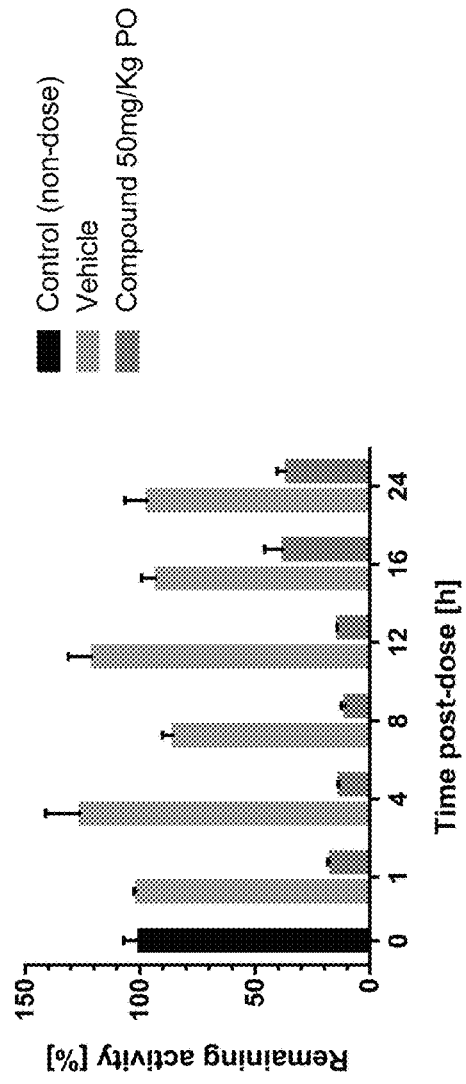
FIG. 6A shows FAP activity in plasma of mice dosed with an exemplary compound after various time points post-administration.
Figure 6B:
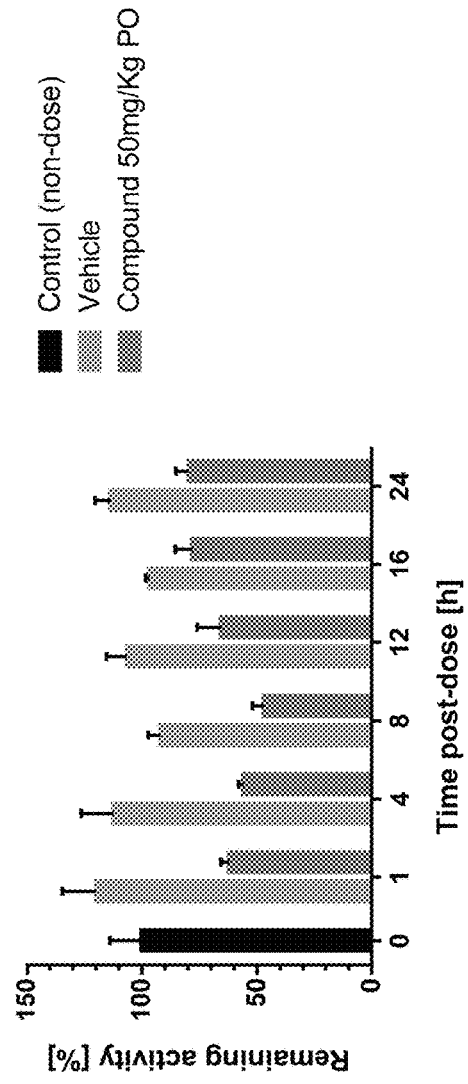
FIG. 6B shows DPPIV activity in plasma of mice dosed with an exemplary compound after various time points post-administration.
Figure 6C:
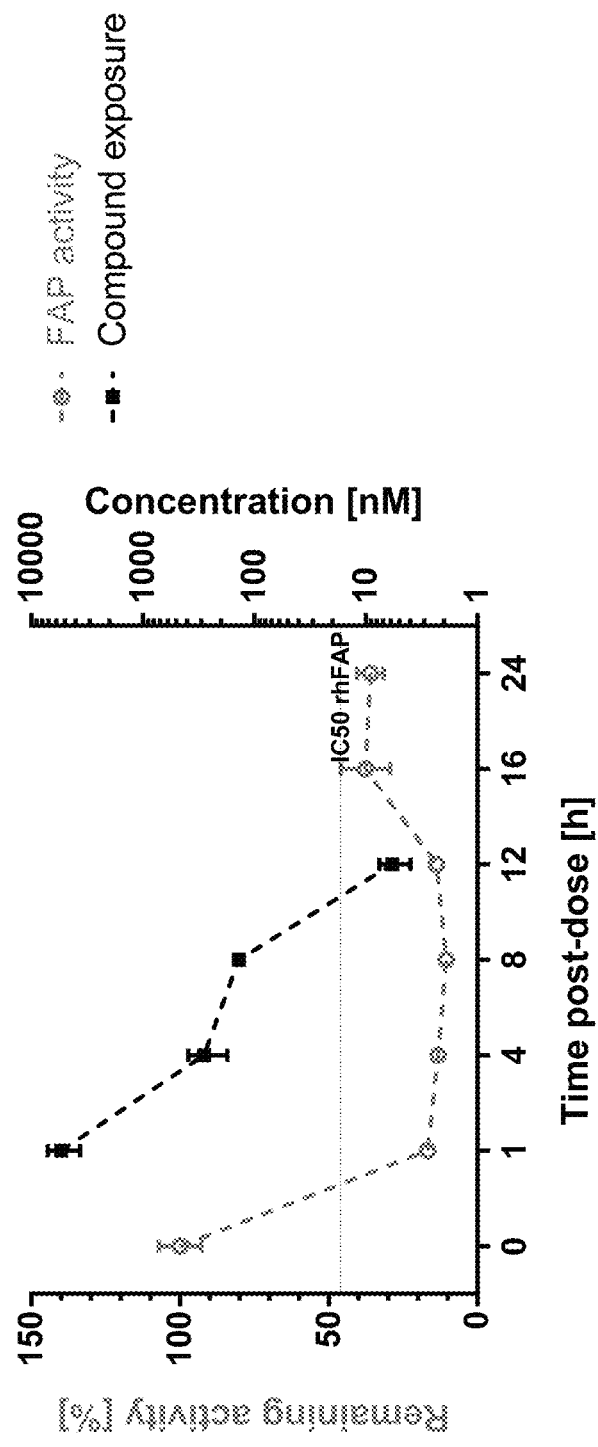
FIG. 6C shows a comparison of FAP activity over time and the compound exposure as measured in in plasma of mice dosed with an exemplary compound.

All fluorescence measurements were corrected subtracting the average fluorescence from blank reactions containing only substrate and assay buffer. To calculate the remaining FAP and DPPIV in plasma from mice dosed with vehicle or compound 13 (an exemplary compound), all fluorescence measurements were normalized against the fluorescence from samples of non-dose group assumed as one hundred percent of activity for each assay. Percentage of remaining FAP activity found in plasma of mice orally dosed with vehicle or compound 13 (an exemplary compound) are shown in FIG. 6A. Percentage of DPPIV activity are summarized in FIG. 6B. A comparison of the FAPα activity and the PK/PD of the compound over time is shown in FIG. 6C Example B10

Tumor Inhibition In Vivo

Female C57/BL6 mice (approximately 8-9 weeks old; 20-21 gr) obtained from the vivarium of Fundación Ciencia & Vida (Santiago, Chile) were maintained in a temperature-controlled room with 12/12 hour light/dark schedule with food and water ad libitum. The mice were acclimated for a minimum period of 4 days upon arrival at the testing facility.

MC38 mouse colon cancer cell line was maintained as monolayer culture in DMEM-F12 (Cat. No.: SH30023.01, Hyclone) supplemented with 10% fetal bovine serum (Cat. No.: 16000, Gibco) and penicillin/streptomycin (Cat. No.: 15140122, Gibco) at 37° C. in an atmosphere with 5% $CO_2$. The cells were routinely subcultured every 3 days to maintain growth at exponential phase. The tumor cells growing in exponential growth phase were harvested using 1×PBS with 0.05% trypsin-EDTA (Cat. No.: 15400054, Gibco), followed by centrifugation at 330 g×3 min in a centrifuge at room temperature. The supernatant was subsequently removed by aspiration. Cell pellet was resuspended in approximately 10× volume of cell culture medium and counted. Cell viability was determined to be >95% by trypan blue staining.

At the day of inoculation, female C57/Bl6 mice (n=15 total) were weighed and identified by marking the tail with numbers using a non-toxic permanent marker. Mice were inoculated subcutaneously in the right lower flank (near the dorsal thigh region) with a single volume of 0.1 mL cell suspension containing approximately $2\times10^6$ MC38 cells in 1×PBS. Tumors were measured three times per week with digital calipers and tumors volumes, expressed in $mm^3$, were calculated with the following formula:

$$\text{Tumor volume } (mm^3) = (a \times b^2)/2$$

where "b" is the smallest diameter and "a" is the largest perpendicular diameter.

Seven days after inoculation, mean tumor volume was about 100 $mm^3$. The mice were weighted and randomized into two experimental groups (n=5-6 mice), and receive the following treatments dosed orally twice daily until end: 1) Vehicle (PEG200 50% in water); or 2) 50 mg/kg test compound 24 in PEG200 50%/water. Body weight of the mice and tumor volume was recorded two or three times per week for a total of 22 days. At day 22, mice were sacrificed and all tumor mass were weighed.

Figure 7:
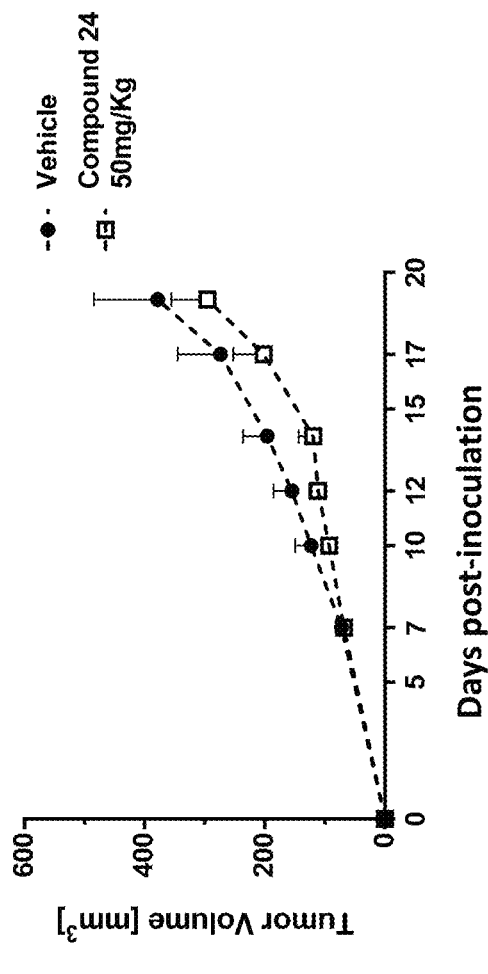
FIG. 7 shows the volume of a MC38 colon cancer cell line-derived xenograft tumor in C57/BL6 mice after oral administration (on day 7) of test compound 24 (50 mg/kg, twice daily) or a vehicle control.
Figure 8:
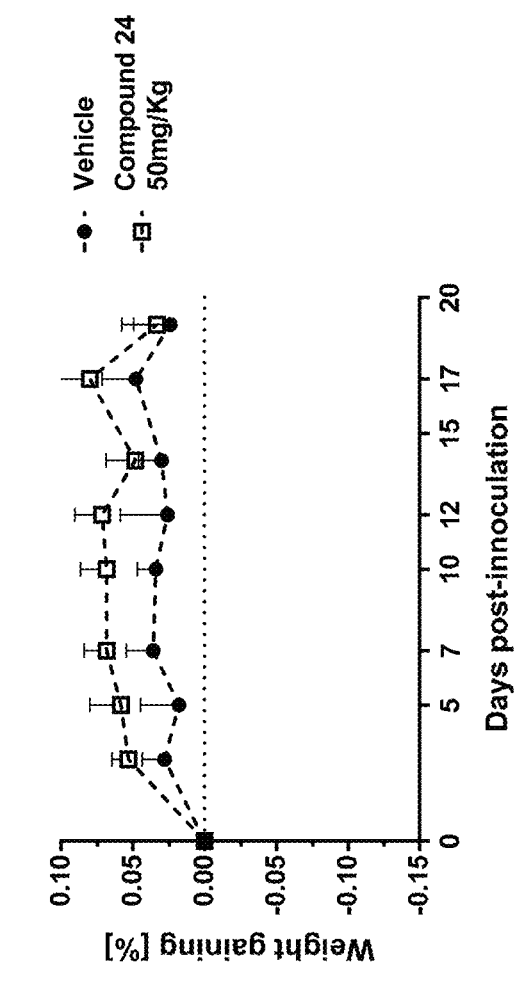
FIG. 8 shows body weight gain of the C47/BL6 mice with the MC38 colon cancer cell line-derived xenograft tumor after administration (day 7) of test compound 24 (50 mg/kg, twice daily) or a vehicle control.

Tumor volume is shown as mean with standard error of mean (SEM) in FIG. 7. Mouse body weight gain is shown as mean with standard error of mean (SEM) in FIG. 8. Individual recording of tumor volume is shown in FIG. 9. Tumor mass weight is shown as mean with standard error of mean (SEM) in FIG. 10. As shown by the figures, mice treated with test compound 24 had a smaller volume of tumor than treatment with the vehicle alone. No statistical significance was observed in these studies.

Example B11

FAPα Enzymatic Activity in Murine Tumors

Mouse tumor proteins are extracted in a lysis buffer (Tris HCl 50 mM pH 7.6, EDTA 1 mM, Glycerol 10%, protease/phosphatase inhibitors cocktail) for 20 min using an ultra Turrax (IKA, #3737000). To assay baseline FAPα enzymatic exopeptidase activity in the tumor extract, 10 µg of tumor extract sample is incubated with 100 µM Z-Gly-Pro-AMC peptide (BACHEM, #L-1145) in PBS 1× for 1 h at 37° C. in 96-well black plates (Nunc, #237108). Inhibitors are pre-incubated with the tumor extract for 15 min at 37° C. before starting the reaction by substrate addition in 96-well black plates (Nunc, #237108). 7-Amino-4-Methylcoumarin (AMC) release is detected measuring fluorescence at Ex/Em 380/460 nm using a Multifunction Microplate Reader (Synergy 4, Biotek). All measurements are carried out in triplicate.

Example B12

PK/PD Studies in Tumors of Murine Cancer Models

B16-F10 murine melanoma model

Male C57Bl/6 mice were engrafted intradermal with $1\times10^6$ B16-F10 murine melanoma cells suspended in 100 µL of sterile PBS 1× (Day 0). On day 2 post-engraftment, groups of animals (n=3) were dosed with vehicle PEG200/$dH_2O$ (50/50 v/v) or compound 13 (an exemplary compound) at 50 mg/Kg orally (PO) twice a day (BID) until day 15.

At terminal day, all mice were sacrificed and immediately tumors and plasma samples were collected and stored at −80° C. prior to being assayed for FAPα enzymatic activity or bioanalysis.

Proteins of murine cancer tumors were extracted in lysis buffer (Tris HCl 50 mM pH 7.6, EDTA 1 mM, Glycerol 10%, protease/phosphatase inhibitors cocktail) using an Ultra Turrax homogenizer (IKA, #3737000). Homogenates were clarified by centrifugation 21,000 g for 20 min at 4° C. Supernatants were collected and proteins were quantified using a BCA Protein assay kit (Cat. No. #23225, Thermo Scientific). All protein samples were adjusted at 2 μg/L with lysis buffer and then aliquoted for storing at −80° C.

For assessment of FAPα activity in tumor homogenates, 10 μg of each tumoral extract were diluted with cFAP buffer assay in a 96-well black plate at final volume of 50 μL and then mixed with 100 μM PRXS-AMC peptide. Reactions were carried out for 1 h at 37° C. AMC release was detected measuring fluorescence at Ex/Em 380/460 nm using a Multifunction Microplate Reader and expressed as relative fluorescence units (RFU). All measurements are carried out as single point.

Figure 11B:
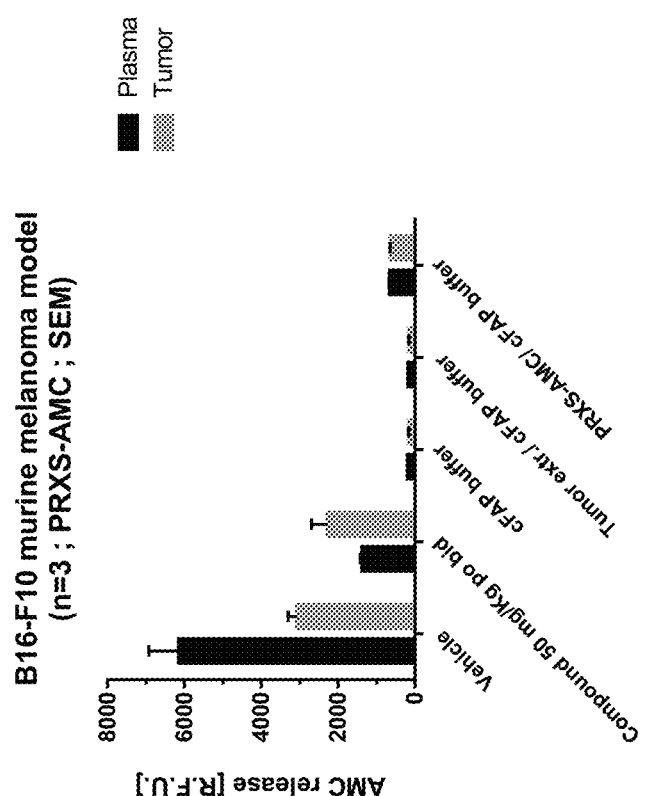
FIG. 11B shows the FAP activity in the plasma and tumor of mice bearing a B16-F10 tumor, which were administered vehicle or compound 13 (an exemplary compound).
Figure 11A:
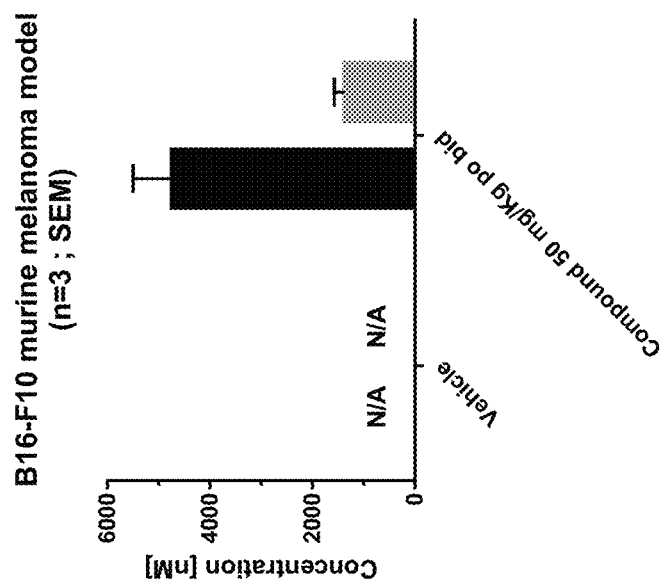
FIG. 11A shows the concentration of an exemplary compound in the plasma and tumor of mice bearing a B16-F10 tumor, which were administered vehicle or compound 13 (an exemplary compound).

Concentrations of compound 13 (an exemplary compound) are shown in FIG. 11A. FAPα activities in plasma and tumor from animals bearing B16-F10 murine melanoma tumors are shown in FIG. 11B.

MC38 Murine Melanoma Model

Female C57B1/6 mice were engrafted subcutaneously with $2 \times 10^6$ MC38 mouse colon cancer cells suspended in 100 μL of sterile PBS 1× (Day 0). On day 12 post-engraftment, mice were randomized based on tumor volume into two experimental groups (n=6) with a mean tumor volume ~160 mm$^3$. Groups of animals received vehicle PEG200/dH$_2$O (50/50 v/v) or compound 13 (an exemplary compound) 50 mg/kg PO bid until day 24.

At terminal day, all mice were sacrificed and immediately tumors and plasma samples were collected and stored at −80° C. prior to being assayed for FAPα enzymatic activity or bioanalysis as described for the B16-F10 murine melanoma model.

Figure 12A:
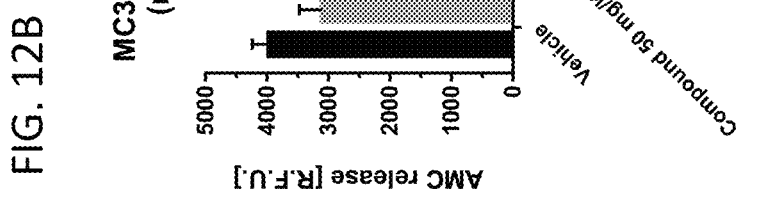
FIG. 12A shows the concentration of an exemplary compound in the plasma and tumor of mice bearing a MC38 tumor, which were administered vehicle or compound 13 (an exemplary compound).
Figure 12B:
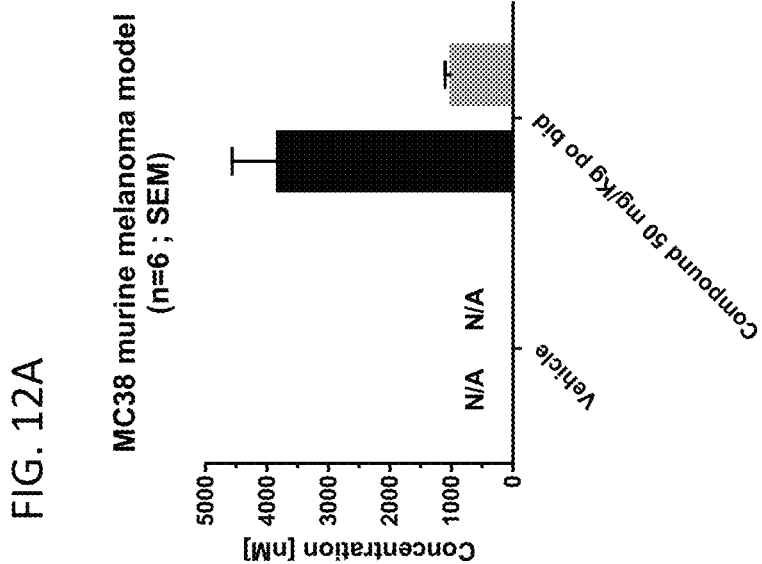
FIG. 12B shows the FAP activity in the plasma and tumor of mice bearing a MC38 tumor, which were administered vehicle or compound 13 (an exemplary compound).

Concentrations of compound 13 (an exemplary compound) are shown in FIG. 12A. FAPα activities in plasma and tumor from animals bearing MC38 murine melanoma tumors are shown in FIG. 12B.

Example B13

In Vitro FAP-Mediated Proteolytic Cleavage of FGF21 Assays

Pharmacological administration of FGF21 to diabetic and obese animal models markedly ameliorates obesity, insulin resistance, dyslipidemia, fatty liver, and hyperglycemia in rodents (Markan, K. R. et. al., Semin Cell Dev Biol, 2016, 53: 85-93), and FGF21 analogs have been efficacious in inducing weight loss and correcting hyperinsulinemia, dyslipidemia, and hypoadiponectinemia in obese people with type 2 diabetes (Gaich, G., et al., Cell Metab, 2013, 18(3): 333-40; Dong, J. Q., et al., Br J Clin Pharmacol, 2015, 80(5): 1051-63). However, in rodents and primates, the half-life of exogenously administered human FGF21 is short (~0.5-2 h) as result of FAP-mediated enzymatic degradation and susceptibility to renal clearance (Hager, T., et al., Anal Chem, 2013. 85(5): 2731-8; Xu, J., et al., Am J Physiol Endocrinol Metab, 2009, 297(5): E1105-14; Kharitonenkov, A., et al., Endocrinology, 2007, 148(2): 774-81). Common half-life extension strategies have improved significantly the PK properties of these FGF21 analogs in vivo; however, proteolytic processing still persists in these analogs (Hecht, R., et al., PLoS One, 2012, 7(11): e49345; Mu, J., et al., Diabetes, 2012, 61(2): 505-12; Camacho, R. C., et al., Eur J Pharmacol, 2013. 715(1-3): 41-5). To determine if the FAP inhibitor compounds described herein can inhibit the FGF-21 cleavage and can offer an oral therapy to augment endo- and/or exo-genous FGF21 action, FAP-mediated digestion of FGF21 in there presence and absence of exemplary FAP inhibitor compounds were compared.

FAP-Mediated Digestion of FGF21 In Vitro

Recombinant human FGF21 (rhFGF21; Cat. No. #2539-FG-025/CF, R&D systems) was incubated overnight (16 h) at 37° C. with recombinant human FAP (rhFAP; Cat. No. #3715-SE-010, R&D systems) in digestion buffer (50 mM Tris pH 7.4, 100 mM NaCl, 0.1 mg/ml bovine serum albumin). Reactions were carried out at final concentrations of 1000 ng/mL hFGF21 and 400, 800 or 1200 ng/mL rhFAP in a volume of 100 μL. For SDS-PAGE analysis, after incubation each sample received immediately 4× Laemmli protein sample buffer (Cat. No. #161-0747, Bio-Rad) supplemented with 0.1 ml 3-mercaptoethanol/10 ml aliquot and then boiled at 95° C. during 10 min. An aliquot of 15 μL of each sample were then loaded onto a reducing 20% Tris-Tricine SDS-PAGE gel. For immunoblot analysis, proteins were separated on SDS-PAGE gels and transferred to PVDF membranes (Cat. No. #1620177, Bio-Rad). For immunodetection, anti-FGF21 (Cat. No. #RD181108100, BioVendor) and anti-rabbit HRP conjugated (Cat. No. #611-1322, Rockland) were used as primary and secondary antibodies, respectively. Proteins were detected using the ECL Western Blotting Substrate (Cat. No. #32106, Thermo Fisher Scientific) and visualized using a ChemiDoc™ Imaging System (Biorad) and Image lab software v5.2.1 build 11.

Figure 13A:
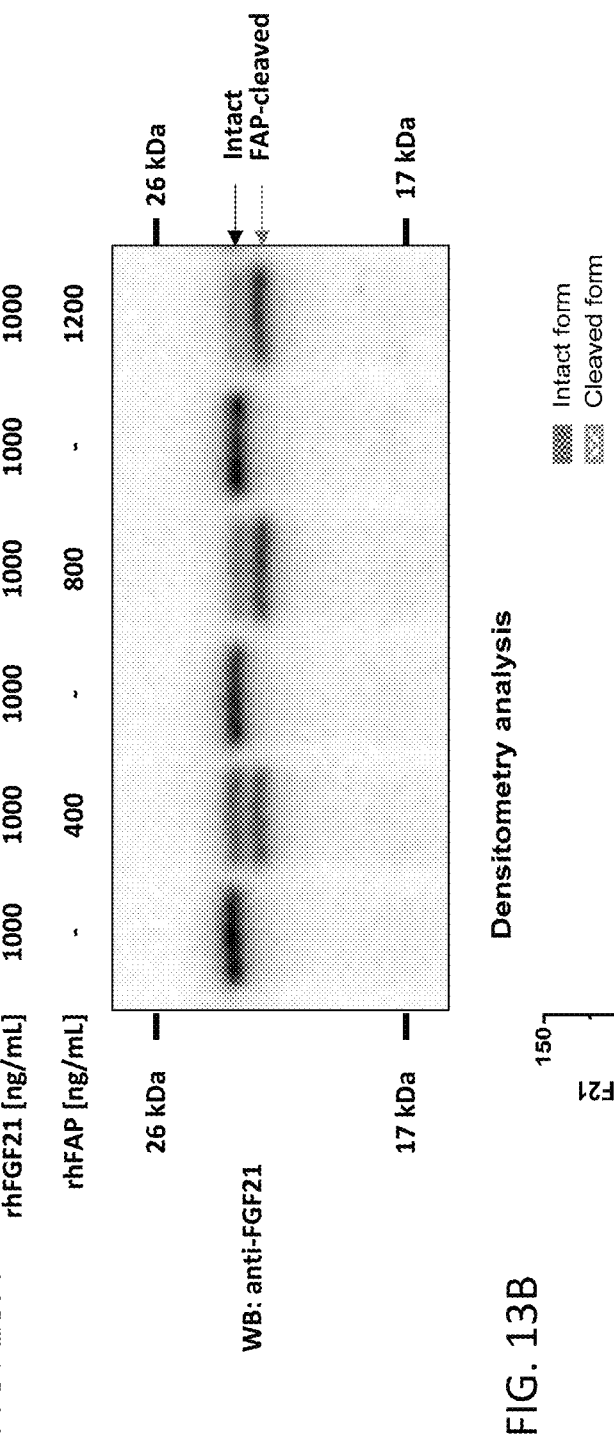
FIG. 13A shows an image of an anti-FGF21 Western Blot demonstrating degradation of rhFGF21 by rhFAP.
Figure 13B:
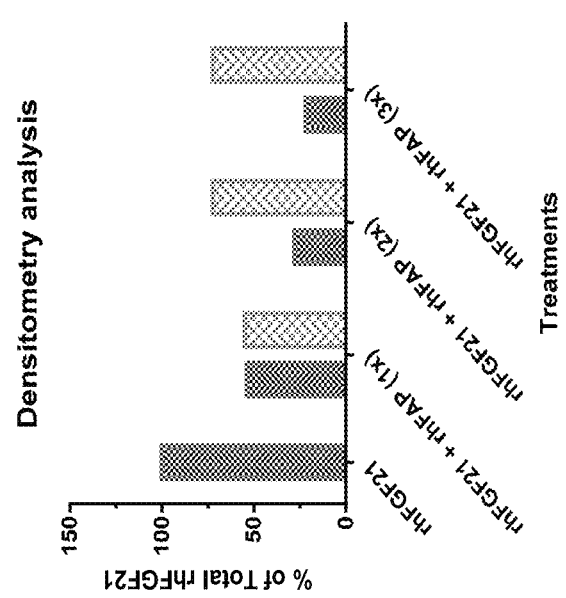
FIG. 13B shows the densitometry analysis of the Western Blot shown in FIG. 13A.

Immunodetection of intact and rhFAP-cleaved forms of rhFGF21 is shown in FIG. 13A and densitometry analysis is shown in FIG. 13B. As shown by the immunoblotting image and densitometry analysis, cleaved form of rhFGF21 increases in an rhFAP concentration-dependent fashion.

Inhibition of FAP-Mediated Digestion of FGF21 In Vitro.

To compare the efficacy for inhibiting the rhFAP-mediated proteolytic processing of rhFGF21, exemplary compounds and the commercial non-selective DDP inhibitor Val-boroPro were tested at low concentrations in the FGF21 cleavage assays in vitro.

Test compounds and Val-boroPro were prepared from powder as 10 mM stock solutions in DMSO and stored in presence of N2 neutral atmosphere at −80° C. Stock solutions were pre-diluted in DMSO to get diluted aliquots at 1 and 0.1 mM. These aliquots were 10-fold diluted again in digestion buffer and then 10 μL of these dilutions were added to 50 μL of rhFAP. The enzyme-inhibitor mixture was allowed to interact for 30 min at 37° C. and then 40 μL of rhFGF21 were added to start the reaction. Reactions were carried out at final concentrations of 1000 ng/mL hFGF21 and 1200 ng/mL rhFAP for 16 h at 37° C. After incubation, samples were boiled immediately in Laemmli protein sample buffer and then proteins were resolved in a reducing 20% Tris-Tricine SDS-PAGE gel. The immunodetection of intact and rhFAP-cleaved forms of rhFGF21 was carried out as described above.

Figure 13C:
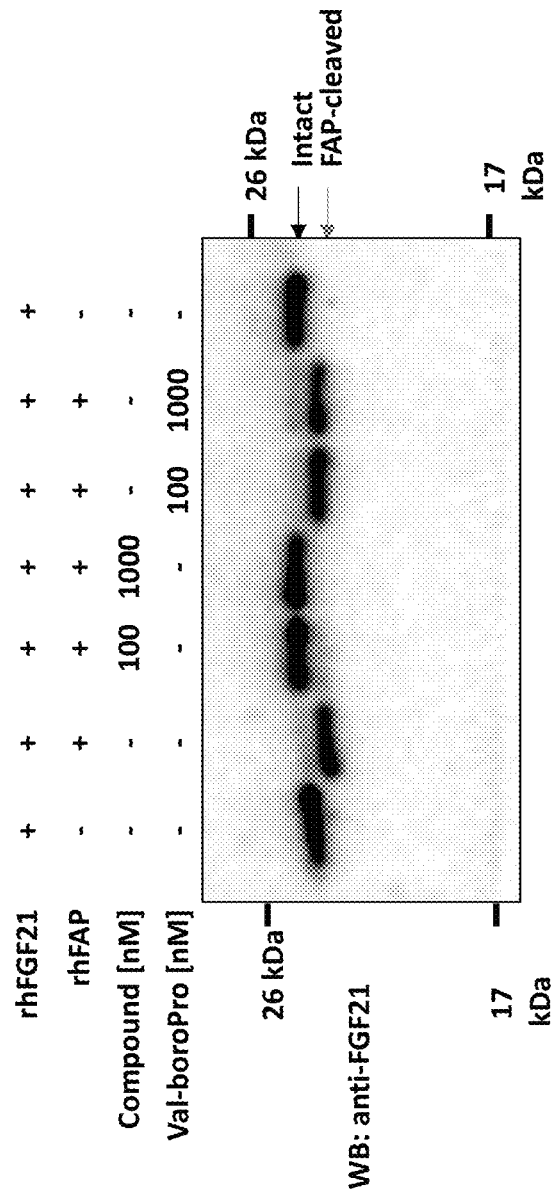
FIG. 13C shows an image of an anti-FGF21 Western Blot demonstrating compound 13 (an exemplary compound)-mediated inhibition of the degradation of rhFGF21 by rhFAP.
Figure 13D:
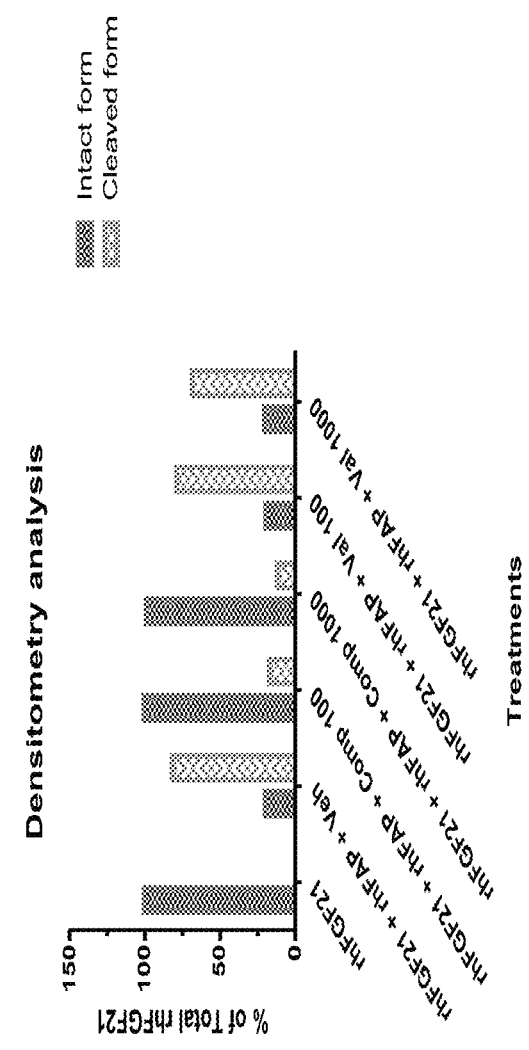
FIG. 13D shows the densitometry analysis of the Western Blot shown in FIG. 13C.

Comparison of efficacy between compound 13 (an exemplary compound) and Val-boroPro at 100 and 1000 nM for inhibiting the proteolytic processing of rhFGF21 by rhFAP in vitro is showed in the FIG. 13C and desitometry analysis is shown in FIG. 13D. As shown by the immunoblotting image and densitometry analysis, the intact form of rhFGF21 is preserved in presence of compound 13 (an exemplary compound) even at a low concentration.

Figure 14A:
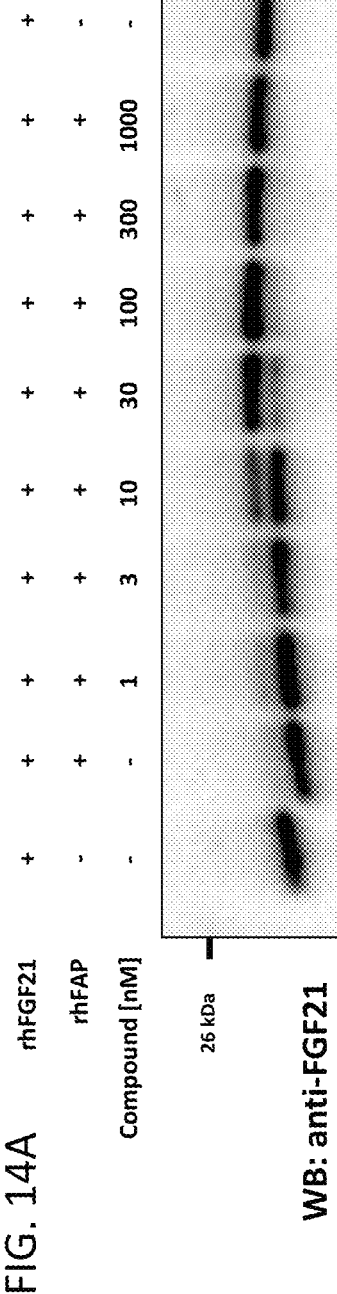
FIG. 14A shows an image of an anti-FGF21 Western Blot demonstrating compound 13 (an exemplary compound)-mediated inhibition of the degradation of rhFGF21 by rhFAP in a dose-dependent manor.
Figure 14B:
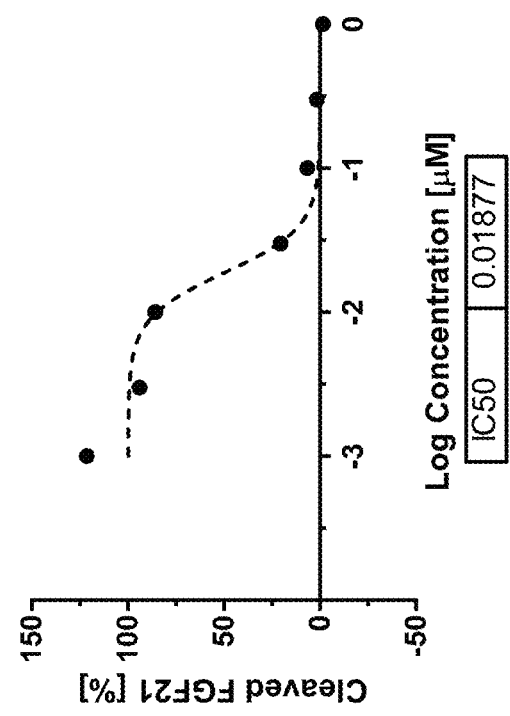
FIG. 14B shows the densitometry analysis of the Western Blot shown in FIG. 14A and the $IC_{50}$ determined from the resulting curve.

Additionally, the $IC_{50}$ for FAP-mediated proteolytic cleavage of FGF21, was determined in the using a serial dilution of compound 13 (an exemplary compound). As shown in FIG. 14A, the exemplary compound inhibited rhFAP-mediate proteolytic processing of FGF21 in a dose-dependent manor in vitro. As shown by the densitometry analysis in FIG. 14B, the exemplary compound showed an $IC_{50}$ in the nanomolar range in FAP-mediated proteolytic cleavage of FGF21 assays.

Example B14 rhFGF21 Administration in Conjunction with FAP Inhibition In Vivo

To determine if exemplary compounds of the invention can contribute to extend the half-life of hFGF21 in vivo, rats were orally dosed with vehicle or compound 13 (an exemplary compound) followed by sub-therapeutic dose of rhFGF21.

Male Sprague Dawley rats, approximately 7-8 weeks old (~250 g), were obtained from the vivarium of Universidad Católica de Chile (Santiago, Chile). Animals were acclimated for a minimum period of 4 days upon arrival at the testing facility. At the day of study, two rats were anesthetized using sevoflurane and subjected to surgical implantation of catheters in carotid artery and jugular vein. Catheter plugs were fixed to the external ends of the catheters and kept patent using an anti-coagulant heparinized saline solution containing 25 U/mL Heparin (Fresenius Kabi, Laboratorio Sanderson) in 0.9% NaCl Apiroflex (Fresenius Kabi, Laboratorio Sanderson). After surgical recovery, rats were weighed and identified by marking the tail with numbers using a non-toxic permanent marker for designation of treatments described in Table 9.

TABLE 9

Experimental treatments of cannulated rats.

| | Dosing #1 | | | Dosing #2 | | |
|---|---|---|---|---|---|---|
| Rat ID# | Treatment | Route | Dose [mg/Kg] | Treatment | Route | Dose [µg/Kg] |
| 1 | Vehicle | PO | — | rhFGF21 | IV | 90 |
| 2 | Compound | PO | 50 | rhFGF21 | IV | 90 |

Compound 13 (an exemplary compound) was formulated at 5 mg/ml in vehicle PEG200/dH$_2$O (50/50, v/v) for oral administration and rhFGF21 was formulated in 0.9% NaCl Apiroflex at 100 µg/mL.

Whole blood samples were collected via the implanted carotid artery catheter from both animals (time point=−15 min) and immediately after the first dose was administered (a single oral dose of 50 mg/Kg vehicle or compound 13 via feeding tubes (15 gauge) to Rat #1 and #2, respectively). After 15 min, a second whole blood sample was collected (time point=0 min) and immediately after the second dose was administered (a single intravenous dose of rhFGF21 90 µg/Kg via the implanted jugular vein catheter). Whole blood samples were then collected at time points: 5, 15, 30, 60, 120, 240 and 480 min post-second dosing. Blood samples were immediately centrifuged at approximately 9000 g at 4° C. for 5 minutes. Plasma was separated and placed into individually labeled cryotube vials and stored at −80° C. prior to be assayed for immunodetection of rhFGF21 by Western blots technique, FAPα activity assays using PRXS-AMC or bioanalysis as described above in previous examples.

For immunodetection, thawed plasma samples were centrifuged 2,000 g for 15 min at 4° C. and then supernatants were transferred into a clean Eppendorf tube. 1.5 µL of each plasma sample were mixed with 11.25 µL of 4× Laemmli protein sample buffer and 32.25 µL of dH$_2$O. Proteins were boiled and then 15 µL of each sample were resolved in a reducing 20% Tris-Tricine SDS-PAGE gel and then immunoblotted for detection of FGF21 as described above.

Figure 15:
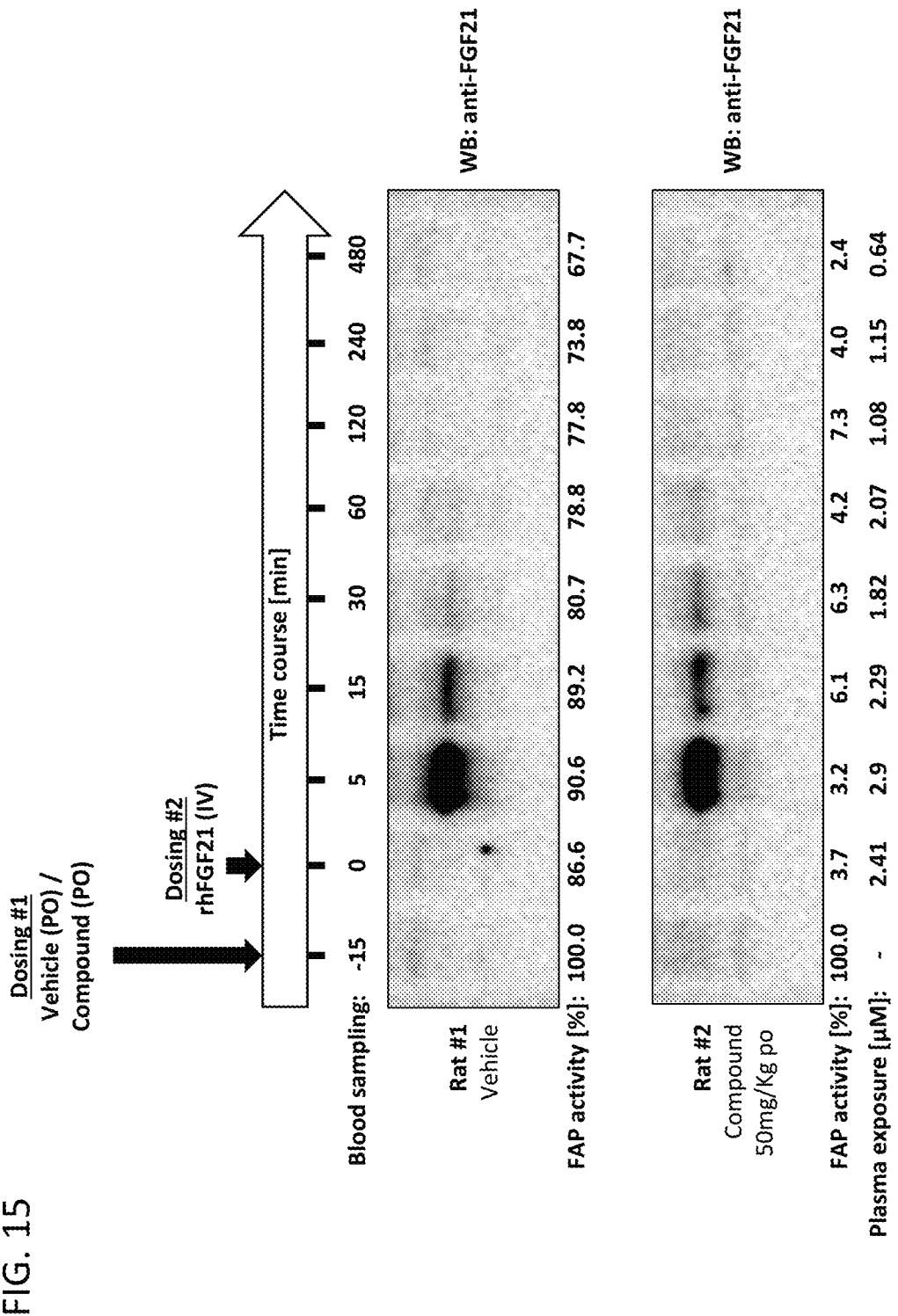
FIG. 15 shows a summary of experimental protocol for orally administering vehicle or compound 13 (an exemplary compound) to rats and subsequently administering rhFGF21 intravenously and also shows resulting anti-FGF21 Western Blots, FAP activity, and plasma exposure levels over time.

Results are summarized in FIG. 15. The administration of compound 13 at an oral single dose of 50 mg/kg potently suppressed the plasma FAP activity. The pre-treatment with the exemplary compound increased the amount of rhFGF21 detected through time in the plasma.

Example B15

Oral PK/PD Studies in Hamsters hFAP hydrolyzes peptides that have both a Glycine (Gly) at P2 and a Proline (Pro) at P1. The Gly-Pro FAP consensus residues at position 170-171 in human FGF21 is conserved in most mammalian species with available FGF21 sequences (including predicted sequences). However, the FGF21 expressed in rats and mice possess Glu-Pro instead of the conserved Gly-Pro at the putative FAP cleavage site. It has been reported that hFAP does not process FGF21 containing the murine sequence (Dunshee, D. R., et al., J Biol Chem, 2016, 291(11): 5986-96). Interestingly, the corresponding peptide from Syrian hamster FGF21 with Leu at the P1' position exhibited significant hydrolysis by hFAP (Dunshee, D. R., et al., J Biol Chem, 2016, 291(11): 5986-96).

To assess the effect of FAP inhibition by an exemplary compound over the cleavage of endogenously produced FGF21, in vivo PK/PD studies were conducted in male Golden Syrian hamsters following single intravenous and oral administration of an exemplary compound.

Male Golden Syrian hamsters were provided by National Laboratory Animal Center (NLAC) in Taiwan. The animals were maintained in a hygienic environment under controlled temperature (20-24° C.) and humidity (50%-80%) with 12 hours light/dark cycles. Free access to standard lab diet [MFG (Oriental Yeast Co., Ltd. Japan)] and autoclaved tap water were granted. All aspects of this work including housing, experimentation and disposal of animals were performed in general accordance with the "Guide for the Care and Use of Laboratory Animals: Eighth Edition" (National Academies Press, Washington, D.C., 2011) under the supervision of veterinarians. In addition, the animal care and use protocol was reviewed and approved by the IACUC at Pharmacology Discovery Services Taiwan, Ltd.

Compound 13 (an exemplary compound) was formulated in dimethyl sulfoxide (DMSO)/Solutol® HS 15 (BASF, Germany)/phosphate buffered saline (PBS, Sigma, USA) (5/5/90, v/v/v) at 0.2 mg/mL for IV injection and polyethylene glycol (PEG) 200 (Sigma, USA)/water for injection (WFI; Tai-Yu, Taiwan) (50/50, v/v) at 1 mg/mL for PO administration. The dosing volumes were 5 mL/kg for IV and 10 mL/kg for PO.

On the day of study, hamsters were anesthetized and subjected to surgical implantation of catheters in the jugular vein. Catheter plugs were fixed to the external ends of the catheters and kept patent using an anti-coagulant heparinized saline solution. After surgical recovery, hamsters were weighed and identified by marking the tail with numbers using a non-toxic permanent marker for designation for IV or PO groups (n=3) as Table 10 details.

TABLE 10

Experimental groups for PK/PD study in hamsters.

| Group ID# | Dose [mg/Kg] | Route | Dosing solution [mg/mL] | Dosing volume [mL/Kg] |
|---|---|---|---|---|
| 1 | 1 | IV | 0.2 | 5 |
| 2 | 10 | PO | 1 | 10 |
| 3 | Non-dose | Control | — | — |

Hamsters from Group 1 received an intravenous bolus via jugular vein of 1 mg/kg of compound 13 (an exemplary compound). On the other hand, hamsters from Group 2 received an intragastric bolus of 10 mg/kg of compound 13 (an exemplary compound) using feeding needles.

Plasma samples were collected at 5, 10, 15, 30, 60, 120, 240, 360, 480 and 1440 minutes post-dose in both IV and PO groups. Hamsters from group 3 were not dosed and were used to collect samples of zero time point and baseline levels of FAP activity and endogenous FGF21.

Blood aliquots (100-150 µL) were collected from jugular vein catheterized hamsters in tubes coated with EDTA-K2, mixed gently, then kept on ice and centrifuged at 2,500×g for 15 minutes at 4° C., within 1 hour of collection. Plasma samples were placed into individually labeled cryotube vials and stored at −80° C. prior to be assayed for FAPα activity assays (Z-Gly-Pro-AMC substrate) and bioanalysis as described above in previous examples.

Figure 16:
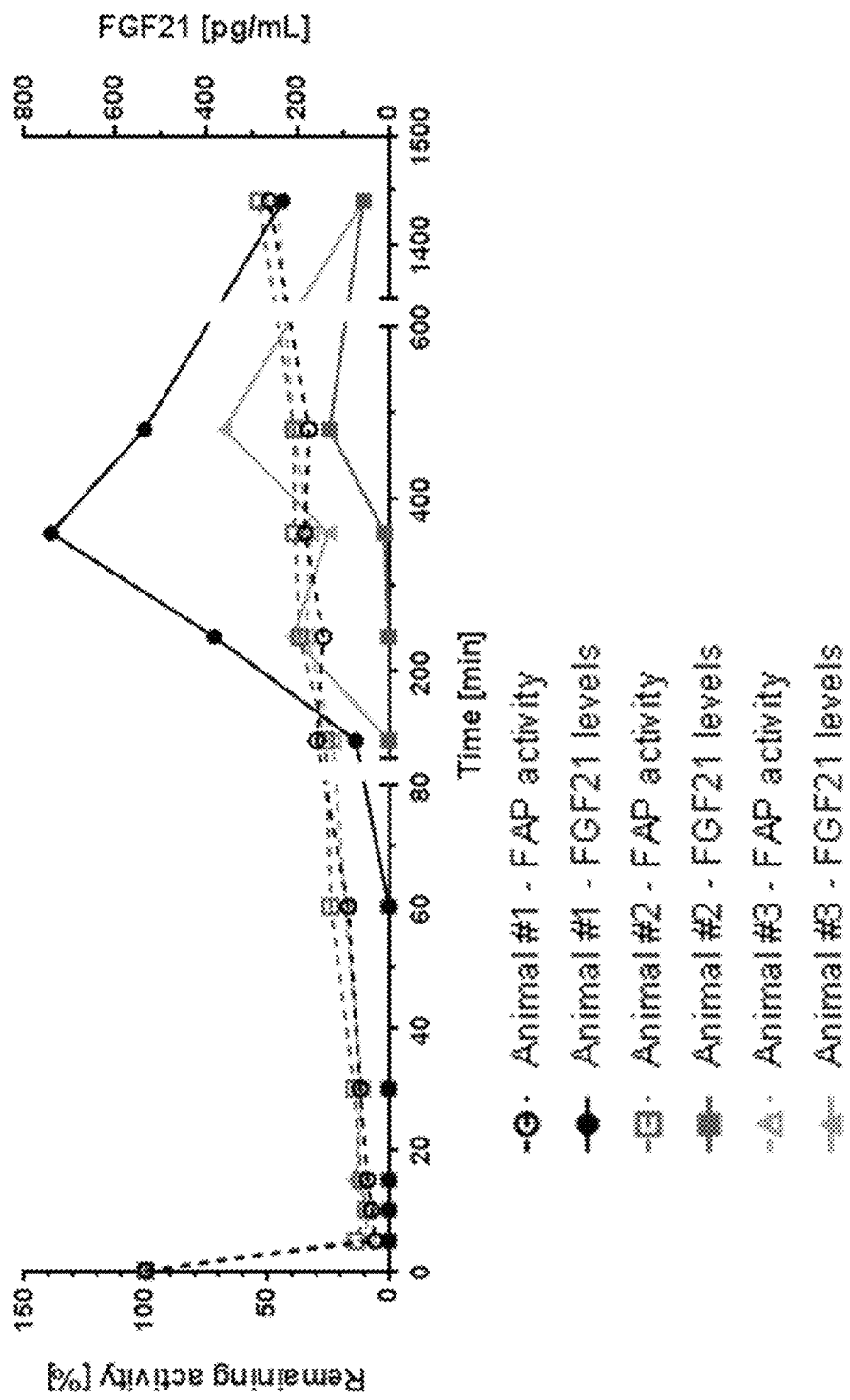
FIG. 16 shows FAP activity and FGF21 levels over time in hamsters after intravenous administration of compound 13 (an exemplary compound).

Levels of endogenous hamster FGF21 in the plasma samples were quantified by using an ELISA kit (Cat. No. #EZRMFGF21-26K, Millipore) according to the manufacturer's instructions. The detection limit was 44.85 pg/ml. Plasma samples of non-dosed animals were analyzed as a pool of plasma. All samples were assayed as single point. The results are shown in FIG. 16.

The $AUC_{last}$ of compound 13 (an exemplary compound) for intravenous and oral administration equaled 255 and 350 hr·ng/mL, respectively. Compared with baseline levels, FAP activity diminished quickly after the administration of compound 13 (an exemplary compound) and although the baseline levels of FGF21 differed between individuals, the levels of total FGF21 increased in the most of hamsters. Importantly, the time course of this increment correlated closely with the inhibition of activity of endogenous FAP in plasma. Therefore, inhibition of FAP in vivo by the administration of an exemplary compound resulted in an increase of endogenous serum FGF21, suggesting protection from cleavage by FAP.

Example B16

Efficacy on Diet-Induced Obesity (DIO) Model in Hamsters

Groups of 10 male golden Syrian hamsters weighing 90±10 g are fed a high fat diet (HFD) (g/100 g: corn oil, 5; coconut oil, 5; cholesterol, 0.2; standard chow, 89.8) throughout the experiment. Seven days after the beginning of the diet, vehicle, ezetimibe (positive control) or an exemplary test compound are administered by oral gavage daily (PO, QD) for 28 consecutive days (Day 1). An extra non-treated group of animals (Group 5) are fed normal diet (control). Body weights (BW) are measured and recorded twice a week.

After fasting overnight, blood is obtained from the retro-orbital sinus of each animal 5 min before daily dosing on Days 1, 8, 15, 22 and 29 after dosing for 0, 7, 14, 21 and 28 days.

The serum obtained from each hamster is assayed for fasted glucose, total cholesterol (Total), low density lipoprotein (LDL), high density lipoprotein (HDL) and triglyceride (TG). Post-treatment values are calculated as a percentage of pre-treatment values. The percent change of treated relative to the vehicle control group is also determined.

At terminal Day 29, all animals are sacrificed and immediately subjected to cardiac puncture for collecting the maximum volume of blood samples. A half of blood sample is processed for serum and is used to assay for terminal adiponectin and insulin by ELISA methods. The other half of blood sample is processed for plasma. Plasma samples are placed into individually labeled cryotube vials and stored at −80° C. prior to FAPα activity assays, quantitation of FGF21 levels by ELISA, and bioanalysis of the exemplary compound as described above in previous examples.

Additionally, tissues such as brain, liver, interscapular BAT, epididymal WAT, pancreas and gastrocnemius muscle are harvested for molecular and biochemical assessments of FGF21 target genes and proteins. Portions of the liver are also collected as non-fixed frozen samples and stained with Oil Red-O staining, or formalin-fixed and paraffin-embedded samples for H&E staining and histopathological analyses.

All references throughout, such as publications, patents, patent applications and published patent applications, are incorporated herein by reference in their entireties.

What is claimed is:
1. A compound of formula (III):

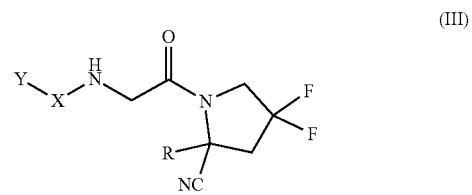

(III)

or a pharmaceutically acceptable salt thereof, wherein:
R is hydrogen, $C_1$-$C_6$ alkyl, $C_3$-$C_8$ cycloalkyl, or $C_6$-$C_{14}$ aryl, wherein the $C_1$-$C_6$ alkyl, $C_3$-$C_8$ cycloalkyl, and $C_6$-$C_{14}$ aryl of R are independently optionally substituted by $R^d$;
X is —C(=O)— or —CH(OH)—;
Y is pyridin-4-yl substituted by $R^{12}$ in the 3-position, wherein
$R^{12}$ is $C^3$—$C_8$ cycloalkyl, $C_4$—$C_8$ cycloalkenyl, 3- to 12-membered heterocyclyl, 5- to 10-membered heteroaryl, or $C_{10}$ aryl, wherein each $R^{12}$ is independently optionally substituted by $R^L$;
each $R^{14}$ is independently hydrogen, $C_1$-$C_6$ alkyl, $C_2$-$C_6$ alkynyl, $C^3$-$C_8$ cycloalkyl, or $C_6$-$C_{14}$ aryl, wherein the $C_1$-$C_6$ alkyl, $C_2$-$C_6$ alkenyl, $C_2$-$C_6$ alkynyl, $C_3$-$C_3$ cycloalkyl, and $C_6$-$C_{14}$ aryl, of $R^{14}$ are independently optionally substituted by halogen, -OH, oxo, cyano, or $C_1$-$C_6$ alkyl optionally substituted by halogen, -OH, or oxo;
$R^{15}$ and $R^{16}$, independently of each other and independently at each occurrence, are hydrogen, $C_1$-$C_6$ alkyl, $C_2$-$C_6$ alkenyl, $C_2$-$C_6$ alkynyl, $C_3$-$C_3$ cycloalkyl, or $C_6$-$C_{14}$ aryl, wherein the $C_1$-$C_6$ alkyl, $C_2$-$C_6$ alkenyl, $C_2$-$C_6$ alkynyl, $C_3$-$C_3$ cycloalkyl, and $C_6$-$C_{14}$ aryl of $R^{15}$ and $R^{16}$ are independently optionally substituted by halogen, -OH, oxo, cyano, or $C_1$-$C_6$ alkyl, optionally substitued by halogen, -OH, or oxo;

$R^d$ is halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, -$OR^{14}$, -$NR^{15}R^{16}$, cyano, or nitro; and each $R^L$ is independently halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, -$OR^{14}$, -$C(O)R^{14}$, -$NR^{15}R^{16}$, cyano, oxo, or nitro.

2. The compound of claim 1, or a pharmaceutically acceptable salt thereof, wherein X is -C(=O)-.

3. The compound of claim 1, or a pharmaceutically acceptable salt thereof, wherein R is hydrogen.

4. A pharmaceutical composition comprising a compound of claim 1, or a pharmaceutically acceptable salt thereof, and a pharmaceutically acceptable carrier.

5. The compound of claim 1, or a pharmaceutically acceptable salt thereof, wherein the compound is selected from the group consisting of:

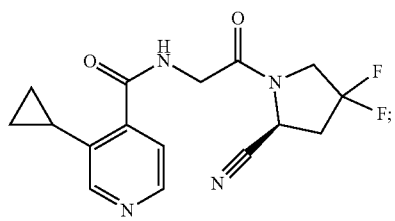

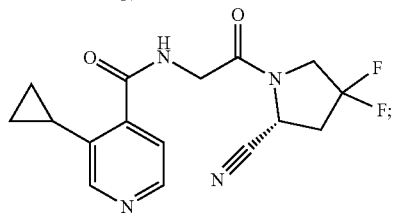

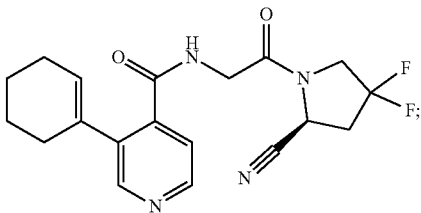

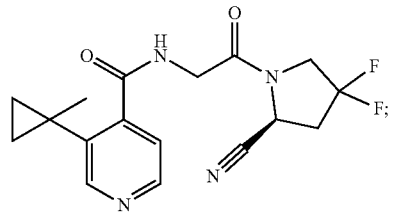

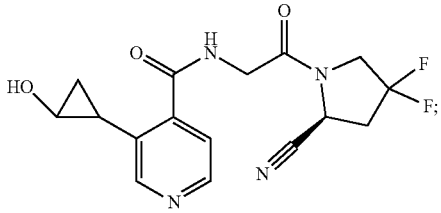

-continued

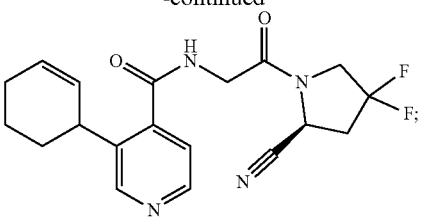

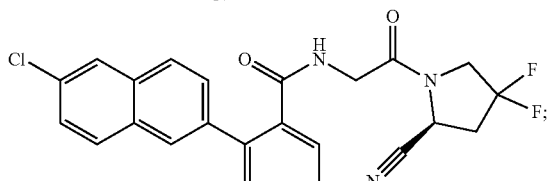

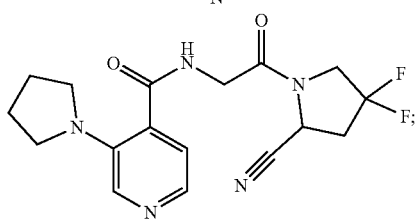

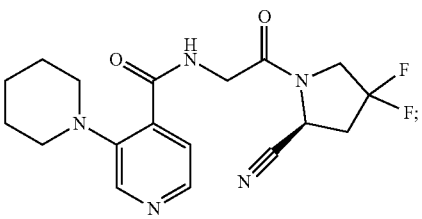

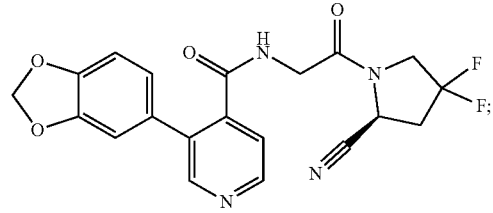

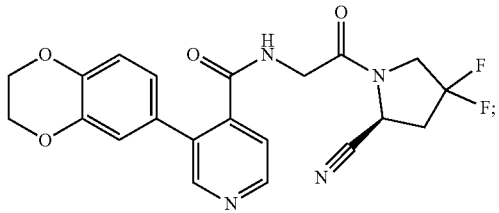

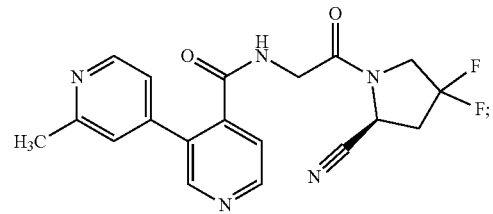

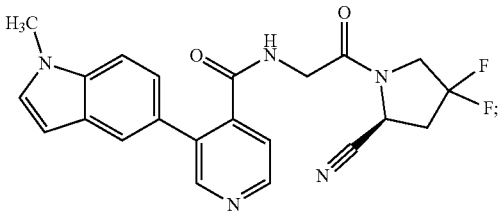

-continued
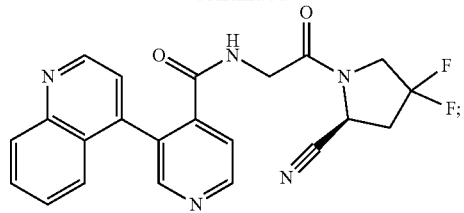
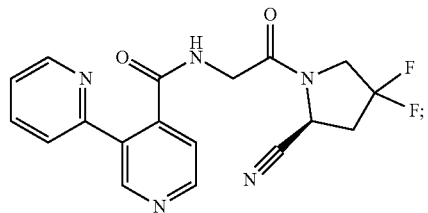
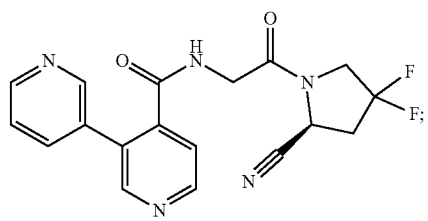
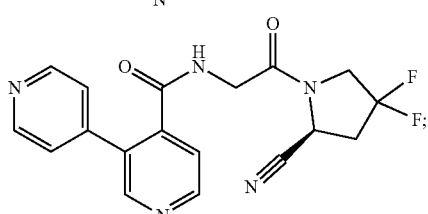
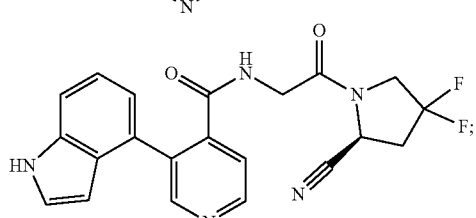
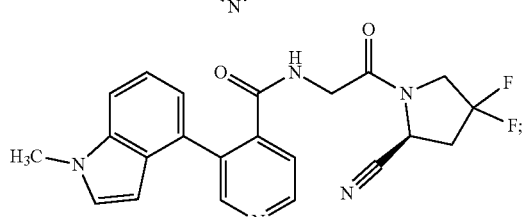
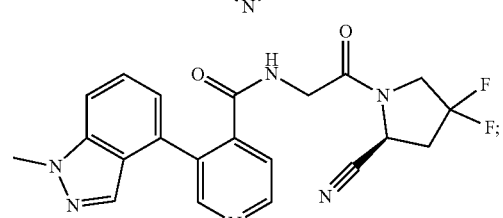
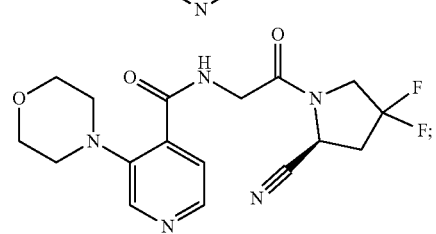
-continued
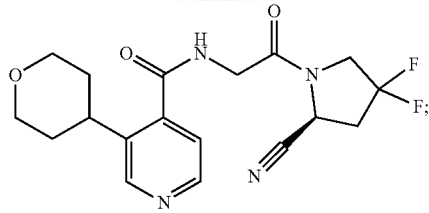
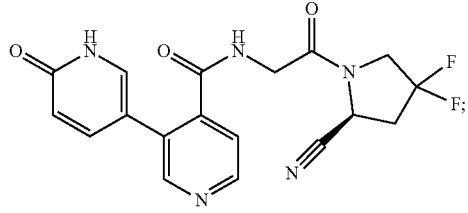
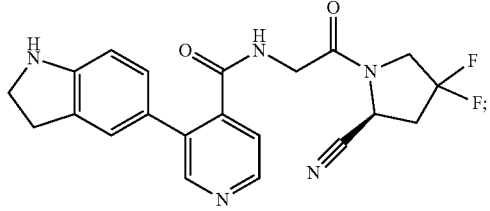
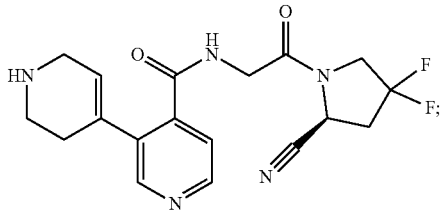
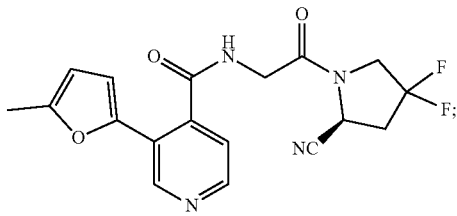
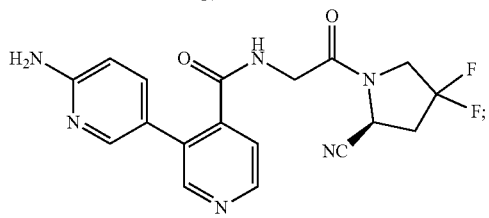
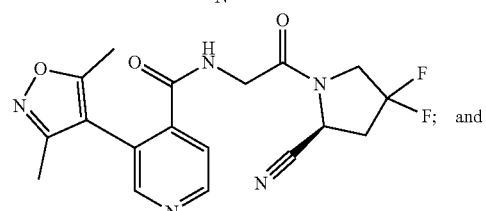; and
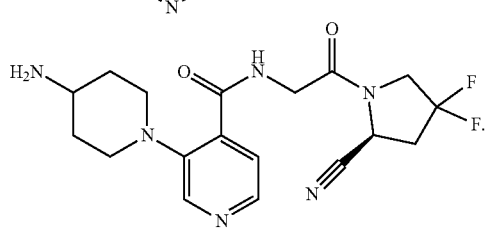.

6. The compound of claim 1, or a pharmaceutically acceptable salt thereof, wherein $R^{12}$ is $C_3$-$C_8$ cycloalkyl optionally substituted by $R^L$.

7. The compound of claim 1, or a pharmaceutically acceptable salt thereof, wherein $R^{12}$ is $C_4$-$C_8$ cycloalkenyl optionally substituted by $R^L$.

8. The compound of claim 1, or a pharmaceutically acceptable salt thereof, wherein $R^{12}$ is 3- to 12-membered heterocyclyl optionally substituted by $^R L$.

9. The compound of claim 1, or a pharmaceutically acceptable salt thereof, wherein $R^{12}$ is 5- to 10-membered heteroaryl optionally substituted by $^R L$.

10. The compound of claim 1, or a pharmaceutically acceptable salt thereof, wherein $R^{12}$ is $C_{10}$ aryl optionally substituted by $R^L$.

11. The compound of claim 1, wherein the compound is

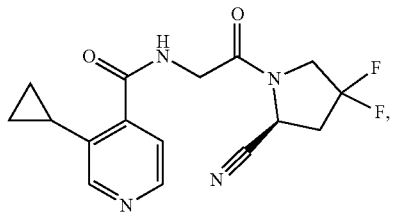 [SMILES: N#C[C@@H]1CC(F)(F)CN1C(=O)CNC(=O)c1ccncc1C1CC1]

or a pharmaceutically acceptable salt thereof.

12. The compound of claim 1, wherein the compound is

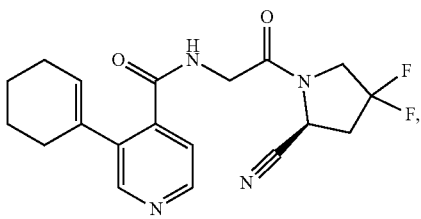 [SMILES: N#C[C@@H]1CC(F)(F)CN1C(=O)CNC(=O)c1ccncc1C1=CCCCC1]

or a pharmaceutically acceptable salt thereof.

13. The compound of claim 1, wherein the compound is

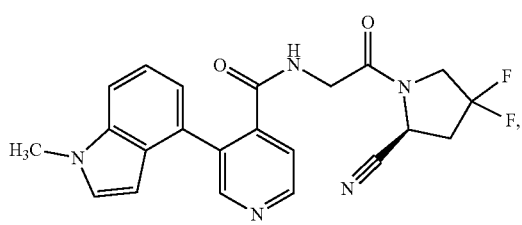 [SMILES: Cn1ccc2c(-c3cnccc3C(=O)NCC(=O)N3CC(F)(F)C[C@H]3C#N)cccc21]

or a pharmaceutically acceptable salt thereof.

14. The compound of claim 1, wherein the compound is

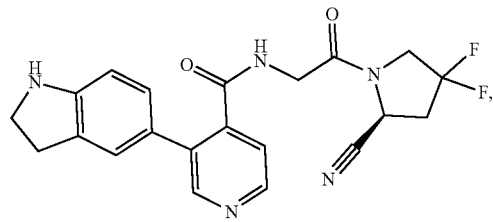 [SMILES: N#C[C@@H]1CC(F)(F)CN1C(=O)CNC(=O)c1ccncc1-c1ccc2c(c1)CCN2]

or a pharmaceutically acceptable salt thereof.

15. The compound of claim 1, wherein the compound is

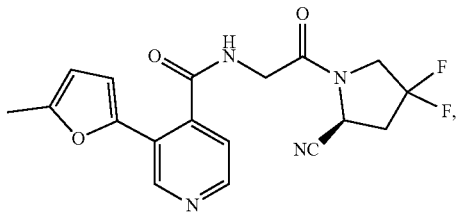 [SMILES: Cc1ccc(-c2cnccc2C(=O)NCC(=O)N2CC(F)(F)C[C@H]2C#N)o1]

or a pharmaceutically acceptable salt thereof.

16. The compound of claim 1, wherein the compound is

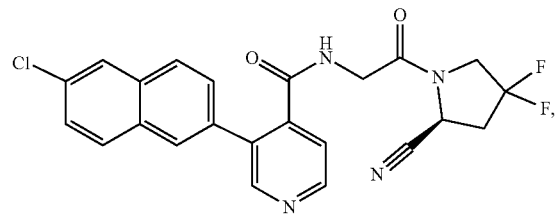 [SMILES: N#C[C@@H]1CC(F)(F)CN1C(=O)CNC(=O)c1ccncc1-c1ccc2cc(Cl)ccc2c1]

or a pharmaceutically acceptable salt thereof.

* * * * *